(12) United States Patent
Izuhara et al.

(10) Patent No.: US 9,347,954 B2
(45) Date of Patent: May 24, 2016

(54) ANTIBODY CAPABLE OF BINDING TO SPECIFIC REGION OF PERIOSTIN, AND METHOD OF MEASURING PERIOSTIN USING THE SAME

(75) Inventors: Kenji Izuhara, Saga (JP); Shoichiro Ohta, Saga (JP); Kazuhiko Arima, Saga (JP); Hiroshi Shiraishi, Saga (JP); Shoichi Suzuki, Saga (JP); Tomoaki Hoshino, Kurume (JP); Yoshinori Azuma, Sagamihara (JP); Junya Ono, Sagamihara (JP)

(73) Assignees: SHINO-TEST CORPORATION, Tokyo (JP); SAGA UNIVERSITY, Saga-Shi (JP); KURUME UNIVERSITY, Kurume-Shi (JP)

( * ) Notice: Subject to any disclaimer, the term of this patent is extended or adjusted under 35 U.S.C. 154(b) by 79 days.

(21) Appl. No.: 14/342,996

(22) PCT Filed: Sep. 6, 2012

(86) PCT No.: PCT/JP2012/072774
§ 371 (c)(1),
(2), (4) Date: Jun. 19, 2014

(87) PCT Pub. No.: WO2013/035799
PCT Pub. Date: Mar. 14, 2013

(65) Prior Publication Data
US 2014/0308685 A1    Oct. 16, 2014

(30) Foreign Application Priority Data

Sep. 6, 2011   (JP) .................. 2011-194323
Mar. 29, 2012  (JP) .................. 2012-077774

(51) Int. Cl.
*C07K 16/18*    (2006.01)
*G01N 33/68*    (2006.01)

(52) U.S. Cl.
CPC ............ *G01N 33/6893* (2013.01); *C07K 16/18* (2013.01); *G01N 2800/12* (2013.01)

(58) Field of Classification Search
CPC ........... C12Q 2600/158; C12Q 1/6886; C07K 16/18; C07K 14/47; C07K 16/00; A61K 2039/505; A61K 38/1709; G01N 33/6893; G01N 2800/12; G01N 33/53
See application file for complete search history.

(56) References Cited

U.S. PATENT DOCUMENTS

| 5,756,664 | A  | 5/1998  | Amann et al. |
| 6,518,063 | B1 | 2/2003  | Ducy et al.  |
| 2003/0073137 | A1 | 4/2003  | Chen et al.  |
| 2003/0152956 | A1 | 8/2003  | Ohtani et al. |
| 2006/0228763 | A1 | 10/2006 | Chen et al.  |
| 2011/0086360 | A1 | 4/2011  | Izuhara et al. |
| 2012/0219977 | A1 | 8/2012  | Garnero et al. |
| 2013/0230861 | A1 | 9/2013  | Izuhara et al. |

FOREIGN PATENT DOCUMENTS

| EP | 1 978 034 A1     | 10/2008 |
| EP | 2 295 599 A1     | 3/2011  |
| JP | H09-229935       | 9/1997  |
| JP | H10-132819 A     | 5/1998  |
| JP | 2005-500059 A    | 1/2005  |
| JP | 2012-058048 A    | 3/2012  |
| WO | WO 98/23963      | 6/1998  |
| WO | WO 02/052006 A1  | 7/2002  |
| WO | WO 2007/077934 A1 | 7/2007 |
| WO | WO 2009/148184 A1 | 12/2009 |
| WO | 2013/148232 A1   | 10/2013 |

OTHER PUBLICATIONS

Shimazaki et al (JEM, vol. 205, No. 2, Feb. 18, 2008 295-303.*
Contié et al., "Development of a New ELISA for Serum Periostin: Evaluation of Growth-Related Changes and Bisphosphonate Treatment in Mice," Calcified Tissue International, Jun. 22, 2010, vol. 87, No. 4, XP19840149A, pp. 341-350.
Extended European Search Report, dated Aug. 4, 2015, for European Application No. 12829373.5, (Continued)

*Primary Examiner* — Shafiqul Haq
*Assistant Examiner* — Carmencita M Belei
(74) *Attorney, Agent, or Firm* — Birch, Stewart, Kolasch & Birch, LLP

(57) ABSTRACT

The present invention provides a method and a reagent for measuring periostin contained in a sample with improved accuracy, a method for improving accuracy in measurement of periostin, and a method of testing for pulmonary fibrosis or interstitial pneumonia with improved accuracy. The antibody of the present invention binds to at least one region selected from the group consisting of an EMI region, an R1 region, an R2 region, and an R3 region of periostin or a cleavage product thereof. The method and the reagent for measuring periostin and the method for improving accuracy in periostin measurement of the present invention is characterized by detecting at least one region selected from the group consisting of an EMI region, an R1 region, an R2 region, and an R3 region of periostin. The method of testing for pulmonary fibrosis or interstitial pneumonia of the present invention includes the steps of a) measuring the amount or concentration of periostin in a sample derived from a subject, which measuring includes detecting at least one region selected from the group consisting of an EMI region, an R1 region, an R2 region, and an R3 region of periostin and b) comparing the amount or concentration of the periostin in the sample derived from the subject with an amount or concentration of periostin in a sample derived from a living body not suffering from pulmonary fibrosis and interstitial pneumonia.

2 Claims, 22 Drawing Sheets

(56) References Cited

OTHER PUBLICATIONS

Kii et al., "Incorporation of Tenascin-C into the Extracellular Matrix by Periostin Underlies an Extracellular Meshwork Architecture," Journal of Biological Chemistry, Jan. 15, 2010, vol. 285, No. 3, XP55203913A, pp. 2028-2039.

Kim et al., "Corneal Dystrophy-associated R124H Mutation Disrupts TGFBI Interaction with Periostin and Causes Mislocalization to the Lysosome," Journal of Biological Chemistry, Jul. 17, 2009, vol. 284, No. 29, XP55174951A, pp. 19580-19591.

Norris et al., "Periostin Promotes a Fibroblastic Lineage Pathway in Atrioventricular Valve Progenitor Cells," Developmental Dynamics, Mar. 30, 2009, vol. 238, No. 5, XP55203979A, pp. 1052-1063.

Okamoto et al., "Periostin, a Matrix Protein, is a Novel Biomarker for Idiopathic Interstitial Pneumonias," European Respiratory Journal, 2011 (first published online: Dec. 22, 2010), vol. 37, No. 5, XP55204016A, pp. 1119-1127.

Shimazaki et al., "Periostin is Essential for Cardiac Healing After Acute Myocardial Infarction," JEM, Feb. 18, 2008, vol. 205, No. 2, XP55174973A, pp. 295-303.

Taniguchi et al., "Periostin Controls Keratinocyte Proliferation and Differentiation by Interacting with the Paracrine IL-1α/IL-6 Loop," Journal of Investigative Dermatology, 2014 (published online Dec. 19, 2013), vol. 134, No. 5, XP55204145A, pp. 1295-1304.

Blanchard et al., "Periostin facilitates eosinophil tissue infiltration in allergic lung and esophageal responses", Mucosal. Immunol., vol. 1, No. 4 (2008) pp. 289-296.

International Search Report issued in International Application No. PCT/JP2012/072774 mailed Oct. 9, 2012.

Orecchia et al., "Identification of a novel cell binding site of periostin involved in tumour growth", European Journal of Cancer, vol. 47 (2011) pp. 2221-2229.

Takayama et al., "Periostin: A novel component of subepithelial fibrosis of bronchial asthma downstream of IL-4 and IL-13 signals", J. Allergy Clin. Immunol., vol. 118 (2006) pp. 98-104.

\* cited by examiner

Figure 1
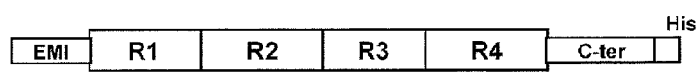
PERIOSTIN
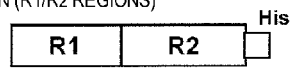
PARTIAL-LENGTH PERIOSTIN (R1/R2 REGIONS)
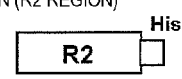
PARTIAL-LENGTH PERIOSTIN (R2 REGION)
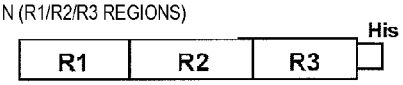
PARTIAL-LENGTH PERIOSTIN (R1/R2/R3 REGIONS)
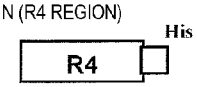
PARTIAL-LENGTH PERIOSTIN (R4 REGION)
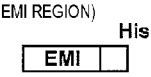
PARTIAL-LENGTH PERIOSTIN (EMI REGION)
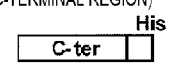
PARTIAL-LENGTH PERIOSTIN (C-TERMINAL REGION)
Figure 2
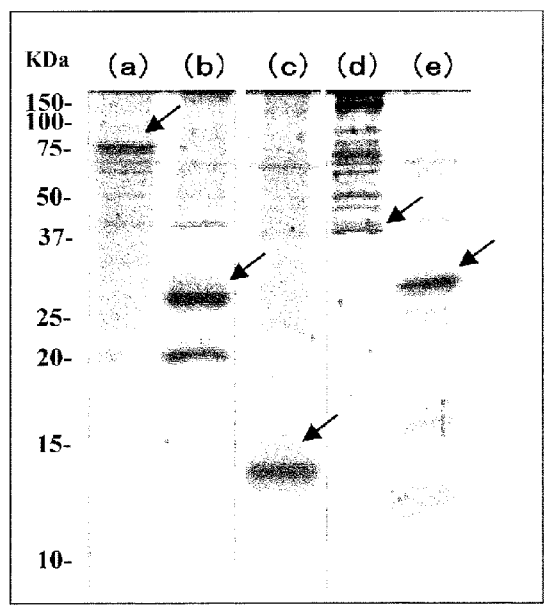

Figure 4

| | Anti-periostin monoclonal antibody | Periostin | Partial-length periostin (R1/R2 regions) | Partial-length periostin (R2 region) | Partial-length periostin (R1/R2/R3 regions) | Partial-length periostin (R4 region) | Partial-length periostin (EMI region) | Partial-length periostin (C-terminal region) | Region recognized as epitope |
|---|---|---|---|---|---|---|---|---|---|
| (1) | SS16A | O | | | O | | | | R3 region |
| (2) | SS17B | O | | | | O | | | R4 region |
| (3) | SS18A | O | O | | O | | | | R1 region |
| (4) | SS19A | O | | | | O | | | R4 region |
| (5) | SS19B | O | | | | | | O | C-terminal region |
| (6) | SS19C | O | O | O | O | | | | R2 region |
| (7) | SS19D | O | | | O | | | | R3 region |
| (8) | SS20A | O | | | | | O | | EMI region |
| (9) | SS21A | O | | | | | | O | C-terminal region |

Figure 7

| ANTI-PERIOSTIN MONOCLONAL ANTIBODY | PERIOSTIN | | |
|---|---|---|---|
| | MULTIMER | MONOMER | CLEAVAGE PRODUCT |
| SS16A | O | O | O |
| SS17B | O | O | |
| SS18A | O | O | O |
| SS19A | O | O | |
| SS19B | O | O | |
| SS19C | O | O | O |
| SS19D | | O | O |
| SS20A | O | O | O |
| SS21A | O | O | |

Figure 18

| | | IMMOBILIZED ANTIBODY | LABELED ANTIBODY | REGION OF PERIOSTIN DETECTED BY IMMOBILIZED ANTIBODY | REGION OF PERIOSTIN DETECTED BY LABELED ANTIBODY | PERIOSTIN (MONOMER, MULTIMER, OR CLEAVAGE PRODUCT) THAT CAN BE MEASURED | SENSITIVITY OF MEASUREMENT | SPECIFICITY OF MEASUREMENT | RATIO OF MEAN VALUE OF MEASURED VALUES OF POSITIVE SAMPLES TO MEAN VALUE OF MEASURED VALUES OF NEGATIVE SAMPLES | AUC VALUE OF ROC CURVE |
|---|---|---|---|---|---|---|---|---|---|---|
| (1) | MEASUREMENT-1 BY A CONVENTIONAL TECHNIQUE | SS18A | SS17B | R1 REGION | R4 REGION | • MULTIMER<br>• MONOMER | 50.0% | 98.1% | 2.1 TIMES | 0.902 |
| (2) | MEASUREMENT-1 BY THE PRESENT INVENTION | SS18A | SS19C | R1 REGION | R2 REGION | • MULTIMER<br>• MONOMER<br>• CLEAVAGE PRODUCT | 84.6% | 98.1% | 2.9 TIMES | 0.980 |
| (3) | MEASUREMENT-2 BY THE PRESENT INVENTION | SS20A | SS19D | EMI REGION | R3 REGION | • MONOMER<br>• CLEAVAGE PRODUCT | 96.2% | 98.1% | 7.7 TIMES | 0.994 |
| (4) | MEASUREMENT-2 BY A CONVENTIONAL TECHNIQUE | SS19D | SS17B | R3 REGION | R4 REGION | • MONOMER | 53.8% | 98.1% | 1.6 TIMES | 0.882 |
| (5) | MEASUREMENT-3 BY A CONVENTIONAL TECHNIQUE | SS19D | SS19A | R3 REGION | R4 REGION | • MONOMER | 61.5% | 98.1% | 2.1 TIMES | 0.889 |
| (6) | MEASUREMENT-4 BY A CONVENTIONAL TECHNIQUE | SS19D | SS21A | R3 REGION | C-TERMINAL REGION | • MONOMER | 7.7% | 98.1% | 1.3 TIMES | 0.493 |
| (7) | MEASUREMENT-3 BY THE PRESENT INVENTION | SS19D | SS20A | R3 REGION | EMI REGION | • MONOMER<br>• CLEAVAGE PRODUCT | 80.8% | 98.1% | 5.8 TIMES | 0.943 |
| (8) | MEASUREMENT-4 BY THE PRESENT INVENTION | SS16A | SS18A | R3 REGION | R1 REGION | • MULTIMER<br>• MONOMER<br>• CLEAVAGE PRODUCT | 76.9% | 98.1% | 2.8 TIMES | 0.912 |
| (9) | MEASUREMENT-5 BY A CONVENTIONAL TECHNIQUE | SS19B | SS17B | C-TERMINAL REGION | R4 REGION | • MULTIMER<br>• MONOMER | 23.1% | 98.1% | 1.3 TIMES | 0.606 |
| (10) | MEASUREMENT-5 BY THE PRESENT INVENTION | SS19C | SS19D | R2 REGION | R3 REGION | • MONOMER<br>• CLEAVAGE PRODUCT | 73.1% | 98.1% | 7.7 TIMES | 0.914 |
| (11) | MEASUREMENT-6 BY THE PRESENT INVENTION | SS20A | SS19C | EMI REGION | R2 REGION | • MULTIMER<br>• MONOMER<br>• CLEAVAGE PRODUCT | 73.1% | 98.1% | 1.8 TIMES | 0.914 |
| (12) | MEASUREMENT-6 BY A CONVENTIONAL TECHNIQUE | SS20A | SS21A | EMI REGION | C-TERMINAL REGION | • MULTIMER<br>• MONOMER | 30.8% | 98.1% | 1.7 TIMES | 0.704 |
| (13) | MEASUREMENT-7 BY A CONVENTIONAL TECHNIQUE | SS18A | SS21A | R1 REGION | C-TERMINAL REGION | • MULTIMER<br>• MONOMER | 23.1% | 98.1% | 1.9 TIMES | 0.691 |

Figure 28

| | | IMMOBILIZED ANTIBODY | LABELED ANTIBODY | REGION OF PERIOSTIN DETECTED BY IMMOBILIZED ANTIBODY | REGION OF PERIOSTIN DETECTED BY LABELED ANTIBODY | PERIOSTIN (MONOMER, MULTIMER, OR CLEAVAGE PRODUCT) THAT CAN BE MEASURED | SENSITIVITY OF MEASUREMENT | SPECIFICITY OF MEASUREMENT | RATIO OF MEAN VALUE OF MEASURED VALUES OF POSITIVE SAMPLES TO MEAN VALUE OF MEASURED VALUES OF NEGATIVE SAMPLES | AUC VALUE OF ROC CURVE |
|---|---|---|---|---|---|---|---|---|---|---|
| <1> | MEASUREMENT BY A CONVENTIONAL TECHNIQUE | SS18A | SS17B | R1 REGION | R4 REGION | •MULTIMER<br>•MONOMER | 43.6% | 98.4% | 2.8 TIMES | 0.872 |
| <2> | MEASUREMENT-(i) BY THE PRESENT INVENTION | SS20A | SS19D | EMI REGION | R3 REGION | •MONOMER<br>•CLEAVAGE PRODUCT | 79.5% | 98.4% | 6.1 TIMES | 0.984 |
| <3> | MEASUREMENT-(ii) BY THE PRESENT INVENTION | SS25A | SS20A | R2 REGION | EMI REGION | •MONOMER<br>•CLEAVAGE PRODUCT | 71.8% | 98.4% | 16.1 TIMES | 0.957 |
| <4> | MEASUREMENT-(iii) BY THE PRESENT INVENTION | SS27A | SS20A | R1 REGION | EMI REGION | •MONOMER<br>•CLEAVAGE PRODUCT | 92.3% | 98.4% | 3.6 TIMES | 0.993 |

SEQUENCE LISTING

```
<160> NUMBER OF SEQ ID NOS: 18

<210> SEQ ID NO 1
<211> LENGTH: 3213
<212> TYPE: DNA
<213> ORGANISM: Homo sapiens
<220> FEATURE:
<221> NAME/KEY: CDS
<222> LOCATION: (12)..(2522)

<400> SEQUENCE: 1
agagactcaa g atg att ccc ttt tta ccc atg ttt tct cta cta ttg ctg      50
            Met Ile Pro Phe Leu Pro Met Phe Ser Leu Leu Leu Leu
            1               5                   10 ctt att gtt aac cct ata aac gcc aac aat cat tat gac aag atc ttg       98
Leu Ile Val Asn Pro Ile Asn Ala Asn Asn His Tyr Asp Lys Ile Leu
    15                  20                  25 gct cat agt cgt atc agg ggt cgg gac caa ggc cca aat gtc tgt gcc      146
Ala His Ser Arg Ile Arg Gly Arg Asp Gln Gly Pro Asn Val Cys Ala
30                  35                  40                  45 ctt caa cag att ttg ggc acc aaa aag aaa tac ttc agc act tgt aag      194
Leu Gln Gln Ile Leu Gly Thr Lys Lys Lys Tyr Phe Ser Thr Cys Lys
                50                  55                  60 aac tgg tat aaa aag tcc atc tgt gga cag aaa acg act gtt tta tat      242
Asn Trp Tyr Lys Lys Ser Ile Cys Gly Gln Lys Thr Thr Val Leu Tyr
            65                  70                  75 gaa tgt tgc cct ggt tat atg aga atg gaa gga atg aaa ggc tgc cca      290
Glu Cys Cys Pro Gly Tyr Met Arg Met Glu Gly Met Lys Gly Cys Pro
        80                  85                  90 gca gtt ttg ccc att gac cat gtt tat ggc act ctg ggc atc gtg gga      338
Ala Val Leu Pro Ile Asp His Val Tyr Gly Thr Leu Gly Ile Val Gly
    95                  100                 105 gcc acc aca acg cag cgc tat tct gac gcc tca aaa ctg agg gag gag      386
Ala Thr Thr Thr Gln Arg Tyr Ser Asp Ala Ser Lys Leu Arg Glu Glu
110                 115                 120                 125 atc gag gga aag gga tcc ttc act tac ttt gca ccg agt aat gag gct      434
Ile Glu Gly Lys Gly Ser Phe Thr Tyr Phe Ala Pro Ser Asn Glu Ala
                130                 135                 140 tgg gac aac ttg gat tct gat atc cgt aga ggt ttg gag agc aac gtg      482
Trp Asp Asn Leu Asp Ser Asp Ile Arg Arg Gly Leu Glu Ser Asn Val
            145                 150                 155 aat gtt gaa tta ctg aat gct tta cat agt cac atg att aat aag aga      530
Asn Val Glu Leu Leu Asn Ala Leu His Ser His Met Ile Asn Lys Arg
        160                 165                 170 atg ttg acc aag gac tta aaa aat ggc atg att att cct tca atg tat      578
Met Leu Thr Lys Asp Leu Lys Asn Gly Met Ile Ile Pro Ser Met Tyr
    175                 180                 185 aac aat ttg ggg ctt ttc att aac cat tat cct aat ggg gtt gtc act      626
Asn Asn Leu Gly Leu Phe Ile Asn His Tyr Pro Asn Gly Val Val Thr
190                 195                 200                 205 gtt aat tgt gct cga atc atc cat ggg aac cag att gca aca aat ggt      674
Val Asn Cys Ala Arg Ile Ile His Gly Asn Gln Ile Ala Thr Asn Gly
                210                 215                 220
```

```
gtt gtc cat gtc att gac cgt gtg ctt aca caa att ggt acc tca att        722
Val Val His Val Ile Asp Arg Val Leu Thr Gln Ile Gly Thr Ser Ile
            225                     230                     235 caa gac ttc att gaa gca gaa gat gac ctt tca tct ttt aga gca gct        770
Gln Asp Phe Ile Glu Ala Glu Asp Asp Leu Ser Ser Phe Arg Ala Ala
            240                     245                     250 gcc atc aca tcg gac ata ttg gag gcc ctt gga aga gac ggt cac ttc        818
Ala Ile Thr Ser Asp Ile Leu Glu Ala Leu Gly Arg Asp Gly His Phe
            255                     260                     265 aca ctc ttt gct ccc acc aat gag gct ttt gag aaa ctt cca cga ggt        866
Thr Leu Phe Ala Pro Thr Asn Glu Ala Phe Glu Lys Leu Pro Arg Gly
270                     275                     280                 285 gtc cta gaa agg ttc atg gga gac aaa gtg gct tcc gaa gct ctt atg        914
Val Leu Glu Arg Phe Met Gly Asp Lys Val Ala Ser Glu Ala Leu Met
                290                     295                     300 aag tac cac atc tta aat act ctc cag tgt tct gag tct att atg gga        962
Lys Tyr His Ile Leu Asn Thr Leu Gln Cys Ser Glu Ser Ile Met Gly
            305                     310                     315 gga gca gtc ttt gag acg ctg gaa gga aat aca att gag ata gga tgt       1010
Gly Ala Val Phe Glu Thr Leu Glu Gly Asn Thr Ile Glu Ile Gly Cys
            320                     325                     330 gac ggt gac agt ata aca gta aat gga atc aaa atg gtg aac aaa aag       1058
Asp Gly Asp Ser Ile Thr Val Asn Gly Ile Lys Met Val Asn Lys Lys
            335                     340                     345 gat att gtg aca aat aat ggt gtg atc cat ttg att gat cag gtc cta       1106
Asp Ile Val Thr Asn Asn Gly Val Ile His Leu Ile Asp Gln Val Leu
350                     355                     360                 365 att cct gat tct gcc aaa caa gtt att gag ctg gct gga aaa cag caa       1154
Ile Pro Asp Ser Ala Lys Gln Val Ile Glu Leu Ala Gly Lys Gln Gln
                370                     375                     380 acc acc ttc acg gat ctt gtg gcc caa tta ggc ttg gca tct gct ctg       1202
Thr Thr Phe Thr Asp Leu Val Ala Gln Leu Gly Leu Ala Ser Ala Leu
            385                     390                     395 agg cca gat gga gaa tac act ttg ctg gca cct gtg aat aat gca ttt       1250
Arg Pro Asp Gly Glu Tyr Thr Leu Leu Ala Pro Val Asn Asn Ala Phe
            400                     405                     410 tct gat gat act ctc agc atg gtt cag cgc ctc ctt aaa tta att ctg       1298
Ser Asp Asp Thr Leu Ser Met Val Gln Arg Leu Leu Lys Leu Ile Leu
415                     420                     425 cag aat cac ata ttg aaa gta aaa gtt ggc ctt aat gag ctt tac aac       1346
Gln Asn His Ile Leu Lys Val Lys Val Gly Leu Asn Glu Leu Tyr Asn
430                     435                     440                 445 ggg caa ata ctg gaa acc atc gga ggc aaa cag ctc aga gtc ttc gta       1394
Gly Gln Ile Leu Glu Thr Ile Gly Gly Lys Gln Leu Arg Val Phe Val
                450                     455                     460 tat cgt aca gct gtc tgc att gaa aat tca tgc atg gag aaa ggg agt       1442
Tyr Arg Thr Ala Val Cys Ile Glu Asn Ser Cys Met Glu Lys Gly Ser
            465                     470                     475 aag caa ggg aga aac ggt gcg att cac ata ttc cgc gag atc atc aag       1490
Lys Gln Gly Arg Asn Gly Ala Ile His Ile Phe Arg Glu Ile Ile Lys
            480                     485                     490 cca gca gag aaa tcc ctc cat gaa aag tta aaa caa gat aag cgc ttt       1538
Pro Ala Glu Lys Ser Leu His Glu Lys Leu Lys Gln Asp Lys Arg Phe
495                     500                     505 agc acc ttc ctc agc cta ctt gaa gct gca gac ttg aaa gag ctc ctg       1586
Ser Thr Phe Leu Ser Leu Leu Glu Ala Ala Asp Leu Lys Glu Leu Leu
510                     515                     520                 525 aca caa cct gga gac tgg aca tta ttt gtg cca acc aat gat gct ttt       1634
Thr Gln Pro Gly Asp Trp Thr Leu Phe Val Pro Thr Asn Asp Ala Phe
```

-continued

```
                        530                 535                 540
aag gga atg act agt gaa gaa aaa gaa att ctg ata cgg gac aaa aat      1682
Lys Gly Met Thr Ser Glu Glu Lys Glu Ile Leu Ile Arg Asp Lys Asn
            545                 550                 555 gct ctt caa aac atc att ctt tat cac ctg aca cca gga gtt ttc att      1730
Ala Leu Gln Asn Ile Ile Leu Tyr His Leu Thr Pro Gly Val Phe Ile
        560                 565                 570 gga aaa gga ttt gaa cct ggt gtt act aac att tta aag acc aca caa      1778
Gly Lys Gly Phe Glu Pro Gly Val Thr Asn Ile Leu Lys Thr Thr Gln
    575                 580                 585 gga agc aaa atc ttt ctg aaa gaa gta aat gat aca ctt ctg gtg aat      1826
Gly Ser Lys Ile Phe Leu Lys Glu Val Asn Asp Thr Leu Leu Val Asn
590                 595                 600                 605 gaa ttg aaa tca aaa gaa tct gac atc atg aca aca aat ggt gta att      1874
Glu Leu Lys Ser Lys Glu Ser Asp Ile Met Thr Thr Asn Gly Val Ile
            610                 615                 620 cat gtt gta gat aaa ctc ctc tat cca gca gac aca cct gtt gga aat      1922
His Val Val Asp Lys Leu Leu Tyr Pro Ala Asp Thr Pro Val Gly Asn
        625                 630                 635 gat caa ctg ctg gaa ata ctt aat aaa tta atc aaa tac atc caa att      1970
Asp Gln Leu Leu Glu Ile Leu Asn Lys Leu Ile Lys Tyr Ile Gln Ile
    640                 645                 650 aag ttt gtt cgt ggt agc acc ttc aaa gaa atc ccc gtg act gtc tat      2018
Lys Phe Val Arg Gly Ser Thr Phe Lys Glu Ile Pro Val Thr Val Tyr
655                 660                 665 aca act aaa att ata acc aaa gtt gtg gaa cca aaa att aaa gtg att      2066
Thr Thr Lys Ile Ile Thr Lys Val Val Glu Pro Lys Ile Lys Val Ile
            670                 675                 680                 685 gaa ggc agt ctt cag cct att atc aaa act gaa gga ccc aca cta aca      2114
Glu Gly Ser Leu Gln Pro Ile Ile Lys Thr Glu Gly Pro Thr Leu Thr
        690                 695                 700 aaa gtc aaa att gaa ggt gaa cct gaa ttc aga ctg att aaa gaa ggt      2162
Lys Val Lys Ile Glu Gly Glu Pro Glu Phe Arg Leu Ile Lys Glu Gly
    705                 710                 715 gaa aca ata act gaa gtg atc cat gga gag cca att att aaa aaa tac      2210
Glu Thr Ile Thr Glu Val Ile His Gly Glu Pro Ile Ile Lys Lys Tyr
720                 725                 730 acc aaa atc att gat gga gtg cct gtg gaa ata act gaa aaa gag aca      2258
Thr Lys Ile Ile Asp Gly Val Pro Val Glu Ile Thr Glu Lys Glu Thr
            735                 740                 745 cga gaa gaa cga atc att aca ggt cct gaa ata aaa tac act agg att      2306
Arg Glu Glu Arg Ile Ile Thr Gly Pro Glu Ile Lys Tyr Thr Arg Ile
750                 755                 760                 765 tct act gga ggt gga gaa aca gaa gaa act ctg aag aaa ttg tta caa      2354
Ser Thr Gly Gly Gly Glu Thr Glu Glu Thr Leu Lys Lys Leu Leu Gln
        770                 775                 780 gaa gag gtc acc aag gtc acc aaa ttc att gaa ggt ggt gat ggt cat      2402
Glu Glu Val Thr Lys Val Thr Lys Phe Ile Glu Gly Gly Asp Gly His
    785                 790                 795 tta ttt gaa gat gaa gaa att aaa aga ctg ctt cag gga gac aca ccc      2450
Leu Phe Glu Asp Glu Glu Ile Lys Arg Leu Leu Gln Gly Asp Thr Pro
800                 805                 810 gtg agg aag ttg caa gcc aac aaa aaa gtt caa ggt tct aga aga cga      2498
Val Arg Lys Leu Gln Ala Asn Lys Lys Val Gln Gly Ser Arg Arg Arg
            815                 820                 825 tta agg gaa ggt cgt tct cag tga aaatccaaaa accagaaaaa aatgtttata    2552
Leu Arg Glu Gly Arg Ser Gln
830                 835 caaccctaag tcaataacct gaccttagaa aattgtgaga gccaagttga cttcaggaac    2612
```

-continued

```
tgaaacatca gcacaaagaa gcaatcatca aataattctg aacacaaatt taatattttt      2672
ttttctgaat gagaaacatg agggaaattg tggagttagc ctcctgtggt aaaggaattg      2732
aagaaaatat aacaccttac acccttttc atcttgacat taaaagttct ggctaacttt      2792
ggaatccatt agagaaaaat ccttgtcacc agattcatta caattcaaat cgaagagttg      2852
tgaactgtta tcccattgaa aagaccgagc cttgtatgta tgttatggat acataaaatg      2912
cacgcaagcc attatctctc catgggaagc taagttataa aaataggtgc ttggtgtaca      2972
aaacttttta tatcaaaagg ctttgcacat ttctatatga gtgggtttac tggtaaatta      3032
tgttattttt tacaactaat tttgtactct cagaatgttt gtcatatgct tcttgcaatg      3092 catattttt aatctcaaac gtttcaataa aaccattttt cagatataaa gagaattact      3152
tcaaattgag taattcagaa aaactcaaga tttaagttaa aaagtggttt ggacttggga      3212
a                                                                      3213
```

<210> SEQ ID NO 2
<211> LENGTH: 836
<212> TYPE: PRT
<213> ORGANISM: Homo sapiens

<400> SEQUENCE: 2

```
Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255
```

```
Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Phe Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Val Gln Arg Leu Leu Lys Leu Ile Leu Gln Asn His
            420                 425                 430

Ile Leu Lys Val Lys Val Gly Leu Asn Glu Leu Tyr Asn Gly Gln Ile
        435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
        515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
        595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Thr Thr Lys
            660                 665                 670

Ile Ile Thr Lys Val Val Glu Pro Lys Ile Lys Val Ile Glu Gly Ser
```

```
            675                 680                 685
Leu Gln Pro Ile Ile Lys Thr Glu Gly Pro Thr Leu Thr Lys Val Lys
        690                 695                 700

Ile Glu Gly Glu Pro Glu Phe Arg Leu Ile Lys Glu Gly Glu Thr Ile
705                 710                 715                 720

Thr Glu Val Ile His Gly Glu Pro Ile Ile Lys Lys Tyr Thr Lys Ile
                725                 730                 735

Ile Asp Gly Val Pro Val Glu Ile Thr Glu Lys Glu Thr Arg Glu Glu
            740                 745                 750

Arg Ile Ile Thr Gly Pro Glu Ile Lys Tyr Thr Arg Ile Ser Thr Gly
        755                 760                 765

Gly Gly Glu Thr Glu Thr Leu Lys Lys Leu Leu Gln Glu Glu Val
770                 775                 780

Thr Lys Val Thr Lys Phe Ile Glu Gly Gly Asp Gly His Leu Phe Glu
785                 790                 795                 800

Asp Glu Glu Ile Lys Arg Leu Leu Gln Gly Asp Thr Pro Val Arg Lys
                805                 810                 815

Leu Gln Ala Asn Lys Lys Val Gln Gly Ser Arg Arg Leu Arg Glu
            820                 825                 830

Gly Arg Ser Gln
        835

<210> SEQ ID NO 3
<211> LENGTH: 267
<212> TYPE: DNA
<213> ORGANISM: Homo sapiens
<220> FEATURE:
<221> NAME/KEY: CDS
<222> LOCATION: (1)..(267)

<400> SEQUENCE: 3 aac aat cat tat gac aag atc ttg gct cat agt cgt atc agg ggt cgg        48
Asn Asn His Tyr Asp Lys Ile Leu Ala His Ser Arg Ile Arg Gly Arg
1               5                   10                  15 gac caa ggc cca aat gtc tgt gcc ctt caa cag att ttg ggc acc aaa        96
Asp Gln Gly Pro Asn Val Cys Ala Leu Gln Gln Ile Leu Gly Thr Lys
                20                  25                  30 aag aaa tac ttc agc act tgt aag aac tgg tat aaa aag tcc atc tgt       144
Lys Lys Tyr Phe Ser Thr Cys Lys Asn Trp Tyr Lys Lys Ser Ile Cys
            35                  40                  45 gga cag aaa acg act gtg tta tat gaa tgt tgc cct ggt tat atg aga       192
Gly Gln Lys Thr Thr Val Leu Tyr Glu Cys Cys Pro Gly Tyr Met Arg
        50                  55                  60 atg gaa gga atg aaa ggc tgc cca gca gtt ttg ccc att gac cat gtt       240
Met Glu Gly Met Lys Gly Cys Pro Ala Val Leu Pro Ile Asp His Val
65                  70                  75                  80 tat ggc act ctg ggc atc gtg gga gcc                                    267
Tyr Gly Thr Leu Gly Ile Val Gly Ala
                85

<210> SEQ ID NO 4
<211> LENGTH: 89
<212> TYPE: PRT
<213> ORGANISM: Homo sapiens

<400> SEQUENCE: 4

Asn Asn His Tyr Asp Lys Ile Leu Ala His Ser Arg Ile Arg Gly Arg
1               5                   10                  15

Asp Gln Gly Pro Asn Val Cys Ala Leu Gln Gln Ile Leu Gly Thr Lys
```

```
                    20                  25                  30

Lys Lys Tyr Phe Ser Thr Cys Lys Asn Trp Tyr Lys Lys Ser Ile Cys
            35                  40                  45

Gly Gln Lys Thr Thr Val Leu Tyr Glu Cys Cys Pro Gly Tyr Met Arg
        50                  55                  60

Met Glu Gly Met Lys Gly Cys Pro Ala Val Leu Pro Ile Asp His Val
65                  70                  75                  80

Tyr Gly Thr Leu Gly Ile Val Gly Ala
                85

<210> SEQ ID NO 5
<211> LENGTH: 372
<212> TYPE: DNA
<213> ORGANISM: Homo sapiens
<220> FEATURE:
<221> NAME/KEY: CDS
<222> LOCATION: (1)..(372)

<400> SEQUENCE: 5 acc aca acg cag cgc tat tct gac gcc tca aaa ctg agg gag gag atc      48
Thr Thr Thr Gln Arg Tyr Ser Asp Ala Ser Lys Leu Arg Glu Glu Ile
1               5                   10                  15 gag gga aag gga tcc ttc act tac ttt gca ccg agt aat gag gct tgg      96
Glu Gly Lys Gly Ser Phe Thr Tyr Phe Ala Pro Ser Asn Glu Ala Trp
            20                  25                  30 gac aac ttg gat tct gat atc cgt aga ggt ttg gag agc aac gtg aat     144
Asp Asn Leu Asp Ser Asp Ile Arg Arg Gly Leu Glu Ser Asn Val Asn
        35                  40                  45 gtt gaa tta ctg aat gct tta cat agt cac atg att aat aag aga atg     192
Val Glu Leu Leu Asn Ala Leu His Ser His Met Ile Asn Lys Arg Met
    50                  55                  60 ttg acc aag gac tta aaa aat ggc atg att att cct tca atg tat aac     240
Leu Thr Lys Asp Leu Lys Asn Gly Met Ile Ile Pro Ser Met Tyr Asn
65                  70                  75                  80 aat ttg ggg ctt ttc att aac cat tat cct aat ggg gtt gtc act gtt     288
Asn Leu Gly Leu Phe Ile Asn His Tyr Pro Asn Gly Val Val Thr Val
                85                  90                  95 aat tgt gct cga atc atc cat ggg aac cag att gca aca aat ggt gtt     336
Asn Cys Ala Arg Ile Ile His Gly Asn Gln Ile Ala Thr Asn Gly Val
            100                 105                 110 gtc cat gtc att gac cgt gtg ctt aca caa att ggt                     372
Val His Val Ile Asp Arg Val Leu Thr Gln Ile Gly
        115                 120

<210> SEQ ID NO 6
<211> LENGTH: 124
<212> TYPE: PRT
<213> ORGANISM: Homo sapiens

<400> SEQUENCE: 6

Thr Thr Thr Gln Arg Tyr Ser Asp Ala Ser Lys Leu Arg Glu Glu Ile
1               5                   10                  15

Glu Gly Lys Gly Ser Phe Thr Tyr Phe Ala Pro Ser Asn Glu Ala Trp
            20                  25                  30

Asp Asn Leu Asp Ser Asp Ile Arg Arg Gly Leu Glu Ser Asn Val Asn
        35                  40                  45

Val Glu Leu Leu Asn Ala Leu His Ser His Met Ile Asn Lys Arg Met
    50                  55                  60

Leu Thr Lys Asp Leu Lys Asn Gly Met Ile Ile Pro Ser Met Tyr Asn
65                  70                  75                  80
```

-continued

```
Asn Leu Gly Leu Phe Ile Asn His Tyr Pro Asn Gly Val Val Thr Val
                85                  90                  95

Asn Cys Ala Arg Ile Ile His Gly Asn Gln Ile Ala Thr Asn Gly Val
            100                 105                 110

Val His Val Ile Asp Arg Val Leu Thr Gln Ile Gly
        115                 120

<210> SEQ ID NO 7
<211> LENGTH: 432
<212> TYPE: DNA
<213> ORGANISM: Homo sapiens
<220> FEATURE:
<221> NAME/KEY: CDS
<222> LOCATION: (1)..(432)

<400> SEQUENCE: 7 acc tca att caa gac ttc att gaa gca gaa gat gac ctt tca tct ttt     48
Thr Ser Ile Gln Asp Phe Ile Glu Ala Glu Asp Asp Leu Ser Ser Phe
1               5                   10                  15 aga gca gct gcc atc aca tcg gac ata ttg gag gcc ctt gga aga gac     96
Arg Ala Ala Ala Ile Thr Ser Asp Ile Leu Glu Ala Leu Gly Arg Asp
            20                  25                  30 ggt cac ttc aca ctc ttt gct ccc acc aat gag gct ttt gag aaa ctt    144
Gly His Phe Thr Leu Phe Ala Pro Thr Asn Glu Ala Phe Glu Lys Leu
        35                  40                  45 cca cga ggt gtc cta gaa agg atc atg gga gac aaa gtg gct tcc gaa    192
Pro Arg Gly Val Leu Glu Arg Ile Met Gly Asp Lys Val Ala Ser Glu
    50                  55                  60 gct ctt atg aag tac cac atc tta aat act ctc cag tgt tct gag tct    240
Ala Leu Met Lys Tyr His Ile Leu Asn Thr Leu Gln Cys Ser Glu Ser
65                  70                  75                  80 att atg gga gga gca gtc ttt gag acg ctg gaa gga aat aca att gag    288
Ile Met Gly Gly Ala Val Phe Glu Thr Leu Glu Gly Asn Thr Ile Glu
                85                  90                  95 ata gga tgt gac ggt gac agt ata aca gta aat gga atc aaa atg gtg    336
Ile Gly Cys Asp Gly Asp Ser Ile Thr Val Asn Gly Ile Lys Met Val
            100                 105                 110 aac aaa aag gat att gtg aca aat aat ggt gtg atc cat ttg att gat    384
Asn Lys Lys Asp Ile Val Thr Asn Asn Gly Val Ile His Leu Ile Asp
        115                 120                 125 cag gtc cta att cct gat tct gcc aaa caa gtt att gag ctg gct gga    432
Gln Val Leu Ile Pro Asp Ser Ala Lys Gln Val Ile Glu Leu Ala Gly
    130                 135                 140

<210> SEQ ID NO 8
<211> LENGTH: 144
<212> TYPE: PRT
<213> ORGANISM: Homo sapiens

<400> SEQUENCE: 8

Thr Ser Ile Gln Asp Phe Ile Glu Ala Glu Asp Asp Leu Ser Ser Phe
1               5                   10                  15

Arg Ala Ala Ala Ile Thr Ser Asp Ile Leu Glu Ala Leu Gly Arg Asp
            20                  25                  30

Gly His Phe Thr Leu Phe Ala Pro Thr Asn Glu Ala Phe Glu Lys Leu
        35                  40                  45

Pro Arg Gly Val Leu Glu Arg Ile Met Gly Asp Lys Val Ala Ser Glu
    50                  55                  60

Ala Leu Met Lys Tyr His Ile Leu Asn Thr Leu Gln Cys Ser Glu Ser
65                  70                  75                  80
```

```
Ile Met Gly Gly Ala Val Phe Glu Thr Leu Glu Gly Asn Thr Ile Glu
                85                  90                  95

Ile Gly Cys Asp Gly Asp Ser Ile Thr Val Asn Gly Ile Lys Met Val
            100                 105                 110

Asn Lys Lys Asp Ile Val Thr Asn Asn Gly Val Ile His Leu Ile Asp
        115                 120                 125

Gln Val Leu Ile Pro Asp Ser Ala Lys Gln Val Ile Glu Leu Ala Gly
    130                 135                 140
```

<210> SEQ ID NO 9
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 9

```
aaa cag caa acc acc ttc acg gat ctt gtg gcc caa tta ggc ttg gca     48
Lys Gln Gln Thr Thr Phe Thr Asp Leu Val Ala Gln Leu Gly Leu Ala
1               5                   10                  15 tct gct ctg agg cca gat gga gaa tac act ttg ctg gca cct gtg aat    96
Ser Ala Leu Arg Pro Asp Gly Glu Tyr Thr Leu Leu Ala Pro Val Asn
            20                  25                  30 aat gca ttt tct gat gat act ctc agc atg gat cag cgc ctc ctt aaa   144
Asn Ala Phe Ser Asp Asp Thr Leu Ser Met Asp Gln Arg Leu Leu Lys
        35                  40                  45 tta att ctg cag aat cac ata ttg aaa gta aaa gtt ggc ctt aat gag   192
Leu Ile Leu Gln Asn His Ile Leu Lys Val Lys Val Gly Leu Asn Glu
    50                  55                  60 ctt tac aac ggg caa ata ctg gaa acc atc gga ggc aaa cag ctc aga   240
Leu Tyr Asn Gly Gln Ile Leu Glu Thr Ile Gly Gly Lys Gln Leu Arg
65                  70                  75                  80 gtc ttc gta tat cgt aca gct gtc tgc att gaa aat tca tgc atg gag   288
Val Phe Val Tyr Arg Thr Ala Val Cys Ile Glu Asn Ser Cys Met Glu
                85                  90                  95 aaa ggg agt aag caa ggg aga aac ggt gcg att cac ata ttc cgc gag   336
Lys Gly Ser Lys Gln Gly Arg Asn Gly Ala Ile His Ile Phe Arg Glu
            100                 105                 110 atc atc aag cca gca                                                351
Ile Ile Lys Pro Ala
        115
```

<210> SEQ ID NO 10
<211> LENGTH: 117
<212> TYPE: PRT
<213> ORGANISM: Homo sapiens

<400> SEQUENCE: 10

```
Lys Gln Gln Thr Thr Phe Thr Asp Leu Val Ala Gln Leu Gly Leu Ala
1               5                   10                  15

Ser Ala Leu Arg Pro Asp Gly Glu Tyr Thr Leu Leu Ala Pro Val Asn
            20                  25                  30

Asn Ala Phe Ser Asp Asp Thr Leu Ser Met Asp Gln Arg Leu Leu Lys
        35                  40                  45

Leu Ile Leu Gln Asn His Ile Leu Lys Val Lys Val Gly Leu Asn Glu
    50                  55                  60

Leu Tyr Asn Gly Gln Ile Leu Glu Thr Ile Gly Gly Lys Gln Leu Arg
65                  70                  75                  80
```

```
Val Phe Val Tyr Arg Thr Ala Val Cys Ile Glu Asn Ser Cys Met Glu
                85                  90                  95

Lys Gly Ser Lys Gln Gly Arg Asn Gly Ala Ile His Ile Phe Arg Glu
            100                 105                 110

Ile Ile Lys Pro Ala
        115

<210> SEQ ID NO 11
<211> LENGTH: 408
<212> TYPE: DNA
<213> ORGANISM: Homo sapiens
<220> FEATURE:
<221> NAME/KEY: CDS
<222> LOCATION: (1)..(408)

<400> SEQUENCE: 11 gag aaa tcc ctc cat gaa aag tta aaa caa gat aag cgc ttt agc acc      48
Glu Lys Ser Leu His Glu Lys Leu Lys Gln Asp Lys Arg Phe Ser Thr
1               5                   10                  15 ttc ctc agc cta ctt gaa gct gca gac ttg aaa gag ctc ctg aca caa      96
Phe Leu Ser Leu Leu Glu Ala Ala Asp Leu Lys Glu Leu Leu Thr Gln
            20                  25                  30 cct gga gac tgg aca tta ttt gtg cca acc aat gat gct ttt aag gga     144
Pro Gly Asp Trp Thr Leu Phe Val Pro Thr Asn Asp Ala Phe Lys Gly
        35                  40                  45 atg act agt gaa gaa aaa gaa att ctg ata cgg gac aaa aat gct ctt     192
Met Thr Ser Glu Glu Lys Glu Ile Leu Ile Arg Asp Lys Asn Ala Leu
50                  55                  60 caa aac atc att ctt tat cac ctg aca cca gga gtt ttc att gga aaa     240
Gln Asn Ile Ile Leu Tyr His Leu Thr Pro Gly Val Phe Ile Gly Lys
65                  70                  75                  80 gga ttt gaa cct ggt gtt act aac att tta aag acc aca caa gga agc     288
Gly Phe Glu Pro Gly Val Thr Asn Ile Leu Lys Thr Thr Gln Gly Ser
                85                  90                  95 aaa atc ttt ctg aaa gaa gta aat gat aca ctt ctg gtg aat gaa ttg     336
Lys Ile Phe Leu Lys Glu Val Asn Asp Thr Leu Leu Val Asn Glu Leu
            100                 105                 110 aaa tca aaa gaa tct gac atc atg aca aca aat ggt gta att cat gtt     384
Lys Ser Lys Glu Ser Asp Ile Met Thr Thr Asn Gly Val Ile His Val
        115                 120                 125 gta gat aaa ctc ctc tat cca gca                                     408
Val Asp Lys Leu Leu Tyr Pro Ala
    130                 135

<210> SEQ ID NO 12
<211> LENGTH: 136
<212> TYPE: PRT
<213> ORGANISM: Homo sapiens

<400> SEQUENCE: 12

Glu Lys Ser Leu His Glu Lys Leu Lys Gln Asp Lys Arg Phe Ser Thr
1               5                   10                  15

Phe Leu Ser Leu Leu Glu Ala Ala Asp Leu Lys Glu Leu Leu Thr Gln
            20                  25                  30

Pro Gly Asp Trp Thr Leu Phe Val Pro Thr Asn Asp Ala Phe Lys Gly
        35                  40                  45

Met Thr Ser Glu Glu Lys Glu Ile Leu Ile Arg Asp Lys Asn Ala Leu
50                  55                  60

Gln Asn Ile Ile Leu Tyr His Leu Thr Pro Gly Val Phe Ile Gly Lys
65                  70                  75                  80
```

-continued

```
Gly Phe Glu Pro Gly Val Thr Asn Ile Leu Lys Thr Thr Gln Gly Ser
             85                  90                  95

Lys Ile Phe Leu Lys Glu Val Asn Asp Thr Leu Leu Val Asn Glu Leu
        100                 105                 110

Lys Ser Lys Glu Ser Asp Ile Met Thr Thr Asn Gly Val Ile His Val
    115                 120                 125

Val Asp Lys Leu Leu Tyr Pro Ala
130                 135

<210> SEQ ID NO 13
<211> LENGTH: 615
<212> TYPE: DNA
<213> ORGANISM: Homo sapiens
<220> FEATURE:
<221> NAME/KEY: CDS
<222> LOCATION: (1)..(615)

<400> SEQUENCE: 13 gac aca cct gtt gga aat gat caa ctg ctg gaa ata ctt aat aaa tta      48
Asp Thr Pro Val Gly Asn Asp Gln Leu Leu Glu Ile Leu Asn Lys Leu
1               5                  10                  15 atc aaa tac atc caa att aag ttt gtt cgt ggt agc acc ttc aaa gaa      96
Ile Lys Tyr Ile Gln Ile Lys Phe Val Arg Gly Ser Thr Phe Lys Glu
            20                  25                  30 atc ccc gtg act gtc tat aca act aaa att ata acc aaa gtt gtg gaa     144
Ile Pro Val Thr Val Tyr Thr Thr Lys Ile Ile Thr Lys Val Val Glu
        35                  40                  45 cca aaa att aaa gtg att gaa ggc agt ctt cag cct att atc aaa act     192
Pro Lys Ile Lys Val Ile Glu Gly Ser Leu Gln Pro Ile Ile Lys Thr
    50                  55                  60 gaa gga ccc aca cta aca aaa gtc aaa att gaa ggt gaa cct gaa ttc     240
Glu Gly Pro Thr Leu Thr Lys Val Lys Ile Glu Gly Glu Pro Glu Phe
65                  70                  75                  80 aga ctg att aaa gaa ggt gaa aca ata act gaa gtg atc cat gga gag     288
Arg Leu Ile Lys Glu Gly Glu Thr Ile Thr Glu Val Ile His Gly Glu
                85                  90                  95 cca att att aaa aaa tac acc aaa atc att gat gga gtg cct gtg gaa     336
Pro Ile Ile Lys Lys Tyr Thr Lys Ile Ile Asp Gly Val Pro Val Glu
            100                 105                 110 ata act gaa aaa gag aca cga gaa gaa cga atc att aca ggt cct gaa     384
Ile Thr Glu Lys Glu Thr Arg Glu Glu Arg Ile Ile Thr Gly Pro Glu
        115                 120                 125 ata aaa tac act agg att tct act gga ggt gga gaa aca gaa gaa act     432
Ile Lys Tyr Thr Arg Ile Ser Thr Gly Gly Gly Glu Thr Glu Glu Thr
    130                 135                 140 ctg aag aaa ttg tta caa gaa gag gtc acc aag gtc acc aaa ttc att     480
Leu Lys Lys Leu Leu Gln Glu Glu Val Thr Lys Val Thr Lys Phe Ile
145                 150                 155                 160 gaa ggt ggt gat ggt cat tta ttt gaa gat gaa gaa att aaa aga ctg     528
Glu Gly Gly Asp Gly His Leu Phe Glu Asp Glu Glu Ile Lys Arg Leu
                165                 170                 175 ctt cag gga gac aca ccc gtg agg aag ttg caa gcc aac aaa aaa gtt     576
Leu Gln Gly Asp Thr Pro Val Arg Lys Leu Gln Ala Asn Lys Lys Val
            180                 185                 190 caa gga tct aga aga cga tta agg gaa ggt cgt tct cag                 615
Gln Gly Ser Arg Arg Arg Leu Arg Glu Gly Arg Ser Gln
        195                 200                 205

<210> SEQ ID NO 14
<211> LENGTH: 205
<212> TYPE: PRT
```

<213> ORGANISM: Homo sapiens

<400> SEQUENCE: 14

```
Asp Thr Pro Val Gly Asn Asp Gln Leu Leu Glu Ile Leu Asn Lys Leu
1               5                   10                  15

Ile Lys Tyr Ile Gln Ile Lys Phe Val Arg Gly Ser Thr Phe Lys Glu
            20                  25                  30

Ile Pro Val Thr Val Tyr Thr Thr Lys Ile Ile Thr Lys Val Val Glu
        35                  40                  45

Pro Lys Ile Lys Val Ile Glu Gly Ser Leu Gln Pro Ile Ile Lys Thr
    50                  55                  60

Glu Gly Pro Thr Leu Thr Lys Val Lys Ile Glu Gly Pro Glu Phe
65                  70                  75                  80

Arg Leu Ile Lys Glu Gly Glu Thr Ile Thr Glu Val Ile His Gly Glu
                85                  90                  95

Pro Ile Ile Lys Lys Tyr Thr Lys Ile Ile Asp Gly Val Pro Val Glu
            100                 105                 110

Ile Thr Glu Lys Glu Thr Arg Glu Glu Arg Ile Ile Thr Gly Pro Glu
        115                 120                 125

Ile Lys Tyr Thr Arg Ile Ser Thr Gly Gly Glu Thr Glu Glu Thr
    130                 135                 140

Leu Lys Lys Leu Leu Gln Glu Glu Val Thr Lys Val Thr Lys Phe Ile
145                 150                 155                 160

Glu Gly Gly Asp Gly His Leu Phe Glu Asp Glu Ile Lys Arg Leu
                165                 170                 175

Leu Gln Gly Asp Thr Pro Val Arg Lys Leu Gln Ala Asn Lys Lys Val
            180                 185                 190

Gln Gly Ser Arg Arg Arg Leu Arg Glu Gly Arg Ser Gln
        195                 200                 205
```

<210> SEQ ID NO 15
<211> LENGTH: 447
<212> TYPE: DNA
<213> ORGANISM: Mus musculus
<220> FEATURE:
<221> NAME/KEY: CDS
<222> LOCATION: (1)..(447)

<400> SEQUENCE: 15

```
atg gaa tgg agc tgg gtc atc ctc ttt ttg gta gca aca gct aca gat      48
Met Glu Trp Ser Trp Val Ile Leu Phe Leu Val Ala Thr Ala Thr Asp
1               5                   10                  15 gtc cac tcc cag gtc caa ctt cag caa cct ggg tct gaa ctg gtg aag      96
Val His Ser Gln Val Gln Leu Gln Gln Pro Gly Ser Glu Leu Val Lys
            20                  25                  30 cct ggg gct tca gtg aag ctg tcc tgc aag gct tct ggc tac acc ttc     144
Pro Gly Ala Ser Val Lys Leu Ser Cys Lys Ala Ser Gly Tyr Thr Phe
        35                  40                  45 acc agc tac tgg atg cac tgg gtg aag cag agc cct gga caa ggc ctt     192
Thr Ser Tyr Trp Met His Trp Val Lys Gln Ser Pro Gly Gln Gly Leu
    50                  55                  60 gag tgg att gga gag att aat cct agc aac ggt cgt act aac tac aat     240
Glu Trp Ile Gly Glu Ile Asn Pro Ser Asn Gly Arg Thr Asn Tyr Asn
65                  70                  75                  80 gag aag ttc aag acc aag gcc aca ctg act gta gac aaa tcc tcc agc     288
Glu Lys Phe Lys Thr Lys Ala Thr Leu Thr Val Asp Lys Ser Ser Ser
                85                  90                  95 aca gcc tac atg caa ctc aac agc ctg aca tct gag gac tct gcg gtc     336
Thr Ala Tyr Met Gln Leu Asn Ser Leu Thr Ser Glu Asp Ser Ala Val
```

```
Thr Ala Tyr Met Gln Leu Asn Ser Leu Thr Ser Glu Asp Ser Ala Val
            100                 105                 110 tat tac tgt gta aga ggg gac gag ggg ttt gct tac tgg ggc caa ggg       384
Tyr Tyr Cys Val Arg Gly Asp Glu Gly Phe Ala Tyr Trp Gly Gln Gly
            115                 120                 125 act ctg gtc act gtc tct gca gcc aaa acg aca ccc cca ccc gtc tat       432
Thr Leu Val Thr Val Ser Ala Ala Lys Thr Thr Pro Pro Pro Val Tyr
130                 135                 140 ccc ctg gcc cct gga                                                   447
Pro Leu Ala Pro Gly
145

<210> SEQ ID NO 16
<211> LENGTH: 149
<212> TYPE: PRT
<213> ORGANISM: Mus musculus

<400> SEQUENCE: 16

Met Glu Trp Ser Trp Val Ile Leu Phe Leu Val Ala Thr Ala Thr Asp
1               5                   10                  15

Val His Ser Gln Val Gln Leu Gln Gln Pro Gly Ser Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Ser Pro Gly Gln Gly Leu
    50                  55                  60

Glu Trp Ile Gly Glu Ile Asn Pro Ser Asn Gly Arg Thr Asn Tyr Asn
65                  70                  75                  80

Glu Lys Phe Lys Thr Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Val Arg Gly Asp Glu Gly Phe Ala Tyr Trp Gly Gln Gly
        115                 120                 125

Thr Leu Val Thr Val Ser Ala Ala Lys Thr Thr Pro Pro Pro Val Tyr
    130                 135                 140

Pro Leu Ala Pro Gly
145

<210> SEQ ID NO 17
<211> LENGTH: 438
<212> TYPE: DNA
<213> ORGANISM: Mus musculus
<220> FEATURE:
<221> NAME/KEY: CDS
<222> LOCATION: (1)..(438)

<400> SEQUENCE: 17 atg gag tca gac aca ctg ctg cta tgg gtg ctg ctg ctc tgg gtt cca       48
Met Glu Ser Asp Thr Leu Leu Leu Trp Val Leu Leu Leu Trp Val Pro
1               5                   10                  15 ggt tcc aca ggt aac att gtg ctg acc caa tct cca gct tct ttg gct       96
Gly Ser Thr Gly Asn Ile Val Leu Thr Gln Ser Pro Ala Ser Leu Ala
            20                  25                  30 gtg tct cta ggg cag agg gcc acc ata tcc tgc agt gcc agt gaa agt       144
Val Ser Leu Gly Gln Arg Ala Thr Ile Ser Cys Ser Ala Ser Glu Ser
        35                  40                  45 gtt gat agt tat ggc agg agt ttt ata cac tgg ttc cag cag aaa cca       192
Val Asp Ser Tyr Gly Arg Ser Phe Ile His Trp Phe Gln Gln Lys Pro
    50                  55                  60
```

-continued

```
gga cag cca ccc aaa ctc ctc atc tat ctt gca tcc tac cta gaa tct      240
Gly Gln Pro Pro Lys Leu Leu Ile Tyr Leu Ala Ser Tyr Leu Glu Ser
65                   70                  75                  80 ggg gtc cct gcc agg ttc agt ggc agt ggg tct agg aca gac ttc acc      288
Gly Val Pro Ala Arg Phe Ser Gly Ser Gly Ser Arg Thr Asp Phe Thr
                85                  90                  95 ctc acc att gat cct gtg gag gct gat gat gct gca acc tat tac tgt      336
Leu Thr Ile Asp Pro Val Glu Ala Asp Asp Ala Ala Thr Tyr Tyr Cys
            100                 105                 110 cac caa aat aat gag gat cct ccg acg ttc ggt gga ggc gcc aag ctg      384
His Gln Asn Asn Glu Asp Pro Pro Thr Phe Gly Gly Gly Ala Lys Leu
        115                 120                 125 gaa atc aaa cgg gct gat gct gca cca act gta tcc atc ttc cca cca      432
Glu Ile Lys Arg Ala Asp Ala Ala Pro Thr Val Ser Ile Phe Pro Pro
    130                 135                 140 tcc agt                                                              438
Ser Ser
145

<210> SEQ ID NO 18
<211> LENGTH: 146
<212> TYPE: PRT
<213> ORGANISM: Mus musculus

<400> SEQUENCE: 18

Met Glu Ser Asp Thr Leu Leu Leu Trp Val Leu Leu Leu Trp Val Pro
1               5                   10                  15

Gly Ser Thr Gly Asn Ile Val Leu Thr Gln Ser Pro Ala Ser Leu Ala
            20                  25                  30

Val Ser Leu Gly Gln Arg Ala Thr Ile Ser Cys Ser Ala Ser Glu Ser
        35                  40                  45

Val Asp Ser Tyr Gly Arg Ser Phe Ile His Trp Phe Gln Gln Lys Pro
    50                  55                  60

Gly Gln Pro Pro Lys Leu Leu Ile Tyr Leu Ala Ser Tyr Leu Glu Ser
65                  70                  75                  80

Gly Val Pro Ala Arg Phe Ser Gly Ser Gly Ser Arg Thr Asp Phe Thr
                85                  90                  95

Leu Thr Ile Asp Pro Val Glu Ala Asp Asp Ala Ala Thr Tyr Tyr Cys
            100                 105                 110

His Gln Asn Asn Glu Asp Pro Pro Thr Phe Gly Gly Gly Ala Lys Leu
        115                 120                 125

Glu Ile Lys Arg Ala Asp Ala Ala Pro Thr Val Ser Ile Phe Pro Pro
    130                 135                 140

Ser Ser
145
```

…

ANTIBODY CAPABLE OF BINDING TO SPECIFIC REGION OF PERIOSTIN, AND METHOD OF MEASURING PERIOSTIN USING THE SAME

TECHNICAL FIELD

The present invention relates to an antibody that binds to a specific region of periostin (also referred to as osteoblastic specific factor 2 or OSF2), which can be a marker of allergic disease and other diseases, a method of measuring periostin contained in a sample using the antibody, a measurement reagent, a method for improving accuracy of the measurement, and a method of testing for pulmonary fibrosis or interstitial pneumonia.

The present invention is useful in the field of life sciences such as clinical examination, clinical pathology, immunology, and medicine and the field of chemistry such as chemical analysis.

BACKGROUND ART

Periostin is an extracellular matrix protein and is composed of an EMI region, an R1 region, an R2 region, an R3 region, an R4 region, and a C-terminal region in this order from the N-terminus to the C-terminus. One of the present inventors, K. Izuhara, has found that measurement of the expression level of the periostin gene is useful as a method of testing for allergic disease and has accomplished an invention relating to a method of testing for allergic disease (see Patent Literature 1 and Non Patent Literature 1).

K. Izuhara has also found that measurement of the expression level of the periostin gene is useful as a method of testing for idiopathic interstitial pneumonia (see Patent Literature 2).

Furthermore, there have been disclosed a polyclonal antibody and a monoclonal antibody against OSF2 (periostin) and a diagnostic method using these antibodies (see Patent Literature 3), an immunoassay of a novel osteoblast specific transcription factor named as Osf2/Cbfa1 using an anti-OSF2 (periostin) antibody (see Patent Literature 4), a purified antibody specifically binding to human periostin and a diagnostic assay for investigating, for example, metastasis of breast cancer to bone using the antibody (see Patent Literature 5), and an antibody against periostin having anti-cell adhesion activity and a method of quantitatively measuring periostin using the antibody (see Patent Literature 6).

However, such measurements of periostin useful for testing various diseases have been required to be improved in accuracy, such as sensitivity and specificity, of the measurement for differentiating patients affected with the diseases from healthy subjects and patients affected with other diseases.

CITATION LIST

Patent Literature

Patent Literature 1: International Publication No. WO02/052006
Patent Literature 2: International Publication No. WO09/148184
Patent Literature 3: Japanese Patent Laid-Open No. H05-268982
Patent Literature 4: National Publication of International Patent Application No. 2002-502250
Patent Literature 5: National Publication of International Patent Application No. 2005-500059
Patent Literature 6: International Publication No. WO07/077,934

Non Patent Literature

Non Patent Literature 1: G. Takayama et al., J. Allergy Clin. Immunol., Vol. 118, pp. 98-104, published in 2006

SUMMARY OF INVENTION

Technical Problem

In the measurement described above utilizing the antigen-antibody reaction of periostin contained in a sample, the accuracy is insufficient.

Accordingly, there has been a risk of misdiagnosis when a measured value of periostin contained in a sample is used in testing for diseases.

Therefore, the measurement utilizing the antigen-antibody reaction of periostin contained in a sample is required to be further improved in accuracy for differentiating patients affected with the diseases from healthy subjects and patients affected with other diseases.

Accordingly, it is an object of the present invention to provide a method and a reagent having improved accuracy in measurement utilizing an antigen-antibody reaction, etc. of periostin contained in a sample. and to provide a method for improving accuracy of measurement and a method of testing for pulmonary fibrosis or interstitial pneumonia with improved accuracy.

Solution to Problem

The present inventors have diligently investigated measurement of periostin contained in samples and have found that the above-mentioned problems can be solved by detecting a specific region of periostin and have accomplished the present invention.

That is, the present invention involves the following aspects:

(1) An antibody that binds to at least one region selected from the group consisting of an EMI region, an R1 region, an R2 region, and an R3 region of periostin or a cleavage product thereof;

(2) The antibody according to (1), wherein the antibody binds to a periostin cleavage product;

(3) The antibody according to (1) or (2), wherein the antibody does not bind to periostin multimers;

(4) The antibody according to any one of (1) to (3), wherein the antibody is a monoclonal antibody;

(5) The antibody according to (4), wherein an amino acid sequence of a heavy chain variable region of the antibody comprises the amino acid sequence set forth in SEQ ID NO: 16 and an amino acid sequence of a light chain variable region of the antibody comprises the amino acid sequence set forth in SEQ ID NO: 18;

(6) A monoclonal antibody produced by a hybridoma selected from the group consisting of a hybridoma cell line SS16A having Accession Number NITE BP-1281, a hybridoma cell line SS18A having Accession Number NITE BP-1282, a hybridoma cell line SS19C having Accession Number NITE BP-1283, a hybridoma cell line SS19D having Accession Number NITE BP-1068, a hybridoma cell line SS20A having Accession Number NITE BP-1284, a hybridoma cell line SS25A having Accession Number NITE BP-1285, and a hybridoma cell line SS27A having Accession Number NITE BP-1286;

(7) A method of measuring periostin contained in a sample, the method comprising:
    detecting at least one region selected from the group consisting of an EMI region, an R1 region, an R2 region, and an R3 region of periostin;
(8) The method according to (7), wherein the method uses the antibody according to any one of (1) to (6);
(9) The method according to (7) or (8), wherein the periostin is a periostin cleavage product;
(10) The method according to any one of (7) to (9), wherein the periostin is not a multimer;
(11) A reagent for measuring periostin or a cleavage product thereof contained in a sample, the reagent comprising a substance that specifically binds to at least one region selected from the group consisting of an EMI region, an R1 region, an R2 region, and an R3 region of periostin;
(12) The reagent according to (11), wherein the substance is the antibody according to any one of (1) to (6);
(13) The reagent according to (11) or (12), wherein the periostin is a periostin cleavage product;
(14) The reagent according to any one of (11) to (13), wherein the periostin is not a multimer;
(15) A method for improving accuracy of periostin measurement, wherein a measurement of an amount or concentration of periostin contained in a sample comprises detecting at least one region selected from the group consisting of an EMI region, an R1 region, an R2 region, and an R3 region of periostin;
(16) The method according to (15), wherein the method uses the antibody according to any one of (1) to (6);
(17) The method according to (15) or (16), wherein the periostin is a periostin cleavage product;
(18) The method according to any one of (15) to (17), wherein the periostin is not a multimer;
(19) A method of testing for pulmonary fibrosis or interstitial pneumonia, the method comprising the steps of:
    a) measuring an amount or concentration of periostin in a sample derived from a subject, wherein the measuring comprises detecting at least one region selected from the group consisting of an EMI region, an R1 region, an R2 region, and an R3 region of periostin; and
    b) comparing the amount or concentration of the periostin in the sample derived from the subject with an amount or concentration of periostin in a sample derived from a living body not suffering from pulmonary fibrosis and interstitial pneumonia;
(20) The method according to (19), wherein the method uses the antibody according to any one of (1) to (6);
(21) The method according to (19) or (20), wherein the periostin is a periostin cleavage product; and
(22) The method according to any one of (19) to (21), wherein the periostin is not a multimer.

Advantageous Effects of Invention

The antibody that binds to at least one region selected from the group consisting of an EMI region, an R1 region, an R2 region, and an R3 region of periostin or a cleavage product thereof according to the present invention (hereinafter, the antibody may be referred to as "anti-periostin specific region antibody") is an antibody having a specificity such that the antibody can bind to at least one region selected from the group consisting of the EMI region, the R1 region, the R2 region, and the R3 region of periostin or a cleavage product thereof.

This antibody can be used in detection of at least one region selected from the group consisting of the EMI region, the R1 region, the R2 region, and the R3 region of periostin.

In addition, the antibody can bind to a periostin cleavage product.

Among the antibodies (anti-periostin specific region antibodies) of the present invention, the antibody that does not bind to periostin multimers is an antibody having a specificity such that the antibody can bind to at least one region selected from the group consisting of the EMI region, the R1 region, the R2 region, and the R3 region of periostin or a cleavage product thereof but does not bind to periostin multimers.

The antibody can bind to a periostin cleavage product but does not bind to periostin multimers.

The method of measuring periostin, the reagent for measuring periostin, the method for improving accuracy of periostin measurement, and the method of testing for pulmonary fibrosis or interstitial pneumonia of the present invention detect at least one region selected from the group consisting of the EMI region, the R1 region, the R2 region, and the R3 region of periostin in the measurement of periostin contained in a sample and thereby can improve, for example, the sensitivity [positive rate (true positive rate) in patient group in the measurement] or the specificity [negative rate (true negative rate: 1-(false positive rate)) in unaffected subject group in the measurement] of the measurement to improve the accuracy of the measurement.

Accordingly, the method of measuring periostin, the reagent for measuring periostin, the method for improving accuracy of periostin measurement, and the method of testing for pulmonary fibrosis or interstitial pneumonia of the present invention can provide accurate measured values of periostin and improve the differentiation of patients affected with the diseases from healthy subjects and patients affected with other diseases to prevent wrong diagnosis.

BRIEF DESCRIPTION OF DRAWINGS

FIG. 1 is a diagram schematically illustrating prepared and obtained periostin and partial-length periostins.

FIG. 2 is a photograph showing the results (gel) of SDS-polyacrylamide gel electrophoresis in investigation of prepared periostin, partial-length periostin (R1/R2 regions), partial-length periostin (R2 region), partial-length periostin (R1/R2/R3 regions), and partial-length periostin (C-terminal region).

FIG. 4 is a table showing the results in investigation for which region of periostin each of the obtained anti-periostin monoclonal antibodies recognizes.

FIG. 7 is a table summarizing the results in investigation of reactivities of the obtained anti-periostin monoclonal antibodies to periostin monomer, multimer, and cleavage product.

FIG. 18 is a table summarizing the measurement results of periostin in human serum.

FIG. 28 is a table summarizing the measurement results of periostin in human serum.

DESCRIPTION OF EMBODIMENTS

Figure 3:
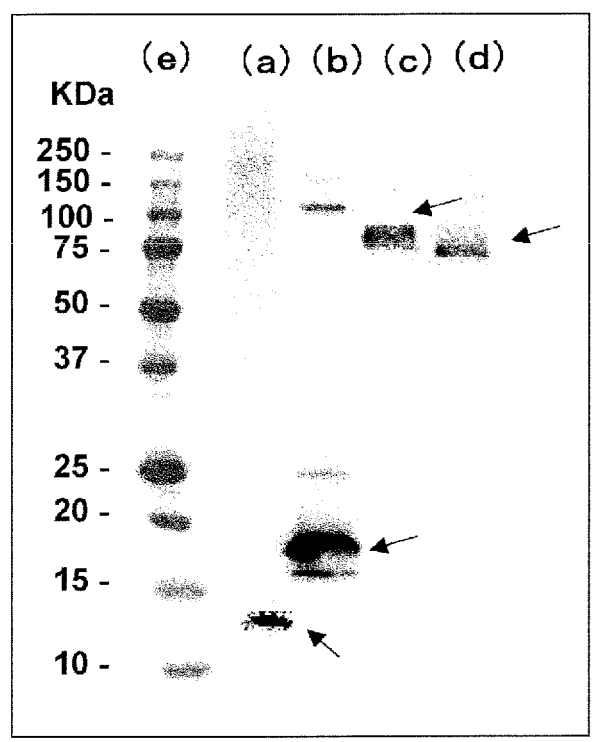
FIG. 3 is a photograph showing the results (polyvinyl difluoride membrane) of SDS-polyacrylamide gel electrophoresis and Western blotting in investigation of prepared partial-length periostin (R4 region) and partial-length periostin (EMI region).

The present invention will now be described in detail. The following embodiments are examples for explaining the present invention and are not intended to limit the present invention to these embodiments. The present invention can be implemented in various forms without deviating from the scope of the present invention.

All publications cited in the specification, for example, prior art documents, patent publication documents, patent documents, and other patent literatures are all incorporated into the specification by reference. The specification encompasses the contents described in the specifications, claims, and drawings of Japanese Patent Application (Application No. 2011-194323), filed on Sep. 6, 2011, and Japanese Patent Application (Application No. 2012-077774), filed on Mar. 29, 2012, based on which the present application claims priority.

[1] Anti-Periostin Specific Region Antibody

1. Antibody

The antibody according to the present invention is an antibody (anti-periostin specific region antibody) that binds to at least one region selected from the group consisting of the EMI region, the R1 region, the R2 region, and the R3 region of periostin or a cleavage product thereof.

That is, the use of the anti-periostin specific region antibody of the present invention in measurement utilizing an antigen-antibody reaction of periostin contained in a sample can improve the accuracy of the measurement.

In the present invention, the anti-periostin specific region antibody may be any antibody that can bind to at least one region selected from the group consisting of the EMI region, the R1 region, the R2 region, and the R3 region of periostin or a cleavage product thereof.

Examples of the anti-periostin specific region antibody include monoclonal antibodies, polyclonal antibodies, antisera, antibody fragments (e.g., Fab and F(ab')$_2$), and single-strand antibodies (scFv) that can bind to at least one region selected from the group consisting of the EMI region, the R1 region, the R2 region, and the R3 region of periostin or a cleavage product thereof.

The anti-periostin specific region antibody may be an antibody the amino acid sequence of which has been modified to that of an animal species different from the animal immunized with an immunogen (e.g., chimera antibody, humanized antibody, or completely humanized antibody) by, for example, a gene recombination technology.

The anti-periostin specific region antibody is preferably a monoclonal antibody.

In the present invention, two or more anti-periostin specific region antibodies may be used.

The anti-periostin specific region antibody of the present invention binds to a cleavage product of periostin (also referred to as "periostin cleavage product").

In the present invention, the periostin cleavage product refers to a polypeptide in which at least the C-terminal region having the amino acid sequence set forth in SEQ ID NO: 14 is deleted from periostin having the amino acid sequence set forth in SEQ ID NO: 2.

Examples of the periostin cleavage product of the present invention include polypeptides in which at least the C-terminal region having the amino acid sequence set forth in SEQ ID NO: 14 and the whole or part of the R4 region having the amino acid sequence set forth in SEQ ID NO: 12 are deleted from periostin having the amino acid sequence set forth in SEQ ID NO: 2.

Examples of the periostin cleavage product of the present invention include polypeptides in which at least the C-terminal region having the amino acid sequence set forth in SEQ ID NO: 14, the whole of the R4 region having the amino acid sequence set forth in SEQ ID NO: 12, and part of the R3 region having the amino acid sequence set forth in SEQ ID NO: 10 are deleted from periostin having the amino acid sequence set forth in SEQ ID NO: 2.

The periostin cleavage products of the present invention are polypeptides that have been discovered by the present inventors. The presence of a periostin cleavage product can be specifically confirmed by, for example, detecting the polypeptides contained in a sample derived from a living body by an immunological method using an antibody of the present invention (e.g., FIGS. 5, 9, and 26).

Examples of the periostin cleavage product include, but not limited to, those having a molecular weight of about 40000 Da (about 40 kDa). The periostin cleavage product is preferably one contained in a sample derived from a living body.

The anti-periostin specific region antibody of the present invention is preferably an antibody that binds to at least one region selected from the group consisting of the EMI region, the R1 region, the R2 region, and the R3 region of periostin or a cleavage product thereof but does not bind to periostin multimers: dimer, trimer, tetramer, and higher multimers of periostin.

That is, the anti-periostin specific region antibody in the present invention that binds to at least one region selected from the group consisting of the EMI region, the R1 region, the R2 region, and the R3 region of periostin or a cleavage product thereof but does not bind to periostin multimers further enhances the improvement in the accuracy of measurement and is therefore preferred.

2. Immunogen

Immunogens for generating anti-periostin specific region antibodies according to the present invention will now be described.

The whole or part of periostin can be used as an immunogen for generating an anti-periostin specific region antibody according to the present invention.

That is, the whole or part of periostin derived from, for example, human, periostin prepared by gene recombination, etc. can be used.

The immunogen for generating the anti-periostin specific region antibody is preferably the whole or part of the EMI region, the R1 region, the R2 region, and/or the R3 region of periostin.

The immunogen for generating the anti-periostin specific region antibody that does not bind to periostin multimers is preferably the whole or part of the EMI region, the R1 region, the R2 region, and/or the R3 region of periostin.

The anti-periostin specific region antibody according to the present invention can be obtained by using the whole or part of the periostin as an immunogen.

The immunogen for generating the anti-periostin specific region antibody may be, for example, a peptide or protein including an amino acid sequence obtained by deletion, substitution, insertion, addition, or modification of one to several (usually one to eight, preferably one to six) amino acid residues of the whole or part of the amino acid sequence of periostin.

It has been reported that an antibody can recognize an amino acid sequence consisting of three amino acids (F. Hudecz et al., J. Immunol. Methods, Vol. 147, pp. 201-210, published in 1992).

Accordingly, a minimum unit of the amino acid sequence as an immunogen for the anti-periostin specific region antibody according to the present invention can be believed to be an amino acid sequence consisting of consecutive three amino acid residues in the whole or part of the amino acid sequence of periostin or in amino acid sequences obtained by deletion, substitution, insertion, addition, or modification of one to several (usually one to eight, preferably one to six) amino acid residues of the whole or part of the amino acid sequence of periostin. Therefore, a tripeptide having an amino acid sequence consisting of any of these consecutive three amino acid residues or a peptide in which an amino acid or a peptide is added to such a tripeptide can be believed to be the minimum unit of the immunogen for the anti-periostin specific region antibody according to the present invention.

The immunogen mentioned above, i.e., a peptide or protein including the whole or part of the amino acid sequence of periostin or a peptide or protein etc. including an amino acid sequence obtained by deletion, substitution, insertion, addition, or modification of one to several (usually one to eight, preferably one to six) amino acid residues of the whole or part of the amino acid sequence of periostin, can be obtained through, for example, extraction from body fluids, cells, tissue, organs, etc. of, for example, human and purification of the extract by known methods and the like.

In the present invention, the peptide or protein including the whole or part of the amino acid sequence of periostin may be obtained by any method and can be obtained by, for example, a known method.

For example, periostin can be obtained by the following method ("G. Takayama et al., J. Allergy Clin. Immunol., Vol. 118, No. 1, pp. 713-723, published in 2006").

(a) A recombinant periostin protein, periostin (nucleotide sequence of the polynucleotide: Accession Number D13666 in the GenBank nucleic acid database (SEQ ID NO: 1), amino acid sequence: Accession Number BAA02837 in the GenBank nucleic acid database (SEQ ID NO: 2)) tagged with V5/His, is expressed in insect S2 cells and is purified.

(b) That is, specifically, transformants of the S2 cells are prepared as follows.

A cDNA encoding the above-mentioned portion of periostin is inserted into a pMT/Bip/V5-His A plasmid (Invitrogen Corporation, Carlsbad, Calif., USA) to construct pMT/Bip/periostin-V5-His A.

S2 cells are transformed through cotransfection with the pMT/Bip/periostin-V5-His A and a plasmid expressing a hygromycin-resistant gene, pAcHygro (Invitrogen Corporation, Carlsbad, Calif., USA), by a known method.

Stable transformants are selected with hygromycin.

Subsequently, periostin having a V5 epitope/His tag at the carboxy terminus is expressed in the S2 cell transformants.

(c) The S2 recombinant periostin protein is purified as follows.

The expression of S2 recombinant periostin protein is induced by adding copper sulfate to the culture medium of the stable S2 cell transformants with the periostin gene.

As a result, the S2 recombinant periostin protein is expressed and secreted in the culture supernatant.

The culture supernatant is dialyzed against phosphate-buffered saline (PBS) and is then mixed with nickel resin (Ni-NTA Agarose, Qiagen GmbH, Hilden, Germany) to allow the S2 recombinant periostin protein to bind to the resin.

The resin is washed to remove contaminants, and the S2 recombinant periostin protein is eluted with a buffer containing imidazole.

The eluted S2 recombinant periostin protein is dialyzed against, for example, PBS to obtain purified periostin protein.

Periostin can also be obtained by the following method.

That is, cDNA of periostin is inserted into a GEX-KG vector ("K. L. Guan et al., Anal. Biochem., Vol. 192, pp. 262-267, published in 1991") and is transfected into E. coli BL21.

The E. coli cells are cultured in an LB medium containing ampicillin, and then periostin tagged with glutathione-S-transferase (GST) is purified from the cells with Glutathione Sepharose 4B (GE Healthcare, Little Chalfont, UK).

The GST is cleaved with thrombin to obtain GST-free periostin.

Periostin the amount (concentration) of which is clear through measurement by a Bradford method can be obtained.

Periostin can also be obtained by the method described in, for example, "I. Takayama et al., J. Biochem., Vol. 146, No. 5, pp. 713-723, published in 2009." The amino acid sequence of periostin is represented by SEQ ID NO: 2 as described above, and the nucleotide sequence of the polynucleotide encoding the amino acid sequence is represented by SEQ ID NO: 1.

The EMI region of periostin can be obtained by, for example, the method described in "I. Kii et al., J. Biol. Chem., Vol. 285, No. 3, pp. 2028-2039, published in 2010" or the method described in "T. Maruhashi et al., J. Biol. Chem., Vol. 285, No. 17, pp. 13294-13303, published in 2010." The amino acid sequence of the EMI region of periostin is represented by SEQ ID NO: 4, and the nucleotide sequence of the polynucleotide encoding the amino acid sequence is represented by SEQ ID NO: 3.

Each of the R1 region, the R2 region, and the R3 region of periostin can be obtained by, for example, the method described in "I. Takayama et al., J. Biochem., Vol. 146, No. 5, pp. 713-723, published in 2009." The amino acid sequences of the R1 region, the R2 region, and the R3 region of periostin are respectively represented by SEQ ID NOs: 6, 8, and 10 and the nucleotide sequences of the polynucleotide encoding the amino acid sequences are respectively represented by SEQ ID NOs: 5, 7, and 9. The amino acid sequences of the R4 region and the C-terminal region of periostin are respectively represented by SEQ ID NOs: 12 and 14 and the nucleotide sequences of the polynucleotide encoding the amino acid sequences are respectively represented by SEQ ID NOs: 11 and 13.

The immunogen can be synthesized by a peptide synthesis method such as liquid-phase synthesis and solid-phase synthesis. An automatic peptide synthesizer may be used, and synthesis can be performed in accordance with the method described in, for example, "Seikagaku Jikken Koza (Course of Biochemical Experiments) 1, Tanpakushitsu no Kagaku (Protein Chemistry) IV," edited by the Japanese Biochemical Society, Tokyo Kagaku Dojin, 1975; Izumiya et al., "Pepuchido Gosei no Kiso to Jikken (Fundamentals and Experiments for Peptide Synthesis," Maruzen, 1985; or "Zoku-Seikagaku Jikken Koza (Course of Biochemical Experiments, 2nd Series) 2, Tanpakushitsu no Kagaku Gekan (Protein Chemistry the last volume)," edited by the Japanese Biochemical Society, Tokyo Kagaku Dojin, 1987. Variants having deletion, substitution, insertion, or addition in the above-mentioned amino acid sequence can also be easily produced.

Furthermore, modification such as introduction of a non-natural amino acid or stabilization of the structure by chemical modification of an amino acid residue or cyclization of the molecule through introduction of a cysteine residue may be performed.

The immunogen may be prepared by a genetic engineering technology using a DNA or RNA including a corresponding nucleic acid nucleotide sequence and may be prepared with reference to, for example, "Zoku-Seikagaku Jikken Koza (Course of Biochemical Experiments, 2nd Series) 1, Idenshi Kenkyu-ho (Methods in Genetic Studies) I," edited by the Japanese Biochemical Society, Tokyo Kagaku Dojin, 1986; "Zoku-Seikagaku Jikken Koza (Course of Biochemical Experiments, 2nd Series) 1, Idenshi Kenkyu-ho (Methods in Genetic Studies) II," edited by the Japanese Biochemical Society, Tokyo Kagaku Dojin, 1986; or "Zoku-Seikagaku Jikken Koza (Course of Biochemical Experiments, 2nd Series) 1, Idenshi Kenkyu-ho (Methods in Genetic Studies) III," edited by the Japanese Biochemical Society, Tokyo Kagaku Dojin, 1987.

Meanwhile, in a case of using a low molecular weight substance as an immunogen, the immunogen is conjugated to a carrier and is then used for immunization of, for example, an animal. However, since there is also a report that a specific antibody was produced using a peptide consisting of five amino acids as an immunogen (Kiyama et al., "The Pharmaceutical Society of Japan, The 112th Annual Meeting Lecture Summaries 3," p. 122, published in 1992), the use of a carrier is not indispensable.

The carrier used in production of an antibody may be any known carrier such as keyhole limpet hemocyanin (KLH), bovine serum albumin (BSA), chicken serum albumin, poly-L-lysine, polyalanyl lysine, dipalmityl lysine, tetanus toxoid, or polysaccharide.

The immunogen may be conjugated to a carrier by any known binding method such as a glutaraldehyde method, a 1-ethyl-3-(3-dimethylaminopropyl)carbodiimide method, a maleimidebenzoyl-N-hydroxysuccinimide ester method, a bisdiazotized benzidine method, or an N-succinimidyl-3-(2-pyridyldithio)propionic acid method.

An immunogen adsorbed to a carrier such as nitrocellulose particles, polyvinylpyrrolidone, or liposome can be also used as an immunogen.

3. Method of Preparing Anti-Periostin Specific Region Polyclonal Antibody

A polyclonal antibody that can bind to at least one region selected from the group consisting of the EMI region, the R1 region, the R2 region, and the R3 region of periostin or a cleavage product thereof, i.e., an anti-periostin specific region polyclonal antibody can be prepared by the following procedure.

The above-described immunogen can be used as an immunogen for producing the anti-periostin specific region polyclonal antibody.

For example, a mammal (e.g., mouse, guinea pig, hamster, rabbit, rat, sheep, goat, bovine, horse, donkey, or camel) or a bird (e.g., chicken, duck, or ostrich) is immunized with the immunogen or a conjugate of the immunogen and a carrier.

The animal immunized with the immunogen or the conjugate of the immunogen and a carrier is preferably an animal whose gene involved in the production of periostin in the body is inactive or deficient, i.e., an animal whose gene involved in the production of periostin is knocked out.

This is because that the risk of binding of periostin produced in the body of the animal to the anti-periostin specific region antibody produced in the body by the immunization with, for example, an immunogen such as periostin and thereby decreasing the antibody activity of the anti-periostin specific region antibody is low in the knockout animal.

In the knockout animal, periostin is not produced in the body of the animal. Consequently, periostin as the immunogen is readily recognized as a foreign substance, and an antibody is highly produced.

Examples of the animal whose gene involved in the production of periostin is inactive or deficient include periostin knockout mice ("H. Rios et al., Molecular and Cellular Biology, Vol. 25, No. 24, pp. 11131-11144, published in 2005").

The amount of the immunogen or the conjugate of the immunogen and a carrier for immunization is determined depending on the types of the immunogen, carrier, and immune animal, the site of immune injection, etc. In a case of mice, 0.1 µg to 5 mg of the immunogen or the conjugate of the immunogen and a carrier is preferably injected into each mouse at each immunization.

The immunogen or the conjugate of the immunogen and a carrier is preferably injected as a mixture with an adjuvant for immunization.

The adjuvant may be a known adjuvant such as Freund's complete adjuvant, Freund's incomplete adjuvant, aluminum hydroxide adjuvant, chemically synthesized adjuvant, or pertussis adjuvant.

The immune injection may be performed into a site such as subcutaneous tissue, a vein, the abdominal cavity, or the back.

After the initial immunization, booster injection of the immunogen or the conjugate of the immunogen and a carrier into a site such as subcutaneous tissue, a vein, the abdominal cavity, or the back is performed at one- to two-week intervals.

The frequency of the booster injection is generally two to six times.

In also the booster injection, the immunogen or the conjugate of the immunogen and a carrier is preferably injected as a mixture with an adjuvant.

After the initial immunization, the antibody titer in serum of the immunized animal is repeatedly measured by, for example, ELISA until the antibody titer reaches plateau. Whole blood collection is then performed, and serum is collected to obtain antiserum containing antibodies.

The antiserum is subjected to purification by salting-out with ammonium sulfate, sodium sulfate, or the like; a method such as ion-exchange chromatography, gel filtration, or affinity chromatography; or a combination thereof to obtain polyclonal antibodies.

The polyclonal antibodies obtained herein include polyclonal antibodies that can bind to at least one region selected from the group consisting of the EMI region, the R1 region, the R2 region, and the R3 region of periostin or a cleavage product thereof (anti-periostin specific region polyclonal antibody) and polyclonal antibodies that do not bind to any of the EMI region, the R1 region, the R2 region, and the R3 region of periostin.

Accordingly, for example, for separation, the resulting polyclonal antibodies are introduced into, for example, an affinity chromatography column in which a protein or peptide including the amino acid sequence of the EMI region, the R1 region, the R2 region, and/or the R3 region of periostin is immobilized, as a ligand, onto a solid phase, and is brought into contact with the protein or peptide.

As a result, the anti-periostin specific region polyclonal antibodies are immobilized onto and captured by the solid phase via the ligand (protein or peptide including the amino acid sequence of the EMI region, the R1 region, the R2 region, and/or the R3 region of periostin) in the column or the like.

In contrast, the polyclonal antibodies that do not bind to any of the EMI region, the R1 region, the R2 region, and the R3 region of periostin do not bind to the ligand (protein and/or peptide including the amino acid sequence of the EMI region, the R1 region, the R2 region, or the R3 region of periostin) in the column or the like and pass through the column or the like.

The anti-periostin specific region polyclonal antibodies bound to the ligand (protein or peptide including the amino acid sequence of the EMI region, the R1 region, the R2 region, and/or the R3 region of periostin) in the column or the like can be separated from the ligand by changing the salt concentration, the pH, or the like and are captured to obtain the anti-periostin specific region polyclonal antibodies.

The resulting anti-periostin specific region polyclonal antibodies can bind to a periostin cleavage product.

In the case of using "the whole or part of the EMI region, the R1 region, the R2 region, and/or the R3 region of periostin" as an immunogen, the treatment of separating the polyclonal antibodies that do not bind to any of the EMI region, the R1 region, the R2 region, and the R3 region of periostin is not necessary.

In obtaining a "polyclonal antibodies that bind to at least one region selected from the group consisting of the EMI region, the R1 region, the R2 region, and the R3 region of periostin or a cleavage product thereof but do not bind to periostin multimers (anti-periostin specific region polyclonal antibody not binding to periostin multimers)," for example, anti-periostin specific region polyclonal antibodies are obtained as described above.

The anti-periostin specific region polyclonal antibodies obtained herein include "anti-periostin specific region polyclonal antibodies that do not bind to periostin multimers" and "anti-periostin specific region polyclonal antibodies that bind to a periostin multimer."

Subsequently, for separation, the resulting anti-periostin specific region polyclonal antibodies are introduced into, for example, an affinity chromatography column in which a periostin multimer is immobilized, as a ligand, onto a solid phase and is brought into contact with the periostin multimer.

As a result, the "anti-periostin specific region polyclonal antibodies that bind to a periostin multimer" is immobilized onto the solid phase via the ligand (periostin multimer) in the column or the like.

In contrast, "the anti-periostin specific region polyclonal antibodies that do not bind to periostin multimers" do not bind to the ligand (periostin multimer) in the column or the like and pass through the column or the like. By capturing them, the "anti-periostin specific region polyclonal antibodies that do not bind to periostin multimers" can be obtained.

Alternatively, for separation, the resulting anti-periostin specific region polyclonal antibodies are brought into contact with, for example, a solid-phase carrier immobilizing a periostin multimer as a ligand, and then the solid-phase carrier is separated to remove the "anti-periostin specific region polyclonal antibodies that bind to a periostin multimer." Consequently, the "anti-periostin specific region polyclonal antibodies that do not bind to periostin multimers" can be obtained from the remaining.

The resulting "anti-periostin specific region polyclonal antibodies that do not bind to periostin multimers" can bind to a periostin cleavage product but do not bind to periostin multimers.

Meanwhile, in immunization of, for example, an animal with a conjugate of an immunogen and a carrier, the resulting polyclonal antibodies include antibodies against the carrier. Accordingly, it is preferable to remove the antibodies against the carrier.

The removal treatment can be performed, for example, by adding the carrier to the resulting polyclonal antibody solution and removing the generated aggregates or by affinity chromatography using the carrier immobilized on an insoluble solid phase.

4. Method of Preparing Anti-Periostin Specific Region Monoclonal Antibody

A monoclonal antibody that can bind to at least one region selected from the group consisting of the EMI region, the R1 region, the R2 region, and the R3 region of periostin or a cleavage product thereof, i.e., an anti-periostin specific region monoclonal antibody, can be prepared by the following procedure.

The monoclonal antibody can be obtained by a hybridoma prepared by a cell fusion method of Koehler et al. (G. Koehler et al., Nature, Vol. 256, pp. 495-497, published in 1975) or by an antibody-producing cell such as a tumorigenic cell infected with a virus such as Epstein-Barr virus.

The monoclonal antibody can also be produced from a cDNA library of antibody genes by a phage display method of McCafferty et al. (M. McCafferty et al., Nature, Vol. 348, pp. 552-554, published in 1990).

For example, a monoclonal antibody can be prepared by the cell fusion method by the following procedure.

(1) A mammal (such as mouse, hamster, rat, or rabbit, e.g., BALB/c inbred mouse) or a bird (such as chicken) etc. is immunized with the immunogen or the conjugate of the immunogen and a carrier.

The animal immunized with the immunogen or the conjugate of the immunogen and a carrier is preferably an animal whose gene involved in the production of periostin in the body is inactive or deficient, i.e., an animal whose gene involved in the production of periostin is knocked out.

This is because that in the knockout animal, the risk of binding of periostin produced in the body of the animal to the anti-periostin specific region antibody produced in the body by the immunization with, for example, an immunogen such as periostin and thereby decreasing the antibody activity of the anti-periostin specific region antibody is low.

In the knockout animal, periostin is not produced in the body. Consequently, periostin as the immunogen is readily recognized as a foreign substance, and an antibody is highly produced.

Examples of the animal whose gene involved in the production of periostin is inactive or deficient include periostin knockout mice ("H. Rios et al., Mol. Cell. Biol., Vol. 25, No. 24, pp. 11131-11144, published in 2005").

The amount of the immunogen or the conjugate of the immunogen and a carrier for immunization is appropriately determined depending on the types of the immune animal, the site of immune injection, etc. In a case of mice, 0.1 µg to 5 mg of the immunogen or the conjugate of the immunogen and a carrier is preferably injected into each mouse at each immunization.

The immunogen or the conjugate of the immunogen and a carrier is preferably injected as a mixture with an adjuvant for immunization.

The adjuvant may be a known adjuvant such as Freund's complete adjuvant, Freund's incomplete adjuvant, aluminum hydroxide adjuvant, chemically synthesized adjuvant, or pertussis adjuvant.

The immune injection may be performed into a site such as subcutaneous tissue, a vein, the abdominal cavity, the footpad, or the back.

(2) After the initial immunization, booster injection of the immunogen or the conjugate of the immunogen and a carrier into a site such as subcutaneous tissue, a vein, the abdominal cavity, the footpad, or the back is performed at one- to two-week intervals.

The frequency of the booster injection is generally two to six times.

In also the booster injection, the immunogen or the conjugate of the immunogen and a carrier is preferably injected as a mixture with an adjuvant.

(3) After the initial immunization, the antibody titer in serum of the immunized animal is repeatedly measured by, for example, ELISA until the antibody titer reaches plateau. A solution of the immunogen or the conjugate of the immunogen and a carrier dissolved in saline (0.9% sodium chloride aqueous solution) is intravenously or intraperitoneally injected as the final immunization.

(4) Three to five days after the final immunization, cells having antibody producibility, such as splenocytes, lymph node cells, or peripheral lymphocytes, of the immunized animal are collected.

(5) The cells having antibody producibility collected from the immunized animal are fused to myeloma cells of, for example, a mammal (such as mouse, nude mouse, or rat). The myeloma cells are preferably those derived from a cell line having deficiency of an enzyme such as hypoxanthine-guanine phosphoribosyltransferase (HGPRT) or thymidine kinase (TK). For example, a BALB/c mouse-derived HGPRT-deficient cell line, such as cell line P3-X63-Ag8 (ATCC TIB9), cell line P3-X63-Ag8-U1 (Japanese Cancer Research Resources Bank (JCRB) 9085), cell line P3-NS1-1-Ag-4-1 (JCRB 0009), cell line P3-X63-Ag8-653 (JCRB 0028), or cell line SP2/O-Ag-14 (JCRB 0029), can be used.

The cell fusion can be performed by using a fusion promoter such as polyethylene glycol (PEG) having various molecular weights, liposome, or hemagglutinating virus of Japan (HVJ) or by electrical fusion.

In a case of HGPRT-deficient or TK-deficient myeloma cells, only the fusion cells (hybridomas) of the cells having antibody producibility and myeloma cells are selectively cultured and proliferated by using a selection medium containing hypoxanthine, aminopterin, and thymidine (HAT medium).

(6) The thus-obtained hybridoma culture supernatant is subjected to measurement by, for example, an immunoassay, such as ELISA or Western blotting, using a protein or peptide including the EMI region, the R1 region, the R2 region, and/or the R3 region of periostin derived from human or another animal (in the measurement of human periostin, human-derived periostin is preferred), and thereby hybridoma producing a "monoclonal antibody (anti-periostin specific region monoclonal antibody) that can bind to at least one region selected from the group consisting of the EMI region, the R1 region, the R2 region, and the R3 region of periostin or a cleavage product thereof" can be selected.

(7) An anti-periostin specific region monoclonal antibody-producing cell line according to the present invention can be isolated by performing combination of the hybridoma selection method and a known cloning method such as a limiting dilution method.

(8) An anti-periostin specific region monoclonal antibody according to the present invention can be obtained by culturing the monoclonal antibody-producing cell line in an appropriate culture medium and collecting it from the culture supernatant. The culture medium used may be a serum-free medium or a low serum-concentration medium. Such a medium is preferred because of easiness in purification of the antibody. For example, a DMEM medium, RPMI1640 medium, or ASF medium 103 can be used.

Alternatively, the monoclonal antibody-producing cell line is intraperitoneally injected into a mammal having compatibility therewith and stimulated with, for example, pristane in advance. After a certain period of time, an anti-periostin specific region monoclonal antibody according to the present invention can also be obtained from the ascites accumulated in the abdominal cavity.

(9) The thus-obtained anti-periostin specific region monoclonal antibody is subjected to salting-out with ammonium sulfate, sodium sulfate, or the like; a method such as ion-exchange chromatography, gel filtration, or affinity chromatography; or a combination thereof to obtain a purified anti-periostin specific region monoclonal antibody.

The resulting anti-periostin specific region monoclonal antibody can bind to a periostin cleavage product.

(10) As described in (6), a hybridoma producing an anti-periostin specific region monoclonal antibody can be selected by measuring the resulting hybridoma culture supernatant by, for example, an immunoassay, such as ELISA or Western blotting, using a protein or peptide including the EMI region, the R1 region, the R2 region, and/or the R3 region of periostin derived from human or another animal. In addition, measurement by, for example, an immunoassay, such as ELISA or Western blotting, using a periostin multimer can select a hybridoma producing a "monoclonal antibody that can bind to at least one region selected from the group consisting of the EMI region, the R1 region, the R2 region, and the R3 region of periostin or a cleavage product thereof but does not bind to periostin multimers (anti-periostin specific region monoclonal antibody that does not bind to periostin multimers)."

(11) An "anti-periostin specific region monoclonal antibody that does not bind to periostin multimers" can be obtained from the hybridoma that produces an "anti-periostin specific region monoclonal antibody that does not bind to periostin multimers" as in (7) to (9).

The resulting "anti-periostin specific region monoclonal antibody that does not bind to periostin multimers" can bind to a periostin cleavage product but does not bind to periostin multimer.

Examples of the monoclonal antibody according to the present invention include a monoclonal antibody wherein an amino acid sequence of a heavy chain variable region of the antibody comprises the amino acid sequence set forth in SEQ ID NO: 16 and an amino acid sequence of a light chain variable region of the antibody comprises the amino acid sequence set forth in SEQ ID NO: 18.

In another aspect, examples of the monoclonal antibody according to the present invention include, but not limited to, a monoclonal antibody produced by a hybridoma selected from the group consisting of the hybridoma cell line SS16A having Accession Number NITE BP-1281, the hybridoma cell line SS18A having Accession Number NITE BP-1282, the hybridoma cell line SS19C having Accession Number NITE BP-1283, the hybridoma cell line SS19D having Accession Number NITE BP-1068, the hybridoma cell line SS20A having Accession Number NITE BP-1284, the hybridoma cell line SS25A having Accession Number NITE BP-1285, and the hybridoma cell line SS27A having Accession Number NITE BP-1286.

[2] Method of Measuring Periostin

1. Outline

The method of measuring periostin of the present invention is a method of measuring periostin contained in a sample and is characterized by detecting at least one region selected from the group consisting of the EMI region, the R1 region, the R2 region, and the R3 region of periostin.

Periostin is composed of an EMI region, an R1 region, an R2 region, an R3 region, an R4 region, and a C-terminal region in this order from the N-terminus to the C-terminus. The method of measuring periostin of the present invention is characterized by detecting at least one region selected from the group consisting of the EMI region, the R1 region, the R2 region, and the R3 region among these regions.

The method of the present invention may be a method of measuring a periostin cleavage product contained in a sample. More specifically, the method may be a method of measuring a periostin cleavage product contained in a sample characterized by detecting at least one region selected from the group consisting of an EMI region, an R1 region, an R2 region, and an R3 region of the periostin cleavage product.

In another aspect, the method of the present invention may be a method of measuring periostin other than periostin multimers. In the present invention, the method of measuring periostin other than multimers means a method that does not detect (or measure) periostin multimers. More specifically, the method of the present invention may be a method of measuring periostin or a periostin cleavage product contained in a sample characterized by detecting at least one region selected from the group consisting of the EMI region, the R1 region, the R2 region, and the R3 region of periostin or a periostin cleavage product but not detecting (or measuring) periostin multimers.

The method of measuring periostin of the present invention is a method that can improve the accuracy of the periostin measurement by detecting at least one region selected from the group consisting of the EMI region, the R1 region, the R2 region, and the R3 region of periostin in the measurement of periostin contained in a sample.

In the method of measuring periostin of the present invention, the phrase "detecting at least one region selected from the group consisting of the EMI region, the R1 region, the R2 region, and the R3 region of periostin" refers to detection of the presence or the amount of at least one region selected from the group consisting of the EMI region, the R1 region, the R2 region, and the R3 region of periostin.

The phrase "detecting at least one region selected from the group consisting of the EMI region, the R1 region, the R2 region, and the R3 region of periostin" will now be more specifically described. In a case of measuring periostin contained in a sample by utilizing a reaction between substances having specific affinity, such as an antigen and an antibody, a saccharide and lectin, a nucleotide chain and a substance specific thereto, or a ligand and a receptor, for example, the use of a substance (specific binding substance) that can specifically bind to at least one region selected from the group consisting of the EMI region, the R1 region, the R2 region, and the R3 region of periostin allows the specific binding substance to bind to at least one region selected from the group consisting of the EMI region, the R1 region, the R2 region, and the R3 region of periostin, and thereby the presence or the amount of at least one region selected from the group consisting of the EMI region, the R1 region, the R2 region, and the R3 region of periostin can be detected. That is, at least one region selected from the group consisting of the EMI region, the R1 region, the R2 region, and the R3 region of periostin can be detected.

For example, when the specific binding substance is an antibody, the presence or the amount of at least one region selected from the group consisting of the EMI region, the R1 region, the R2 region, and the R3 region of periostin can be detected by, for example, using an antibody (anti-periostin specific region antibody) that can bind to at least one region selected from the group consisting of the EMI region, the R1 region, the R2 region, and the R3 region of periostin or a cleavage product thereof. That is, at least one region selected from the group consisting of the EMI region, the R1 region, the R2 region, and the R3 region of periostin can be detected.

The method of measuring periostin of the present invention may detect any one of the EMI region, the R1 region, the R2 region, and the R3 region of periostin or may detect two or more of the EMI region, the R1 region, the R2 region, and the R3 region of periostin.

The method of measuring periostin of the present invention is preferably a method utilizing an antigen-antibody reaction in measurement of periostin contained in a sample and uses an antibody (anti-periostin specific region antibody) that binds to at least one region selected from the group consisting of the EMI region, the R1 region, the R2 region, and the R3 region of periostin or a cleavage product thereof.

As the anti-periostin specific region antibody, the antibodies described in the section "[1] Anti-periostin specific region antibody," for example, the following antibodies, can be used:

(i) Antibody that binds to at least one region selected from the group consisting of the EMI region, the R1 region, the R2 region, and the R3 region of periostin or a cleavage product thereof;

(ii) Antibody that binds to a periostin cleavage product;

(iii) Antibody that binds to at least one region selected from the group consisting of the EMI region, the R1 region, the R2 region, and the R3 region of periostin or a cleavage product thereof but does not bind to periostin multimers;

(iv) Antibody that binds to periostin cleavage products but does not bind to periostin multimers;

(v) Monoclonal antibody that binds to at least one region selected from the group consisting of the EMI region, the R1 region, the R2 region, and the R3 region of periostin or a cleavage product thereof;

(vi) Monoclonal antibody that binds to a periostin cleavage product;

(vii) Monoclonal antibody that binds to at least one region selected from the group consisting of the EMI region, the R1 region, the R2 region, and the R3 region of periostin or a cleavage product thereof but does not bind to periostin multimers;

(viii) Monoclonal antibody wherein an amino acid sequence of a heavy chain variable region of the antibody comprises the amino acid sequence set forth in SEQ ID NO: 16 and an amino acid sequence of a light chain variable region of the antibody comprises the amino acid sequence set forth in SEQ ID NO: 18; and (ix) Monoclonal antibody produced by a hybridoma selected from the group consisting of the hybridoma cell line SS16A having Accession Number NITE BP-1281, the hybridoma cell line SS18A having Accession Number NITE BP-1282, the hybridoma cell line SS19C having Accession Number NITE BP-1283, the hybridoma cell line SS19D having Accession Number NITE BP-1068, the hybridoma cell line SS20A having Accession Number NITE BP-1284, the hybridoma cell line SS25A having Accession Number NITE BP-1285, and the hybridoma cell line SS27A having Accession Number NITE BP-1286.

In the method of measuring periostin of the present invention, for example, when two molecules of antibodies bind to one molecule of periostin, both of these antibodies are required to be anti-periostin specific region antibodies.

For example, in a sandwich assay of ELISA using an enzyme-labeled antibody and a immobilized antibody, both the enzyme-labeled antibody and the immobilized antibody to be bound to periostin contained in a sample are required to be anti-periostin specific region antibodies.

Meanwhile, among the anti-periostin specific region antibodies according to the present invention, the use of an anti-periostin specific region antibody that does not bind to periostin multimers in the method of measuring periostin contained in a sample utilizing an antigen-antibody reaction can further enhance the improvement in accuracy of the measurement and is therefore preferred. In the method of measuring periostin of the present invention, for example, when two molecules of antibodies bind to one molecule of periostin, if one antibody is an anti-periostin specific region antibody that does not bind to periostin multimers, the other antibody is not necessarily required to be an anti-periostin specific region antibody that does not bind to periostin multimers as long as it is an anti-periostin specific region antibody.

For example, in a sandwich assay of ELISA using an enzyme-labeled antibody and a immobilized antibody, when one of the enzyme-labeled antibody and the immobilized antibody to be bound to periostin contained in a sample is an anti-periostin specific region antibody that does not bind to periostin multimers, the other antibody is not necessarily required to be an anti-periostin specific region antibody that does not bind to periostin multimers as long as it is an anti-periostin specific region antibody.

The anti-periostin specific region antibody is not limited to a single type of antibody, and multiple types of antibodies may be simultaneously used.

The details of the anti-periostin specific region antibody are as described in the section "[1] Anti-periostin specific region antibody."

The method of measuring periostin of the present invention can improve the accuracy of measurement and is suitable for measurement for testing the presence of disease or the severity (e.g., symptom) thereof.

The method of measuring periostin of the present invention is more suitable for measurement for testing the presence of cancer or lung disease or the severity (e.g., symptom) thereof.

The method of measuring periostin of the present invention is further suitable for measurement for testing the presence of cholangiocarcinoma, pulmonary fibrosis, or interstitial pneumonia or the severity (e.g., symptom) thereof.

The method of measuring periostin of the present invention is still more suitable for measurement for testing the presence of pulmonary fibrosis or interstitial pneumonia or the severity (e.g., symptom) thereof.

The method of measuring periostin of the present invention is particularly suitable for measurement for testing the presence of interstitial pneumonia or the severity (e.g., symptom) thereof.

2. Method of Measurement Utilizing Antigen-Antibody Reaction

The method of measuring periostin of the present invention is preferably a method of measuring periostin contained in a sample utilizing an antigen-antibody reaction and uses an anti-periostin specific region antibody. The intended effect can be achieved by using the anti-periostin specific region antibody regardless of the principle of the measurement.

Examples of the method utilizing an antigen-antibody reaction in measurement of periostin contained in a sample include enzyme immunoassays (ELISA and EIA), fluoroimmunoassays (FIAs), radioimmunoassays (RIAs), luminescence immunoassays (LIAs), enzyme antibody techniques, fluorescence antibody techniques, immunochromatographies, immunonephelometries, latex nephelometries, latex agglutination assays, erythrocyte agglutination assays, particle agglutination assays, the method described in, for example, Japanese Patent Laid-Open No. H09-229936 or Japanese Patent Laid-Open No. H10-132819 using a carrier having a surface onto which a substance that specifically binds to a substance to be measured (analyte) is immobilized so as to cover the surface and using particles onto which a substance that specifically binds to the substance to be measured (analyte) is immobilized, and the enzyme-linked ligandsorbent assay (ELSA) described by Dahlbeack et al. (Thromb. Haemost., Vol. 79, pp. 767-772, published in 1998; International Publication No. WO98/23963).

To the measurement in the method of measuring periostin of the present invention can be applied any of sandwich assay, competitive assay, and homogeneous method.

The measurement in the method of measuring periostin of the present invention may be carried out manually or with an apparatus such as an analyzer.

3. Sample

The sample in the present invention may be any sample such as biological samples having a possibility of containing periostin, e.g., body fluids such as blood, serum, plasma, urine, semen, cerebrospinal fluid, saliva, ascites, and amniotic fluid; and extracts from organs such as blood vessels or the liver, tissues, or cells.

The sample to be subjected to the measurement is preferably in a liquid form. If a sample is not a liquid, the sample may be converted into a liquid sample by a known pretreatment process such as extraction or solubilization treatment.

A sample may be optionally subjected to concentration treatment.

A sample may be optionally diluted with a diluent before the measurement.

For example, the dilution may be performed by adding a diluent to a sample before the sample is brought into contact with and is allowed to bind to an anti-periostin specific region antibody.

The diluent may be any of various aqueous solvents.

For example, an aqueous solvent such as water, saline, or a buffer solution such as tris(hydroxymethyl)aminomethane buffer [Tris buffer], phosphate buffer, or phosphate-buffered saline can be used.

These buffers preferably have a pH in the range of 5 to 10.

In a case of using blood (whole blood) as the sample, the whole blood sample is preferably mixed with a water or a hypotonic solution such as an aqueous solvent containing a surfactant to rupture the erythrocytes, which allows the subsequent measurement to be performed without difficulty.

4. Substance to be Measured

In the present invention, the substance to be measured is periostin.

The periostin includes a monomer, dimer, trimer, tetramer, or higher multimer of periostin, or a periostin cleavage product (e.g., a periostin cleavage product having a molecular weight of about 40 KDa), and these are all substances to be measured in the present invention.

The substance to be measured in the present invention is preferably a periostin monomer or a periostin cleavage product.

That is, periostin other than periostin multimers (throughout the specification, also referred to as "periostin other than multimers") is preferred as a substance to be measured.

The periostin cleavage product is particularly preferred as the periostin, i.e., as the substance to be measured in the present invention.

That is, periostin other than a periostin monomer and periostin multimers is particularly preferred as substances to be measured.

5. Immunoassay Using Labeled Antibody

When the measurement in the method of measuring periostin of the present invention is implemented by an immunoassay using a labeled antibody, such as an enzyme immunoassay, fluoroimmunoassay, radioimmunoassay, or luminescence immunoassay, i.e., by a measuring method utilizing an antigen-antibody reaction using a labeled antibody, the method can be carried out by, for example, a sandwich assay or a competitive assay. In the sandwich assay, the immobilized antibody and the labeled antibody to be bound to periostin contained in a sample are both required to be anti-periostin specific region antibodies.

In the measurement by a sandwich assay as described above, when one of the enzyme-labeled antibody and the immobilized antibody is an anti-periostin specific region antibody that does not bind to periostin multimers, the other antibody is not necessarily required to be an anti-periostin specific region antibody that does not bind to periostin multimers as long as it is an anti-periostin specific region antibody.

The solid-phase carrier used in the immunoassay using a labeled antibody can have a shape such as a microcapsule, bead, microplate (microtiter plate), test tube, stick, or test strip made of a material such as polystyrene, polycarbonate, polyvinyl toluene, polypropylene, polyethylene, polyvinyl chloride, nylon, polymethacrylate, polyacrylamide, latex, liposome, gelatin, agarose, cellulose, Sepharose (registered trademark), glass, a metal, ceramics, or a magnetic material.

An antibody such as the anti-periostin specific region antibody can be immobilized onto a solid-phase carrier by adsorption and/or binding through a known method such as physical adsorption, chemical binding, or the both.

The physical adsorption can be carried out by a known method, for example, by mixing and bringing into contact an antibody such as the anti-periostin specific region antibody with a solid-phase carrier in a solution such as a buffer or by bringing into contact an antibody such as the anti-periostin specific region antibody dissolved in, for example, a buffer with a solid-phase carrier.

The chemical binding can be carried out by a known method described in, for example, "RINSHO BYORI (Clinical Pathology), extra issue, special edition No. 53, Rinsho Kensa notameno Immunoassei—Gijutsu to Oyo—(Immunoassay for clinical test—its technique and application—)," edited by the Japan Society of Clinical Pathology, Rinsho Byori Kanko Kai, published in 1983; or "Shin Seikagaku Jikken Koza (New Course of Biochemical Experiments) 1, Tanpakushitsu (Protein) IV," edited by the Japanese Biochemical Society, Tokyo Kagaku Dojin, published in 1991, by mixing and bringing into contact an antibody such as the anti-periostin specific region antibody and a solid-phase carrier with a bivalent crosslinking reagent such as glutaraldehyde, carbodiimide, imidoester, or maleimide to allow the amino group, carboxyl group, thiol group, aldehyde group, or hydroxy group etc. of the antibody such as the anti-periostin specific region antibody and the solid-phase carrier to react with the reagent.

Furthermore, if treatment for inhibiting non-specific reaction or natural aggregation of the solid-phase carrier etc. is needed, the surface or the internal surface of the solid-phase carrier onto which an antibody such as the anti-periostin specific region antibody is immobilized may be treated by a known method for blocking (masking) the solid-phase carrier, for example, by bringing into contact and coating the surface or the internal surface with a protein such as bovine serum albumin (BSA), human serum albumin (HSA), casein, gelatin, ovalbumin, or a salt thereof; a surfactant; or skim milk.

The labeling substance that can be used in the enzyme immunoassay is, for example, peroxidase (POD), alkaline phosphatase (ALP), β-galactosidase, urease, catalase, glucose oxidase, lactic acid dehydrogenase, or amylase.

The labeling substance that can be used in the fluoroimmunoassay is, for example, fluorescein isothiocyanate, tetramethylrhodamine isothiocyanate, substituted rhodamine isothiocyanate, or dichlorotriazine isothiocyanate.

The labeling substance that can be used in the radioimmunoassay is, for example, tritium, iodine$^{125}$, or odine$^{131}$.

The labeling substance that can be used in the luminescence immunoassay is, for example, NADH-FMNH$_2$-luciferase, luminol-hydrogen peroxide-POD, acridinium ester, or a dioxetane compound.

An antibody such as the anti-periostin specific region antibody and the labeling substance such as an enzyme can be bound to each other in accordance with a known method described in, for example, "RINSHO BYORI (Clinical Pathology), extra issue, special edition No. 53, Rinsho Kensa notameno Immunoassei—Gijutsu to Oyo—(Immunoassay for clinical test—its technique and application—)," edited by the Japan Society of Clinical Pathology, Rinsho Byori Kanko Kai, published in 1983; or "Shin Seikagaku Jikken Koza (New Course of Biochemical Experiments) 1, Tanpakusitsu (Protein) IV," edited by the Japanese Biochemical Society, Tokyo Kagaku Dojin, published in 1991, by mixing and bringing into contact an antibody such as the anti-periostin specific region antibody and the labeling substance with a bivalent crosslinking reagent such as glutaraldehyde, carbodiimide, imidoester, or maleimide to allow the amino group, carboxyl group, thiol group, aldehyde group, or hydroxy group etc. of an antibody such as the anti-periostin specific region antibody and the labeling substance to react with the reagent.

The measurement can be carried out by a known method (for example, "RINSHO BYORI (Clinical Pathology), extra issue, special edition No. 53, Rinsho Kensa notameno Immunoassei—Gijutsu to Oyo—(Immunoassay for clinical test—its technique and application—)," edited by the Japan Society of Clinical Pathology, Rinsho Byori Kanko Kai, published in 1983; "Koso Men-eki Sokutei-ho (Enzyme Immunoassay)" edited by Eiji Ishikawa et al., third edition, Igaku-Shoin Ltd., published in 1987; or "Tanpakushitsu Kakusan Koso (Protein, Nucleic Acid and Enzyme) Supplement No. 31, Koso Men-eki Sokutei-ho (Enzyme Immunoassay)," edited by Tsunehiro Kitagawa et al., Kyoritsu Shuppan Co., Ltd., published in 1987).

For example, a sample is reacted with a immobilized antibody and a labeled antibody simultaneously or is reacted with a immobilized antibody and then, after washing, with a labeled antibody to form a complex of "solid-phase carrier=immobilized antibody=periostin=labeled antibody."

Unbound labeled antibody is removed by washing, and only the amount (concentration) of periostin contained in a sample can be measured from the amount of the labeled antibody bound to the solid-phase carrier via the "immobilized antibody=periostin" or the amount of unbound labeled antibody.

Specifically, in the enzyme immunoassay, for example, an enzyme conjugated to an antibody as a label is reacted with a substrate under optimum conditions, and the amount of the enzyme reaction product is measured by, for example, an optical method.

In the fluoroimmunoassay, for example, the fluorescence intensity of the fluorescent label is measured. In the radioimmunoassay, for example, the radiation dose of the radioactive label is measured.

In the luminescence immunoassay, for example, the amount of luminescence of the light emission reaction system is measured.

6. Immunoassay by Agglutination Assay

When the measurement in the method of measuring periostin of the present invention is implemented by, for example, an immunonephelometry, latex nephelometry, latex agglutination assay, erythrocyte agglutination assay, or particle agglutination assay in which the generation of immune complex aggregates is measured through measurement of the transmitted light or scattered light by an optical method or visual measurement, that is, when periostin is measured by a method (agglutination assay) of measuring the generation of aggregates of a complex by an antigen-antibody reaction, the antibody to be bound to periostin contained in a sample is required to be an anti-periostin specific region antibody.

In the measurement by the agglutination assay, the anti-periostin specific region antibody may be an anti-periostin specific region antibody that does not bind to periostin multimers, which enhances the improvement in accuracy and is therefore preferred.

The solvent in the measurement by the agglutination assay can be, for example, phosphate buffer, glycine buffer, tris (hydroxymethyl)aminomethane buffer [Tris buffer], or Good's buffer and may further contain a reaction promoter such as polyethylene glycol or a non-specific reaction inhibitor.

The solid-phase carrier for immobilizing an antibody such as the anti-periostin specific region antibody can be particles made of a material such as polystyrene, a styrene-styrenesulfonate copolymer, an acrylonitrile-butadiene-styrene copolymer, a vinyl chloride-acrylate ester copolymer, a vinyl acetate-acrylic acid copolymer, polyacrolein, a styrene-methacrylic acid copolymer, a styrene-glycidyl (meth)acrylic acid copolymer, a styrene-butadiene copolymer, a methacrylic acid polymer, an acrylic acid polymer, latex, gelatin, liposome, microcapsule, erythrocyte, silica, alumina, carbon black, a metal compound, a metal, ceramics, or a magnetic material.

An antibody such as the anti-periostin specific region antibody can be immobilized onto the solid-phase carrier by a known method such as physical adsorption, chemical binding, or the both.

The physical adsorption can be carried out by a known method, for example, by mixing and bringing into contact an antibody such as the anti-periostin specific region antibody with a solid-phase carrier in a solution such as a buffer or by bringing into contact an antibody such as the anti-periostin specific region antibody dissolved in, for example, a buffer with a solid-phase carrier.

The chemical binding can be carried out by a known method described in, for example, "RINSHO BYORI (Clinical Pathology), extra issue, special edition No. 53, Rinsho Kensa notameno Immunoassei—Gijutsu to Oyo—(Immunoassay for clinical test—its technique and application —)," edited by the Japan Society of Clinical Pathology, Rinsho Byori Kanko Kai, published in 1983; or "Shin Seikagaku Jikken Koza (New Course of Biochemical Experiments) 1, Tanpakushitsu (Protein) IV," edited by the Japanese Biochemical Society, Tokyo Kagaku Dojin, published in 1991, by mixing and bringing into contact an antibody such as the anti-periostin specific region antibody and a solid-phase carrier with a bivalent crosslinking reagent such as glutaraldehyde, carbodiimide, imidoester, or maleimide to allow the amino group, carboxyl group, thiol group, aldehyde group, or hydroxy group etc. of the antibody such as the anti-periostin specific region antibody and the solid-phase carrier to react with the reagent.

Furthermore, if treatment for inhibiting non-specific reaction or natural aggregation of the solid-phase carrier etc. is needed, the surface or the internal surface of the solid-phase carrier onto which an antibody such as the anti-periostin specific region antibody is immobilized may be treated by a known method for blocking (masking) the solid-phase carrier, for example, by bringing into contact and coating the surface or the internal surface with a protein such as bovine serum albumin (BSA), human serum albumin (HSA), casein, gelatin, ovalbumin, or a salt thereof; a surfactant; or skim milk.

In the case of employing the latex nephelometry as the principle of measurement, the latex particles used as the solid-phase carrier may have any particle diameter. From the viewpoints of, for example, the degree of generation of aggregates by binding of the latex particles via a substance to be measured (periostin) and easiness in measurement of the generated aggregates, the latex particles preferably have an average particle diameter of 0.04 to 1 µm.

In the case of employing the latex nephelometry as the principle of measurement, the optimum concentration of the latex particles onto which an antibody such as the anti-periostin specific region antibody is immobilized varies depending on various conditions such as the concentration of periostin in a sample, the distribution density of an antibody such as the anti-periostin specific region antibody on the latex particle surfaces, the particle diameter of the latex particles, and the mixing ratio of a sample and a measurement reagent.

In general, the concentration of the latex particles onto which an "antibody such as the anti-periostin specific region antibody" is immobilized is 0.005 to 1% (w/v) in a reaction solution mixture during the reaction to be measured by mixing a sample and a measurement reagent for an antigen-antibody reaction between the "antibody such as the anti-periostin specific region antibody" immobilized onto the latex particles and "periostin" contained in the sample. In this case, the measurement reagent contains the "latex particles onto which the antibody such as the anti-periostin specific region antibody" at a concentration to give such a concentration in the reaction solution mixture.

In the case of employing an indirect agglutination assay such as a latex agglutination assay, erythrocyte agglutination assay, or particle agglutination assay as the principle of measurement, the particles used as the solid-phase carrier may have any particle diameter and preferably have an average particle diameter within the range of 0.01 to 100 µm and more preferably within the range of 0.5 to 10 µm, and preferably have a specific gravity within the range of 1 to 10 and more preferably within the range of 1 to 2.

Examples of the container used in the measurement employing an indirect agglutination assay such as a latex agglutination assay, erythrocyte agglutination assay, or particle agglutination assay as the principle of measurement include test tubes, microplates (microtiter plates), and trays made of glass, polystyrene, polyvinyl chloride, or polymethacrylate.

In these containers, the bottom of a solution receiving portion (e.g., the well of a microplate) preferably has a shape having a slant from the center toward the periphery, such as a U-shaped, V-shaped, or UV-shaped.

The measurement can be carried out by a known method etc. For example, in the measurement by an optical method, a sample is allowed to react with an antibody such as the anti-periostin specific region antibody or an "antibody such as the anti-periostin specific region antibody immobilized onto a solid-phase carrier," and the transmitted light or scattered light is measured by an end point assay or rate assay.

In the case of visual measurement, a sample is allowed to react with an "antibody such as the anti-periostin specific region antibody immobilized onto a solid-phase carrier" in the container such as a plate or a microplate, and the state of aggregation is visually measured.

The measurement may be performed using a device such as a microplate reader, instead of the visual measurement, An example of measuring procedure will now be described.

For example, a measurement reagent containing a "solid-phase carrier onto which an anti-periostin specific region antibody is immobilized" is prepared. Alternatively, a measurement reagent containing a "solid-phase carrier onto which an anti-periostin specific region antibody is immobilized" and a measurement reagent containing an "aqueous solvent" etc. are prepared.

Subsequently, for example, the measurement reagent containing the "solid-phase carrier onto which an anti-periostin specific region antibody is immobilized" and a sample are mixed to bring the sample into contact with the "solid-phase carrier onto which an anti-periostin specific region antibody is immobilized."

As a result, an antigen-antibody reaction between the "anti-periostin specific region antibody" of the "solid-phase carrier onto which an anti-periostin specific region antibody is immobilized" and "periostin" contained in the sample occurs.

Subsequently, the resulting aggregates of a complex of the "solid-phase carrier onto which an anti-periostin specific region antibody is immobilized" (anti-periostin specific region antibody=solid-phase carrier=anti-periostin specific region antibody) and "periostin," ( . . . [periostin]-[anti-periostin specific region antibody=solid-phase carrier=anti-periostin specific region antibody]-[periostin]-[anti-periostin specific region antibody=solid-phase carrier=anti-periostin specific region antibody]-[periostin]. . . ), are measured.

The measurement of the generated complex aggregates is carried out by measuring, for example, the absorbance of transmitted light or scattered light of a reaction solution mixture containing the complex aggregates during the reaction to be measured by an end point assay or a rate assay.

The measured value such as the absorbance obtained by measuring a sample is compared to the measured value such as the absorbance obtained by measuring a standard substance (sample having a known periostin concentration), and the concentration (quantitative value) of periostin contained in the sample is calculated.

The measurement of the absorbance etc. may be carried out by measuring, for example, transmitted light or scattered light and may be carried out by single wavelength measurement or double wavelength measurement (difference or ratio between those at two wavelengths).

The measurement wavelength is usually selected from the range of 340 to 1000 nm.

The measurement of periostin according to the present invention may be carried out manually or with an apparatus such as an analyzer.

The analyzer may be a general purpose automatic analyzer or a dedicated analyzer (special purpose machine).

The measurement of periostin according to the present invention may be carried out by a one-step method (one-reagent method) or by a plurality of procedure steps such as a two-step method (two-reagent method).

The measurement of periostin will now be described in more detail by a method employing a latex nephelometry as the principle of measurement as an example.

(1) The following reagents are prepared as reagents for measuring periostin.

First Reagent:
Buffer (aqueous solvent)
Second Reagent:
Buffer containing "latex particles onto which an anti-periostin specific region antibody is immobilized"

(2) A certain amount of a sample such as serum and a certain amount of the first reagent are mixed, and the mixture is left to stand at a certain temperature for a certain time.

The mixing ratio (quantity ratio) of the sample and the first reagent may be appropriately selected.

The temperature during the leaving to stand is preferably a certain temperature within the range of room temperature (1° C. to 30° C.) or lukewarmness (30° C. to 40° C.) (for example, 37° C.).

(3) After the certain time, a certain amount of the second reagent is added to and mixed with the mixture of the sample and the first reagent, and the resulting reaction mixture solution is left to stand at a certain temperature for a certain time.

As a result, the sample is brought into contact with the "latex particles onto which an anti-periostin specific region antibody is immobilized."

The amount of the second reagent added may be appropriately selected.

The temperature during the leaving to stand is preferably a certain temperature within the range of room temperature (1° C. to 30° C.) or lukewarmness (30° C. to 40° C.) (for example, 37° C.).

The time for the leaving to stand is preferably a certain time of 1 minute or more and 10 minutes or less and more preferably a certain time of 3 minutes or more and 5 minutes or less.

The second reagent is added to and mixed with the mixture of the sample and the first reagent to cause an antigen-antibody reaction between the anti-periostin specific region antibody immobilized onto the latex particles and periostin contained in the sample.

The antigen-antibody reaction generates crosslinking such as " . . . [periostin]-[anti-periostin specific region antibody=latex particle=anti-periostin specific region antibody]-[periostin]-[anti-periostin specific region antibody=latex particle=anti-periostin specific region antibody]-[periostin]. . . " and thereby generates aggregates of the complex of "latex particles onto which an anti-periostin specific region antibody is immobilized" via periostin.

(4) The amount of the generated complex aggregates, i.e., the amount of periostin contained in the sample, is determined by measuring a decrease in the intensity of the transmitted light (an increase in absorbance) or an increase in the intensity of the scattered light at an appropriate wavelength, which is a signal caused by the generated aggregates of the complex of the latex particles by irradiating the reaction solution mixture with light, with an analyzer or spectrophotometer etc.

(5) The amount (concentration) of periostin contained in the sample subjected to the measurement is calculated by comparing "the measured value obtained by measuring the sample [value of the decrease in the intensity of the transmitted light (the increase in absorbance) or the increase in the intensity of the scattered light]" with "the measured value [value of the decrease in the intensity of the transmitted light (the increase in absorbance) or the increase in the intensity of the scattered light] obtained by measuring a standard substance [sample containing a known concentration of periostin] such as a standard solution or a standard serum."

7. Other Components for Measurement

In the method of measuring periostin of the present invention, various aqueous solvents can be used as the solvent.

Examples of the aqueous solvents include purified water, saline, and various buffers such as tris(hydroxymethyl)aminomethane buffer [Tris buffer], phosphate buffer, and phosphate-buffered saline.

The pH of such a buffer may be appropriately selected without particular limitation and is usually selected within the range of 3 to 12.

The method of measuring periostin of the present invention may appropriately use one or more of proteins such as bovine serum albumin (BSA), human serum albumin (HSA), casein and salts thereof; various salts; various saccharides; skim milk; serum of various animals such as normal rabbit serum; various preservatives such as sodium azide and antibiotics; activators; reaction promoters; sensitivity enhancers such as polyethylene glycol; non-specific reaction inhibitors; and various surfactants such as nonionic surfactants, amphoteric surfactants, and anionic surfactants, in addition to the reagent components, e.g., the antibody such as the anti-periostin specific region antibody, the solid-phase carrier onto which the antibody such as the anti-periostin specific region antibody is immobilized, and/or the antibody such as the anti-periostin specific region antibody labeled with a labeling substance such as an enzyme.

The concentration of such additives used in the measurement is not particularly limited and is preferably 0.001 to 10% (W/V) and particularly preferably 0.01 to 5% (W/V).

Examples of the surfactants include nonionic surfactants such as sorbitan fatty acid ester, glycerol fatty acid ester, decaglycerol fatty acid ester, polyoxyethylene sorbitan fatty acid ester, polyoxyethylene glycerol fatty acid ester, polyethylene glycol fatty acid ester, polyoxyethylene alkyl ether, polyoxyethylene phytosterol, phytostanol, polyoxyethylene polyoxypropylene alkyl ether, polyoxyethylene alkylphenyl ether, polyoxyethylene castor oil, hydrogenated castor oil, and polyoxyethylene lanolin; amphoteric surfactants such as betaine acetate; and anionic surfactants such as polyoxyethylene alkyl ether sulfate and polyoxyethylene alkyl ether acetate.

[3] Reagent for Measuring Periostin or Cleavage Product Thereof.

1. Outline

The reagent for measuring periostin or a cleavage product thereof of the present invention is a reagent for measuring periostin or a cleavage product thereof contained in a sample characterized by detecting at least one region selected from the group consisting of the EMI region, the R1 region, the R2 region, and the R3 region of periostin.

Periostin is composed of an EMI region, an R1 region, an R2 region, an R3 region, an R4 region, and a C-terminal region in this order from the N-terminus to the C-terminus. The reagent measuring periostin or a cleavage product thereof of the present invention is characterized by detecting at least one region selected from the group consisting of the EMI region, the R1 region, the R2 region, and the R3 region among these regions.

In another aspect, the reagent for measuring periostin or a cleavage product thereof of the present invention includes a substance (specific binding substance) that specifically binds to at least one region selected from the group consisting of the EMI region, the R1 region, the R2 region, and the R3 region of periostin or a cleavage product thereof. In the present invention, the specific binding substance refers to a substance that specifically binds to at least one region selected from the group consisting of the EMI region, the R1 region, the R2 region, and the R3 region of periostin or a cleavage product thereof. Examples of such a substance include lectin, substances that specifically bind to nucleotide chains (e.g., aptamer), antibodies and fragments thereof, receptors, and polypeptides or oligopeptides that specifically bind to any of the regions. When the specific binding substance is an antibody, examples of the antibody include, but not limited to, the antibodies (i) to (ix) described in the section "1. Outline in [2] Method of measuring periostin." When the specific binding substance is a polypeptide or oligopeptide, examples of the peptide include peptides from peptide phage display libraries.

The measurement reagent of the present invention may be a reagent for measuring a periostin cleavage product contained in a sample. More specifically, the measurement reagent may be a reagent containing a substance that specifically binds to at least one region selected from the group consisting of the EMI region, the R1 region, the R2 region, and the R3 region of a periostin cleavage product to measure a periostin cleavage product contained in a sample.

In another aspect, the measurement reagent of the present invention may be a reagent for measuring periostin other than multimers. In the present invention, a reagent for measuring periostin other than multimers means a reagent that does not detect (or measure) periostin multimers. More specifically, the measurement reagent of the present invention may be a reagent for measuring periostin or a periostin cleavage product contained in a sample and containing a substance that specifically binds to at least one region selected from the group consisting of the EMI region, the R1 region, the R2 region, and the R3 region of periostin or a periostin cleavage product but does not bind to periostin multimers.

The substance (specific binding substance) that specifically binds to any of the regions is described as above.

The reagent for measuring periostin or a cleavage product thereof of the present invention is a measurement reagent that can improve the accuracy of periostin measurement by detecting at least one region selected from the group consisting of the EMI region, the R1 region, the R2 region, and the R3 region of periostin in the measurement of periostin or a cleavage product thereof contained in a sample.

In the reagent for measuring periostin or a cleavage product thereof of the present invention, the phrase "detecting at least one region selected from the group consisting of the EMI region, the R1 region, the R2 region, and the R3 region of periostin" refers to detection of the presence or the amount of at least one region selected from the group consisting of the EMI region, the R1 region, the R2 region, and the R3 region of periostin.

The phrase "detecting at least one region selected from the group consisting of the EMI region, the R1 region, the R2 region, and the R3 region of periostin" will now be more specifically described. In a case of measuring periostin or a cleavage product thereof contained in a sample by utilizing a reaction between substances having specific affinity, such as an antigen and an antibody, a saccharide and lectin, a nucleotide chain and a substance specific thereto, or a ligand and a receptor, the presence or the amount of at least one region selected from the group consisting of the EMI region, the R1 region, the R2 region, and the R3 region of periostin or a cleavage product thereof can be detected by, for example, using a specific binding substance that can specifically bind to at least one region selected from the group consisting of the EMI region, the R1 region, the R2 region, and the R3 region of periostin. That is, at least one region selected from the group consisting of the EMI region, the R1 region, the R2 region, and the R3 region of periostin or a cleavage product thereof can be detected.

For example, when the specific binding substance is an antibody, the presence or the amount of at least one region selected from the group consisting of the EMI region, the R1 region, the R2 region, and the R3 region of periostin or a cleavage product thereof can be detected by, for example, using an antibody (anti-periostin specific region antibody) that can bind to at least one region selected from the group consisting of the EMI region, the R1 region, the R2 region, and the R3 region of periostin or a cleavage product thereof. That is, at least one region selected from the group consisting of the EMI region, the R1 region, the R2 region, and the R3 region of periostin or a cleavage product thereof can be detected.

Meanwhile, the reagent for measuring periostin or a cleavage product thereof of the present invention may be a reagent for detecting any one of the EMI region, the R1 region, the R2 region, and the R3 region of periostin or a cleavage product thereof or may be a reagent for detecting two or more of the EMI region, the R1 region, the R2 region, and the R3 region of periostin or a cleavage product thereof.

The reagent for measuring periostin or a cleavage product thereof of the present invention is a reagent for measuring periostin or a cleavage product thereof contained in a sample utilizing an antigen-antibody reaction and preferably contains an antibody (anti-periostin specific region antibody) that binds to at least one region selected from the group consisting of the EMI region, the R1 region, the R2 region, and the R3 region of periostin or a cleavage product thereof.

Examples of the anti-periostin specific region antibody include, but not limited to, the antibodies (i) to (ix) described in the section "1. Outline in [2] Method of measuring periostin."

In the reagent for measuring periostin or a cleavage product thereof of the present invention, for example, when two molecules of antibodies bind to one molecule of periostin, both of these antibodies are required to be anti-periostin specific region antibodies for measuring periostin contained in a sample using this measurement reagent.

For example, when the measurement of periostin is a sandwich assay of ELISA using an enzyme-labeled antibody and a immobilized antibody, both the enzyme-labeled antibody and the immobilized antibody to be bound to periostin contained in a sample are required to be anti-periostin specific region antibodies.

Meanwhile, among the anti-periostin specific region antibodies according to the present invention, the addition of an anti-periostin specific region antibody that does not bind to periostin multimers to the reagent for measuring periostin contained in a sample utilizing an antigen-antibody reaction can further enhance the improvement in accuracy of the measurement and is therefore preferred. In the measurement of periostin using the reagent for measuring periostin or a cleavage product thereof of the present invention, for example, when two molecules of antibodies bind to one molecule of periostin, if one antibody is an anti-periostin specific region antibody that does not bind to periostin multimers, the other antibody is not necessarily required to be an anti-periostin specific region antibody that does not bind to periostin multimers as long as it is an anti-periostin specific region antibody.

For example, in the measurement of periostin by a sandwich assay of ELISA using an enzyme-labeled antibody and a immobilized antibody, when one of the enzyme-labeled antibody and the immobilized antibody to be bound to periostin contained in a sample is an anti-periostin specific region antibody that does not bind to periostin multimers, the other antibody is not necessarily required to be an anti-periostin specific region antibody that does not bind to periostin multimers as long as it is an anti-periostin specific region antibody.

The anti-periostin specific region antibody is not limited to a single type of antibody, and multiple types of antibodies may be used.

The details of the anti-periostin specific region antibody are as described in the section "[1] Anti-periostin specific region antibody."

The reagent for measuring periostin or a cleavage product thereof of the present invention can improve the accuracy of measurement and is suitable for measurement for testing the presence of a disease or the severity (e.g., symptom) thereof.

The reagent for measuring periostin or a cleavage product thereof of the present invention is more suitable for measurement for testing the presence of cancer or lung disease or the severity (e.g., symptom) thereof.

The reagent for measuring periostin or a cleavage product thereof of the present invention is further suitable for measurement for testing the presence of cholangiocarcinoma, pulmonary fibrosis, or interstitial pneumonia or the severity (e.g., symptom) thereof.

The reagent for measuring periostin or a cleavage product thereof of the present invention is still more suitable for measurement for testing the presence of pulmonary fibrosis or interstitial pneumonia or the severity (e.g., symptom) thereof.

The reagent for measuring periostin or a cleavage product thereof of the present invention is particularly suitable for measurement for testing the presence of interstitial pneumonia or the severity (e.g., symptom) thereof.

2. Sample

The samples in the present invention are as described in "3. Sample" in "[2] Method of measuring periostin."

3. Substance to be Measured

The substance to be measured in the present invention are as described in "4. Substance to be measured" in "[2] Method of measuring periostin."

4. Measurement Reagent Utilizing Antigen-Antibody Reaction

The reagent for measuring periostin or a cleavage product thereof of the present invention is a reagent for measuring periostin or a cleavage product thereof contained in a sample utilizing an antigen-antibody reaction and preferably contains an anti-periostin specific region antibody, and the intended effect can be achieved as long as the anti-periostin specific region antibody is contained, regardless of the principle of the periostin measurement.

Examples of the principle of measurement of periostin or a cleavage product thereof by the reagent of the present invention include enzyme immunoassays (ELISA and EIA), fluoroimmunoassays (FIAs), radioimmunoassays (RIAs), luminescence immunoassays (LIAs), enzyme antibody techniques, fluorescence antibody techniques, immunochromatographies, immunonephelometries, latex nephelometries, latex agglutination assays, erythrocyte agglutination assays, particle agglutination assays, the method described in, for example, Japanese Patent Laid-Open No. H09-229936 or Japanese Patent Laid-Open No. H10-132819 using a carrier having a surface onto which a substance that specifically binds to a substance to be measured (analyte) is immobilized so as to cover the surface and using particles onto which a substance that specifically binds to the substance to be measured (analyte) is immobilized, and the enzyme-linked ligandsorbent assay (ELSA) described by Dahlbeack et al. (Thromb. Haemost., Vol. 79, pp. 767-772, published in 1998; International Publication No. WO98/23963).

To the measurement with the reagent for measuring periostin or a cleavage product thereof of the present invention can be applied any method of sandwich assay, competitive assay, and homogeneous method.

The measurement with the reagent for measuring periostin or a cleavage product thereof of the present invention may be carried out manually or with an apparatus such as an analyzer.

The reagent for measuring periostin or a cleavage product thereof of the present invention may be composed of a single measurement reagent.

In this case, the anti-periostin specific region antibody is contained in the single measurement reagent.

The reagent for measuring periostin or a cleavage product thereof of the present invention may be composed of two or more measurement reagents.

In this case, the anti-periostin specific region antibody may be contained in one of the two or more measurement reagents or may be contained in the two or more measurement reagents.

For example, when the reagent for measuring periostin or a cleavage product thereof of the present invention is composed of two measurement reagents, a first reagent and a second reagent, the anti-periostin specific region antibody may be contained in only the first reagent or the second reagent or may be contained in both the first reagent and the second reagent.

As the solvent for the reagent for measuring periostin or a cleavage product thereof of the present invention, various aqueous solvents can be used.

Examples of the aqueous solvents include water, saline, and various buffers such as tris(hydroxymethyl)aminomethane buffer [Tris buffer], phosphate buffer, and phosphate-buffered saline.

The pH of such a buffer may be appropriately selected without particular limitation and is usually selected within the range of 5 to 10.

The reagent for measuring periostin or a cleavage product thereof of the present invention may appropriately contain one or more of proteins such as bovine serum albumin (BSA), human serum albumin (HSA), casein and salts thereof; various metal ions such as calcium ions; various salts such as calcium salts; various saccharides; skim milk; serum of various animals such as normal rabbit serum; various preservatives such as sodium azide and antibiotics; activators; reaction promoters; sensitivity enhancers such as polyethylene glycol; non-specific reaction inhibitors; and various surfactants such as nonionic surfactants, amphoteric surfactants, and anionic surfactants, in addition to the anti-periostin specific region antibody and the like.

The concentration of such additives contained in the reagent measuring periostin or a cleavage product thereof of the present invention is not particularly limited and is preferably 0.001 to 10% (W/V) and particularly preferably 0.01 to 5% (W/V).

Examples of the surfactant include nonionic surfactants such as sorbitan fatty acid ester, glycerol fatty acid ester, decaglycerol fatty acid ester, polyoxyethylene sorbitan fatty acid ester, polyoxyethylene glycerol fatty acid ester, polyethylene glycol fatty acid ester, polyoxyethylene alkyl ether, polyoxyethylene phytosterol, phytostanol, polyoxyethylene polyoxypropylene alkyl ether, polyoxyethylene alkylphenyl ether, polyoxyethylene castor oil, hydrogenated castor oil, and polyoxyethylene lanolin; amphoteric surfactants such as betaine acetate; and anionic surfactants such as polyoxyethylene alkyl ether sulfate and polyoxyethylene alkyl ether acetate.

The reagent for measuring periostin or a cleavage product thereof of the present invention can be sold alone or used alone for measuring periostin or a cleavage product thereof contained in a sample.

The reagent for measuring periostin or a cleavage product thereof of the present invention can be sold in combination with another reagent or used for measuring periostin or a cleavage product thereof contained in a sample in combination with one or more other reagents.

Examples of the one or more other reagents include buffers, sample diluents, reagent diluents, reagents containing labeling substances, reagents containing substances that generate signals such as color development, and reagents containing substances for calibration.

The reagent for measuring periostin or a cleavage product thereof of the present invention may be a reagent for measuring periostin containing a first reagent containing an aqueous solvent and a second reagent containing an anti-periostin specific region antibody.

The reagent for measuring periostin or a cleavage product thereof of the present invention is preferably a measurement reagent kit.

5. Measurement Reagent Employing Immunoassay Using Labeled Antibody as the Principle of Measurement When the principle of the measurement using the reagent for measuring periostin or a cleavage product thereof of the present invention is an immunoassay using a labeled antibody, such as an enzyme immunoassay, fluoroimmunoassay, radioimmunoassay, or luminescence immunoassay, i.e., a measuring method utilizing an antigen-antibody reaction using a labeled antibody, the measurement can be carried out by, for example, a sandwich assay or a competitive assay. In the sandwich assay, both the immobilized antibody and the labeled antibody to be bound to periostin contained in a sample are required to be anti-periostin specific region antibodies.

In the measurement by a sandwich assay as described above, when one of the labeled antibody and the immobilized antibody is an anti-periostin specific region antibody that does not bind to periostin multimers, the other antibody is not necessarily required to be an anti-periostin specific region antibody that does not bind to periostin multimers as long as it is an anti-periostin specific region antibody.

In the reagent for measuring periostin or a cleavage product thereof of the present invention employing the measuring method utilizing an antigen-antibody reaction using a labeled antibody as the principle of measurement, the details of the measuring method utilizing an antigen-antibody reaction using a labeled antibody are as described in "5. Immunoassay using labeled antibody" in "[2] Method of measuring periostin."

6. Measurement Reagent Employing Immunoassay by Agglutination Assay as the Principle of Measurement When the reagent for measuring periostin or a cleavage product thereof of the present invention measures the generation of immune complex aggregates, as in an immunonephelometry, latex nephelometry, latex agglutination assay, erythrocyte agglutination assay, or particle agglutination assay, by measuring the transmitted light or scattered light by an optical method or visual measurement, that is, when the principle of measurement is a method (agglutination assay) of measuring the generation of aggregates of a complex by an antigen-antibody reaction, the antibody to be bound to periostin contained in a sample is required to be an anti-periostin specific region antibody.

When the principle of measurement is the agglutination assay, the anti-periostin specific region antibody may be an anti-periostin specific region antibody that does not bind to periostin multimers, which enhances the improvement in accuracy and is therefore preferred.

When the principle of measurement is the agglutination assay, the reagent for measuring periostin or a cleavage product thereof of the present invention contains an "anti-periostin specific region antibody" or a "solid-phase carrier onto which an anti-periostin specific region antibody is immobilized."

When the reagent for measuring periostin or a cleavage product thereof of the present invention is composed of two measurement reagents, the "anti-periostin specific region antibody" or the "solid-phase carrier onto which an anti-periostin specific region antibody is immobilized" is preferably contained in the second reagent.

When the reagent for measuring periostin or a cleavage product thereof of the present invention is composed of two or more measurement reagents, the reagent other than the reagent containing the "anti-periostin specific region antibody" or the "solid-phase carrier onto which an anti-periostin specific region antibody is immobilized," i.e., the reagent not containing both the "anti-periostin specific region antibody" and the "solid-phase carrier onto which an anti-periostin specific region antibody is immobilized," may be, for example, a reagent containing the aqueous solvent.

For example, in a case of employing the latex nephelometry as the principle of measurement, the latex particles used as the solid-phase carrier may have any particle diameter. From the viewpoints of, for example, the degree of generation of aggregates by binding of the latex particles via a substance to be measured (periostin) and easiness in measurement of the generated aggregates, the latex particles preferably have an average particle diameter of 0.04 to 1 μm.

In a case of employing the latex nephelometry as the principle of measurement, the optimum concentration of the latex particles onto which an antibody such as the anti-periostin specific region antibody is immobilized varies depending on various conditions such as the concentration of periostin in a sample, the distribution density of an antibody such as the anti-periostin specific region antibody on the latex particle surfaces, the particle diameter of the latex particles, and the mixing ratio of a sample and a measurement reagent.

In general, the concentration of the latex particles onto which an "antibody such as the anti-periostin specific region antibody" is immobilized is 0.005 to 1% (w/v) in a reaction solution mixture during the reaction to be measured by mixing a sample and a measurement reagent for an antigen-antibody reaction between the "antibody such as the anti-periostin specific region antibody" immobilized onto the latex particles and "periostin" contained in the sample. In this case, the measurement reagent contains the "latex particles onto which the antibody such as the anti-periostin specific region antibody" at a concentration to give such a concentration in the reaction solution mixture.

In a case of employing an indirect agglutination assay such as a latex agglutination assay, erythrocyte agglutination assay, or particle agglutination assay as the principle of measurement, the particles used as the solid-phase carrier may have any particle diameter and preferably have an average particle diameter within the range of 0.01 to 100 μm and more preferably within the range of 0.5 to 10 μm, and preferably have a specific gravity within the range of 1 to 10 and more preferably within the range of 1 to 2.

Examples of the container used in the measurement employing an indirect agglutination assay such as a latex agglutination assay, erythrocyte agglutination assay, or particle agglutination assay as the principle of measurement include test tubes, microplates (microtiter plates), and trays made of glass, polystyrene, polyvinyl chloride, or polymethacrylate.

In these containers, the bottom of a solution receiving portion (e.g., the well of a microplate) preferably has a shape having a slant from the center toward the periphery, such as a U-like shape, V-like shape, or UV-like shape.

The reagent for measuring periostin or a cleavage product thereof of the present invention may contain a first reagent containing an aqueous solvent and a second reagent containing a solid-phase carrier onto which an anti-periostin specific region antibody is immobilized.

In the reagent for measuring periostin or a cleavage product thereof of the present invention, the solid-phase carrier is preferably latex particles.

In the reagent for measuring periostin or a cleavage product thereof of the present invention employing a method of measuring the generation of aggregates of a complex by an antigen-antibody reaction as the principle of measurement, the details of the method of measuring the generation of aggregates of a complex by an antigen-antibody reaction are as described in "6. Immunoassay by agglutination assay" in "[2] Method of measuring periostin."

[4] Method for Improving Accuracy of Periostin Measurement

1. Outline

The method for improving accuracy of periostin measurement of the present invention is characterized by detecting at least one region selected from the group consisting of the EMI region, the R1 region, the R2 region, and the R3 region of periostin in the measurement of the amount or concentration of periostin contained in a sample.

Periostin is composed of an EMI region, an R1 region, an R2 region, an R3 region, an R4 region, and a C-terminal region in this order from the N-terminus to the C-terminus. The method for improving accuracy of periostin measurement of the present invention is characterized by detecting at least one region selected from the group consisting of the EMI region, the R1 region, the R2 region, and the R3 region among these regions.

The improving method of the present invention may be characterized by detecting at least one region selected from the group consisting of the EMI region, the R1 region, the R2 region, and the R3 region of a periostin cleavage product in the measurement of the amount or concentration of a periostin cleavage product contained in a sample.

In another aspect, the improving method of the present invention may be characterized by detecting at least one region selected from the group consisting of the EMI region, the R1 region, the R2 region, and the R3 region of periostin or a periostin cleavage product but not detecting (or measuring) periostin multimers in the measurement of the amount or concentration of periostin other than multimers.

The method for improving accuracy of periostin measurement of the present invention is a method for improving accuracy of periostin measurement by detecting at least one region selected from the group consisting of the EMI region, the R1 region, the R2 region, and the R3 region of periostin in the measurement of the amount or concentration of periostin contained in a sample.

In the method for improving accuracy of periostin measurement of the present invention, the phrase "detecting at least one region selected from the group consisting of the EMI region, the R1 region, the R2 region, and the R3 region of periostin" refers to detection of the presence or the amount of at least one region selected from the group consisting of the EMI region, the R1 region, the R2 region, and the R3 region of periostin.

The phrase "detecting at least one region selected from the group consisting of the EMI region, the R1 region, the R2 region, and the R3 region of periostin" will now be more specifically described. In a case of measuring periostin contained in a sample by utilizing a reaction between substances having specific affinity, such as an antigen and an antibody, a saccharide and lectin, a nucleotide chain and a substance specific thereto, or a ligand and a receptor, for example, the use of a specific binding substance that can specifically bind to at least one region selected from the group consisting of the EMI region, the R1 region, the R2 region, and the R3 region of periostin allows the specific binding substance to bind to at least one region selected from the group consisting of the EMI region, the R1 region, the R2 region, and the R3 region of periostin, and thereby the presence or the amount of at least one region selected from the group consisting of the EMI region, the R1 region, the R2 region, and the R3 region of periostin can be detected. That is, at least one region selected from the group consisting of the EMI region, the R1 region, the R2 region, and the R3 region of periostin can be detected.

For example, when the specific binding substance is an antibody, the use of an antibody (anti-periostin specific region antibody) that can bind to at least one region selected from the group consisting of the EMI region, the R1 region, the R2 region, and the R3 region of periostin or a cleavage product thereof allows the anti-periostin specific region antibody to bind to at least one region selected from the group consisting of the EMI region, the R1 region, the R2 region, and the R3 region of periostin, and thereby the presence or the amount of at least one region selected from the group consisting of the EMI region, the R1 region, the R2 region, and the R3 region of periostin can be detected. That is, at least one region selected from the group consisting of the EMI region, the R1 region, the R2 region, and the R3 region of periostin can be detected.

The method for improving accuracy of periostin measurement of the present invention may detect any one of the EMI region, the R1 region, the R2 region, and the R3 region of periostin or may detect two or more of the EMI region, the R1 region, the R2 region, and the R3 region of periostin.

The method for improving accuracy of periostin measurement of the present invention preferably uses an antibody (anti-periostin specific region antibody) that binds to at least one region selected from the group consisting of the EMI region, the R1 region, the R2 region, and the R3 region of periostin or a cleavage product thereof in the measurement utilizing the antigen-antibody reaction of periostin contained in a sample.

Examples of the anti-periostin specific region antibody include, but not limited to, the antibodies (i) to (ix) described in the section "1. Outline in [2] Method of measuring periostin."

In the method for improving accuracy of periostin measurement of the present invention, for example, when two molecules of antibodies bind to one molecule of periostin for measuring periostin contained in a sample, both of these antibodies are required to be anti-periostin specific region antibodies.

For example, when the measurement of periostin is a sandwich assay of ELISA using an enzyme-labeled antibody and a immobilized antibody, both the enzyme-labeled antibody and the immobilized antibody to be bound to periostin contained in a sample are required to be anti-periostin specific region antibodies.

Meanwhile, among the anti-periostin specific region antibodies according to the present invention, the use of an anti-periostin specific region antibody that does not bind to periostin multimers in measurement of periostin contained in a sample utilizing an antigen-antibody reaction can further enhance the improvement in accuracy of the measurement and is therefore preferred. In the method for improving accuracy of periostin measurement of the present invention, for example, when two molecules of antibodies bind to one molecule of periostin, if one antibody is an anti-periostin specific region antibody that does not bind to periostin multimers, the other antibody is not necessarily required to be an anti-periostin specific region antibody that does not bind to periostin multimers as long as it is an anti-periostin specific region antibody.

For example, when the measurement of periostin is a sandwich assay of ELISA using an enzyme-labeled antibody and a immobilized antibody, and one of the enzyme-labeled antibody and the immobilized antibody to be bound to periostin contained in a sample is an anti-periostin specific region antibody that does not bind to periostin multimers, the other antibody is not necessarily required to be an anti-periostin specific region antibody that does not bind to periostin multimers as long as it is an anti-periostin specific region antibody.

The anti-periostin specific region antibody is not limited to a single type of antibody, and multiple types of antibodies may be simultaneously used.

The details of the anti-periostin specific region antibody are as described in the section "[1] Anti-periostin specific region antibody."

The method for improving accuracy of periostin measurement of the present invention can improve the accuracy of periostin measurement and is suitable for measurement for testing the presence of a disease or the severity (e.g., symptom) thereof.

The method for improving accuracy of periostin measurement of the present invention is more suitable for measurement for testing the presence of cancer or lung disease or the severity (e.g., symptom) thereof.

The method for improving accuracy of periostin measurement of the present invention is further suitable for measurement for testing the presence of cholangiocarcinoma, pulmonary fibrosis, or interstitial pneumonia or the severity (e.g., symptom) thereof.

The method for improving accuracy of periostin measurement of the present invention is still more suitable for measurement for testing the presence of pulmonary fibrosis or interstitial pneumonia or the severity (e.g., symptom) thereof.

The method for improving accuracy of periostin measurement of the present invention is particularly suitable for measurement for testing the presence of interstitial pneumonia or the severity (e.g., symptom) thereof.

2. Sample

The samples in the present invention are as described in "3. Sample" in "[2] Method of measuring periostin."

3. Substance to be Measured

The substances to be measured in the present invention are as described in "4. Substance to be measured" in "[2] Method of measuring periostin."

4. Measurement Utilizing Antigen-Antibody Reaction

The method for improving accuracy of periostin measurement of the present invention preferably uses an anti-periostin specific region antibody in the measurement utilizing an antigen-antibody reaction of periostin contained in a sample. The intended effect can be achieved by using the anti-periostin specific region antibody regardless of the principle of the measurement.

Examples of the principle of periostin measurement in the method for improving accuracy of periostin measurement of the present invention include enzyme immunoassays (ELISA and EIA), fluoroimmunoassays (FIAs), radioimmunoassays (RIAs), luminescence immunoassays (LIAs), enzyme antibody techniques, fluorescence antibody techniques, immunochromatographies, immunonephelometries, latex nephelometries, latex agglutination assays, erythrocyte agglutination assays, particle agglutination assays, the method described in, for example, Japanese Patent Laid-Open No. H09-229936 or Japanese Patent Laid-Open No. H10-132819 using a carrier having a surface onto which a substance that specifically binds to a substance to be measured (analyte) is immobilized so as to cover the surface and using particles onto which a substance that specifically binds to the substance to be measured (analyte) is immobilized, and the enzyme-linked ligandsorbent assay (ELSA) described by Dahlbeack et al. (Thromb. Haemost., Vol. 79, pp. 767-772, published in 1998; International Publication No. WO98/23963).

To the periostin measurement in the method for improving accuracy of periostin measurement of the present invention can be applied any method of sandwich assay, competitive assay, and homogeneous method.

The periostin measurement in the method for improving accuracy of periostin measurement of the present invention may be carried out manually or with an apparatus such as an analyzer.

The periostin measurement in the method for improving accuracy of periostin measurement of the present invention may use a single measurement reagent (one-reagent method or one-step method).

In this case, the anti-periostin specific region antibody is contained in the single measurement reagent.

The periostin measurement in the method for improving accuracy of periostin measurement of the present invention may use two or more measurement reagents (multi-reagent method or multi-step method).

In this case, the anti-periostin specific region antibody may be contained in one of the two or more measurement reagents or may be contained in the two or more measurement reagents.

For example, when the periostin measurement in the method for improving accuracy of periostin measurement of the present invention uses two measurement reagents, a first reagent and a second reagent, the anti-periostin specific region antibody may be contained in only the first reagent or the second reagent or may be contained in both the first reagent and the second reagent.

In the method for improving accuracy of periostin measurement of the present invention, each of the above-mentioned aqueous solvents can be used as a solvent in the periostin measurement.

In the measurement of periostin in the method for improving accuracy of periostin measurement of the present invention, the details of the measuring method utilizing an antigen-antibody reaction using a labeled antibody are as described in "5. Immunoassay using labeled antibody" in "[2] Method of measuring periostin."

In the method for improving accuracy of periostin measurement of the present invention, the details of the method of measuring the generation of aggregates of a complex by an antigen-antibody reaction in the periostin measurement are as described in "6. Immunoassay by agglutination assay" in "[2] Method of measuring periostin."

In the method for improving accuracy of periostin measurement of the present invention, the details of the "other components for measurement" in the periostin measurement are as described in "7. Other components for measurement" in "[2] Method of measuring periostin."

[5] Method of Testing for Pulmonary Fibrosis or Interstitial Pneumonia

1. Outline

The method of testing for pulmonary fibrosis or interstitial pneumonia of the present invention includes the steps of:

a) measuring an amount or concentration of periostin in a sample derived from a subject, wherein the measuring comprises detecting at least one region selected from the group consisting of the EMI region, the R1 region, the R2 region, and the R3 region of periostin; and b) comparing the amount or concentration of the periostin in the sample derived from the subject with an amount or concentration of periostin in a sample derived from a living body not suffering from pulmonary fibrosis and interstitial pneumonia.

Periostin is composed of an EMI region, an R1 region, an R2 region, an R3 region, an R4 region, and a C-terminal region in this order from the N-terminus to the C-terminus. In the method of testing for pulmonary fibrosis or interstitial pneumonia of the present invention, the measurement of periostin contained in a sample includes a step of detecting at least one region selected from the group consisting of the EMI region, the R1 region, the R2 region, and the R3 region among these regions.

The method of testing for pulmonary fibrosis or interstitial pneumonia of the present invention further includes a step of comparing the amount or concentration of periostin in a sample derived from a subject with an amount or concentration of periostin in a sample derived from a living body not suffering from pulmonary fibrosis and interstitial pneumonia.

The method of testing for pulmonary fibrosis or interstitial pneumonia of the present invention is a testing method that can improve the sensitivity or specificity of the measurement to improve the accuracy of the measurement of periostin contained in a sample by detecting at least one region selected from the group consisting of the EMI region, the R1 region, the R2 region, and the R3 region of periostin.

Accordingly, the method of testing for pulmonary fibrosis or interstitial pneumonia of the present invention is a testing method that can obtain an accurate measured value of periostin and can improve the differentiation of patients affected with the diseases from healthy subjects and patients affected with other diseases to prevent wrong diagnosis.

The testing method of the present invention may include a step of measuring a periostin cleavage product in a sample derived from a subject. More specifically, the testing method of the present invention may include the steps of:

a) measuring an amount or concentration of a periostin cleavage product in a sample derived from a subject, wherein the measuring comprises detecting at least one region selected from the group consisting of the EMI region, the R1 region, the R2 region, and the R3 region of a periostin cleavage product; and b) comparing the amount or concentration of the periostin cleavage product in the sample derived from the subject with an amount or concentration of a periostin cleavage product in a sample derived from a living body not suffering from pulmonary fibrosis and interstitial pneumonia.

In another aspect, the method of testing of the present invention may include detection (measurement) of periostin other than multimers. More specifically, the testing method of the present invention may include the steps of:

a) measuring an amount or concentration of periostin or a periostin cleavage product in a sample derived from a subject, wherein the measuring comprises detecting at least one region selected from the group consisting of the EMI region, the R1 region, the R2 region, and the R3 region of periostin or a periostin cleavage product but not detecting periostin multimers; and b) comparing the amount or concentration of the periostin or the periostin cleavage product in the sample derived from the subject with an amount or concentration of periostin or a periostin cleavage product in a sample derived from a living body not suffering from pulmonary fibrosis and interstitial pneumonia.

In the method of testing for pulmonary fibrosis or interstitial pneumonia of the present invention, the phrase "detecting at least one region selected from the group consisting of the EMI region, the R1 region, the R2 region, and the R3 region of periostin" refers to detection of the presence or the amount of at least one region selected from the group consisting of the EMI region, the R1 region, the R2 region, and the R3 region of periostin.

The phrase "detecting at least one region selected from the group consisting of the EMI region, the R1 region, the R2 region, and the R3 region of periostin" will now be more specifically described. In a case of measuring periostin contained in a sample by utilizing a reaction between substances having specific affinity, such as an antigen and an antibody, a saccharide and lectin, a nucleotide chain and a substance specific thereto, or a ligand and a receptor, for example, the use of a specific binding substance that can specifically bind to at least one region selected from the group consisting of the EMI region, the R1 region, the R2 region, and the R3 region of periostin allows the specific binding substance to bind to at least one region selected from the group consisting of the EMI region, the R1 region, the R2 region, and the R3 region of periostin, and thereby the presence or the amount of at least one region selected from the group consisting of the EMI region, the R1 region, the R2 region, and the R3 region of periostin can be detected. That is, at least one region selected from the group consisting of the EMI region, the R1 region, the R2 region, and the R3 region of periostin can be detected.

For example, when the specific binding substance is an antibody, the use of an antibody (anti-periostin specific region antibody) that can bind to at least one region selected from the group consisting of the EMI region, the R1 region, the R2 region, and the R3 region of periostin or a cleavage product thereof allows the anti-periostin specific region antibody to bind to at least one region selected from the group consisting of the EMI region, the R1 region, the R2 region, and the R3 region of periostin, and thereby the presence or the amount of at least one region selected from the group consisting of the EMI region, the R1 region, the R2 region, and the R3 region of periostin can be detected. That is, at least one region selected from the group consisting of the EMI region, the R1 region, the R2 region, and the R3 region of periostin can be detected.

The method of testing for pulmonary fibrosis or interstitial pneumonia of the present invention may detect any one of the EMI region, the R1 region, the R2 region, and the R3 region of periostin or may detect two or more of the EMI region, the R1 region, the R2 region, and the R3 region of periostin.

The method of testing for pulmonary fibrosis or interstitial pneumonia of the present invention preferably uses an antibody (anti-periostin specific region antibody) that binds to at least one region selected from the group consisting of the EMI region, the R1 region, the R2 region, and the R3 region of periostin or a cleavage product thereof in the measurement utilizing the antigen-antibody reaction of periostin contained in a sample.

Examples of the anti-periostin specific region antibody include, but not limited to, the antibodies (i) to (ix) described in the section "1. Outline in [2] Method of measuring periostin."

In the method of testing for pulmonary fibrosis or interstitial pneumonia of the present invention, for example, when two molecules of antibodies bind to one molecule of periostin for measuring periostin contained in a sample, both of these antibodies are required to be anti-periostin specific region antibodies.

For example, when the measurement of periostin is a sandwich assay of ELISA using an enzyme-labeled antibody and a immobilized antibody, both the enzyme-labeled antibody and the immobilized antibody to be bound to periostin contained in a sample are required to be anti-periostin specific region antibodies.

Meanwhile, among the anti-periostin specific region antibodies according to the present invention, the use of an anti-periostin specific region antibody that does not bind to periostin multimers in measurement of periostin contained in a sample utilizing an antigen-antibody reaction can further enhance the improvement in accuracy of the measurement and is therefore preferred. In the method of testing for pulmonary fibrosis or interstitial pneumonia of the present invention, for example, when two molecules of antibodies bind to one molecule of periostin, if one antibody is an anti-periostin specific region antibody that does not bind to periostin multimers, the other antibody is not necessarily required to be an anti-periostin specific region antibody that does not bind to periostin multimers as long as it is an anti-periostin specific region antibody.

For example, when the measurement of periostin is a sandwich assay of ELISA using an enzyme-labeled antibody and a immobilized antibody, and one of the enzyme-labeled antibody and the immobilized antibody to be bound to periostin contained in a sample is an anti-periostin specific region antibody that does not bind to periostin multimers, the other antibody is not necessarily required to be an anti-periostin specific region antibody that does not bind to periostin multimers as long as it is an anti-periostin specific region antibody.

The anti-periostin specific region antibody is not limited to a single type of antibody, and multiple types of antibodies may be simultaneously used.

The details of the anti-periostin specific region antibody are as described in the section "[1] Anti-periostin specific region antibody."

The method of testing for pulmonary fibrosis or interstitial pneumonia of the present invention is suitable for testing the presence of pulmonary fibrosis or interstitial pneumonia or the severity (e.g., symptom) thereof.

The method of testing for pulmonary fibrosis or interstitial pneumonia of the present invention is particularly suitable for testing the presence of pulmonary fibrosis or the severity (e.g., symptom) thereof.

The method of testing for pulmonary fibrosis or interstitial pneumonia of the present invention particularly suitable for testing the presence of interstitial pneumonia or the severity (e.g., symptom) thereof.

2. Sample

The samples in the present invention are as described in "3. Sample" in "[2] Method of measuring periostin."

3. Substance to be Measured

The substances to be measured in the present invention are as described in "4. Substance to be measured" in "[2] Method of measuring periostin."

4. Measurement Utilizing Antigen-Antibody Reaction

The method of testing for pulmonary fibrosis or interstitial pneumonia of the present invention is preferably a method of testing pulmonary fibrosis or interstitial pneumonia by measuring periostin contained in a sample utilizing an antigen-antibody reaction and uses an anti-periostin specific region antibody. The intended effect can be achieved by using the anti-periostin specific region antibody regardless of the principle of measurement.

Examples of the principle of periostin measurement in the method of testing for pulmonary fibrosis or interstitial pneumonia of the present invention include enzyme immunoassays (ELISA and EIA), fluoroimmunoassays (FIAs), radioimmunoassays (RIAs), luminescence immunoassays (LIAs), enzyme antibody techniques, fluorescence antibody techniques, immunochromatographies, immunonephelometries, latex nephelometries, latex agglutination assays, erythrocyte agglutination assays, particle agglutination assays, the method described in, for example, Japanese Patent Laid-Open No. H09-229936 or Japanese Patent Laid-Open No. H10-132819 using a carrier having a surface onto which a substance that specifically binds to a substance to be measured (analyte) is immobilized so as to cover the surface and using particles onto which a substance that specifically binds to the substance to be measured (analyte) is immobilized, and the enzyme-linked ligandsorbent assay (ELSA) described by Dahlbeack et al. (Thromb. Haemost., Vol. 79, pp. 767-772, published in 1998; International Publication No. WO98/23963).

To the periostin measurement in the method of testing for pulmonary fibrosis or interstitial pneumonia of the present invention can be applied any method of sandwich assay, competitive assay, and homogeneous method.

The periostin measurement in the method of testing for pulmonary fibrosis or interstitial pneumonia of the present invention may be carried out manually or with an apparatus such as an analyzer.

The periostin measurement in the method of testing for pulmonary fibrosis or interstitial pneumonia of the present invention may use a single measurement reagent (one-reagent method or one-step method).

In this case, the anti-periostin specific region antibody is contained in the single measurement reagent.

The periostin measurement in the method of testing for pulmonary fibrosis or interstitial pneumonia of the present invention may use two or more measurement reagents (multi-reagent method or multi-step method).

In this case, the anti-periostin specific region antibody may be contained in one of the two or more measurement reagents or may be contained in the two or more measurement reagents.

For example, when the periostin measurement in the method of testing for pulmonary fibrosis or interstitial pneumonia of the present invention uses two measurement reagents, a first reagent and a second reagent, the anti-periostin specific region antibody may be contained in only the first reagent or the second reagent or may be contained in both the first reagent and the second reagent.

In the method of testing for pulmonary fibrosis or interstitial pneumonia of the present invention, each of the above-mentioned aqueous solvents can be used as a solvent in the periostin measurement.

In the measurement of periostin in the method of testing for pulmonary fibrosis or interstitial pneumonia of the present invention, the details of the measuring method utilizing an antigen-antibody reaction using a labeled antibody are as described in "5. Immunoassay using labeled antibody" in "[2] Method of measuring periostin."

In the method of testing for pulmonary fibrosis or interstitial pneumonia of the present invention, the details of the method of measuring the generation of aggregates of a complex by an antigen-antibody reaction in the periostin measurement are as described in "6. Immunoassay by agglutination assay" in "[2] Method of measuring periostin."

In the method of testing for pulmonary fibrosis or interstitial pneumonia of the present invention, the details of the "other components for measurement" in the periostin measurement are as described in "7. Other components for measurement" in "[2] Method of measuring periostin."

5. Comparison of Amount or Concentration of Periostin

In the method of testing for pulmonary fibrosis or interstitial pneumonia of the present invention, periostin contained in a sample is measured by detecting at least one region selected from the group consisting of the EMI region, the R1 region, the R2 region, and the R3 region of periostin as described above, and the amount or concentration of periostin in a sample derived from a subject is compared with the amount or concentration of periostin in a sample derived from a living body not suffering from pulmonary fibrosis and interstitial pneumonia.

That is, in the method of testing for pulmonary fibrosis or interstitial pneumonia of the present invention, the amount or concentration of periostin in a sample derived from a subject measured by detecting at least one region selected from the group consisting of the EMI region, the R1 region, the R2 region, and the R3 region of periostin is compared with the amount or concentration of periostin in a sample derived from a living body not suffering from pulmonary fibrosis and interstitial pneumonia measured by detecting at least one region selected from the group consisting of the EMI region, the R1 region, the R2 region, and the R3 region of periostin.

The details of detection of at least one region selected from the group consisting of the EMI region, the R1 region, the R2 region, and the R3 region of periostin in the measurement of periostin contained in a sample are as described above.

In the comparison of the amount or concentration of periostin in a sample derived from a subject with the amount or concentration of periostin in a sample derived from a living body not suffering from pulmonary fibrosis and interstitial pneumonia, an amount or concentration of periostin in a sample derived from a subject higher than that of periostin in a sample derived from a living body not suffering from pulmonary fibrosis and interstitial pneumonia demonstrates a high probability that the subject is suffering from pulmonary fibrosis or interstitial pneumonia.

In addition, an increase in the amount or concentration of periostin in samples derived from a subject demonstrates a high probability that the symptom of pulmonary fibrosis or interstitial pneumonia of the subject is worsening.

For example, when the amount or concentration of periostin in a sample derived from a subject is higher than that of periostin in a sample (control sample) derived from a living body not suffering from pulmonary fibrosis and interstitial pneumonia by, for example, about 20% or more, about 30% or more, about 40% or more, about 50% or more, about 60% or more, about 70% or more, about 80% or more, about 90% or more, about 95% or more, or about 100% or more, it can be determined that the risk of suffering from pulmonary fibrosis or interstitial pneumonia is high.

Herein, the difference between (i) the amount or concentration of periostin in a sample derived from a subject and (ii) the amount or concentration of periostin in a sample (control sample) derived from a living body not suffering from pulmonary fibrosis and interstitial pneumonia is a critical value for detection or diagnosis of pulmonary fibrosis or interstitial pneumonia and may be established, for example, as follows.

First, the amounts or concentrations of periostin in samples derived from two or more pulmonary fibrosis or interstitial pneumonia patients are measured, and the average value (A) thereof is determined. On this occasion, the number of patients as the object is two or more, for example, 5 or more, 10 or more, 50 or more, or 100 or more. Separately, the amounts or concentrations of periostin in two or more control samples are measured, and the average value (B) thereof is determined. On this occasion, the number of control samples as the object is two or more, for example, 5 or more, 10 or more, 50 or more, or 100 or more. By how many percent the average value of the amounts or concentrations of periostin in the biological samples derived from the pulmonary fibrosis or interstitial pneumonia patients is higher than the average value of the amounts or concentrations of periostin in the control samples is determined by calculating the value (%) of $[(A-B)/B] \times 100$ from the resulting average values A and B. The thus-determined value is set as the difference (critical value) between (i) the amount or concentration of periostin in a sample derived from a subject and (ii) the amount or concentration of periostin in a control sample. That is, when the difference between the amount or concentration of periostin in a case of (i) and the amount or concentration of periostin in a case of (ii) is larger than the difference determined above (e.g., when the difference is statistically significantly large), it can be determined that the risk of suffering from pulmonary fibrosis or interstitial pneumonia is high.

In the method of testing for pulmonary fibrosis or interstitial pneumonia of the present invention, it is preferable to increase the number of patients as the object and the number of healthy subjects and the like as the object (e.g., healthy subjects and subjects not suffering from pulmonary fibrosis and interstitial pneumonia) by incorporating the measured values of amount or concentration of periostin in samples into the average values (A) and (B). The increase in number of cases can improve the precision of detection or diagnosis of pulmonary fibrosis or interstitial pneumonia. The determined average value (B) of the amounts or concentrations of periostin in control samples may be used as "(ii) the amount or concentration of periostin in control samples."

In some other aspects of the present invention, it may be determined that the risk of suffering from pulmonary fibrosis or interstitial pneumonia is high when the measured amount or concentration of periostin in a sample derived from a subject is not less than a certain amount of the protein.

The "certain amount of protein" for determining that the risk of suffering from pulmonary fibrosis or interstitial pneumonia is high can be determined by, for example, as follows. First, the amounts or concentrations of periostin in samples derived from two or more pulmonary fibrosis or interstitial pneumonia patients are measured. On this occasion, the number of patients as the object is two or more, for example, 5 or more, 10 or more, 50 or more, or 100 or more. Separately, the amounts or concentrations of periostin in two or more control samples are also measured. On this occasion, the number of control samples as the object is two or more, for example, 5 or more, 10 or more, 50 or more, or 100 or more. An optimal threshold (cut-off value) of amount or concentration of periostin that allows extraction of the group of samples derived from pulmonary fibrosis or interstitial pneumonia patients is determined by statistical processing of all values of the group of samples derived from pulmonary fibrosis or interstitial pneumonia patients and the control sample group. Examples of the statistical processing include analysis using a receiver-operating-characteristics (ROC) curve.

EXAMPLES

The present invention will now be described in detail by Examples etc., but is not limited to the following Examples etc.

Reference Example 1

Preparation of Periostin and Partial-Length Periostins

In order to, for example, specify epitopes of antibodies, the following periostin and partial-length periostins (those consisting of portions of periostin) were prepared.

(1) Preparation of Periostin

A recombinant periostin protein, periostin (nucleotide sequence: the nucleotide sequence listed with Accession Number D13666 in the GenBank nucleic acid database, amino acid sequence: the amino acid sequence listed with Accession Number BAA02837 in the GenBank nucleic acid database), tagged with V5/His was expressed in insect S2 cells and was purified.

Specifically, transformants of the S2 cells were prepared as follows.

A cDNA encoding the above-mentioned portion of periostin was inserted into a pMT/Bip/V5-His A plasmid (Invitrogen Corporation, Carlsbad, Calif., USA) to construct pMT/Bip/periostin-V5-His A.

Subsequently, S2 cells were transformed through cotransfection with the pMT/Bip/periostin-V5-His A and a plasmid expressing a hygromycin-resistant gene, pAcHygro (Invitrogen Corporation, Carlsbad, Calif., USA), by a known method.

Subsequently, stable transformants were selected with hygromycin.

Periostin having a V5/His tag at the carboxy terminus was expressed in the S2 cell transformants.

The S2 recombinant periostin protein having six histidines at the C-terminus was purified as follows.

The expression of S2 recombinant periostin protein was induced by adding copper sulfate to the culture medium of the stable S2 cell transformants with the periostin gene.

As a result, the S2 recombinant periostin protein was expressed and secreted in the culture supernatant.

Subsequently, the culture supernatant was dialyzed against phosphate-buffered saline (PBS) [an aqueous solution (pH 7.4) containing 137 mM sodium chloride, 2.68 mM potassium chloride, 1.47 mM potassium dihydrogenphosphate, and 8.04 mM disodium hydrogenphosphate] and was then mixed with nickel resin (Ni-NTA Agarose, Qiagen GmbH, Hilden, Germany) to bind the S2 recombinant periostin protein to the resin.

Subsequently, the resin was washed to remove contaminants, and the S2 recombinant periostin protein was eluted with a buffer containing imidazole to obtain periostin.

The DNA sequence of the constructed plasmid was investigated to confirm that the intended sequence was incorporated.

(2) Preparation of Partial-Length Periostin Composed of R1 Region and R2 Region of Periostin A partial-length periostin having six histidine residues at the C-terminus and composed of the R1 region and the R2 region of periostin (hereinafter, referred to as "partial-length periostin (R1/R2 regions)") was prepared and obtained in accordance with the description in a known document (e.g., 1. Takayama et al., J. Biochem., Vol. 146, No. 5, pp. 713-723, published in 2009).

The DNA sequence of the constructed plasmid was investigated to confirm that the intended sequence was incorporated.

(3) Preparation of Partial-Length Periostin Composed of R2 Region of Periostin

A partial-length periostin having six histidine residues at the C-terminus and composed of the R2 region of periostin (hereinafter, referred to as "partial-length periostin (R2 region)") was prepared and obtained in accordance with the description in a known document (e.g., I. Takayama et al., J. Biochem., Vol. 146, No. 5, pp. 713-723, published in 2009).

The DNA sequence of the constructed plasmid was investigated to confirm that the intended sequence was incorporated.

(4) Preparation of Partial-Length Periostin Composed of R1 Region, R2 Region and R3 Region of Periostin A partial-length periostin having six histidine residues at the C-terminus and composed of the R1 region, the R2 region and the R3 region of periostin (hereinafter, referred to as "partial-length periostin (R1/R2/R3 regions)") was prepared and obtained in accordance with the description in a known document (e.g., I. Takayama et al., J. Biochem., Vol. 146, No. 5, pp. 713-723, published in 2009).

The DNA sequence of the constructed plasmid was investigated to confirm that the intended sequence was incorporated.

(5) Preparation of Partial-Length Periostin Composed of R4 Region of Periostin

A partial-length periostin having six histidine residues at the C-terminus and composed of the R4 region of periostin (hereinafter, referred to as "partial-length periostin (R4 region)") was prepared and obtained in accordance with the description in a known document (e.g., I. Takayama et al., J. Biochem., Vol. 146, No. 5, pp. 713-723, published in 2009).

The DNA sequence of the constructed plasmid was investigated to confirm that the intended sequence was incorporated.

(6) Preparation of Partial-Length Periostin Composed of EMI Region of Periostin

A partial-length periostin having six histidine residues at the C-terminus and composed of the EMI region of periostin (hereinafter, referred to as "partial-length periostin (EMI region)") was prepared and obtained in accordance with the description in a known document (e.g., I. Takayama et al., J. Biochem., Vol. 146, No. 5, pp. 713-723, published in 2009).

The DNA sequence of the constructed plasmid was investigated to confirm that the intended sequence was incorporated.

(7) Preparation of Partial-Length Periostin Composed of C-Terminal Region of Periostin A partial-length periostin having six histidine residues at the C-terminus and composed of the C-terminal region of periostin (hereinafter, referred to as "partial-length periostin (C-terminal region)") was prepared and obtained in accordance with the description in a known document (e.g., I. Takayama et al., J. Biochem., Vol. 146, No. 5, pp. 713-723, published in 2009).

The DNA sequence of the constructed plasmid was investigated to confirm that the intended sequence was incorporated.

FIG. 1 schematically shows the periostin, partial-length periostin (R1/R2 regions), partial-length periostin (R2 region), partial-length periostin (R1/R2/R3 regions), partial-length periostin (R4 region), partial-length periostin (EMI region), and partial-length periostin (C-terminal region).

Reference Example 2

Verification of Prepared Periostin and Partial-Length Periostins

I. Verification of Periostin, Partial-Length Periostin (R1/R2 Regions), Partial-Length Periostin (R2 Region), Partial-Length Periostin (R1/R2/R3 Regions), and Partial-Length Periostin (C-Terminal Region)

Periostin, partial-length periostin (R1/R2 regions), partial-length periostin (R2 region), partial-length periostin (R1/R2/R3 regions), and partial-length periostin (C-terminal region) prepared in Reference Example 1 were verified by SDS-polyacrylamide gel electrophoresis.

1. Reagent

The following reagents (1) to (11) were prepared.

(1) Acrylamide Solution

An acrylamide solution [30% acrylamide preservation solution] was prepared by mixing 29.2 g of acrylamide and 0.8 g of N,N'-methylene-bis-acrylamide with pure water and making the final volume to 100 mL.

(2) SDS-1.5 M Tris Solution

An SDS-1.5 M Tris solution [0.4% SDS-1.5 M Tris-hydrochloric acid buffer] was prepared by mixing 18.2 g of tris (hydroxymethyl)aminomethane [Tris] and 0.4 g of sodium dodecyl sulfate [SDS] with pure water, adjusting the pH to 8.8 with hydrochloric acid, and making the final volume to 100 mL.

(3) SDS-0.5 M Tris Solution

An SDS-0.5 M Tris solution [0.4% SDS-0.5 M Tris-hydrochloric acid buffer] was prepared by mixing 6.1 g of tris (hydroxymethyl)aminomethane [Tris] and 0.4 g of sodium dodecyl sulfate [SDS] with pure water, adjusting the pH to 6.8 with hydrochloric acid, and making the final volume to 100 mL.

(4) Ammonium Persulfate Solution

An ammonium persulfate solution [10% ammonium persulfate aqueous solution] was prepared by mixing 100 mg of ammonium persulfate with pure water and making the final volume to 1 mL.

(5) TEMED Solution

N,N,N',N'-tetramethylethylenediamine (Nacalai Tesque, Inc., Kyoto, Japan) was used.

(6) Running Buffer for Electrophoresis Chamber

A running buffer for electrophoresis chamber [0.1% SDS-192 mM glycine-25 mM Tris buffer] was prepared by mixing 1.5 g of tris(hydroxymethyl)aminomethane [Tris], 0.5 g of sodium dodecyl sulfate [SDS], and 7.2 g of glycine with pure water and making the final volume to 500 mL.

(7) SYPRO Ruby Fixing Solution

A SYPRO Ruby fixing solution was prepared by mixing 10 mL of methanol and 7 mL of acetic acid with 83 mL of pure water.

(8) SYPRO Ruby Staining Solution

As a SYPRO Ruby staining solution, SYPRO Ruby protein gel stain available from Molecular Probes (Eugene, Oreg., USA) was used.

(9) SYPRO Ruby Decoloring Solution

A SYPRO Ruby decoloring solution was prepared by mixing 10 mL of methanol and 7 mL of acetic acid with 83 mL of pure water.

(10) Sample Treating Solution

A sample treating solution [4% SDS-12% 2-mercaptoethanol-20% glycerin-100 mM Tris buffer] was prepared by mixing 0.4 g of sodium dodecyl sulfate [SDS], 1.2 mL of 2-mercaptoethanol, 1 mL of 1 M tris(hydroxymethyl)aminomethane [Tris]-hydrochloric acid buffer (pH 6.8), and 2 mL of glycerin with pure water and making the final volume to 10 mL.

2. Sample

Samples used were the following periostin and partial-length periostins prepared in (1) to (4) and (7) in Reference Example 1 and the following molecular weight markers.

(a) Periostin
(b) Partial-length periostin (R1/R2 regions)
(c) Partial-length periostin (R2 region)
(d) Partial-length periostin (R1/R2/R3 regions)
(e) Partial-length periostin (C-terminal region)
(f) Molecular weight markers [Precision Plus Protein All Blue Standards, marker molecular weight: 10 KDa, 15 KDa, 20 KDa, 25 KDa, 37 KDa, 50 KDa, 75 KDa, 100 KDa, 150 KDa, and 250 KDa, BIO-RAD Laboratories, Inc., Hercules, Calif., USA]

3. Electrophoresis

The samples in 2 were subjected to SDS-polyacrylamide gel electrophoresis using the reagents prepared in 1 by the following procedure.

(1) A separating gel solution containing 13.5% acrylamide was prepared using the reagents prepared in (1), (2), (4), and (5) of 1 and pure water.

The separating gel solution was poured into an assembled glass plate and was overlaid with pure water, followed by gelation for 30 minutes.

(2) A stacking gel solution containing 1.3% acrylamide was prepared using the reagents prepared in (1), (3), (4), and (5) of 1 and pure water.

The pure water in the glass plate in (1) was discarded. A small amount of the stacking gel solution was poured into the glass plate for washing, and the remaining stacking gel solution was then poured. Subsequently, a sample comb was inserted thereinto, and gelation was performed for 30 minutes.

(3) The samples (a) to (e) in 2 were each mixed with the sample treating solution in (10) of 1 at a quantity ratio of 1:1, followed by treatment at 100° C. for 10 minutes.

(4) The running buffer for electrophoresis chamber in (6) of 1 was put in a lower electrophoresis chamber. Subsequently, the sample comb was pulled out from the gel in (2). The gel was washed and was then set to the electrophoresis chamber. Subsequently, the running buffer for electrophoresis chamber in (6) of 1 was put in an upper electrophoresis chamber.

(5) The samples treated in (3) each in an amount of 20 µl, and the sample of molecular weight markers (f) in 2 in an amount of 5 µL were poured into the respective comb holes of the gel in (4).

Herein, the samples treated in (3) and the sample of molecular weight markers (f) in 2 were poured into the gel in such a manner that "periostin," "partial-length periostin (R1/R2 regions)," "partial-length periostin (R2 region)," "partial-length periostin (R1/R2/R3 regions)," and "partial-length periostin (C-terminal region)" were poured in this order, from the left, into lane (a), lane (b), lane (c), lane (d), and lane (e) and that the "molecular weight markers" were poured into the lane on the left of lane (a).

(6) Subsequently, electrophoresis was performed at a current of 30 mA for 60 minutes.

(7) After completion of the electrophoresis in (6), the gel was taken out from the glass plate and was immersed in the SYPRO Ruby fixing solution in (7) of 1 with gently shaking for 30 minutes for fixing.

(8) The gel after the fixing in (7) was immersed in the SYPRO Ruby staining solution in (8) of 1 with gently shaking for 3 hours for staining.

(9) The gel after the staining in (8) was immersed in the SYPRO Ruby decoloring solution in (9) of 1 with gently shaking for 30 minutes for decoloring.

(10) The gel after the decoloring in (9) was photographed.

4. Results

FIG. 2 shows the gels photographed in (10) of 3.

The electrophoretic profile of the gel demonstrates that the bands (indicated with arrows) of "periostin" (the lane indicated with (a)), "partial-length periostin (R1/R2 regions)" (the lane indicated with (b)), "partial-length periostin (R2 region)" (the lane indicated with (c)), "partial-length periostin (R1/R2/R3 regions)" (the lane indicated with (d)), and "partial-length periostin (C-terminal region)" (the lane indicated with (e)) prepared in (1) to (4) and (7) in Reference Example 1 were present at the positions corresponding to their molecular weights.

That is, it was confirmed that "periostin," "partial-length periostin (R1/R2 regions)," "partial-length periostin (R2 region),""partial-length periostin (R1/R2/R3 regions)," and "partial-length periostin (C-terminal region)" were prepared.

II. Verification of Partial-Length Periostin (R4 Region) and Partial-Length Periostin (EMI Region)

The partial-length periostin (R4 region) and the partial-length periostin (EMI region) prepared in Reference Example 1 were verified by SDS-polyacrylamide gel electrophoresis and Western blotting.

[1] SDS-Polyacrylamide Gel Electrophoresis

1. Reagent

The following reagents (1) to (4) were prepared.

(1) SDS-Polyacrylamide Gel

Funakoshi Easy-Gel (III) Precast-gel (15%) (Funakoshi Co., Ltd., Tokyo, Japan) was used.

(2) Running Buffer for Electrophoresis Chamber

A running buffer for electrophoresis chamber [0.1% SDS-192 mM glycine-25 mM Tris buffer] was prepared as described in (6) of 1 in I.

(3) Sample Treating Solution

A sample treating solution [4% SDS-12% 2-mercaptoethanol-20% glycerin-100 mM Tris buffer] was prepared as described in (10) of 1 in I.

2. Sample

Samples used were the following periostin and the partial-length periostins prepared in (1), (5), and (6) in Reference Example 1.

In addition, periostin (a partial-length periostin) lacking exon 17, exon 18, and exon 21 at the C-terminal region of periostin and having six histidine residues at the C-terminus (hereinafter, referred to as "partial-length periostin ($\Delta$17/18/21)") was prepared in accordance with the description in a known document (e.g., I. Takayama et al., J. Biochem., Vol. 146, No. 5, pp. 713-723, published in 2009) and was used as a sample. [The DNA sequence of the constructed plasmid was investigated to confirm that the intended sequence was incorporated.]

The following molecular weight markers were also used as a sample.

(a) Partial-length periostin (EMI region)
(b) Partial-length periostin (R4 region)
(c) Periostin
(d) Partial-length periostin ($\Delta$17/18/21)
(e) Molecular weight markers [Precision Plus Protein All Blue Standards, marker molecular weight: 10 KDa, 15 KDa, 20 KDa, 25 KDa, 37 KDa, 50 KDa, 75 KDa, 100 KDa, 150 KDa, and 250 KDa, BIO-RAD Laboratories, Inc., Hercules, Calif., USA]

3. Electrophoresis

The samples in 2 were subjected to SDS-polyacrylamide gel electrophoresis by the following procedure using the reagents prepared in 1, and a gel having periostin, partial-length periostins, and other samples at the positions corresponding to their molecular weights was obtained.

(1) The samples (a) to (d) in 2 were each mixed with the sample treating solution in (3) of 1 at a quantity ratio of 1:1, followed by boiling treatment at 100° C. for 10 minutes.

(2) The running buffer for electrophoresis chamber in (2) of 1 was put in a lower electrophoresis chamber. Subsequently, the SDS-polyacrylamide gel in (1) of 1 was set to the electrophoresis chamber. The running buffer for electrophoresis chamber in (2) of 1 was put in an upper electrophoresis chamber.

(3) The samples treated in (1) each in an amount of 20 µL and the sample of molecular weight markers (e) in 2 in an amount of 5 µL were poured into the respective comb holes of the gel in (2).

Herein, the samples treated in (1) and the sample of molecular weight markers (e) in 2 were poured into the gel in such a manner that "partial-length periostin (EMI region)," "partial-length periostin (R4 region)," "periostin," and "partial-length periostin ($\Delta$17/18/21)" were poured in this order, from the left, into lane (a), lane (b), lane (c), and lane (d) and that the "molecular weight markers" were poured into lane (e) on the left of lane (a).

(4) Subsequently, electrophoresis was performed at a current of 30 mA for 60 minutes.

(5) After completion of the electrophoresis in (4), the gel was taken out from the glass plate.

[2] Western Blotting

1. Western Blotting (1) The gel obtained in 3 of [1] was transferred by a semi-dry system using Trans-Blot SD cell (BIO-RAD Laboratories, Inc., Hercules, Calif., USA) in accordance with the attached instruction.

The gel obtained in 3 of [1] was placed on a transferring apparatus.

Subsequently, a 9 cm×9 cm polyvinyl difluoride membrane (BIO-RAD Laboratories, Inc., Hercules, Calif., USA) was placed on the gel, and transfer was performed using a buffer for transfer composed of 48 mM tris(hydroxymethyl)aminomethane [Tris], 39 mM glycine, 0.0375% (W/V) sodium dodecyl sulfate [SDS], and 20% (V/V) methanol at a current of 200 mA for 2 hours. The periostin or partial-length periostin was transferred from the gel to the polyvinyl difluoride membrane.

(2) The polyvinyl difluoride membrane after the transfer of the periostin and partial-length periostins was immersed in 20 mL of a blocking solution [50 mM tris(hydroxymethyl)aminomethane buffer [Tris buffer] (pH 8.0) containing 0.5% casein, 100 mM sodium chloride, and 0.1% sodium azide] at 25° C. for 2 hours for blocking.

(3) The membrane was then washed by shaking in 20 mL of a washing solution [phosphate-buffered saline containing 0.05% Tween 20] for 10 minutes. This procedure was carried out three times.

(4) An antibody solution was prepared by dissolving 100 µg of a rat-derived antibody against the histidine tag of the periostin and partial-length periostin in 20 mL of phosphate-buffered saline. The polyvinyl difluoride membrane subjected to the procedure in (3) was immersed in the antibody solution at room temperature for 18 hours for reaction.

(5) The polyvinyl difluoride membrane subjected to the procedure in (4) was washed by shaking in 20 mL of the washing solution for 10 minutes. This procedure was carried out three times.

(6) Separately, peroxidase-labeled anti-rat IgG antibody (GE Healthcare, Little Chalfont, UK) was diluted to 2000 times with PBS to prepare 20 mL of a solution. The polyvinyl difluoride membrane in (5) was immersed in the resulting solution at room temperature for 1 hour for reaction.

(7) The polyvinyl difluoride membrane was washed by shaking in 20 mL of the washing solution for 10 minutes. This procedure was carried out three times.

(8) The polyvinyl difluoride membrane in (7) was immersed in 2 mL of ECL Western Blotting Detection Reagents (GE Healthcare, Little Chalfont, UK) at room temperature for 1 minute for light emission.

(9) The polyvinyl difluoride membrane subjected to light emission in (8) was photographed.

2. Results

FIG. 3 shows the polyvinyl difluoride membrane photographed in (9) of 1.

The Western blotting image of the polyvinyl difluoride membrane demonstrates that the bands (indicated with arrows) of "periostin" (the lane indicated with (c)), "partial-length periostin (EMI region)" (the lane indicated with (a)), and "partial-length periostin (R4 region)" (the lane indicated with (b)) prepared in (1), (5), and (6) in Reference Example 1 and "partial-length periostin (Δ17/18/21)" (the lane indicated with (d)) prepared in 2 of [1] were present at the positions corresponding to their molecular weights.

That is, it was confirmed that "periostin," "partial-length periostin (EMI region)," "partial-length periostin (R4 region)," and "partial-length periostin (Δ17/18/21)" were prepared.

Example 1

Preparation of Anti-Periostin Monoclonal Antibody—First Time

An anti-periostin monoclonal antibody was prepared by the following procedure (first time).

(1) A chemical synthetic adjuvant, Titer Max Gold (Funakoshi Co., Ltd., Tokyo, Japan), was mixed with the periostin solution prepared in (1) in Reference Example 1 at a volume ratio of 1:1.

(2) The mixture of the periostin solution in an amount of 10 to 50 μg and Titer Max Gold was subcutaneously injected into the footpad of each female rat as an immunogen and, after 10 to 14 days, further subcutaneously injected in an amount of 10 to 50 μg into the footpad of the rat as an immunogen.

The rats used were Wistar rats [female, 6- to 8-week old] (Charles River Laboratories Japan, Inc., Yokohama-shi, Kanagawa, Japan).

(3) Cells of the popliteal fossa, inguinal region, or iliac lymph node of the immunized rats, 3 to 4 days after the final immunization, were mixed with myeloma cells (Sp2/O cells) at a ratio of 1:1 to 10:1. Polyethylene glycol (PEG 1500, Roche Diagnostics GmbH, Germany) was added to the mixture for cell fusion by a common method. Grown hybridoma colonies were selected.

Specifically, the cell fusion was performed as follows.

The mixture of the lymph node cells and myeloma cells (Sp2/O cells) was centrifuged to remove the supernatant and was then suspended in 1 mL of polyethylene glycol (PEG 1500, Roche Diagnostics GmbH, Germany) at room temperature over 1 minute. The suspension was stirred at 37° C. for 1 minute.

To the suspension was added a serum-free culture medium in an amount of 1 mL over 1 minute and then in an amount of 10 mL over 1 minute.

The cells were washed several times and were then suspended in a culture medium containing hypoxanthine, aminopterin, and thymidine. The suspension was dispensed in a 96-well microtiter plate, and the cells were cultured at 37° C. in the presence of 5% $CO_2$.

Grown monoclonal antibody-producing cell lines (hybridoma cell lines) were selected 7 to 14 days after the cell fusion with an ELISA system by immobilizing the same periostin as that used as the immunogen and using the hybridoma cell culture supernatant as a primary antibody.

The ELISA was specifically performed as follows.

The above-mentioned periostin in a concentration of 1 μg/mL was dispensed in a 96-well microtiter plate, followed by immobilization for several hours.

The solution for the immobilization was washed out. The hybridoma cell culture supernatant was added to each well and was left to stand for 1 hour at room temperature.

The hybridoma cell culture supernatant was washed out. Subsequently, a peroxidase-labeled goat anti-rat IgG antibody (GE Healthcare, Little Chalfont, UK) as a secondary antibody was added, followed by leaving to stand for 1 hour at room temperature.

The secondary antibody was washed out. Subsequently, an ABTS peroxidase substrate (KPL, Inc., Gaithersburg, Md., USA) was added for developing a color, followed by measurement of absorbance at 405 nm.

A clone was established from grown hybridoma cell lines and was named as cell line SS16A.

(4) IgG was purified from this selected monoclonal antibody-producing cell line as follows.

The monoclonal antibody-producing cell line was cultured with a GIT culture medium (Nihon Pharmaceutical Co., Ltd., Tokyo, Japan) in a $CO_2$ incubator at 37° C.

After the culturing, IgG in the supernatant was immobilized to a protein G column (GE Healthcare, Little Chalfont, UK).

The immobilized IgG was eluted with 50 mM citric acid aqueous solution (pH 2.6).

A 1 M tris(hydroxymethyl)aminomethane buffer [Tris buffer] was added to the eluate at a volume ratio of 1:4 to purify IgG to obtain a rat anti-periostin monoclonal antibody, from the monoclonal antibody-producing cell line.

That is, a rat anti-periostin monoclonal antibody (hereinafter, referred to as "anti-periostin monoclonal antibody (SS16A)") was obtained from monoclonal antibody-producing cell line SS16A.

Example 2

Preparation of Anti-Periostin Monoclonal Antibody—Second Time

An anti-periostin monoclonal antibody was prepared again, separately from Example 1, in accordance with the description in (1) to (4) in Example 1 (second time).

As a result, a clone was established from grown hybridoma cell lines and was named as cell line SS17B.

A rat anti-periostin monoclonal antibody (hereinafter, referred to as "anti-periostin monoclonal antibody (SS17B)") was obtained from monoclonal antibody-producing cell line SS17B.

Example 3

Preparation of Anti-Periostin Monoclonal Antibody—Third Time

An anti-periostin monoclonal antibody was prepared for the third time, separately from Examples 1 and 2, in accordance with the description in (1) to (4) in Example 1 (third time).

As a result, a clone was established from grown hybridoma cell lines and was named as cell line SS18A.

A rat anti-periostin monoclonal antibody (hereinafter, referred to as "anti-periostin monoclonal antibody (SS18A)") was obtained from monoclonal antibody-producing cell line SS18A.

Example 4

Preparation of Anti-Periostin Monoclonal Antibody—Fourth Time

An anti-periostin monoclonal antibody was prepared, separately from Examples 1 to 3, by the following procedure (fourth time).

(1) A chemical synthetic adjuvant, Titer Max Gold (Funakoshi Co., Ltd., Tokyo, Japan), was mixed with the periostin solution prepared in (1) in Reference Example 1 at a volume ratio of 1:1.

(2) The mixture of the periostin solution in an amount of 10 to 50 μg and Titer Max Gold was injected into the abdominal cavity of each mouse as an immunogen and, after 10 to 14 days, further injected in an amount of 10 to 50 μg into the abdominal cavity of the mouse as an immunogen.

The mice used were periostin knockout mice (BALB/c) prepared in accordance with the description in a document by Rios et al. (H. Rios et al., Molecular and Cellular Biology, Vol. 25, No. 24, pp. 11131-11144, published in 2005).

(3) Splenocytes of the immunized mice, 3 to 4 days after the final immunization, were mixed with myeloma cells (Sp2/O cells) at a ratio of 1:1 to 10:1. Polyethylene glycol (PEG 1500, Roche Diagnostics GmbH, Germany) was added to the mixture for cell fusion by a common method. Grown hybridoma colonies were selected.

Specifically, the cell fusion was performed as follows.

The mixture of the splenocytes and myeloma cells (Sp2/O cells) was centrifuged to remove the supernatant and was then suspended in 1 mL of polyethylene glycol (PEG 1500, Roche Diagnostics GmbH, Germany) at room temperature over 1 minute. The suspension was stirred at 37° C. for 1 minute.

To the suspension was added a serum-free culture medium in an amount of 1 mL over 1 minute and then in an amount of 10 mL over 1 minute.

The cells were washed several times and were then suspended in a culture medium containing hypoxanthine, aminopterin, and thymidine. The suspension was dispensed in a 96-well microtiter plate, and the cells were cultured at 37° C. in the presence of 5% $CO_2$.

Grown monoclonal antibody-producing cell lines (hybridoma cell lines) were selected 7 to 14 days after the cell fusion with an ELISA system by immobilizing the same periostin as that used as the immunogen and using the hybridoma cell culture supernatant as a primary antibody.

The ELISA was specifically performed as follows.

The above-mentioned periostin in a concentration of 1 μg/mL was dispensed in a 96-well microtiter plate, followed by immobilization for several hours.

The solution for the immobilization was washed out. The hybridoma cell culture supernatant was added to each well, followed by leaving to stand for 1 hour at room temperature.

The hybridoma cell culture supernatant was washed out. Subsequently, a peroxidase-labeled sheep anti-mouse IgG antibody (GE Healthcare, Little Chalfont, UK) as a secondary antibody was added, followed by leaving to stand for 1 hour at room temperature.

The secondary antibody was washed out. Subsequently, an ABTS peroxidase substrate (KPL, Inc., Gaithersburg, Md., USA) was added for developing a color, followed by measurement of absorbance at 405 nm.

Four clones were established from grown hybridoma cell lines and were named as cell line SS19A, cell line SS19B, cell line SS19C, and cell line SS19D.

(4) IgG was purified from each of the selected monoclonal antibody-producing cell lines as follows.

The monoclonal antibody-producing cell line was cultured with a GIT culture medium (Nihon Pharmaceutical Co., Ltd., Tokyo, Japan) in a $CO_2$ incubator at 37° C.

After the culturing, IgG in the supernatant was immobilized to a protein G column (GE Healthcare, Little Chalfont, UK).

The immobilized IgG was eluted with 50 mM citric acid aqueous solution (pH 2.6).

A 1 M tris(hydroxymethyl)aminomethane [Tris] buffer was added to the eluate at a volume ratio of 1:4 to purify IgG to obtain a mouse anti-periostin monoclonal antibody, from the monoclonal antibody-producing cell line.

Mouse anti-periostin monoclonal antibodies (hereinafter, referred to as "anti-periostin monoclonal antibody (SS19A)," "anti-periostin monoclonal antibody (SS19B)," "anti-periostin monoclonal antibody (SS19C)," and "anti-periostin monoclonal antibody (SS19D)") were respectively obtained from monoclonal antibody-producing cell lines SS19A, SS19B, SS19C, and SS19D.

As a representative example of these antibodies, the amino acid sequence of the heavy chain variable region of the anti-periostin monoclonal antibody (SS19D) is shown in SEQ ID NO: 16, and the nucleotide sequence of a polynucleotide encoding the amino acid sequence is shown in SEQ ID NO: 15. The amino acid sequence of the light chain variable region of the antibody is shown in SEQ ID NO: 18, and the nucleotide sequence of a polynucleotide encoding the amino acid sequence is shown in SEQ ID NO: 17.

That is, the antibodies of the present invention include a monoclonal antibody, wherein an amino acid sequence of a heavy chain variable region of the antibody includes the amino acid sequence set forth in SEQ ID NO: 16 and an amino acid sequence of a light chain variable region of the antibody includes the amino acid sequence set forth in SEQ ID NO: 18.

Example 5

Preparation of Anti-Periostin Monoclonal Antibody—Fifth Time

An anti-periostin monoclonal antibody was prepared, separately from Examples 1 to 4, in accordance with the description in (1) to (4) in Example 4 (fifth time).

As a result, a clone was established from grown hybridoma cell lines and was named as cell line SS20A.

A mouse anti-periostin monoclonal antibody (hereinafter, referred to as "anti-periostin monoclonal antibody (SS20A)") was obtained from monoclonal antibody-producing cell line SS20A.

Example 6

Preparation of Anti-Periostin Monoclonal Antibody—Sixth Time

An anti-periostin monoclonal antibody was prepared, separately from Examples 1 to 5, in accordance with the description in (1) to (4) in Example 1 (sixth time).

As a result, a clone was established from grown hybridoma cell lines and was named as cell line SS21A.

A rat anti-periostin monoclonal antibody (hereinafter, referred to as "anti-periostin monoclonal antibody (SS21A)") was obtained from monoclonal antibody-producing cell line SS21A.

Example 7

Investigation of Recognition Site of Anti-Periostin Monoclonal Antibody

Each of the anti-periostin monoclonal antibodies obtained in Examples 1 to 6 was investigated for which region of periostin the anti-periostin monoclonal antibody recognizes.

1. Measurement (1) Solutions of periostin and partial-length periostins [the following (a) to (g)] prepared in (1) to (7) in Reference Example 1 were each prepared to have a concentration of 5 µg/mL with phosphate-buffered saline. The solutions and phosphate-buffered saline as a control each in an amount of 50 µL were poured into the respective wells of a 96-well microtiter plate (Thermo Fisher Scientific Inc., IL, USA), followed by leaving to stand at 5° C. for 18 hours for immobilizing the periostin and the partial-length periostins to the respective wells of the microtiter plate.

(a) "Periostin"
(b) "Partial-length periostin (R1/R2 regions)"
(c) "Partial-length periostin (R2 region)"
(d) "Partial-length periostin (R1/R2/R3 regions)"
(e) "Partial-length periostin (R4 region)"
(f) "Partial-length periostin (EMI region)"
(g) "Partial-length periostin (C-terminal region)"

(2) Subsequently, each well of the microtiter plate in (1) was washed with a washing solution [Tris buffer (TBS) containing 0.05% Tween 20] three times.

(3) Subsequently, the anti-periostin monoclonal antibodies [the following (i) to (ix)] obtained in Examples 1 to 6 each in an amount of 50 µL were poured into the respective wells of the microtiter plate washed in (2) and were left to stand at 25° C. for 1 hour for reacting the anti-periostin monoclonal antibodies with the periostin and partial-length periostins immobilized to the wells of the microtiter plate.

(i) "Anti-periostin monoclonal antibody (SS16A)"
(ii) "Anti-periostin monoclonal antibody (SS17B)"
(iii) "Anti-periostin monoclonal antibody (SS18A)"
(iv) "Anti-periostin monoclonal antibody (SS19A)"
(v) "Anti-periostin monoclonal antibody (SS19B)"
(vi) "Anti-periostin monoclonal antibody (SS19C)"
(vii) "Anti-periostin monoclonal antibody (SS19D)"
(viii) "Anti-periostin monoclonal antibody (SS20A)"
(ix) "Anti-periostin monoclonal antibody (SS21A)"

(4) Subsequently, each well of the microtiter plate in (3) was washed with the washing solution three times.

(5) Subsequently, a POD-labeled anti-rat IgG antibody (GE Healthcare, Little Chalfont, UK) or POD-labeled anti-mouse IgG antibody (GE Healthcare, Little Chalfont, UK) diluted to 2000 times with phosphate-buffered saline was poured in an amount of 50 µL into each well of the microtiter plate washed in (4), followed by leaving to stand at 25° C. for 1 hour for reaction.

In the pouring of the POD-labeled anti-IgG antibody into the wells of the microtiter plate, when the POD-labeled anti-IgG antibody was "anti-periostin monoclonal antibody (SS16A)," "anti-periostin monoclonal antibody (SS17B)," "anti-periostin monoclonal antibody (SS18A)," or "anti-periostin monoclonal antibody (SS21A)," the POD-labeled anti-rat IgG antibody was poured into the wells of the microtiter plate.

When the POD-labeled anti-IgG antibody was "anti-periostin monoclonal antibody (SS19A)," "anti-periostin monoclonal antibody (SS19B)," "anti-periostin monoclonal antibody (SS19C)," "anti-periostin monoclonal antibody (SS19D)," or "anti-periostin monoclonal antibody (SS20A)," the POD-labeled anti-mouse IgG antibody was poured into the wells of the microtiter plate.

(6) Subsequently, each well of the microtiter plate in (5) was washed with the washing solution three times.

(7) Subsequently, a chromogenic substrate solution prepared by mixing Peroxidase Substrate Solution A (KPL, Inc., USA) with Peroxidase Substrate Solution B (KPL, Inc., USA) at a ratio of 1:1 was poured in an amount of 50 µL into each well of the microtiter plate washed in (6), followed by leaving to stand at 25° C. for 10 minutes for reaction of developing a color.

(8) Subsequently, the absorbance in each well of the microtiter plate in (7) at 405 nm was measured with a spectrophotometer.

Based on the measurement results of the absorbance, if the difference between the obtained measured values of absorbance in the well immobilizing periostin or a partial-length periostin and the measured values of absorbance in the control well (into which phosphate-buffered saline was poured instead of periostin or partial-length periostins) is 0.2 or more, an anti-periostin monoclonal antibody was determined to have bound to the periostin or the partial-length periostin immobilized to the well of the microtiter plate.

That is, when the difference in absorbance is 0.2 or more, the anti-periostin monoclonal antibody was determined to recognize any region of the periostin or the partial-length periostin immobilized to the well of the microtiter plate.

2. Results (1) FIG. 4 shows the measurement results in 1.

In the figure, the symbol "○" means a combination of an anti-periostin monoclonal antibody and periostin or a partial-length periostin in which the difference in absorbance described above was 0.2 or more as measured after the anti-periostin monoclonal antibody was reacted with the periostin or partial-length periostins, i.e., a combination determined that the anti-periostin monoclonal antibody bound to periostin or the partial-length periostin.

Based on the measurement results, the region of periostin recognized by each of the anti-periostin monoclonal antibodies was determined. The results are shown in the right-end column in the figure.

(2) The measurement results demonstrate that "anti-periostin monoclonal antibody (SS16A)" bound to only "periostin" and "partial-length periostin (R1/R2/R3 regions)" among the above-mentioned periostin and partial-length periostins and did not bind to "partial-length periostin (R1/R2 regions)," "partial-length periostin (R2 region)," "partial-length periostin (R4 region)," "partial-length periostin (EMI region)," and "partial-length periostin (C-terminal region)."

It was confirmed from the results that "anti-periostin monoclonal antibody (SS16A)" recognized the R3 region of periostin as an epitope.

(3) The measurement results demonstrate that "anti-periostin monoclonal antibody (SS17B)" bound to only "periostin" and "partial-length periostin (R4 region)" among the above-mentioned periostin and partial-length periostins and did not bind to "partial-length periostin (R1/R2 regions)," "partial-length periostin (R2 region)," "partial-length periostin (R1/R2/R3 regions)," "partial-length periostin (EMI region)," and "partial-length periostin (C-terminal region)."

It was confirmed from the results that "anti-periostin monoclonal antibody (SS17B)" recognized the R4 region of periostin as an epitope.

(4) The measurement results demonstrate that "anti-periostin monoclonal antibody (SS18A)" bound to only "periostin," "partial-length periostin (R1/R2 regions)," and "partial-length periostin (R1/R2/R3 regions)" among the above-mentioned periostin and partial-length periostins and did not bind to "partial-length periostin (R2 region)," "partial-length periostin (R4 region)," "partial-length periostin (EMI region)," and "partial-length periostin (C-terminal region)."

It was confirmed from the results that "anti-periostin monoclonal antibody (SS18A)" recognized the R1 region of periostin as an epitope.

(5) The measurement results demonstrate that "anti-periostin monoclonal antibody (SS19A)" bound to only "periostin" and "partial-length periostin (R4 region)" among the above-mentioned periostin and partial-length periostins and did not bind to "partial-length periostin (R1/R2 regions)," "partial-length periostin (R2 region)," "partial-length periostin (R1/R2/R3 regions)," "partial-length periostin (EMI region)," and "partial-length periostin (C-terminal region)."

It was confirmed from the results that "anti-periostin monoclonal antibody (SS19A)" recognized the R4 region of periostin as an epitope.

(6) The measurement results demonstrate that "anti-periostin monoclonal antibody (SS19B)" bound to only "periostin" and "partial-length periostin (C-terminal region)" among the above-mentioned periostin and partial-length periostins and did not bind to "partial-length periostin (R1/R2 regions)," "partial-length periostin (R2 region)," "partial-length periostin (R1/R2/R3 regions)," "partial-length periostin (R4 region)," and "partial-length periostin (EMI region)."

It was confirmed from the results that "anti-periostin monoclonal antibody (SS19B)" recognized the C-terminal region of periostin as an epitope.

(7) The measurement results demonstrate that "anti-periostin monoclonal antibody (SS19C)" bound to only "periostin," "partial-length periostin (R1/R2 regions)," "partial-length periostin (R2 region)," and "partial-length periostin (R1/R2/R3 regions)" among the above-mentioned periostin and partial-length periostins and did not bind to "partial-length periostin (R4 region)," "partial-length periostin (EMI region)," and "partial-length periostin (C-terminal region)."

It was confirmed from the results that "anti-periostin monoclonal antibody (SS19C)" recognized the R2 region of periostin as an epitope.

(8) The measurement results demonstrate that "anti-periostin monoclonal antibody (SS19D)" bound to only "periostin" and "partial-length periostin (R1/R2/R3 regions)" among the above-mentioned periostin and partial-length periostins and did not bind to "partial-length periostin (R1/R2 regions)," "partial-length periostin (R2 region)," "partial-length periostin (R4 region)," "partial-length periostin (EMI region)," and "partial-length periostin (C-terminal region)."

It was confirmed from the results that "anti-periostin monoclonal antibody (SS19D)" recognized the R3 region of periostin as an epitope.

(9) The measurement results demonstrate that "anti-periostin monoclonal antibody (SS20A)" bound to only "periostin" and "partial-length periostin (EMI region)" among the above-mentioned periostin and partial-length periostins and did not bind to "partial-length periostin (R1/R2 regions)," "partial-length periostin (R2 region)," "partial-length periostin (R1/R2/R3 regions)," "partial-length periostin (R4 region)," and "partial-length periostin (C-terminal region)."

It was confirmed from the results that "anti-periostin monoclonal antibody (SS20A)" recognized the EMI region of periostin as an epitope.

(10) The measurement results demonstrate that "anti-periostin monoclonal antibody (SS21A)" bound to only "periostin" and "partial-length periostin (C-terminal region)" among the above-mentioned periostin and partial-length periostins and did not bind to "partial-length periostin (R1/R2 regions)," "partial-length periostin (R2 region)," "partial-length periostin (R1/R2/R3 regions)," "partial-length periostin (R4 region)," and "partial-length periostin (EMI region)."

It was confirmed from the results that "anti-periostin monoclonal antibody (SS21A)" recognized the C-terminal region of periostin as an epitope.

Example 8

Investigation of Reactivity of Anti-Periostin Monoclonal Antibody

The reactivities of the anti-periostin monoclonal antibodies obtained in Examples 1 to 6 to periostin monomer, multimer, and cleavage product were investigated.

[1] Anti-Periostin Monoclonal Antibodies Derived from Cell Lines Other than Cell Line SS19B The reactivities of "anti-periostin monoclonal antibody (SS16A)," "anti-periostin monoclonal antibody (SS17B)," "anti-periostin monoclonal antibody (SS18A)," "anti-periostin monoclonal antibody (SS19A)," "anti-periostin monoclonal antibody (SS19C)," "anti-periostin monoclonal antibody (SS19D)," "anti-periostin monoclonal antibody (SS20A)," and "anti-periostin monoclonal antibody (SS21A)" to periostin monomer, multimer, and cleavage product were investigated as follows.

1. Immunoprecipitation Treatment (1) The following anti-periostin monoclonal antibodies (a) to (h) obtained in Examples 1 to 6 each in an amount of 5 μg were put into the respective 1.5-mL tubes.

(a) "Anti-periostin monoclonal antibody (SS16A)"
(b) "Anti-periostin monoclonal antibody (SS17B)"
(c) "Anti-periostin monoclonal antibody (SS18A)"
(d) "Anti-periostin monoclonal antibody (SS19A)"
(e) "Anti-periostin monoclonal antibody (SS19C)"
(f) "Anti-periostin monoclonal antibody (SS19D)"
(g) "Anti-periostin monoclonal antibody (SS20A)"
(h) "Anti-periostin monoclonal antibody (SS21A)"

(2) Subsequently, 20 μL of Protein G Sepharose (GE Healthcare, Little Chalfont, UK) and 1 mL of phosphate-buffered saline were added to each tube in (1).

The tubes were then rotated at 5° C. for 1 hour to immobilize the anti-periostin monoclonal antibodies to the Protein G Sepharose.

(3) Subsequently, the tubes in (2) were centrifuged.

After removal of the supernatant, 1 mL of a blocking solution [50 mM tris(hydroxymethyl)aminomethane buffer [Tris buffer] (pH 8.0) containing 0.5% casein, 100 mM sodium chloride, and 0.1% sodium azide] was added to 20 μL of the "anti-periostin monoclonal antibody-immobilized Protein G Sepharose" in each tube.

Each tube was then rotated at 5° C. for 2 hours to block the surface of Protein G Sepharose to which the anti-periostin monoclonal antibody was not immobilized.

(4) Subsequently, the tubes in (3) were centrifuged.

After removal of the supernatant, 1 mL of "partial-length periostin (Δ17/18/21)," in 2 of [1] of II in Reference Example 2, diluted with the blocking solution to 100 ng/mL was added to 20 μL of the "anti-periostin monoclonal antibody-immobilized Protein G Sepharose" in each tube.

It is separately demonstrated that periostin monomer, multimer, and cleavage product are contained in "partial-length periostin (Δ17/18/21)" (hereinafter, the "partial-length periostin (Δ17/18/21)" may also be referred to as "mixture of periostin monomer, multimer, and cleavage product).

The tubes were then rotated at 5° C. for 18 hours to bring each of the periostin monomer, multimer, and cleavage product contained in the "mixture of periostin monomer, multimer, and cleavage product" into contact with "anti-periostin monoclonal antibody immobilized to Protein G Sepharose."

Herein, the "anti-periostin monoclonal antibody" immobilized to Protein G Sepharose binds to at least one of periostin monomer, multimer, and cleavage product that is recognized by this antibody.

(5) Subsequently, the tubes in (4) were centrifuged.

After removal of the supernatant, Protein G Sepharose in each tube was washed with phosphate-buffered saline to thoroughly remove free periostin monomer, multimer, and cleavage product that did not bind to the "anti-periostin monoclonal antibody" immobilized to Protein G Sepharose (i.e., periostin monomer, multimer, and cleavage products that were not recognized and not bound by the "anti-periostin monoclonal antibody").

Through the procedure described above, "a conjugate of the anti-periostin monoclonal antibody immobilized to Protein G Sepharose and a periostin monomer, multimer, or cleavage product recognized and bound by the antibody," that is, a "conjugate, "Protein G Sepharose"-"anti-periostin monoclonal antibody"-"periostin monomer, multimer, or cleavage product recognized and bound by the anti-periostin monoclonal antibody,"" was prepared for each monoclonal antibody.

2. SDS-Polyacrylamide Gel Electrophoresis (1) Reagent

The following reagents (a) to (c) were prepared.

(a) SDS-polyacrylamide Gel

Funakoshi Easy-Gel (III) Precast-gel (10%) (Funakoshi Co., Ltd., Tokyo, Japan) was used.

(b) Running Buffer for Electrophoresis Chamber

A running buffer for electrophoresis chamber [0.1% SDS-192 mM glycine-25 mM Tris buffer] was prepared in accordance with the description in (6) of 1 of I in Reference Example 2.

(c) Sample Treating Solution

A sample treating solution [1% SDS-1% 2-mercaptoethanol-20% glycerin-50 mM Tris buffer] was prepared by mixing 0.1 g of sodium dodecyl sulfate [SDS], 0.1 mL of 2-mercaptoethanol, 0.5 mL of 1 M tris(hydroxymethyl)aminomethane [Tris]-hydrochloric acid buffer (pH 6.8), and 2 mL of glycerin with pure water and then making the final volume to 10 mL.

(2) Sample

Samples used were the "conjugates, "Protein G Sepharose"-"anti-periostin monoclonal antibody"-"periostin monomer, multimer, or cleavage product recognized and bound by the anti-periostin monoclonal antibody,"" in the tubes treated in (5) of 1.

The molecular weight markers [Precision Plus Protein All Blue Standards, marker molecular weight: 10 KDa, 15 KDa, 20 KDa, 25 KDa, 37 KDa, 50 KDa, 75 KDa, 100 KDa, 150 KDa, and 250 KDa, BIO-RAD Laboratories, Inc., Hercules, Calif., USA] were also used as samples.

(3) Electrophoresis

The samples in (2) were subjected to SDS-polyacrylamide gel electrophoresis using the reagents prepared in (1) by the following procedure.

(a) The sample treating solution in (c) of (1) was mixed in an amount of 13 µL with 20 µL of each sample containing the "conjugate, "Protein G Sepharose"-"anti-periostin monoclonal antibody"-"periostin monomer, multimer, or cleavage product recognized and bound by the anti-periostin monoclonal antibody,"" in each tube in (2), followed by boiling treatment at 100° C. for 5 minutes.

The "conjugate, "Protein G Sepharose"-"anti-periostin monoclonal antibody"-"periostin monomer, multimer, or cleavage product recognized and bound by the anti-periostin monoclonal antibody,"" in each of the samples is dissociated into "Protein G Sepharose," the "anti-periostin monoclonal antibody," and the "periostin monomer, multimer, or cleavage product recognized and bound by the anti-periostin monoclonal antibody" by mixing with the sample treating solution.

That is, the "Protein G Sepharose," the "anti-periostin monoclonal antibody," and the "periostin monomer, multimer, or cleavage product recognized and bound by the anti-periostin monoclonal antibody" were turned into free states by mixing with the added sample treating solution.

(b) The running buffer for electrophoresis chamber in (b) of (1) was put in a lower electrophoresis chamber. Subsequently, the SDS-polyacrylamide gel in (a) of (1) was set to the electrophoresis chamber. The running buffer for electrophoresis chamber in (b) of (1) was put in an upper electrophoresis chamber.

(c) The samples treated in (a) were centrifuged, and the supernatants each in an amount of 10 µL were poured into the respective comb holes of the gel in (b). (Herein, "Protein G Sepharose" is removed by collecting the supernatant after centrifugation. The supernatant contains "anti-periostin monoclonal antibody" and "periostin monomer, multimer, or cleavage product recognized and bound by the anti-periostin monoclonal antibody."

The sample of molecular weight markers in (2) was poured in an amount of 5 µL into a comb hole of the gel in (b).

The supernatants and the molecular weight markers mentioned above were poured into the gel such that the lanes of the gel were for the molecular weight markers (i) and "supernatants each containing an "anti-periostin monoclonal antibody" and a "periostin monomer, multimer, or cleavage product recognized and bound by the anti-periostin monoclonal antibody"" (ii) to (ix) in this order from the left.

(i) Molecular weight markers (ii) "Supernatant containing "anti-periostin monoclonal antibody (SS16A)" and a "periostin monomer, multimer, or cleavage product recognized and bound by anti-periostin monoclonal antibody (SS16A)""

(iii) "Supernatant containing "anti-periostin monoclonal antibody (SS17B)" and a "periostin monomer, multimer, or cleavage product recognized and bound by anti-periostin monoclonal antibody (SS17B)""

(iv) "Supernatant containing "anti-periostin monoclonal antibody (SS18A)" and a "periostin monomer, multimer, or cleavage product recognized and bound by anti-periostin monoclonal antibody (SS18A)""

(v) "Supernatant containing "anti-periostin monoclonal antibody (SS19A)" and a "periostin monomer, multimer, or cleavage product recognized and bound by anti-periostin monoclonal antibody (SS19A)""

(vi) "Supernatant containing "anti-periostin monoclonal antibody (SS19C)" and a "periostin monomer, multimer, or cleavage product recognized and bound by anti-periostin monoclonal antibody (SS19C)""

(vii) "Supernatant containing "anti-periostin monoclonal antibody (SS19D)" and a "periostin monomer, multimer, or cleavage product recognized and bound by anti-periostin monoclonal antibody (SS19D)""

(viii) "Supernatant containing "anti-periostin monoclonal antibody (SS20A)" and a "periostin monomer, multimer, or cleavage product recognized and bound by anti-periostin monoclonal antibody (SS20A)""

(ix) "Supernatant containing "anti-periostin monoclonal antibody (SS21A)" and a "periostin monomer, multimer, or cleavage product recognized and bound by anti-periostin monoclonal antibody (SS21A)""

The lane at the right end of the gel was used as a negative control lane into which no sample was poured.

(d) Subsequently, electrophoresis was performed at a current of 20 mA for 90 minutes.

(e) After completion of the electrophoresis in (d), the gel was taken out from the glass plate.

Through the procedure described above, a gel having the periostin monomer, multimer, and cleavage product recognized and bound by anti-periostin monoclonal antibodies at the positions corresponding to their molecular weights was obtained.

3. Western Blotting (1) The gel obtained in (e) of (3) in 2 was transferred by a semi-dry system using Trans-Blot SD cell (BIO-RAD Laboratories, Inc., Hercules, Calif., USA) in accordance with the attached instruction.

The gel obtained in (e) of (3) in 2 was placed on a transferring apparatus.

Subsequently, a 9 cm×9 cm polyvinyl difluoride membrane (BIO-RAD Laboratories, Inc., Hercules, Calif., USA) was placed on the gel, and transfer was performed using a buffer for transfer composed of 48 mM tris(hydroxymethyl)aminomethane [Tris], 39 mM glycine, 0.0375% (W/V) sodium dodecyl sulfate (SDS), and 20% (V/V) methanol at a current of 200 mA for 2 hours. The proteins, such as the "periostin monomer, multimer, and cleavage product recognized and bound by anti-periostin monoclonal antibodies," positioned in the gel according to their molecular weights were transferred from the gel to the polyvinyl difluoride membrane.

(2) The polyvinyl difluoride membrane to which proteins, such as the "periostin monomer, multimer, and cleavage product recognized and bound by anti-periostin monoclonal antibodies," were transferred was immersed in 20 mL of a blocking solution [50 mM tris(hydroxymethyl)aminomethane buffer [Tris buffer] (pH 8.0) containing 0.5% casein, 100 mM sodium chloride, and 0.1% sodium azide] at 25° C. for 2 hours for blocking.

(3) Subsequently, the polyvinyl difluoride membrane was washed by shaking in 20 mL of a washing solution (phosphate-buffered saline containing 0.05% Tween 20) for 10 minutes. This procedure was carried out three times.

(4) "Anti-periostin monoclonal antibody (SS17B)," which can recognize and bind to periostin monomer and multimer as described below, obtained in Example 2 was labeled with biotin using Sulfo-NHS-LC-Biotin (Thermo Fisher Scientific Inc., IL, USA, Product Code No. 21335) to give biotin-labeled "anti-periostin monoclonal antibody (SS17B)."

"Anti-periostin monoclonal antibody (SS19C)," which can recognize and bind to periostin monomer, multimer, and cleavage product as described below, obtained in Example 4 was labeled with biotin using Sulfo-NHS-LC-Biotin (Thermo Fisher Scientific Inc., IL, USA, Product Code No. 21335) to give biotin-labeled "anti-periostin monoclonal antibody (SS19C)."

The biotin-labeled "anti-periostin monoclonal antibody (SS17B)" and biotin-labeled "anti-periostin monoclonal antibody (SS19C)" were each diluted with a labeled antibody diluent (containing sodium azide) [50 mM tris(hydroxymethyl)aminomethane buffer [Tris buffer] (pH 8.0) containing 0.5% casein, 100 mM sodium chloride, and 0.1% sodium azide] to 5 µg/mL to prepare a biotin-labeled antibody mixture solution.

The polyvinyl difluoride membrane washed in (3) was immersed in the biotin-labeled antibody mixture solution at room temperature overnight for reaction.

The procedure described above allowed the "periostin monomer, multimer, or cleavage product recognized and bound by an anti-periostin monoclonal antibody" transferred to the polyvinyl difluoride membrane to react with the biotin-labeled "anti-periostin monoclonal antibody (SS17B)" or biotin-labeled "anti-periostin monoclonal antibody (SS19C)."

(5) The polyvinyl difluoride membrane subjected to the procedure in (4) was washed by shaking in 20 mL of the washing solution for 5 minutes. This procedure was carried out three times.

(6) Subsequently, the polyvinyl difluoride membrane in (5) was immersed in a peroxidase-labeled streptavidin solution prepared by diluting POD-labeled streptavidin (Stereospecific Detection Technologies GmbH, Germany) to 15000 times with a labeled antibody diluent [50 mM tris(hydroxymethyl)aminomethane buffer [Tris buffer] (pH 8.0) containing 0.5% casein and 100 mM sodium chloride] at room temperature for 90 minutes for reaction.

(7) The polyvinyl difluoride membrane subjected to the procedure in (6) was washed by shaking in 20 mL of the washing solution for 5 minutes. This procedure was carried out three times.

(8) The polyvinyl difluoride membrane in (7) was immersed in 20 mL of phosphate-buffered saline containing 0.025% 3,3'-diaminobenzidine tetrahydrochloride and 0.01% hydrogen peroxide at room temperature for 15 minutes for developing a color.

As a result, in the polyvinyl difluoride membrane, the positions corresponding to the molecular weights of the periostin monomer, multimer, and cleavage product recognized and bound by the anti-periostin monoclonal antibodies were colored.

(9) The polyvinyl difluoride membrane subjected to color development in (8) was photographed.

The reactivity of each anti-periostin monoclonal antibody to the monomer, multimer, and cleavage product of periostin was investigated from the presence and the position (molecular weight) of coloring on the polyvinyl difluoride membrane.

Figure 5:
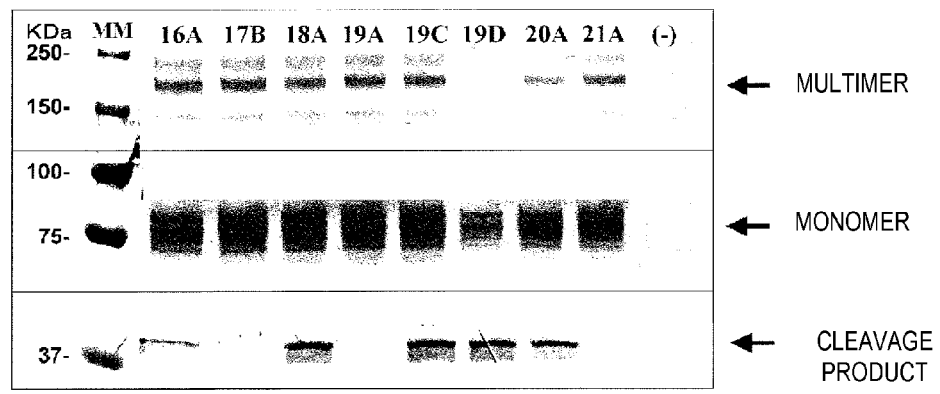
FIG. 5 is a photograph showing the results (polyvinyl difluoride membrane) in investigation of reactivities of the obtained anti-periostin monoclonal antibodies (derived from cell lines other than cell line SS19B) to periostin monomer, multimer, and cleavage product.

4. Results (1) FIG. 5 shows the polyvinyl difluoride membrane photographed in (9) of 3.

In the figure, the lanes show, from the left, the molecular weight markers (lane indicated by "MM"), periostin recognized and bound by "anti-periostin monoclonal antibody (SS16A)" (lane indicated by "16A"), periostin recognized and bound by "anti-periostin monoclonal antibody (SS17B)" (lane indicated by "17B"), periostin recognized and bound by "anti-periostin monoclonal antibody (SS18A)" (lane indicated by "18A"), periostin recognized and bound by "anti-periostin monoclonal antibody (SS19A)" (lane indicated by "19A"), periostin recognized and bound by "anti-periostin monoclonal antibody (SS19C)" (lane indicated by "19C"), periostin recognized and bound by "anti-periostin monoclonal antibody (SS19D)" (lane indicated by "19D"), periostin recognized and bound by "anti-periostin monoclonal antibody (SS20A)" (lane indicated by "20A"), periostin recognized and bound by "anti-periostin monoclonal antibody (SS21A)" (lane indicated by "21A"), and the negative control (lane indicated by "(-)").

In the figure, the broad band observed between the molecular weight markers of 150 and 250 KDa represents a periostin multimer (which is presumed as a trimer from the molecular weight); the broad band observed from near the molecular weight marker of 75 KDa towards the higher molecular weight side represents a periostin monomer from the molecular weight; and the broad band near the molecular weight marker of 37 KDa represents a periostin cleavage product from the molecular weight.

(2) The figure demonstrates that in the lane of periostin recognized and bound by "anti-periostin monoclonal antibody (SS16A)," coloring was observed at all positions representing the periostin multimer, monomer, and cleavage product. It was therefore confirmed that "anti-periostin monoclonal antibody (SS16A)" recognizes and binds to all of periostin multimer, monomer, and cleavage product.

(3) The figure demonstrates that in the lane of periostin recognized and bound by "anti-periostin monoclonal antibody (SS17B)," coloring was observed at the positions representing the periostin multimer and monomer but not observed at the position representing the periostin cleavage product. It was therefore confirmed that "anti-periostin monoclonal antibody (SS17B)" recognizes and binds to periostin multimer and monomer but does not recognize and not bind to periostin cleavage products.

(4) The figure demonstrates that in the lane of periostin recognized and bound by "anti-periostin monoclonal antibody (SS18A)," coloring was observed at all positions representing the periostin multimer, monomer, and cleavage product. It was therefore confirmed that "anti-periostin monoclonal antibody (SS18A)" recognizes and binds to all of periostin multimer, monomer, and cleavage product.

(5) The figure demonstrates that in the lane of periostin recognized and bound by "anti-periostin monoclonal antibody (SS19A)," coloring was observed at the positions representing the periostin multimer and monomer but not observed at the position representing the periostin cleavage product. It was therefore confirmed that "anti-periostin monoclonal antibody (SS19A)" recognizes and binds to periostin multimer and monomer but does not recognize and not bind to periostin cleavage products.

(6) The figure demonstrates that in the lane of periostin recognized and bound by "anti-periostin monoclonal antibody (SS19C)," coloring was observed at all positions representing the periostin multimer, monomer, and cleavage product. It was therefore confirmed that "anti-periostin monoclonal antibody (SS19C)" recognizes and binds to all of periostin multimer, monomer, and cleavage product.

(7) The figure demonstrates that in the lane of periostin recognized and bound by "anti-periostin monoclonal antibody (SS19D)," coloring was observed at the positions representing the periostin monomer and cleavage product but not observed at the position representing the periostin multimer. It was therefore confirmed that "anti-periostin monoclonal antibody (SS19D)" recognizes and binds to periostin monomer and cleavage product but does not recognize and not bind to periostin multimers.

(8) The figure demonstrates that in the lane of periostin recognized and bound by "anti-periostin monoclonal antibody (SS20A)," coloring was observed at all positions representing the periostin multimer, monomer, and cleavage product. It was therefore confirmed that "anti-periostin monoclonal antibody (SS20A)" recognizes and binds to all of periostin multimer, monomer, and cleavage product.

(9) The figure demonstrates that in the lane of periostin recognized and bound by "anti-periostin monoclonal antibody (SS21A)," coloring was observed at the positions representing the periostin multimer and monomer but not observed at the position representing the periostin cleavage product. It was therefore confirmed that "anti-periostin monoclonal antibody (SS21A)" recognizes and binds to periostin multimer and monomer but does not recognize and not bind to periostin cleavage products.

(10) It was also demonstrated that in the lane of negative control at the right end of the figure, no coloring was observed and it was therefore confirmed that non-specific binding and coloring did not occur.

[2] Anti-Periostin Monoclonal Antibody Derived from Cell Line SS19B

The reactivities of "anti-periostin monoclonal antibody (SS19B)" to periostin monomer, multimer, and cleavage product were investigated as follows.

1. SDS-Polyacrylamide Gel Electrophoresis (1) Reagent

The following reagents (a) to (c) were prepared.

(a) SDS-polyacrylamide Gel

Funakoshi Easy-Gel (III) Precast-gel (10%)(Funakoshi Co., Ltd., Tokyo, Japan) was used.

(b) Running Buffer for Electrophoresis Chamber

A running buffer for electrophoresis chamber [0.1% SDS-192 mM glycine-25 mM Tris buffer] was prepared in accordance with the description in (6) of 1 of I in Reference Example 2.

(c) Sample Treating Solution

A sample treating solution [1% SDS-1% 2-mercaptoethanol-20% glycerin-50 mM Tris buffer] was prepared in accordance with the description in (c) of (1) of 2 in [1].

(2) Sample

"Partial-length periostin (Δ17/18/21)" in 2 of [1] of II in Reference Example 2, that is, the "mixture of periostin monomer, multimer, and cleavage product" was used in an amount of 50 ng as a reference sample.

As described above, the "mixture of periostin monomer, multimer, and cleavage product" ("partial-length periostin (Δ17/18/21)") is known to contain the monomer, multimer, and cleavage product of periostin.

Molecular weight markers [Precision Plus Protein All Blue Standards, marker molecular weight: 10 KDa, 15 KDa, 20 KDa, 25 KDa, 37 KDa, 50 KDa, 75 KDa, 100 KDa, 150 KDa, and 250 KDa, BIO-RAD Laboratories, Inc., Hercules, Calif., USA] were also used as a sample.

(3) Electrophoresis

The samples in (2) were subjected to SDS-polyacrylamide gel electrophoresis using the reagents prepared in (1) by the following procedure.

(a) The sample treating solution in (c) of (1) was mixed in an amount of 13 μL with 20 μL of the "mixture of periostin monomer, multimer, and cleavage product" in (2), followed by boiling treatment at 100° C. for 5 minutes.

(b) The running buffer for electrophoresis chamber in (b) of (1) was put in a lower electrophoresis chamber. Subsequently, the SDS-polyacrylamide gel in (a) of (1) was set to the electrophoresis chamber. The buffer for electrophoresis chamber in (b) of (1) was put in an upper electrophoresis chamber.

(c) The sample treated in (a) was centrifuged, and 10 μL of the resulting supernatant was poured into a comb hole of the gel in (b).

In addition, 5 μL of the sample of molecular weight markers in (2) was poured into a comb hole of the gel in (b).

The supernatant and the molecular weight markers mentioned above were poured into the gel such that the lanes of the gel were for molecular weight markers (i) and "supernatant containing "periostin monomer, multimer, and cleavage product"" (ii) in this order from the left.

(i) Molecular weight markers (ii) "Supernatant containing "periostin monomer, multimer, and cleavage product""

(d) Subsequently, electrophoresis was performed at a current of 20 mA for 90 minutes.

(e) After completion of the electrophoresis in (d), the gel was taken out from the glass plate.

Through the procedure described above, a gel having the periostin monomer, multimer, and cleavage product at positions corresponding to their molecular weights was obtained.

2. Western Blotting (1) "Anti-periostin monoclonal antibody (SS19B)" obtained by Example 4 was labeled with biotin using Sulfo-NHS-LC-Biotin (Thermo Fisher Scientific Inc., IL, USA, Product Code No. 21335). The resulting biotin-labeled "anti-periostin monoclonal antibody (SS19B)" was diluted with the labeled antibody diluent (containing sodium azide) to 5 µg/mL to prepare a solution of the biotin-labeled "anti-periostin monoclonal antibody (SS19B)."

(2) A procedure was performed in accordance with the description in (1) to (9) of 3 in [1] except that the solution of the biotin-labeled "anti-periostin monoclonal antibody (SS19B)" in (1) was used instead of the mixture solution of the biotin-labeled "anti-periostin monoclonal antibody (SS17B)" and the biotin-labeled "anti-periostin monoclonal antibody (SS19C)" in (4) of 3 in [1].

By this procedure, the periostin monomer, multimer, and cleavage product positioned according to their molecular weights in the gel obtained in (3) in 1 were transferred to the polyvinyl difluoride membrane; the transferred periostin monomer, multimer, and cleavage product were brought into contact with the biotin-labeled "anti-periostin monoclonal antibody (SS19B)" for reaction; and the binding therebetween was investigated.

This Western blotting provided a colored polyvinyl difluoride membrane.

The reactivity of "anti-periostin monoclonal antibody (SS19B)" to the monomer, multimer, and cleavage product of periostin was investigated by the presence and the position (molecular weight) of coloring on the polyvinyl difluoride membrane.

Figure 6:
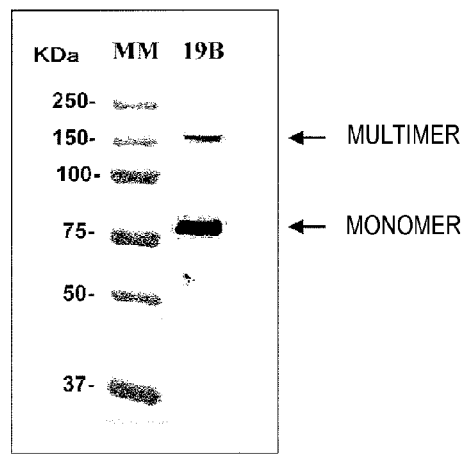
FIG. 6 is a photograph showing the results (polyvinyl difluoride membrane) in investigation of reactivity of the obtained anti-periostin monoclonal antibody (derived from cell line SS19B) to periostin monomer, multimer, and cleavage product.

3. Results (1) FIG. 6 shows the polyvinyl difluoride membrane prepared in 2.

In the figure, the lanes show, from the left, the molecular weight markers (lane indicated by "MM") and periostin recognized and bound by "anti-periostin monoclonal antibody (SS19B)" (lane indicated by "19B").

In the figure, the broad band at the higher molecular weight side than the molecular weight marker of 150 KDa represents a periostin multimer from the molecular weight; and the broad band at the higher molecular weight side than the molecular weight marker of 75 KDa represents a periostin monomer from the molecular weight.

(2) This figure demonstrates that in the lane of periostin (monomer, multimer, and cleavage product) with which "anti-periostin monoclonal antibody (SS19B)" reacted, coloring was observed at the positions representing the periostin multimer and monomer.

However, no coloring (band) is observed on the lower molecular weight side than the band representing the periostin monomer. That is, no coloring is observed at the position representing periostin cleavage products.

Accordingly, it was confirmed that "anti-periostin monoclonal antibody (SS19B)" recognizes and binds to periostin multimer and monomer but does not recognize and not bind to periostin cleavage products.

[3] Conclusion

The reactivities of the anti-periostin monoclonal antibodies obtained in Examples 1 to 6 to periostin monomer, multimer, and cleavage product are summarized in FIG. 7.

In the figure, a periostin monomer, multimer, or cleavage product recognized and bound by an anti-periostin monoclonal antibody is indicated with the symbol "○."

The figure demonstrates that all anti-periostin monoclonal antibodies can recognize and bind to periostin monomers.

The figure demonstrates that the following anti-periostin monoclonal antibodies cannot recognize and not bind to periostin cleavage products:

"anti-periostin monoclonal antibody (SS17B),"
"anti-periostin monoclonal antibody (SS19A),"
"anti-periostin monoclonal antibody (SS19B)," and
"anti-periostin monoclonal antibody (SS21A)."

The figure demonstrates that the following anti-periostin monoclonal antibodies can recognize and bind to periostin cleavage products:

"anti-periostin monoclonal antibody (SS16A),"
"anti-periostin monoclonal antibody (SS18A),"
"anti-periostin monoclonal antibody (SS19C),"
"anti-periostin monoclonal antibody (SS19D)," and
"anti-periostin monoclonal antibody (SS20A)."

The figure also demonstrates that the following anti-periostin monoclonal antibody can recognize and bind to a periostin cleavage product but cannot recognize and not bind to periostin multimers:

"anti-periostin monoclonal antibody (SS19D)."

Cell line SS19D is a monoclonal antibody-producing cell line producing "anti-periostin monoclonal antibody (SS19D)" and has been deposited in the NITE Patent Microorganisms Depositary, National Institute of Technology and Evaluation (2-5-8 Kazusakamatari, Kisarazu-shi, Chiba, Japan) under "Accession No. NITE P-1068" on Feb. 22, 2011. [Cell line SS19D, a monoclonal antibody-producing cell line producing "anti-periostin monoclonal antibody (SS19D)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Feb. 7, 2012 [transfer date: Feb. 9, 2012] (Accession No. NITE BP-1068)].

Cell line SS16A is a monoclonal antibody-producing cell line producing "anti-periostin monoclonal antibody (SS16A)" and has been deposited in the NITE Patent Microorganisms Depositary, National Institute of Technology and Evaluation (2-5-8 Kazusakamatari, Kisarazu-shi, Chiba, Japan) under "Reference No. NITE AP-1281" on Mar. 16, 2012. Cell line SS16A, a monoclonal antibody-producing cell line producing "anti-periostin monoclonal antibody (SS16A)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Jul. 19, 2012 [transfer date: Jul. 19, 2012] (Accession No. NITE BP-1281).

Cell line SS18A is a monoclonal antibody-producing cell line producing "anti-periostin monoclonal antibody (SS18A)" and has been deposited in the NITE Patent Microorganisms Depositary, National Institute of Technology and Evaluation (2-5-8 Kazusakamatari, Kisarazu-shi, Chiba, Japan) under "Reference No. NITE AP-1282" on Mar. 16, 2012. Cell line SS18A, a monoclonal antibody-producing cell line producing "anti-periostin monoclonal antibody (SS18A)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Jul. 19, 2012 [transfer date: Jul. 19, 2012] (Accession No. NITE BP-1282).

Cell line SS19C is a monoclonal antibody-producing cell line producing "anti-periostin monoclonal antibody (SS19C)" and has been deposited in the NITE Patent Microorganisms Depositary, National Institute of Technology and Evaluation (2-5-8 Kazusakamatari, Kisarazu-shi, Chiba, Japan) under "Reference No. NITE AP-1283" on Mar. 16, 2012. Cell line SS19C, a monoclonal antibody-producing cell line producing "anti-periostin monoclonal antibody (SS19C)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Jul. 19, 2012 [transfer date: Jul. 19, 2012] (Accession No. NITE BP-1283).

Cell line SS20A is a monoclonal antibody-producing cell line producing "anti-periostin monoclonal antibody (SS20A)" and has been deposited in the NITE Patent Microorganisms Depositary, National Institute of Technology and Evaluation (2-5-8 Kazusakamatari, Kisarazu-shi, Chiba, Japan) under "Reference No. NITE AP-1284" on Mar. 16, 2012. Cell line SS20A, a monoclonal antibody-producing cell line producing "anti-periostin monoclonal antibody (SS20A)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Jul. 19, 2012 [transfer date: Jul. 19, 2012] (Accession No. NITE BP-1284).

Example 9

Detection of Periostin in Human Serum

Periostin in human serum was detected by immunoprecipitation, electrophoresis, and Western blotting.

[1] Serum of Healthy Subject

Periostin in serum of a healthy subject was investigated as follows.

1. Immunoprecipitation Treatment (1) A bed volume of 100 µL of NHS-activated Sepharose (GE Healthcare, Little Chalfont, UK) was put in a 1.5-mL tube, followed by centrifugation to remove the supernatant.

(2) NHS-activated Sepharose was suspended by adding 1 mM hydrochloric acid to the tube in (1). Immediately thereafter, centrifugation was performed to remove the supernatant.

(3) To the tube in (2) added was 85 µg (in terms of amount of protein) of "anti-periostin monoclonal antibody (SS19C)" (an antibody recognizing and binding to all of the periostin monomer, multimer, and cleavage product) obtained in Example 4 in a solvent of 0.1 M sodium carbonate-0.5 M sodium chloride solution (pH 8.3).

The tube was then incubated at 25° C. for 1 hour with stirring to immobilize "anti-periostin monoclonal antibody (SS19C)" to NHS-activated Sepharose.

(4) Subsequently, the tube in (3) was centrifuged.

After removal of the supernatant, 1 mL of a blocking solution [0.5 M 2-aminoethanol-0.5 M sodium chloride (pH 8.3)] was added to the tube containing the NHS-activated Sepharose to which "anti-periostin monoclonal antibody (SS19C)" was immobilized.

The tube was then left to stand at 25° C. for 1 hour for blocking the surface of NHS-activated Sepharose to which "anti-periostin monoclonal antibody (SS19C)" was not immobilized.

(5) Subsequently, the tube in (4) was centrifuged.

After removal of the supernatant, 1 mL of 20% ethanol was added to the tube, followed by storage at 4° C. for 18 hours.

(6) Separately, new 1.5-mL tubes were prepared, and a bed volume of 10 µL of "NHS-activated Sepharose to which "anti-periostin monoclonal antibody (SS19C)" (8.5 µg) immobilized" in (5) was added to each of the new tubes.

(7) Serum of a healthy subject was added in an amount of 25 µL, 50 µL, or 100 µL to the respective tubes prepared above.

These tubes were then rotated at 5° C. for 18 hours to bring periostin (a monomer, multimer, or cleavage product) contained in the serum of the healthy subject into contact with ""anti-periostin monoclonal antibody (SS19C)" immobilized to NHS-activated Sepharose."

(8) Subsequently, the tubes (containing the serum of the healthy subject in an amount of 25, 50, or 100 µL) in (7) were centrifuged.

After removal of the supernatant, NHS-activated Sepharose in each tube was washed with a washing solution [10 mM tris(hydroxymethyl)aminomethane [Tris]-150 mM sodium chloride-0.05% Tween 20 (pH 8.0)] three times to thoroughly remove free periostin (monomer, multimer, and cleavage product) that did not bind to ""anti-periostin monoclonal antibody (SS19C)" immobilized to NHS-activated Sepharose."

Through the procedure described above, a "conjugate of "anti-periostin monoclonal antibody (SS19C) immobilized to NHS-activated Sepharose" and a "periostin monomer, multimer, or cleavage product contained in a sample (serum of a healthy subject),"" i.e., a "conjugate, "NHS-activated Sepharose"-"anti-periostin monoclonal antibody (SS19C)"-"periostin monomer, multimer, or cleavage product contained in a sample (serum of a healthy subject),"" was prepared.

2. SDS-Polyacrylamide Gel Electrophoresis (1) Reagent

The following reagents (a) to (h) were prepared.

(a) Acrylamide Solution

An acrylamide solution [30% acrylamide preservation solution] was prepared in accordance with the description in (1) of 1 of I in Reference Example 2.

(b) SDS-1.5 M Tris Solution

An SDS-1.5 M Tris solution [0.4% SDS-1.5 M Tris-hydrochloric acid buffer] was prepared in accordance with the description in (2) of 1 of I in Reference Example 2.

(c) SDS-0.5 M Tris Solution

An SDS-0.5 M Tris solution [0.4% SDS-0.5 M Tris-hydrochloric acid buffer] was prepared in accordance with the description in (3) of 1 of I in Reference Example 2.

(d) Ammonium Persulfate Solution

An ammonium persulfate solution [10% ammonium persulfate aqueous solution] was prepared in accordance with the description in (4) of 1 of I in Reference Example 2.

(e) TEMED Solution

N,N,N',N'-tetramethylethylenediamine (Nacalai Tesque, Inc., Kyoto, Japan) was used as described in (5) of 1 of I in Reference Example 2.

(f) Running Buffer for Electrophoresis Chamber

A running buffer for electrophoresis chamber [0.1% SDS-192 mM glycine-25 mM Tris buffer] was prepared in accordance with the description in (6) of 1 of I in Reference Example 2.

(g) Sample Treating Solution (Containing Reducing Agent)

A sample treating solution (containing a reducing agent) [4% SDS-12% 2-mercaptoethanol-20% glycerin-100 mM Tris buffer] was prepared by mixing 0.4 g of sodium dodecyl sulfate [SDS], 1.2 mL of 2-mercaptoethanol (reducing agent), 1 mL of 1 M tris(hydroxymethyl)aminomethane [Tris]-hydrochloric acid buffer (pH 6.8), and 2 mL of glycerin with pure water and then making the final volume to 10 mL.

(h) Sample Treating Solution (not Containing Reducing Agent)

A sample treating solution (not containing any reducing agent) [1% SDS-20% glycerin-100 mM Tris buffer] was prepared by mixing 0.4 g of sodium dodecyl sulfate [SDS], 1 mL of 1 M tris(hydroxymethyl)aminomethane [Tris]-hydrochloric acid buffer (pH 6.8), and 2 mL of glycerin with pure water and then making the final volume to 10 mL.

(2) Sample

The "conjugate, "NHS-activated Sepharose"-"anti-periostin monoclonal antibody (SS19C)"-"periostin monomer, multimer, or cleavage product contained in a sample (serum of a healthy subject),"" in each tube (in which the amount of the serum of the healthy subject was 25 μL, 50 μL, or 100 μL) treated in (8) of 1 was used as the sample as follows.

"Partial-length periostin (Δ17/18/21)" in 2 of [1] of II in Reference Example 2, i.e., the "mixture of periostin monomer, multimer, and cleavage product" was used in an amount of 800 ng as a reference sample as follows.

As described above, the "mixture of periostin monomer, multimer, and cleavage product" ("partial-length periostin (Δ17/18/21)") is known to contain the monomer, multimer, and cleavage product of periostin.

Molecular weight markers [Precision Plus Protein All Blue Standards, marker molecular weight: 10 KDa, 15 KDa, 20 KDa, 25 KDa, 37 KDa, 50 KDa, 75 KDa, 100 KDa, 150 KDa, and 250 KDa, BIO-RAD Laboratories, Inc., Hercules, Calif., USA] were also used as a sample as follows.

(a) "Conjugate, "NHS-activated Sepharose"-"anti-periostin monoclonal antibody (SS19C)"-"periostin monomer, multimer, or cleavage product contained in a sample (serum of a healthy subject)"" (the amount of serum of the healthy subject: 100 μL)

(b) "Conjugate, "NHS-activated Sepharose"-"anti-periostin monoclonal antibody (SS19C)"-"periostin monomer, multimer, or cleavage product contained in a sample (serum of a healthy subject)"" (the amount of serum of the healthy subject: 50 μL)

(c) "Conjugate, "NHS-activated Sepharose"-"anti-periostin monoclonal antibody (SS19C)"-"periostin monomer, multimer, or cleavage product contained in a sample (serum of a healthy subject)"" (the amount of serum of the healthy subject: 25 μL)

(d) Reference sample (mixture of periostin monomer, multimer, and cleavage product)

(e) Molecular weight markers [marker molecular weights: 10 KDa, 15 KDa, 20 KDa, 25 KDa, 37 KDa, 50 KDa, 75 KDa, 100 KDa, 150 KDa, and 250 KDa]

(3) Electrophoresis

The samples in (2) were subjected to SDS-polyacrylamide gel electrophoresis using the reagents prepared in (1) by the following procedure.

(a) A separating gel solution containing 7.5% acrylamide was prepared using the reagents prepared in (a), (b), (d), and (e) in (1) and pure water.

The separating gel solution was poured into an assembled glass plate and was overlaid with pure water, followed by gelation for 30 minutes.

(b) A stacking gel solution containing 1.3% acrylamide was prepared using the reagents prepared in (a), (c), (d), and (e) in (1) and pure water.

The pure water in the glass plate in (a) was discarded, and a small amount of the stacking gel solution was poured into the glass plate for washing and then the remaining stacking gel solution was poured. Subsequently, a sample comb was inserted thereinto, and gelation was performed for 30 minutes.

(c) The sample treating solution (containing a reducing agent) in (g) of (1) was mixed in an amount of 20 μL with 10 μL of each of the samples (a) to (d) in (2), followed by boiling treatment at 100° C. for 10 minutes in the presence of the reducing agent.

The "conjugate, "NHS-activated Sepharose"-"anti-periostin monoclonal antibody (SS19C)"-"periostin monomer, multimer, or cleavage product contained in a sample (serum of a healthy subject),"" in each of the samples (a) to (c) in (2) is dissociated into "NHS-activated Sepharose," "anti-periostin monoclonal antibody (SS19C)," and the "periostin monomer, multimer, or cleavage product contained in the sample (serum of a healthy subject)" by mixing with the sample treating solution (containing a reducing agent).

That is, "NHS-activated Sepharose," "anti-periostin monoclonal antibody (SS19C)," and the "periostin monomer, multimer, or cleavage product contained in the sample (serum of a healthy subject)" were turned into free states by mixing the conjugate with the added sample treating solution.

(d) The running buffer for electrophoresis chamber in (f) of (1) was put in a lower electrophoresis chamber. Subsequently, the sample comb was pulled out from the gel in (b), washed, and then set to the electrophoresis chamber. Subsequently, the running buffer for electrophoresis chamber in (f) of (1) was put in an upper electrophoresis chamber.

(e) The samples treated in (c) were each centrifuged, and 20 μL of each supernatant was poured into the respective comb holes of the gel in (d).

The sample of molecular weight markers in (e) of (2) was poured in an amount of 5 μL into a comb hole of the gel in (d).

The supernatants and the molecular weight markers mentioned above were poured into the gel such that the lanes of the gel were for the supernatants of the "periostin monomer, multimer, or cleavage product contained in the following samples (serum of a healthy subject)" (i) to (iii), the supernatant of the reference sample (mixture of periostin monomer, multimer, and cleavage product) (iv), and the molecular weight markers (v) in this order from the left.

(i) Supernatant of the "periostin monomer, multimer, or cleavage product contained in the sample (serum of the healthy subject)" (the amount of serum of the healthy subject: 100 μL)

(ii) Supernatant of the "periostin monomer, multimer, or cleavage product contained in the sample (serum of the healthy subject)" (the amount of serum of the healthy subject: 50 μL)

(iii) Supernatant of the "periostin monomer, multimer, or cleavage product contained in the sample (serum of the healthy subject)" (the amount of serum of the healthy subject: 25 μL)

(iv) Supernatant of the reference sample (mixture of periostin monomer, multimer, and cleavage product)

(v) Molecular weight markers (f) Subsequently, electrophoresis was performed at a current of 30 mA for 60 minutes.

(g) After completion of the electrophoresis in (f), the gel was taken out from the glass plate.

Through the procedure described above, in the case of using a reducing agent in (c), a gel having periostin (monomer, multimer, or cleavage product) contained in the samples (serum of the healthy subject) at the positions corresponding to their molecular weights was obtained.

(h) In the case of not using a reducing agent in (c), a gel having periostin (monomer, multimer, or cleavage product) contained in the samples (serum of the healthy subject) at the positions corresponding to their molecular weights was obtained in accordance with the description in (a) to (g) except that the treatment in (c) was performed in the absence of the reducing agent by using the sample treating solution (not containing any reducing agent) in (h) of (1) instead of the sample treating solution (containing a reducing agent) and that only the supernatants were poured into the comb holes of the gel in (e) without pouring the sample of molecular weight markers.

3. Western Blotting (1) The gels obtained in (g) and (h) of (3) in 2 were transferred by a wet system using a Mini Protean II Cell kit (BIO-RAD Laboratories, Inc., Hercules, Calif., USA) in accordance with the attached instruction.

The gels obtained in (g) and (h) of (3) in 2 were each placed on a transferring apparatus.

Subsequently, a 6 cm×9 cm polyvinyl difluoride membrane (Millipore Corporation, MA, USA) was placed on each gel, and transfer was performed using a buffer for transfer composed of 25 mM tris(hydroxymethyl)aminomethane [Tris], 39 mM glycine, 0.0375% (W/V) sodium dodecyl sulfate (SDS), and 20% (V/V) methanol at a current of 65 mA for 2 hours. The proteins, such as periostin (monomer, multimer, and cleavage product) contained in the samples (serum of the healthy subject), on the gel were transferred from the gel to the polyvinyl difluoride membrane.

(2) The polyvinyl difluoride membranes to which proteins, such as periostin (monomer, multimer, and cleavage product) contained in the samples (serum of the healthy subject), were transferred were each immersed in 50 mL of Tris-buffered saline [10 mM tris(hydroxymethyl)aminomethane [Tris]-150 mM sodium chloride (pH 8.0)] containing 4% skim milk and 0.05% Tween 20 at room temperature for 1 hour for blocking.

(3) Subsequently, the polyvinyl difluoride membranes were each washed by shaking in 20 mL of a washing solution (phosphate-buffered saline containing 0.05% Tween 20) for 10 minutes. This procedure was carried out three times.

(4) "Anti-periostin monoclonal antibody (SS19C)" (an antibody recognizing and binding to all of periostin monomer, multimer, and cleavage product) obtained in Example 4 was diluted to 1 µg/mL with Tris-buffered saline [10 mM tris(hydroxymethyl)aminomethane [Tris]-150 mM sodium chloride (pH 8.0)] containing 4% skim milk and 0.05% Tween 20 to prepare a solution of this antibody.

The polyvinyl difluoride membranes washed in (3) were each immersed in the antibody solution at 4° C. overnight for reaction.

By this procedure, periostin (monomer, multimer, or cleavage product) contained in the samples (serum of the healthy subject) transferred to the polyvinyl difluoride membrane was reacted with "anti-periostin monoclonal antibody (SS19C)" in the antibody solution.

(5) The polyvinyl difluoride membranes subjected to the procedure in (4) were each washed by shaking in 50 mL of the washing solution for 10 minutes. This procedure was carried out three times.

(6) Subsequently, a peroxidase-labeled anti-mouse IgG antibody solution was prepared by diluting TrueBlot ULTRA (eBioscience, Inc., San Diego, Calif., USA) to 3000 times with Tris-buffered saline [10 mM tris(hydroxymethyl)aminomethane [Tris]-150 mM sodium chloride (pH 8.0)] containing 4% skim milk.

The polyvinyl difluoride membranes in (4) were each immersed in the peroxidase-labeled anti-mouse IgG antibody solution at room temperature for 45 minutes for reaction.

(7) The polyvinyl difluoride membranes were each washed by shaking in 50 mL of the washing solution for 5 minutes. This procedure was carried out three times.

(8) The polyvinyl difluoride membranes in (7) were each immersed in 2 mL of ECL Western Blotting Detection Reagents (GE Healthcare, Little Chalfont, UK) at room temperature for 1 minute for light emission.

By this procedure, light emission was caused at the positions corresponding to the molecular weights of periostin (monomer, multimer, and cleavage product).

(9) The polyvinyl difluoride membranes subjected to light emission in (8) were photographed.

The presence of periostin (monomer, multimer, or cleavage product) contained in each sample (serum of the healthy subject) was confirmed by the presence and the position (molecular weight) of light emission on the polyvinyl difluoride membrane.

Figure 8:
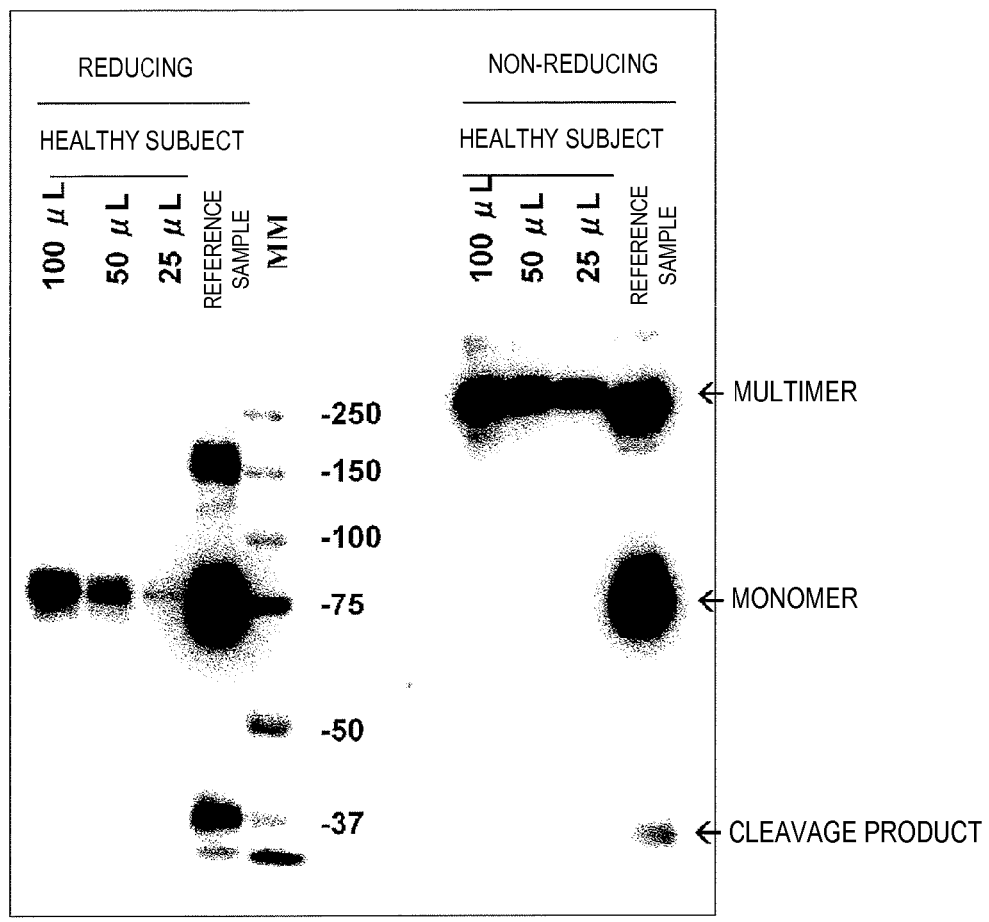
FIG. 8 is a photograph showing the results (polyvinyl difluoride membrane) in investigation of periostin in serum of healthy subjects by immunoprecipitation, electrophoresis, and Western blotting.

4. Results (1) FIG. 8 shows photographs of the polyvinyl difluoride membranes obtained in (9) of 3.

In the figure, the pattern on the left side is the polyvinyl difluoride membrane subjected to electrophoresis in the presence of a reducing agent using a sample treating solution (containing the reducing agent); and the pattern on the right side is the polyvinyl difluoride membrane subjected to electrophoresis in the absence of a reducing agent using a sample treating solution (not containing any reducing agent).

In the pattern on the left side, the lanes show, from the left, the case where the tube containing 100 µl of the serum of the healthy subject in (7) of 1 (lane indicated by "100 µL"), the case where the tube containing 50 µL of the serum of the healthy subject in (7) of 1 (lane indicated by "50 µL"), the case where the tube containing 25 µL of the serum of the healthy subject in (7) of 1 (lane indicated by "25 µL"), the reference sample (mixture of periostin monomer, multimer, and cleavage product) in (d) of (2) of 2 (lane indicated by "reference sample"), and the sample of molecular weight markers in (e) of (2) of 2 (lane indicated by "MM").

In the pattern on the left side, the broad band observed from near the molecular weight marker of 150 KDa towards the higher molecular weight side represents a periostin multimer (which is presumed as a dimer from the molecular weight) from the molecular weight; the broad band near the molecular weight marker of 75 KDa represents a periostin monomer from the molecular weight; and the broad band near the molecular weight marker of 37 KDa represents a periostin cleavage product from the molecular weight.

In the pattern on the right side, the lanes show, from the left, the case where the tube containing 100 µL of the serum of the healthy subject in (7) of 1 (lane indicated by "100 µL"), the case where the tube containing 50 µL of the serum of the healthy subject in (7) of 1 (lane indicated by "50 µL"), the case where the tube containing 25 µL of the serum of the healthy subject in (7) of 1 (lane indicated by "25 µL"), and the reference sample (mixture of periostin monomer, multimer, and cleavage product) in (d) of (2) of 2 (lane indicated by "reference sample").

In the pattern on the right side, the broad band observed from near the molecular weight marker of 250 KDa towards the higher molecular weight side represents a periostin multimer (which is presumed as a trimer from the molecular weight) from the molecular weight; the broad band near the molecular weight marker of 75 KDa represents a periostin monomer from the molecular weight; and the broad band near the molecular weight marker of 37 KDa represents a periostin cleavage product from the molecular weight.

(2) The pattern on the left side of the figure demonstrates that in the serum of a healthy subject subjected to electrophoresis in the presence of a reducing agent using a sample treating solution (containing the reducing agent), in all amounts of the serum, no light emission was observed at either positions corresponding to the periostin multimer and cleavage product and light emission was observed only at the position corresponding to the periostin monomer.

(3) The pattern on the right side of the figure demonstrates that in the serum of a healthy subject subjected to electrophoresis in the absence of a reducing agent using a sample treating solution (not containing any reducing agent), in all amounts of the serum, no light emission was observed at either positions corresponding to the periostin monomer and cleavage product and light emission was observed only at the position corresponding to the periostin multimer.

[2] Serum of Pulmonary Fibrosis Patient

Periostin in serum of pulmonary fibrosis patients was investigated as follows.

1. Immunoprecipitation Treatment

The procedure in accordance with the description in (1) to (8) of 1 in [1] was performed except that "addition of serum of a healthy subject in an amount of 25 µL, 50 µL, or 100 µL to the respective tubes" in (7) of 1 in [1] was changed to "addition of serum of three pulmonary fibrosis patients and a healthy subject each in an amount of 1 mL to the respective (1.5-mL) tubes" to prepare each "conjugate of "anti-periostin monoclonal antibody (SS19C) immobilized to NHS-activated Sepharose" and a "periostin monomer, multimer, or cleavage product contained in the sample (serum of the pulmonary fibrosis patient or the healthy subject),"" i.e., a "conjugate, "NHS-activated Sepharose"-"anti-periostin monoclonal antibody (SS19C)"-"periostin monomer, multimer, or cleavage product contained in a sample (serum of a pulmonary fibrosis patient or a healthy subject),"" for periostin (monomer, multimer, and cleavage product) contained in serum of the pulmonary fibrosis patients and healthy subject.

2. SDS-Polyacrylamide Gel Electrophoresis (1) Reagent

Each reagent was prepared in accordance with the description in (a) to (h) of (1) of 2 in [1].

(2) Sample

The "conjugate, "NHS-activated Sepharose"-"anti-periostin monoclonal antibody (SS19C)"-"periostin monomer, multimer, or cleavage product contained in a sample (serum of a pulmonary fibrosis patient or a healthy subject),"" prepared in 1 was used as a sample as follows.

As a reference sample, 800 ng of "partial-length periostin (Δ17/18/21)" in 2 of [1] of II in Reference Example 2, i.e., a "mixture of periostin monomer, multimer, and cleavage product" was used as follows.

As described above, the "mixture of periostin monomer, multimer, and cleavage product" ("partial-length periostin (Δ17/18/21)") is known to contain the monomer, multimer, and cleavage product of periostin.

Molecular weight markers [Precision Plus Protein All Blue Standards, marker molecular weight: 10 KDa, 15 KDa, 20 KDa, 25 KDa, 37 KDa, 50 KDa, 75 KDa, 100 KDa, 150 KDa, and 250 KDa, BIO-RAD Laboratories, Inc., Hercules, Calif., USA] were also used as a sample as follows.

(a) "Conjugate, "NHS-activated Sepharose"-"anti-periostin monoclonal antibody (SS19C)"-"periostin monomer, multimer, or cleavage product contained in a sample (serum of a healthy subject)""

(b) "Conjugate, "NHS-activated Sepharose"-"anti-periostin monoclonal antibody (SS19C)"-"periostin monomer, multimer, or cleavage product contained in a sample (serum of a first pulmonary fibrosis patient)""

(c) "Conjugate, "NHS-activated Sepharose"-"anti-periostin monoclonal antibody (SS19C)"-"periostin monomer, multimer, or cleavage product contained in a sample (serum of a second pulmonary fibrosis patient)""

(d) "Conjugate, "NHS-activated Sepharose"-"anti-periostin monoclonal antibody (SS19C)"-"periostin monomer, multimer, or cleavage product contained in a sample (serum of a third pulmonary fibrosis patient)""

(e) Reference sample (mixture of periostin monomer, multimer, and cleavage product)

(f) Molecular weight markers [marker molecular weights: 10 KDa, 15 KDa, 20 KDa, 25 KDa, 37 KDa, 50 KDa, 75 KDa, 100 KDa, 150 KDa, and 250 KDa]

(3) Electrophoresis

The samples in (2) were subjected to SDS-polyacrylamide gel electrophoresis using the reagents prepared in (1).

A gel having periostin (monomer, multimer, and cleavage product) contained in each sample (serum of a pulmonary fibrosis patient or healthy subject) at the position corresponding to its molecular weight was obtained by performing electrophoresis in the presence of a reducing agent using a sample treating solution (containing the reducing agent) in accordance with the description in (a) to (g) of (3) of 2 in [1] except for the following matters (a) and (b).

(a) A "separating gel solution containing 9% acrylamide" was prepared instead of the "separating gel solution containing 7.5% acrylamide" in (a) of (3) of 2 in [1]

(b) The molecular weight markers, the supernatant of "periostin monomer, multimer, or cleavage product contained in a sample (serum of the healthy subject)," the supernatant of "periostin monomer, multimer, or cleavage product contained in a sample (serum of the first pulmonary fibrosis patient)," the supernatant of "periostin monomer, multimer, or cleavage product contained in a sample (serum of the second pulmonary fibrosis patient)," the supernatant of "periostin monomer, multimer, or cleavage product contained in a sample (serum of the third pulmonary fibrosis patient)," and the supernatant of the reference sample (mixture of periostin monomer, multimer, and cleavage product) were poured in this order from the left lane into the comb holes of a gel, instead of pouring the supernatant of "periostin monomer, multimer, or cleavage product contained in each of samples (i) to (iii) (serum of the healthy subject)," the supernatant of the reference sample (mixture of periostin monomer, multimer, and cleavage product) in (iv), and the molecular weight markers in (v) in this order from the left lane into the comb holes of the gel in (e) of (3) of 2 in [1].

3. Western Blotting

The gel obtained by SDS-polyacrylamide gel electrophoresis in 2 performed in accordance with the description in (1) to (9) of 3 in [1] was subjected to transfer to a polyvinyl difluoride membrane and light emission at the positions corresponding to the molecular weights of periostin (monomer, multimer, or cleavage product) to investigate the presence of periostin (monomer, multimer, or cleavage product) in the serum of the pulmonary fibrosis patients and the healthy subject from the presence and the position of light emission on the polyvinyl difluoride membrane.

Figure 9:
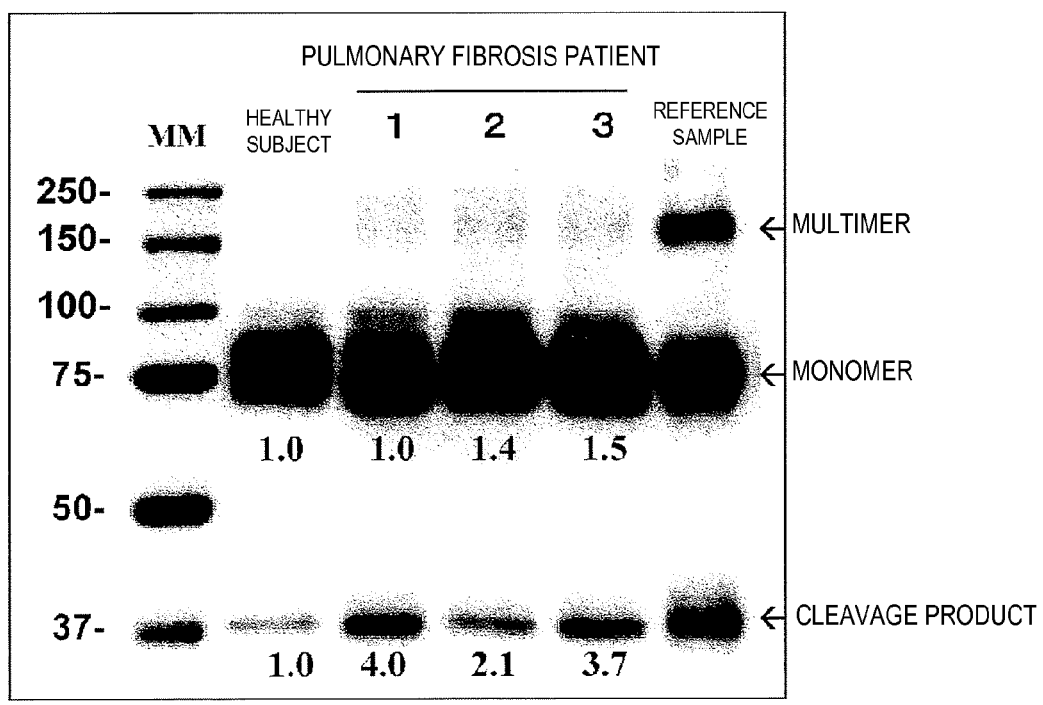
FIG. 9 is a photograph showing the results (polyvinyl difluoride membrane) in investigation of periostin in serum of pulmonary fibrosis patients by immunoprecipitation, electrophoresis, and Western blotting.

4. Results (1) FIG. 9 shows the polyvinyl difluoride membrane obtained in 3.

In this figure, the lanes show, from the left, the samples in 1, i.e., the sample of molecular weight markers (lane indicated by "MM"), the sample of serum of the healthy subject (lane indicated by "healthy subject"), the sample of serum of the first pulmonary fibrosis patient (lane indicated by "pulmonary fibrosis patient 1"), the sample of serum of the second pulmonary fibrosis patient (lane indicated by "pulmonary fibrosis patient 2"), the sample of serum of the third pulmonary fibrosis patient (lane indicated by "pulmonary fibrosis patient 3"), and the reference sample (mixture of periostin monomer, multimer, and cleavage product) (lane indicated by "reference sample").

In this figure, the broad band near the molecular weight marker of 150 KDa represents a periostin multimer (which is presumed as a dimer from the molecular weight) from the molecular weight; the broad band near the molecular weight marker of 75 KDa represents a periostin monomer from the molecular weight; and the broad band near the molecular weight marker of 37 KDa represents a periostin cleavage product from the molecular weight.

In the figure, the numerical value shown under each band of the samples of pulmonary fibrosis patients represents the relative intensity (relative ratio) of the emission band, provided that the emission intensity of the corresponding band in the sample of the healthy subject is 1.0.

(2) The figure demonstrates that in the serum sample of a healthy subject subjected to electrophoresis in the presence of a reducing agent using a sample treating solution (containing the reducing agent), light emission was observed at the position corresponding to a periostin monomer, slight light emission was observed at the position corresponding to a periostin cleavage product, and no light emission was observed at the position corresponding to periostin multimers.

(3) The figure demonstrates that in the serum samples of pulmonary fibrosis patients subjected to electrophoresis in the presence of a reducing agent using a sample treating solution (containing the reducing agent), in all serum samples of three pulmonary fibrosis patients, light emission was observed at the positions corresponding to a periostin monomer and a cleavage product, and no light emission was observed at the position corresponding to periostin multimers.

(4) Provided that the emission intensity of the band of the sample of the healthy subject is 1.0, the relative intensities (relative ratios) of the emission bands of samples of the three pulmonary fibrosis patients shown in the figure are 1.0 to 1.5 in the bands at the position corresponding to a monomer. This demonstrates that the amounts of the periostin monomer in the serum samples of the pulmonary fibrosis patients were equivalent to or slightly higher than that in the healthy subject.

The relative intensities (relative ratios) of serum samples of the three pulmonary fibrosis patients were 2.1 to 4.0 in the bands at the position corresponding to a cleavage product. This demonstrates that the amounts of the periostin cleavage product in the serum samples of the pulmonary fibrosis patients were twice or more the amount in the serum sample of the healthy subject and therefore that the amounts of the periostin cleavage product in the pulmonary fibrosis patients were significantly higher than that in the healthy subject.

It was confirmed from these results that in the pattern of bands obtained by a series of treatments in electrophoresis in the presence of a reducing agent using a sample treating solution (containing the reducing agent), the amounts of periostin monomer and multimer are substantially the same between a healthy subject and a pulmonary fibrosis patient, but the amount of a periostin cleavage product significantly differs between a healthy subject and a pulmonary fibrosis patient such that the amount of the periostin cleavage product of a pulmonary fibrosis patient is obviously higher than that of a healthy subject.

That is, the results described above demonstrate that pulmonary fibrosis patients cannot be differentiated from healthy subjects by measuring a periostin monomer and/or multimer, but can be differentiated from healthy subjects by measuring a periostin cleavage product.

Example 10

Measurement-1 of Periostin in Human Serum

Periostin in human serum was measured to investigate the effects of the antibodies, the measuring method, the measurement reagents, the method for improving accuracy, and the method of testing for pulmonary fibrosis or interstitial pneumonia of the present invention.

[1] Measurement by a Conventional Technique

Periostin in human serum was measured by a conventional technique as follows.

1. Sample

Samples used were the following human serum (1) to (3).

(1) Serum of pulmonary fibrosis patients (37 patients in total)

(2) Serum of interstitial pneumonia [associated with collagen vascular disease] patients (40 patients in total)

(3) Serum of healthy subjects (66 subjects in total)

2. Measurement

The periostin concentration in each sample was measured and calculated by enzyme immunosorbent assay (ELISA) using anti-periostin monoclonal antibodies as follows.

(1) The "anti-periostin monoclonal antibody (SS18A)" (an antibody recognizing and binding to the R1 region of periostin and recognizing and binding to all of periostin monomer, multimer, and cleavage product) obtained in Example 3 was diluted to 2 µg/mL with phosphate-buffered saline (PBS) [an aqueous solution (pH 7.4) containing 137 mM sodium chloride, 2.68 mM potassium chloride, 1.47 mM potassium dihydrogenphosphate, and 8.04 mM disodium hydrogenphosphate]. The resulting antibody solution was poured in an amount of 100 µL into each well of a 96-well microtiter plate (Thermo Fisher Scientific Inc., IL, USA) and was then left to stand at 25° C. for 18 hours to immobilize "anti-periostin monoclonal antibody (SS18A)" to each well of the microtiter plate.

(2) Subsequently, the solution in each well of the microtiter plate in (1) was removed, and 250 µL of a blocking solution [50 mM tris(hydroxymethyl)aminomethane buffer [Tris buffer] (pH 8.0) containing 0.5% casein, 100 mM sodium chloride, and 0.1% sodium azide] was then poured into each well, followed by leaving to stand at 4° C. for 18 hours.

(3) Subsequently, each well of the microtiter plate in (2) was washed with washing solution-2 [phosphate-buffered saline (PBS) containing 0.05% Tween 20] three times.

(4) Subsequently, the samples (1) to (3) in 1 were each diluted to 200 times with a sample diluent [50 mM tris(hydroxymethyl)aminomethane buffer [Tris buffer] (pH 8.0) containing 0.5% casein, 100 mM sodium chloride, and 0.1% sodium azide], and the resulting sample solutions each in an amount of 100 µL were poured into the respective wells of the microtiter plate in (3), followed by leaving to stand at 25° C. for 18 hours for reaction.

This process allowed periostin contained in the samples to bind to "anti-periostin monoclonal antibody (SS18A)" immobilized to the wells.

(5) Subsequently, each well of the microtiter plate in (4) was washed with washing solution-2 five times.

(6) A peroxidase (POD)-labeled anti-periostin monoclonal antibody prepared by labeling "anti-periostin monoclonal antibody (SS17B)" (an antibody recognizing and binding to the R4 region of periostin and capable of recognizing and binding to periostin monomer and multimer, but not capable of recognizing and binding to periostin cleavage products) obtained in Example 2 with POD was diluted to 50 ng/mL with the sample diluent in (4), and 100 μL of the resulting labeled antibody solution was poured into each well of the microtiter plate in (5), followed by leaving to stand at 25° C. for 90 minutes for reaction.

This process allowed the POD-labeled "anti-periostin monoclonal antibody (SS17B)" to bind to periostin that had bound to the immobilized "anti-periostin monoclonal antibody (SS18A)."

(7) Subsequently, each well of the microtiter plate in (6) was washed with washing solution-2 five times.

(8) Subsequently, 100 μL of a POD substrate solution [20 mM citrate buffer containing 0.8 mM 3,3',5,5'-tetramethylbenzidine (TMBZ), 2.5 mM hydrogen peroxide, and 30 mM disodium hydrogenphosphate] was poured into each well of the microtiter plate in (7), followed by leaving to stand at 25° C. for 10 minutes for reaction of developing a color.

(9) The reaction was then stopped by pouring 0.7 N sulfuric acid into each well of the microtiter plate in (8).

(10) Subsequently, the absorbance at 450 nm of each well of the microtiter plate in (9) was measured with a spectrophotometer.

(11) A dilution series of periostin was prepared by diluting periostin prepared in (1) in Reference Example 1 with the sample diluent in (4) and was used as reference samples.

Periostin in the reference samples was measured in accordance with the description in (1) to (10) to describe a standard curve of "periostin concentration-absorbance" (calibration curve) for enzyme immunosorbent assay (ELISA) using the anti-periostin monoclonal antibodies.

(12) The periostin concentration in each sample was determined from the absorbance of each well of the microtiter plate measured in (10), based on the standard curve of "periostin concentration-absorbance" (calibration curve) described in (11).

[2] Measurement-A by the Present Invention

Periostin in human serum was measured according to the present invention as follows.

1. Sample

Samples used were human serum (1) to (3) in 1 in [1].

2. Measurement

The periostin concentration in each sample was measured in accordance with the description in (1) to (12) of 2 in [1] except that "anti-periostin monoclonal antibody (SS19C)" (an antibody recognizing and binding to the R2 region of periostin and recognizing and binding to all of periostin monomer, multimer, and cleavage product) obtained in Example 4 was used instead of "anti-periostin monoclonal antibody (SS17B)" as the anti-periostin monoclonal antibody labeled with POD in (6) of 2 in [1].

[3] Measurement-B by the Present Invention

Periostin in human serum was measured according to the present invention as follows.

1. Sample

Samples used were human serum (1) to (3) in 1 in [1].

2. Measurement

The periostin concentration in each sample was measured and calculated by enzyme immunosorbentassay (ELISA) using anti-periostin monoclonal antibodies as follows.

(1) "Anti-periostin monoclonal antibody (SS20A)" (an antibody recognizing and binding to the EMI region of periostin and recognizing and binding to all of periostin monomer, multimer, and cleavage product) obtained in Example 5 was diluted to 2 μg/mL with phosphate-buffered saline (PBS) [an aqueous solution (pH 7.4) containing 137 mM sodium chloride, 2.68 mM potassium chloride, 1.47 mM potassium dihydrogenphosphate, and 8.04 mM disodium hydrogenphosphate]. The resulting antibody solution was poured in an amount of 100 μL into each well of a 96-well microtiter plate (Thermo Fisher Scientific Inc., IL, USA) and was then left to stand at 25° C. for 18 hours to immobilize "anti-periostin monoclonal antibody (SS20A)" to each well of the microtiter plate.

(2) Subsequently, the solution in each well of the microtiter plate in (1) was removed, and 250 μL of a blocking solution [50 mM tris(hydroxymethyl)aminomethane buffer [Tris buffer] (pH 8.0) containing 0.5% casein, 100 mM sodium chloride, and 0.1% sodium azide) was then poured into each well, followed by leaving to stand at 4° C. for 18 hours.

(3) Subsequently, each well of the microtiter plate in (2) was washed with washing solution-2 [phosphate-buffered saline (PBS) containing 0.05% Tween 20] three times.

(4) Subsequently, the samples in 1 were each diluted to 200 times with a sample diluent [50 mM tris(hydroxymethyl)aminomethane buffer [Tris buffer] (pH 8.0) containing 0.5% casein, 100 mM sodium chloride, and 0.1% sodium azide), and the resulting sample solutions each in an amount of 100 μL were poured into the respective wells of the microtiter plate in (3), followed by leaving to stand at 25° C. for 18 hours for reaction.

This process allowed periostin contained in the samples to bind to the anti-periostin monoclonal antibody immobilized to the wells.

(5) Subsequently, each well of the microtiter plate in (4) was washed with washing solution-2 five times.

(6) A biotin-labeled anti-periostin monoclonal antibody prepared by labeling "anti-periostin monoclonal antibody (SS19D)" (an antibody recognizing and binding to the R3 region of periostin and capable of recognizing and binding to periostin monomer and cleavage product, but not capable of recognizing and binding to periostin multimers) obtained in Example 4 with biotin was diluted to 50 ng/mL with the sample diluent in (4). The resulting labeled antibody solution was poured in an amount of 100 into each well of the microtiter plate in (5), followed by leaving to stand at 25° C. for 90 minutes for reaction.

This process allowed the biotin-labeled "anti-periostin monoclonal antibody (SS19D)" to bind to periostin that had bound to the immobilized "anti-periostin monoclonal antibody (SS20A)."

(7) Subsequently, each well of the microtiter plate in (6) was washed with washing solution-2 five times.

(8) Streptavidin (Stereospecific Detection Technologies GmbH, Germany) labeled with peroxidase (POD) was diluted to 15000 times with a diluent [50 mM tris(hydroxymethyl)aminomethane buffer [Tris buffer] (pH 8.0) containing 0.5% casein and 100 mM sodium chloride]. The resulting labeled streptavidin solution was poured in an amount of 100 μL into each well of the microtiter plate in (7), followed by leaving to stand at 25° C. for 60 minutes for reaction.

(9) Subsequently, 100 μL of a POD substrate solution [20 mM citrate buffer (pH 3.9) containing 0.8 mM 3,3',5,5'-tetramethylbenzidine (TMBZ), 2.5 mM hydrogen peroxide, and 30 mM disodium hydrogenphosphate] was poured into each well of the microtiter plate in (8), followed by leaving to stand at 25° C. for 10 minutes for reaction of developing a color.

(10) The reaction was then stopped by pouring 0.7 N sulfuric acid into each well of the microtiter plate in (9).

(11) Subsequently, the absorbance at 450 nm of each well of the microtiter plate in (10) was measured with a spectrophotometer.

(12) A dilution series of periostin was prepared by diluting periostin prepared in (1) in Reference Example 1 with the sample diluent in (4) and was used as reference samples.

Periostin in the reference samples was measured in accordance with the description in (1) to (11) to describe a standard curve of "periostin concentration-absorbance" (calibration curve) for enzyme immunosorbentassay (ELISA) using the anti-periostin monoclonal antibodies.

(13) The periostin concentration in each sample was determined from the absorbance of each well of the microtiter plate measured in (11), based on the standard curve of "periostin concentration-absorbance" (calibration curve) described in (12).

Figure 10:
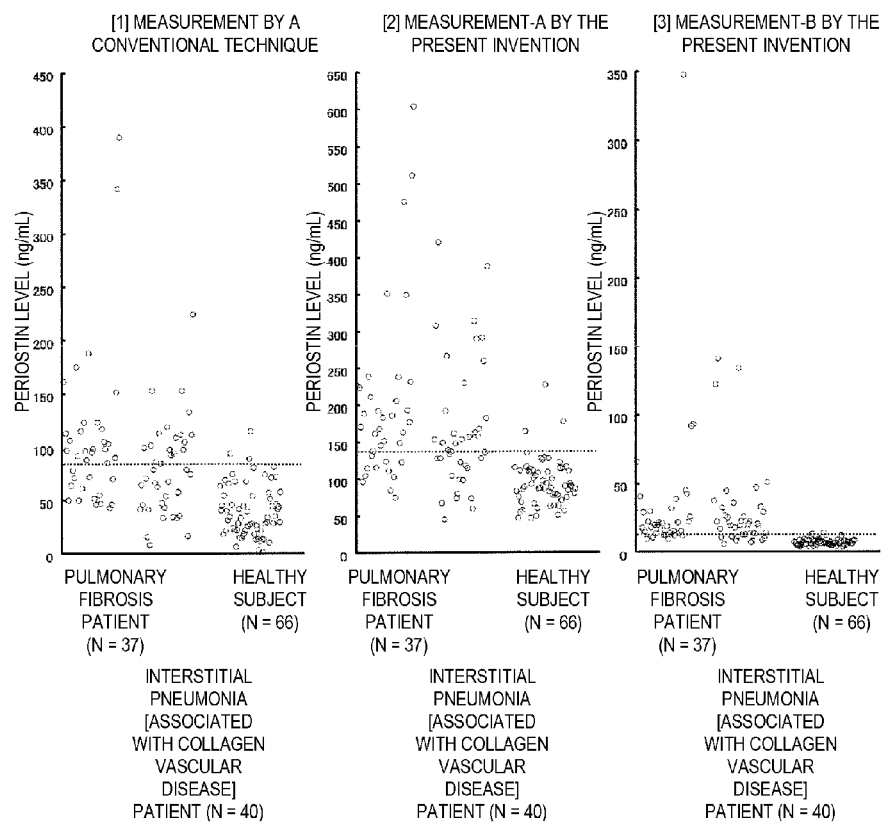
FIG. 10 includes graphs showing the measurement results of periostin in human serum.

[4] Results (1) FIG. 10 shows the measurement results of "Measurement by a conventional technique" in [1], "Measurement-A by the present invention" in [2], and "Measurement-B by the present invention" in [3].

(2) In this figure, the horizontal axis indicates the classification of samples subjected to measurement, and the vertical axis indicates the measured values of concentrations (ng/mL) of periostin in the samples.

The symbol "○" plotted in the figure denotes the measured values of concentration of periostin contained in each sample.

The sensitivity and specificity of each measurement were calculated using a cut-off value of 82 ng/mL in "Measurement by a conventional technique," a cut-off value of 136 ng/mL in "Measurement-A by the present invention," and a cut-off value of 14 ng/mL in "Measurement-B by the present invention."

In the figure, the lines parallel to the horizontal axes denote the cut-off values.

(3) In "Measurement by a conventional technique" in [1], the sensitivity of the measurement was 62.2% when calculated for serum samples of pulmonary fibrosis patients (37 patients in total). The sensitivity of the measurement was 45.0% when calculated for serum samples of interstitial pneumonia [associated with collagen vascular disease] patients (40 patients in total). The calculated specificity of the measurement was 95.5%.

(4) In "Measurement-A by the present invention" in [2], the sensitivity of the measurement was 70.3% when calculated for serum samples of pulmonary fibrosis patients (37 patients in total). The sensitivity of the measurement was 62.5% when calculated for serum samples of interstitial pneumonia [associated with collagen vascular disease] patients (40 patients in total). The calculated specificity of the measurement was 95.5%.

(5) In "Measurement-B by the present invention" in [3], the sensitivity of the measurement was 78.4% when calculated for serum samples of pulmonary fibrosis patients (37 patients in total). The sensitivity of the measurement was 72.5% when calculated for serum samples of interstitial pneumonia [associated with collagen vascular disease] patients (40 patients in total). The calculated specificity of the measurement was 98.5%.

(6) The measurement results above demonstrate that in "Measurement-A by the present invention" in [2] using "anti-periostin monoclonal antibody (SS18A)" recognizing and binding to the R1 region of periostin as a immobilized antibody and "anti-periostin monoclonal antibody (SS19C)" recognizing and binding to the R2 region of periostin as a labeled antibody, the sensitivity of the measurement was improved by 8.1 points in the results of serum samples of pulmonary fibrosis patients (37 patients in total) and by 17.5 points in the results of serum samples of interstitial pneumonia [associated with collagen vascular disease] patients (40 patients in total), compared to "Measurement by a conventional technique" in [1] using "anti-periostin monoclonal antibody (SS18A)" recognizing and binding to the R1 region of periostin as a immobilized antibody and "anti-periostin monoclonal antibody (SS17B)" recognizing and binding to the R4 region of periostin as a labeled antibody.

That is, it was confirmed from the results that in the measurement of periostin according to the present invention using an antibody binding to at least one region selected from the group consisting of the EMI region, the R1 region, the R2 region, and the R3 region of periostin or cleavage products thereof and detecting at least one region selected from the group consisting of the EMI region, the R1 region, the R2 region, and the R3 region of periostin, the sensitivity of the measurement can be improved and the accuracy of the measurement can be improved.

It was also confirmed from the results that in the measurement of periostin according to the present invention using an antibody binding to a periostin cleavage product, the sensitivity of the measurement can be improved and the accuracy of the measurement can be improved.

It was also confirmed from the results that the method of testing for pulmonary fibrosis or interstitial pneumonia according to the present invention can improve the measurement sensitivity, specificity, or the like and can improve the measurement accuracy to give an accurate measurement value of periostin and that the method can improve the differentiation of pulmonary fibrosis or interstitial pneumonia patients from healthy subjects and patients affected with other diseases to prevent wrong diagnosis.

(7) It is also demonstrated from the measurement results that in "Measurement-B by the present invention" in [3] using "anti-periostin monoclonal antibody (SS20A)" recognizing and binding to the EMI region of periostin as a immobilized antibody and "anti-periostin monoclonal antibody (SS19D)" recognizing and binding to the R3 region of periostin as a labeled antibody, the sensitivity of the measurement was improved by 16.2 points in the results of serum samples of pulmonary fibrosis patients (37 patients in total) and by 27.5 points in the results of serum samples of interstitial pneumonia [associated with collagen vascular disease] patients (40 patients in total) and the specificity of the measurement was improved by 3.0 points, compared to "Measurement by a conventional technique" in [1] using "anti-periostin monoclonal antibody (SS18A)" recognizing and binding to the R1 region of periostin as a immobilized antibody and "anti-periostin monoclonal antibody (SS17B)" recognizing and binding to the R4 region of periostin as a labeled antibody.

That is, it was confirmed from the results that in the measurement of periostin according to the present invention using an antibody binding to at least one region selected from the group consisting of the EMI region, the R1 region, the R2 region, and the R3 region of periostin or cleavage products thereof but not binding to periostin multimers and detecting at least one region selected from the group consisting of the EMI region, the R1 region, the R2 region, and the R3 region of periostin, the sensitivity of the measurement can be significantly improved, the specificity of the measurement can be improved, and the accuracy of the measurement can be improved.

It was also confirmed from the results that in the measurement of periostin according to the present invention using an antibody capable of binding to a periostin cleavage product but not binding to periostin multimers, the sensitivity of the measurement can be significantly improved, the specificity of the measurement can be improved, and the accuracy of the measurement can be improved.

It was also confirmed from the results that the method of testing for pulmonary fibrosis or interstitial pneumonia according to the present invention using an antibody capable of binding to a periostin cleavage product but not binding to periostin multimers can significantly improve the measurement sensitivity, specificity, or the like and can improve the measurement accuracy to give an accurate measurement value of periostin and that the method can further improve the differentiation of pulmonary fibrosis or interstitial pneumonia patients from healthy subjects and patients affected with other diseases to prevent wrong diagnosis.

Example 11

ROC Analysis of the Measurement Results of Periostin in Human Serum

Periostin in human serum was measured, and a Receiver Operating Characteristic (ROC) curve of the measurement results was described for analysis.

1. Sample

Samples used were the following human serum (1) and (2).

(1) Positive Sample (77 Samples in Total)

Serum of pulmonary fibrosis patients (37 patients in total) and serum of interstitial pneumonia [associated with collagen vascular disease] patients (40 patients in total) were used as positive samples.

(2) Negative Sample (66 Samples in Total)

Serum of healthy subjects (66 subjects in total) was used as negative samples.

2. Measurement

The periostin concentration in each sample was measured and calculated by enzyme immunosorbentassay (ELISA) using anti-periostin monoclonal antibodies as follows.

(1) Measurement-a by a Conventional Technique (a) "Anti-periostin monoclonal antibody (SS18A)" (an antibody recognizing and binding to the R1 region of periostin and recognizing and binding to all of periostin monomer, multimer, and cleavage product) obtained in Example 3 was diluted to 2 μg/mL with phosphate-buffered saline (PBS) [an aqueous solution (pH 7.4) containing 137 mM sodium chloride, 2.68 mM potassium chloride, 1.47 mM potassium dihydrogenphosphate, and 8.04 mM disodium hydrogenphosphate]. The resulting antibody solution was poured in an amount of 100 μL into each well of a 96-well microtiter plate (Thermo Fisher Scientific Inc., IL, USA) and was then left to stand at 25° C. for 18 hours to immobilize "anti-periostin monoclonal antibody (SS18A)" to each well of the microtiter plate.

(b) Subsequently, the solution in each well of the microtiter plate in (a) was removed, and 250 μL of a blocking solution [50 mM tris(hydroxymethyl)aminomethane buffer [Tris buffer] (pH 8.0) containing 0.5% casein, 100 mM sodium chloride, and 0.1% sodium azide] was then poured into each well, followed by leaving to stand at 4° C. for 18 hours.

(c) Subsequently, each well of the microtiter plate in (b) was washed with washing solution-2 [phosphate-buffered saline (PBS) containing 0.05% Tween 20] three times.

(d) Subsequently, samples (1) and (2) in 1 were each diluted to 200 times with a sample diluent [50 mM tris(hydroxymethyl)aminomethane buffer [Tris buffer] (pH 8.0) containing 0.5% casein, 100 mM sodium chloride, and 0.1% sodium azide], and the resulting sample solutions each in an amount of 100 μL were poured into the respective wells of the microtiter plate in (c), followed by leaving to stand at 25° C. for 18 hours for reaction.

This process allowed periostin contained in the samples to bind to "anti-periostin monoclonal antibody (SS18A)" immobilized to the wells.

(e) Subsequently, each well of the microtiter plate in (d) was washed with washing solution-2 five times.

(f) A biotin-labeled anti-periostin monoclonal antibody prepared by labeling "anti-periostin monoclonal antibody (SS17B)" (an antibody recognizing and binding to the R4 region of periostin and capable of recognizing and binding to periostin monomer and multimer, but not capable of recognizing and binding to periostin cleavage products) obtained in Example 2 with biotin was diluted to 50 ng/mL with the sample diluent in (d). The resulting labeled antibody solution was poured in an amount of 100 μL into each well of the microtiter plate in (e), followed by leaving to stand at 25° C. for 90 minutes for reaction.

This process allowed the biotin-labeled "anti-periostin monoclonal antibody (SS17B)" to bind to periostin that had bound to the immobilized "anti-periostin monoclonal antibody (SS18A)".

(g) Subsequently, each well of the microtiter plate in (f) was washed with washing solution-2 five times.

(h) Streptavidin (Stereospecific Detection Technologies GmbH, Germany) labeled with peroxidase (POD) was diluted to 15000 times with a diluent [50 mM tris(hydroxymethyl)aminomethane buffer [Tris buffer] (pH 8.0) containing 0.5% casein and 100 mM sodium chloride]. The resulting labeled streptavidin solution was poured in an amount of 100 μL into each well of the microtiter plate in (g), followed by leaving to stand at 25° C. for 60 minutes for reaction.

(i) Subsequently, 100 μL of a POD substrate solution [20 mM citrate buffer (pH 3.9) containing 0.8 mM 3,3',5,5'-tetramethylbenzidine (TMBZ), 2.5 mM hydrogen peroxide, and 30 mM disodium hydrogenphosphate] was poured into each well of the microtiter plate in (h), followed by leaving to stand at 25° C. for 10 minutes for reaction of developing a color.

(j) The reaction was then stopped by pouring 0.7 N sulfuric acid into each well of the microtiter plate in (i).

(k) Subsequently, the absorbance at 450 nm of each well of the microtiter plate in (j) was measured with a spectrophotometer.

(l) A dilution series of periostin was prepared by diluting periostin prepared in (1) in Reference Example 1 with the sample diluent in (d) and was used as reference samples.

Periostin in the reference samples was measured in accordance with the description in (a) to (k) to describe a standard curve of "periostin concentration-absorbance" (calibration curve) for enzyme immunosorbentassay (ELISA) using the anti-periostin monoclonal antibodies.

(m) The periostin concentration in each sample was determined from the absorbance of each well of the microtiter plate measured in (k), based on the standard curve of "periostin concentration-absorbance" (calibration curve) described in (l).

(n) Generation of ROC Curve

An ROC curve was described from the measurements of concentrations of periostin in the positive samples (1) in 1 and the negative samples (2) in 1 measured in (m).

In the generation of the ROC curve, the assumed distribution was nonparametric, and the confidence level was set to 95%.

This measurement using "anti-periostin monoclonal antibody (SS18A)" as a immobilized antibody and "anti-periostin monoclonal antibody (SS17B)" as a labeled antibody can measure periostin multimer and monomer, as obvious from the investigation results in Example 8 and FIG. 7.

(2) Measurement-a by the Present Invention

An ROC curve was described by determining the periostin concentration in each sample through measurement and treatment in accordance with the description in (a) to (n) of (1) except that "anti-periostin monoclonal antibody (SS19C)" (an antibody recognizing and binding to the R2 region of periostin and recognizing and binding to all of periostin monomer, multimer, and cleavage product) obtained in Example 4 was used instead of "anti-periostin monoclonal antibody (SS17B)" as the anti-periostin monoclonal antibody labeled with biotin in (f) of (1).

In the generation of the ROC curve, the assumed distribution was nonparametric, and the confidence level was set to 95%.

This measurement using "anti-periostin monoclonal antibody (SS18A)" as a immobilized antibody and "anti-periostin monoclonal antibody (SS19C)" as a labeled antibody can measure periostin multimer, monomer, and cleavage product, as obvious from the investigation results in Example 8 and FIG. 7.

(3) Measurement-b by the Present Invention

An ROC curve was described by determining the periostin concentration in each sample through measurement and treatment in accordance with the description in (a) to (n) of (1) except that "anti-periostin monoclonal antibody (SS20A)" (an antibody recognizing and binding to the EMI region of periostin and recognizing and binding to all of periostin monomer, multimer, and cleavage product) obtained in Example 5 was used instead of "anti-periostin monoclonal antibody (SS18A)" as the anti-periostin monoclonal antibody immobilized to the well of the microtiter plate in (a) of (1) and that "anti-periostin monoclonal antibody (SS19D)" (an antibody recognizing and binding to the R3 region of periostin and capable of recognizing and binding to periostin monomer and cleavage product, but not capable of recognizing and binding to periostin multimers) obtained in Example 4 was used instead of "anti-periostin monoclonal antibody (SS17B)" as the anti-periostin monoclonal antibody labeled with biotin in (f) of (1).

In the generation of the ROC curve, the assumed distribution was nonparametric, and the confidence level was set to 95%.

This measurement using "anti-periostin monoclonal antibody (SS20A)" as a immobilized antibody and "anti-periostin monoclonal antibody (SS19D)" as a labeled antibody can measure periostin monomer and cleavage product, as obvious from the investigation results in Example 8 and FIG. 7.

(4) Measurement-b by a Conventional Technique

An ROC curve was described by determining the periostin concentration in each sample through measurement and treatment in accordance with the description in (a) to (n) of (1) except that "anti-periostin monoclonal antibody (SS19D)" (an antibody recognizing and binding to the R3 region of periostin and capable of recognizing and binding to periostin monomer and cleavage product, but not capable of recognizing and binding to periostin multimers) obtained in Example 4 was used instead of "anti-periostin monoclonal antibody (SS18A)" as the anti-periostin monoclonal antibody immobilized to the well of the microtiter plate in (a) of (1).

In the generation of the ROC curve, the assumed distribution was nonparametric, and the confidence level was set to 95%.

The measurement using "anti-periostin monoclonal antibody (SS19D)" as a immobilized antibody and "anti-periostin monoclonal antibody (SS17B)" as a labeled antibody can measure only a periostin monomer, as obvious from the investigation results in Example 8 and FIG. 7.

(5) Measurement-c by the Present Invention

An ROC curve of a measuring system that can measure only a periostin cleavage product was described by calculation.

Specifically, an ROC curve was described by subtracting the measurement results in "Measurement-b by a conventional technique" in (4) from the measurement results in "Measurement-b by the present invention" in (3). [That is, an ROC curve of a measuring system that can measure only a periostin cleavage product was generated by subtracting the measurement results (those measured only a periostin monomer) in (4) from the measurement results (those measured periostin monomer and cleavage product) in (3).]

Figure 11:
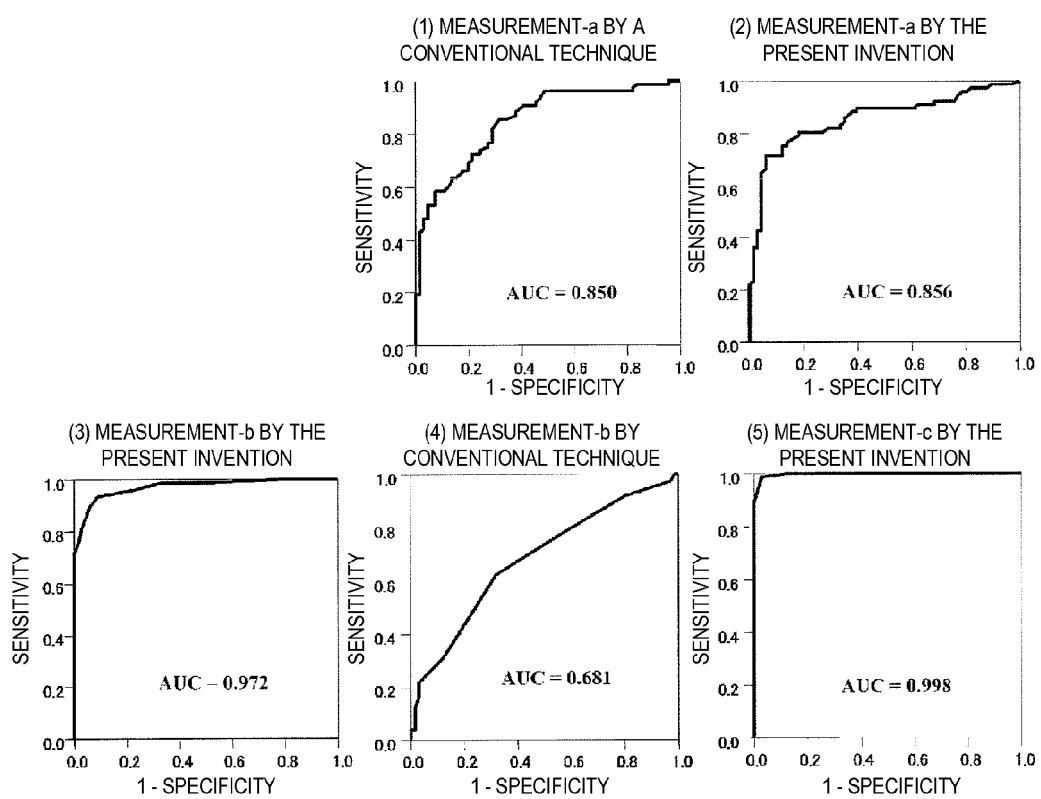
FIG. 11 includes graphs showing the ROC curves of measurement results of periostin in human serum.

3. Results (1) FIG. 11 shows all ROC curves described as described above based on, for example, the measurements results of concentrations of periostin contained in the positive serum samples of pulmonary fibrosis patients and interstitial pneumonia [associated with collagen vascular disease] patients and negative serum samples of healthy subjects.

In the figure, the horizontal axis in each ROC curve indicates the value of "1-specificity" in the measurement, and the vertical axis indicates the "sensitivity" of the measurement.

The "AUC" in each ROC curve in the figure is an abbreviation of Area Under the Curve, and the value thereof denotes the area under the ROC curve. A higher value of the AUC means higher sensitivity and specificity of the measurement, i.e., higher accuracy of the measurement, and is therefore preferred in the measurement.

Each ROC curve will now be described.

(2) In "Measurement-a by a conventional technique" in (1) of 2, i.e., in a measuring system using "anti-periostin monoclonal antibody (SS18A)" recognizing and binding to the R1 region of periostin as a immobilized antibody and "anti-periostin monoclonal antibody (SS17B)" recognizing and binding to the R4 region of periostin as a labeled antibody to detect the R1 region and the R4 region of periostin and capable of measuring periostin multimer and monomer, the AUC value calculated from the ROC curve was 0.850.

(3) In "Measurement-a by the present invention" in (2) of 2, i.e., in a measuring system using "anti-periostin monoclonal antibody (SS18A)" recognizing and binding to the R1 region of periostin as a immobilized antibody and "anti-periostin monoclonal antibody (SS19C)" recognizing and binding to the R2 region of periostin as a labeled antibody to detect the R1 region and the R2 region of periostin and capable of measuring periostin multimer, monomer, and cleavage product, the AUC value calculated from the ROC curve was 0.856.

(4) In "Measurement-b by the present invention" in (3) of 2, i.e., in a measuring system using "anti-periostin monoclonal antibody (SS20A)" recognizing and binding to the EMI region of periostin as a immobilized antibody and "anti-periostin monoclonal antibody (SS19D)" recognizing and binding to the R3 region of periostin as a labeled antibody to detect the EMI region and the R3 region of periostin and capable of measuring periostin monomer and cleavage product, the AUC value calculated from the ROC curve was 0.972.

(5) In "Measurement-b by a conventional technique" in (4) of 2, i.e., in a measuring system using "anti-periostin monoclonal antibody (SS19D)" recognizing and binding to the R3 region of periostin as a immobilized antibody and "anti-periostin monoclonal antibody (SS17B)" recognizing and binding to the R4 region of periostin as a labeled antibody to detect the R3 region and the R4 region of periostin and capable of measuring only a periostin monomer, the AUC value calculated from the ROC curve was 0.681.

(6) In "Measurement-c by the present invention" in (5) of 2, i.e., in a measuring system capable of measuring only a periostin cleavage product by subtracting the measurement results in "Measurement-b by a conventional technique" in (4) of 2 from the measurement results in "Measurement-b by the present invention" in (3) of 2, the AUC value calculated from the ROC curve was 0.998.

(7) The results above demonstrate that in the ROC curve (AUC=0.856) of "Measurement-a by the present invention" in (2) of 2, the ROC curve (AUC=0.972) of "Measurement-b by the present invention" in (3) of 2, and the ROC curve (AUC=0.998) of "Measurement-c by the present invention" in (5) of 2, each detecting at least one region selected from the group consisting of the EMI region, the R1 region, the R2 region, and the R3 region of periostin, i.e., using antibodies binding to periostin cleavage products (i.e., capable of measuring periostin cleavage products), the AUC values were higher than those of the ROC curve (AUC=0.681) of "Measurement-b by a conventional technique" in (4) of 2 and the ROC curve (AUC=0.850) of "Measurement-a by a conventional technique" in (1) of 2, each detecting a region other than "the EMI region, the R1 region, the R2 region, and the R3 region of periostin," i.e., detecting the R4 region and/or the C-terminal region of periostin and not capable of measuring periostin cleavage products. The results therefore demonstrate improvements in the sensitivity and specificity, i.e., the accuracy, of each measurement.

In particular, in the ROC curves of "Measurement-b by the present invention" (AUC=0.972) in (3) of 2 and "Measurement-c by the present invention" (AUC=0.998) in (5) of 2 each using an antibody that binds to a periostin cleavage product and does not bind to periostin multimers (i.e., each capable of measuring a periostin cleavage product, but not capable of measuring periostin multimers), the AUC values were significantly high. This demonstrates significant improvements in the sensitivity and specificity, i.e., the accuracy, of each measurement.

That is, it was confirmed from the results that the method of measuring periostin, the reagent for measuring periostin, and the method for improving accuracy in periostin measurement of the present invention can improve the measurement sensitivity, specificity, or the like and can improve the measurement accuracy.

It was also confirmed from the results that the method of testing for pulmonary fibrosis or interstitial pneumonia of the present invention can improve the measurement sensitivity, specificity, or the like and can improve the measurement accuracy to give an accurate measurement value of periostin and that the method can improve the differentiation of pulmonary fibrosis or interstitial pneumonia patients from healthy subjects and patients affected with other diseases to prevent wrong diagnosis.

Example 12

Measurement-2 of Periostin in Human Serum

The effects of the antibody, the method of measurement, the reagent for measurement, and the method for improving accuracy of the present invention were investigated by measuring periostin in human serum.

1. Sample

Samples used were the following human serum (1) and (2).

(1) Positive Sample (26 Samples in Total)

Serum of pulmonary fibrosis patients (16 patients in total) and serum of interstitial pneumonia [associated with collagen vascular disease] patients (10 patients in total) were used as positive samples.

(2) Negative Sample (54 Samples in Total)

Serum of healthy subjects (54 subjects in total) was used as negative samples.

2. Measurement

The periostin concentration in each sample was measured and calculated by enzyme immunosorbentassay (ELISA) using anti-periostin monoclonal antibodies as follows.

(1) Measurement-1 by a Conventional Technique (a) "Anti-periostin monoclonal antibody (SS18A)" (an antibody recognizing and binding to the R1 region of periostin and recognizing and binding to all of periostin monomer, multimer, and cleavage product) obtained in Example 3 was diluted to 2 µg/mL with phosphate-buffered saline (PBS) [an aqueous solution (pH 7.4) containing 137 mM sodium chloride, 2.68 mM potassium chloride, 1.47 mM potassium dihydrogenphosphate, and 8.04 mM disodium hydrogenphosphate]. The resulting antibody solution was poured in an amount of 100 µL into each well of a 96-well microtiter plate (Thermo Fisher Scientific Inc., IL, USA) and was then left to stand at 25° C. for 18 hours to immobilize "anti-periostin monoclonal antibody (SS18A)" to each well of the microtiter plate.

(b) Subsequently, the solution in each well of the microtiter plate in (a) was removed, and 250 µL of a blocking solution [50 mM tris(hydroxymethyl)aminomethane buffer [Tris buffer] (pH 8.0) containing 0.5% casein, 100 mM sodium chloride, and 0.1% sodium azide] was then poured into each well, followed by leaving to stand at 4° C. for 18 hours.

(c) Subsequently, each well of the microtiter plate in (b) was washed with washing solution-2 [phosphate-buffered saline (PBS) containing 0.05% Tween 20] three times.

(d) Subsequently, the samples (1) and (2) in 1 were each diluted to 200 times with a sample diluent [50 mM tris(hydroxymethyl)aminomethane buffer [Tris buffer] (pH 8.0) containing 0.5% casein, 100 mM sodium chloride, and 0.1% sodium azide]. The resulting sample solutions each in an amount of 100 µL were poured into the respective wells of the microtiter plate in (c), followed by leaving to stand at 25° C. for 18 hours for reaction.

This process allowed periostin contained in each sample to bind to "anti-periostin monoclonal antibody (SS18A)" immobilized to the wells.

(e) Subsequently, each well of the microtiter plate in (d) was washed with washing solution-2 five times.

(f) "Anti-periostin monoclonal antibody (SS17B)" (an antibody recognizing and binding to the R4 region of periostin and capable of recognizing and binding to periostin monomer and multimer, but not capable of recognizing and binding to periostin cleavage products) obtained in Example 2 was labeled with biotin. The biotin-labeled anti-periostin monoclonal antibody was diluted to 50 ng/mL with the sample diluent in (d), and 100 µL of the resulting labeled antibody solution was poured into each well of the microtiter plate in (e), followed by leaving to stand at 25° C. for 90 minutes for reaction.

This process allowed the biotin-labeled "anti-periostin monoclonal antibody (SS17B) to bind to periostin that had bound to the immobilized "anti-periostin monoclonal antibody (SS18A)."

(g) Subsequently, each well of the microtiter plate in (f) was washed with washing solution-2 five times.

(h) Streptavidin (Stereospecific Detection Technologies GmbH, Germany) labeled with peroxidase (POD) was diluted to 15000 times with a diluent [50 mM tris(hydroxymethyl)aminomethane buffer [Tris buffer] (pH 8.0) containing 0.5% casein and 100 mM sodium chloride]. The resulting labeled streptavidin solution was poured in an amount of 100 μL into each well of the microtiter plate in (g), followed by leaving to stand at 25° C. for 60 minutes for reaction.

(i) Subsequently, 100 μL of a POD substrate solution [20 mM citrate buffer (pH 3.9) containing 0.8 mM 3,3',5,5'-tetramethylbenzidine (TMBZ), 2.5 mM hydrogen peroxide, and 30 mM disodium hydrogenphosphate] was poured into each well of the microtiter plate in (h), followed by leaving to stand at 25° C. for 10 minutes for reaction of developing a color.

(j) The reaction was then stopped by pouring 0.7 N sulfuric acid into each well of the microtiter plate in (i).

(k) Subsequently, the absorbance at 450 nm of each well of the microtiter plate in (j) was measured with a spectrophotometer.

(l) A dilution series of periostin was prepared by diluting periostin prepared in (1) in Reference Example 1 with the sample diluent in (d) and was used as reference samples.

Periostin in the reference samples was measured in accordance with the description in (a) to (k) to describe a standard curve of "periostin concentration-absorbance" (calibration curve) for enzyme immunosorbentassay (ELISA) using the anti-periostin monoclonal antibodies.

(m) The concentration of periostin contained in each sample was determined from the absorbance of each well of the microtiter plate measured in (k), based on the standard curve of "periostin concentration-absorbance" (calibration curve) described in (l).

This measurement using "anti-periostin monoclonal antibody (SS18A)" as a immobilized antibody and "anti-periostin monoclonal antibody (SS17B)" as a labeled antibody can measure periostin multimer and monomer, as obvious from the investigation results in Example 8 and FIG. 7.

(2) Measurement-1 by the Present Invention

The periostin concentration in each sample was determined through measurement and treatment in accordance with the description in (a) to (m) of (1) except that "anti-periostin monoclonal antibody (SS19C)" (an antibody recognizing and binding to the R2 region of periostin and recognizing and binding to all of periostin monomer, multimer, and cleavage product) obtained in Example 4 was used instead of "anti-periostin monoclonal antibody (SS17B)" as the anti-periostin monoclonal antibody labeled with biotin in (f) of (1).

This measurement using "anti-periostin monoclonal antibody (SS18A)" as a immobilized antibody and "anti-periostin monoclonal antibody (SS19C)" as a labeled antibody can measure periostin multimer, monomer, and cleavage product, as obvious from the investigation results in Example 8 and FIG. 7.

(3) Measurement-2 by the Present Invention

The periostin concentration in each sample was determined through measurement and treatment in accordance with the description in (a) to (m) of (1) except that "anti-periostin monoclonal antibody (SS20A)" (an antibody recognizing and binding to the EMI region of periostin and recognizing and binding to all of periostin monomer, multimer, and cleavage product) obtained in Example 5 was used instead of "anti-periostin monoclonal antibody (SS18A)" as the anti-periostin monoclonal antibody immobilized to the wells of the microtiter plate in (a) of (1) and that "anti-periostin monoclonal antibody (SS19D)" (an antibody recognizing and binding to the R3 region of periostin and capable of recognizing and binding to periostin monomer and cleavage product, but not capable of recognizing and binding to periostin multimers) obtained in Example 4 was used instead of "anti-periostin monoclonal antibody (SS17B)" as the anti-periostin monoclonal antibody labeled with biotin in (f) of (1).

This measurement using "anti-periostin monoclonal antibody (SS20A)" as a immobilized antibody and "anti-periostin monoclonal antibody (SS19D)" as a labeled antibody can measure periostin monomer and cleavage product, as obvious from the investigation results in Example 8 and FIG. 7.

(4) Measurement-2 by a Conventional Technique

The periostin concentration in each sample was determined through measurement and treatment in accordance with the description in (a) to (m) of (1) except that "anti-periostin monoclonal antibody (SS19D)" (an antibody recognizing and binding to the R3 region of periostin and capable of recognizing and binding to periostin monomer and cleavage product, but not capable of recognizing and binding to periostin multimers) obtained in Example 4 was used instead of "anti-periostin monoclonal antibody (SS18A)" as the anti-periostin monoclonal antibody immobilized to the wells of the microtiter plate in (a) of (1).

This measurement using "anti-periostin monoclonal antibody (SS19D)" as a immobilized antibody and "anti-periostin monoclonal antibody (SS17B)" as a labeled antibody can measure only a periostin monomer, as obvious from the investigation results in Example 8 and FIG. 7.

(5) Measurement-3 by a Conventional Technique

The periostin concentration in each sample was determined through measurement and treatment in accordance with the description in (a) to (m) of (1) except that "anti-periostin monoclonal antibody (SS19D)" (an antibody recognizing and binding to the R3 region of periostin and capable of recognizing and binding to periostin monomer and cleavage product, but not capable of recognizing and binding to periostin multimers) obtained in Example 4 was used instead of "anti-periostin monoclonal antibody (SS18A)" as the anti-periostin monoclonal antibody immobilized to the wells of the microtiter plate in (a) of (1) and that "anti-periostin monoclonal antibody (SS19A)" (an antibody recognizing and binding to the R4 region of periostin and capable of recognizing and binding to periostin monomer and multimer, but not capable of recognizing and binding to periostin cleavage products) obtained in Example 4 was used instead of "anti-periostin monoclonal antibody (SS17B)" as the anti-periostin monoclonal antibody labeled with biotin in (f) of (1).

This measurement using "anti-periostin monoclonal antibody (SS19D)" as a immobilized antibody and "anti-periostin monoclonal antibody (SS19A)" as a labeled antibody can measure only a periostin monomer, as obvious from the investigation results in Example 8 and FIG. 7.

(6) Measurement-4 by a Conventional Technique

The periostin concentration in each sample was determined through measurement and treatment in accordance with the description in (a) to (m) of (1) except that "anti-periostin monoclonal antibody (SS19D)" (an antibody recognizing and binding to the R3 region of periostin and capable of recognizing and binding to periostin monomer and cleavage product, but not capable of recognizing and binding to periostin multimers) obtained in Example 4 was used instead of "anti-periostin monoclonal antibody (SS18A)" as the anti-periostin monoclonal antibody immobilized to the wells of the microtiter plate in (a) of (1) and that "anti-periostin monoclonal antibody (SS21A)" (an antibody recognizing and binding to the C-terminal region of periostin and capable of recognizing and binding to periostin monomer and multimer, but not capable of recognizing and binding to periostin cleavage products) obtained in Example 6 was used instead of "anti-periostin monoclonal antibody (SS17B)" as the anti-periostin monoclonal antibody labeled with biotin in (f) of (1).

This measurement using "anti-periostin monoclonal antibody (SS19D)" as a immobilized antibody and "anti-periostin monoclonal antibody (SS21A)" as a labeled antibody can measure only a periostin monomer, as obvious from the investigation results in Example 8 and FIG. 7.

(7) Measurement-3 by the Present Invention

The periostin concentration in each sample was determined through measurement and treatment in accordance with the description in (a) to (m) of (1) except that "anti-periostin monoclonal antibody (SS19D)" (an antibody recognizing and binding to the R3 region of periostin and capable of recognizing and binding to periostin monomer and cleavage product, but not capable of recognizing and binding to periostin multimers) obtained in Example 4 was used instead of "anti-periostin monoclonal antibody (SS18A)" as the anti-periostin monoclonal antibody immobilized to the wells of the microtiter plate in (a) of (1) and that "anti-periostin monoclonal antibody (SS20A)" (an antibody recognizing and binding to the EMI region of periostin and recognizing and binding to all of periostin monomer, multimer, and cleavage product) obtained in Example 5 was used instead of "anti-periostin monoclonal antibody (SS17B)" as the anti-periostin monoclonal antibody labeled with biotin in (f) of (1).

This measurement using "anti-periostin monoclonal antibody (SS19D)" as a immobilized antibody and "anti-periostin monoclonal antibody (SS20A)" as a labeled antibody can measure periostin monomer and cleavage product, as obvious from the investigation results in Example 8 and FIG. 7.

(8) Measurement-4 by the Present Invention

The periostin concentration in each sample was determined through measurement and treatment in accordance with the description in (a) to (m) of (1) except that "anti-periostin monoclonal antibody (SS16A)" (an antibody recognizing and binding to the R3 region of periostin and recognizing and binding to all of periostin monomer, multimer, and cleavage product) obtained in Example 1 was used instead of "anti-periostin monoclonal antibody (SS18A)" as the anti-periostin monoclonal antibody immobilized to the wells of the microtiter plate in (a) of (1) and that "anti-periostin monoclonal antibody (SS18A)" (an antibody recognizing and binding to the R1 region of periostin and recognizing and binding to all of periostin monomer, multimer, and cleavage product) obtained in Example 3 was used instead of "anti-periostin monoclonal antibody (SS17B)" as the anti-periostin monoclonal antibody labeled with biotin in (f) of (1).

This measurement using "anti-periostin monoclonal antibody (SS16A)" as a immobilized antibody and "anti-periostin monoclonal antibody (SS18A)" as a labeled antibody can measure periostin multimer, monomer, and cleavage product, as obvious from the investigation results in Example 8 and FIG. 7.

(9) Measurement-5 by a Conventional Technique

The periostin concentration in each sample was determined through measurement and treatment in accordance with the description in (a) to (m) of (1) except that "anti-periostin monoclonal antibody (SS19B)" (an antibody recognizing and binding to the C-terminal region of periostin and capable of recognizing and binding to periostin monomer and multimer, but not capable of recognizing and binding to periostin cleavage products) obtained in Example 4 was used instead of "anti-periostin monoclonal antibody (SS18A)" as the anti-periostin monoclonal antibody immobilized to the wells of the microtiter plate in (a) of (1).

This measurement using "anti-periostin monoclonal antibody (SS19B)" as a immobilized antibody and "anti-periostin monoclonal antibody (SS17B)" as a labeled antibody can measure periostin multimer and monomer, as obvious from the investigation results in Example 8 and FIG. 7.

(10) Measurement-5 by the Present Invention

The periostin concentration in each sample was determined through measurement and treatment in accordance with the description in (a) to (m) of (1) except that "anti-periostin monoclonal antibody (SS19C)" (an antibody recognizing and binding to the R2 region of periostin and recognizing and binding to all of periostin monomer, multimer, and cleavage product) obtained in Example 4 was used instead of "anti-periostin monoclonal antibody (SS18A)" as the anti-periostin monoclonal antibody immobilized to the wells of the microtiter plate in (a) of (1) and that "anti-periostin monoclonal antibody (SS19D)" (an antibody recognizing and binding to the R3 region of periostin and capable of recognizing and binding to periostin monomer and cleavage product, but not capable of recognizing and binding to periostin multimers) obtained in Example 4 was used instead of "anti-periostin monoclonal antibody (SS17B)" as the anti-periostin monoclonal antibody labeled with biotin in (f) of (1).

This measurement using "anti-periostin monoclonal antibody (SS19C)" as a immobilized antibody and "anti-periostin monoclonal antibody (SS19D)" as a labeled antibody can measure periostin monomer and cleavage product, as obvious from the investigation results in Example 8 and FIG. 7.

(11) Measurement-6 by the Present Invention

The periostin concentration in each sample was determined through measurement and treatment in accordance with the description in (a) to (m) of (1) except that "anti-periostin monoclonal antibody (SS20A)" (an antibody recognizing and binding to the EMI region of periostin and recognizing and binding to all of periostin monomer, multimer, and cleavage product) obtained in Example 5 was used instead of "anti-periostin monoclonal antibody (SS18A)" as the anti-periostin monoclonal antibody immobilized to the wells of the microtiter plate in (a) of (1) and that "anti-periostin monoclonal antibody (SS19C)" (an antibody recognizing and binding to the R2 region of periostin and recognizing and binding to all of periostin monomer, multimer, and cleavage product) obtained in Example 4 was used instead of "anti-periostin monoclonal antibody (SS17B)" as the anti-periostin monoclonal antibody labeled with biotin in (f) of (1).

This measurement using "anti-periostin monoclonal antibody (SS20A)" as a immobilized antibody and "anti-periostin monoclonal antibody (SS19C)" as a labeled antibody can measure periostin multimer, monomer, and cleavage product, as obvious from the investigation results in Example 8 and FIG. 7.

(12) Measurement-6 by a Conventional Technique

The periostin concentration in each sample was determined through measurement and treatment in accordance with the description in (a) to (m) of (1) except that "anti-periostin monoclonal antibody (SS20A)" (an antibody recognizing and binding to the EMI region of periostin and recognizing and binding to all of periostin monomer, multimer, and cleavage product) obtained in Example 5 was used instead of "anti-periostin monoclonal antibody (SS18A)" as the anti-periostin monoclonal antibody immobilized to the wells of the microtiter plate in (a) of (1) and that "anti-periostin monoclonal antibody (SS21A)" (an antibody recognizing and binding to the C-terminal region of periostin and capable of recognizing and binding to periostin monomer and multimer, but not capable of recognizing and binding to periostin cleavage products) obtained in Example 6 was used instead of "anti-periostin monoclonal antibody (SS17B)" as the anti-periostin monoclonal antibody labeled with biotin in (f) of (1).

This measurement using "anti-periostin monoclonal antibody (SS20A)" as a immobilized antibody and "anti-periostin monoclonal antibody (SS21A)" as a labeled antibody can measure periostin multimer and monomer, as obvious from the investigation results in Example 8 and FIG. 7.

(13) Measurement-7 by a Conventional Technique

The periostin concentration in each sample was determined through measurement and treatment in accordance with the description in (a) to (m) of (1) except that "anti-periostin monoclonal antibody (SS21A)" (an antibody recognizing and binding to the C-terminal region of periostin and capable of recognizing and binding to periostin monomer and multimer, but not capable of recognizing and binding to periostin cleavage products) obtained in Example 6 was used instead of "anti-periostin monoclonal antibody (SS17B)" as the anti-periostin monoclonal antibody labeled with biotin in (f) of (1).

This measurement using "anti-periostin monoclonal antibody (SS18A)" as a immobilized antibody and "anti-periostin monoclonal antibody (SS21A)" as a labeled antibody can measure periostin multimer and monomer, as obvious from the investigation results in Example 8 and FIG. 7.

Figure 12:
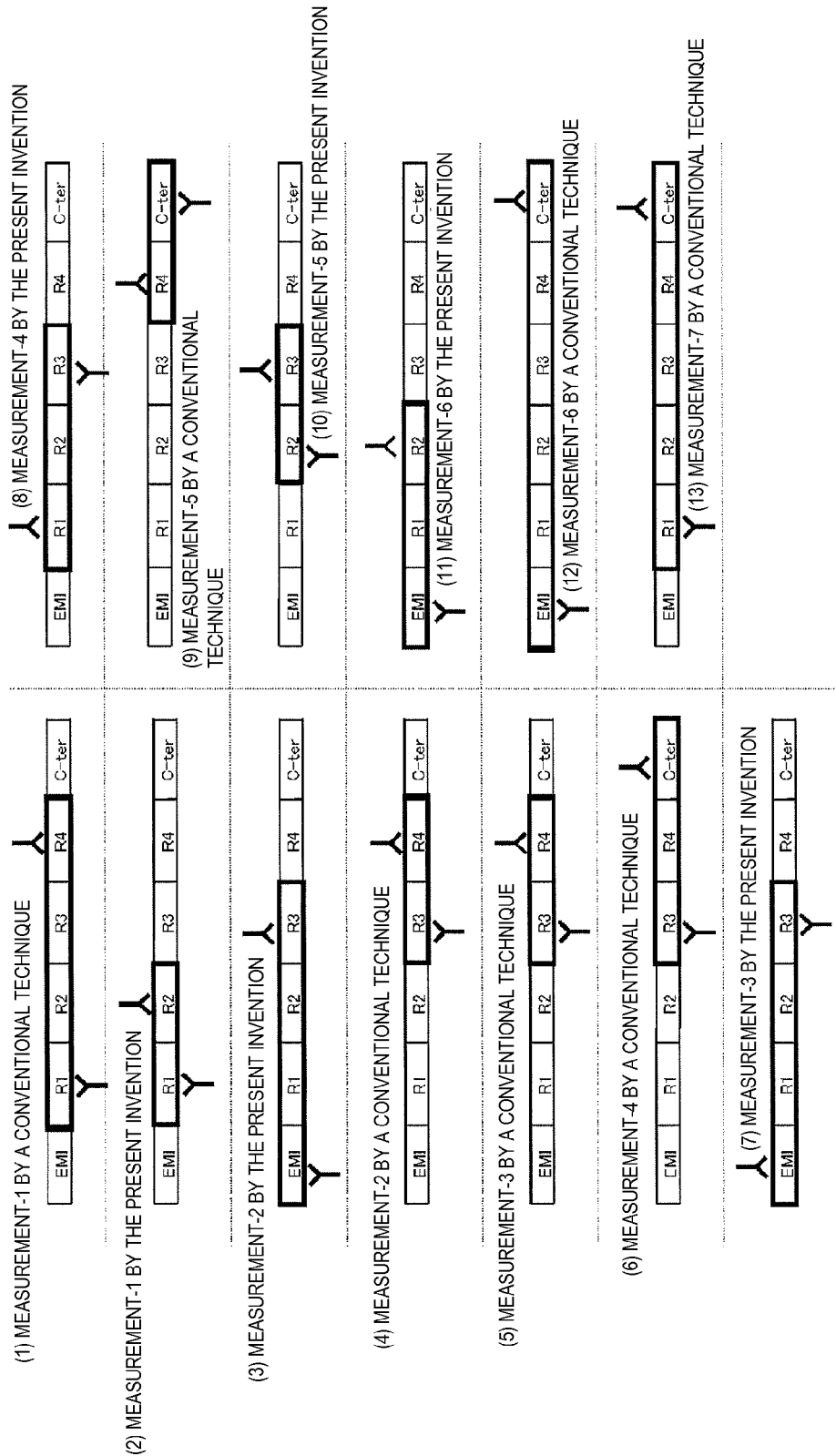
FIG. 12 includes diagrams schematically illustrating, for example, for which regions of periostin the immobilized antibody and the labeled antibody used in measurement of periostin in human serum recognize.

(14) FIG. 12 schematically shows periostin regions which the immobilized antibody and the labeled antibody used in each of measurements (1) to (13) of periostin recognize and bind to (that is, the periostin regions detected by each measurement) and further shows the periostin fragment recognized in each measurement.

In this schematic diagram, "EMI," "R1," "R2," "R3," "R4," and "C-ter" respectively denote the EMI region, the R1 region, the R2 region, the R3 region, the R4 region, and the C-terminal region of periostin.

In this schematic diagram, the region with the lower symbol "Y" indicates the region of periostin recognized and bound (i.e., detected) by the immobilized antibody used in measurement, and the region with the upper symbol "Y" indicates the region of periostin recognized and bound (i.e., detected) by the labeled antibody used in measurement.

In this schematic diagram, the region surrounded with the bold line recognized and bound (i.e., detected) by the immobilized antibody and the region recognized and bound (i.e., detected) by the labeled antibody and the regions lying therebetween.

Figure 13:
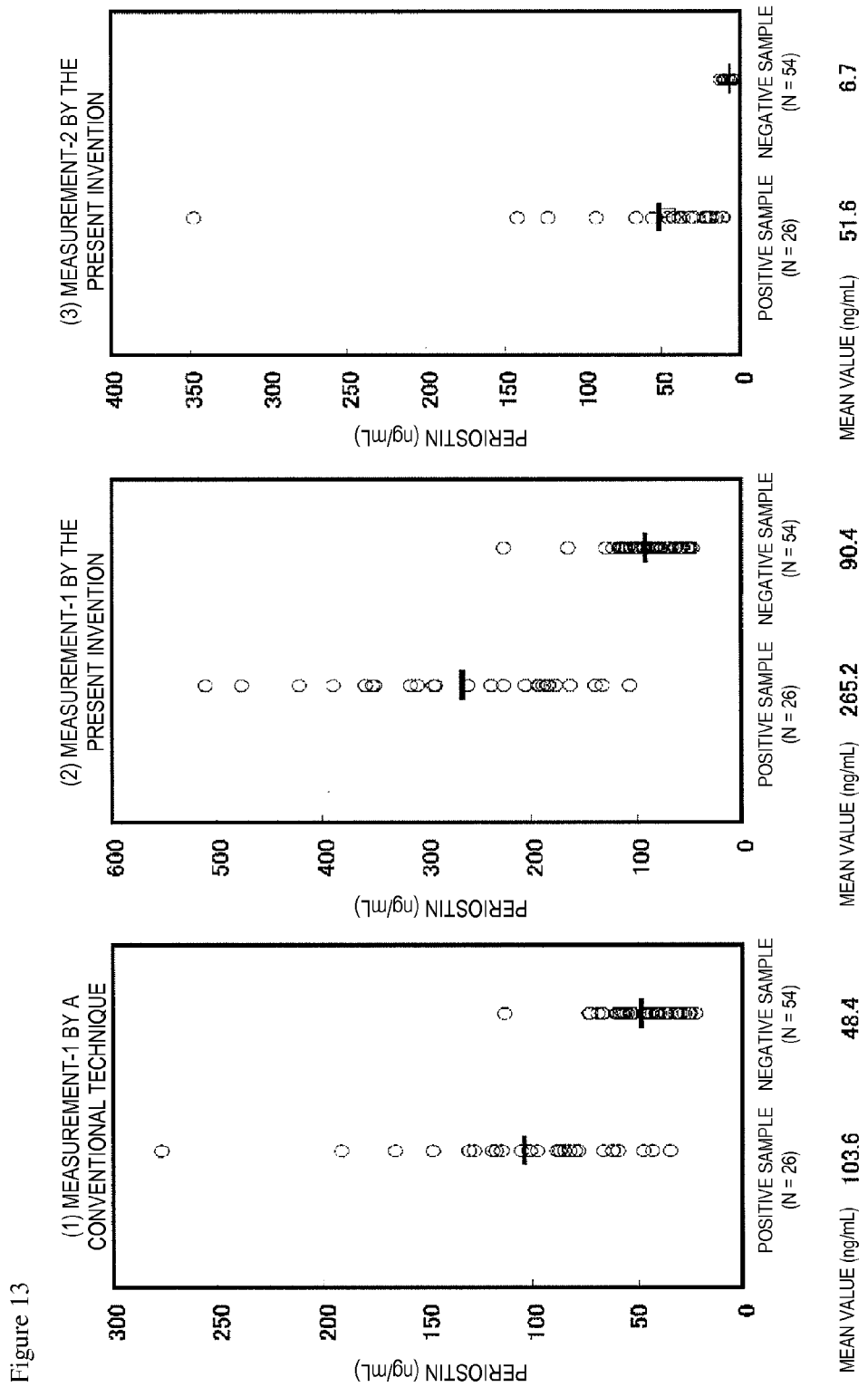
FIG. 13 includes graphs showing the measurement results of periostin in human serum.
Figure 14:
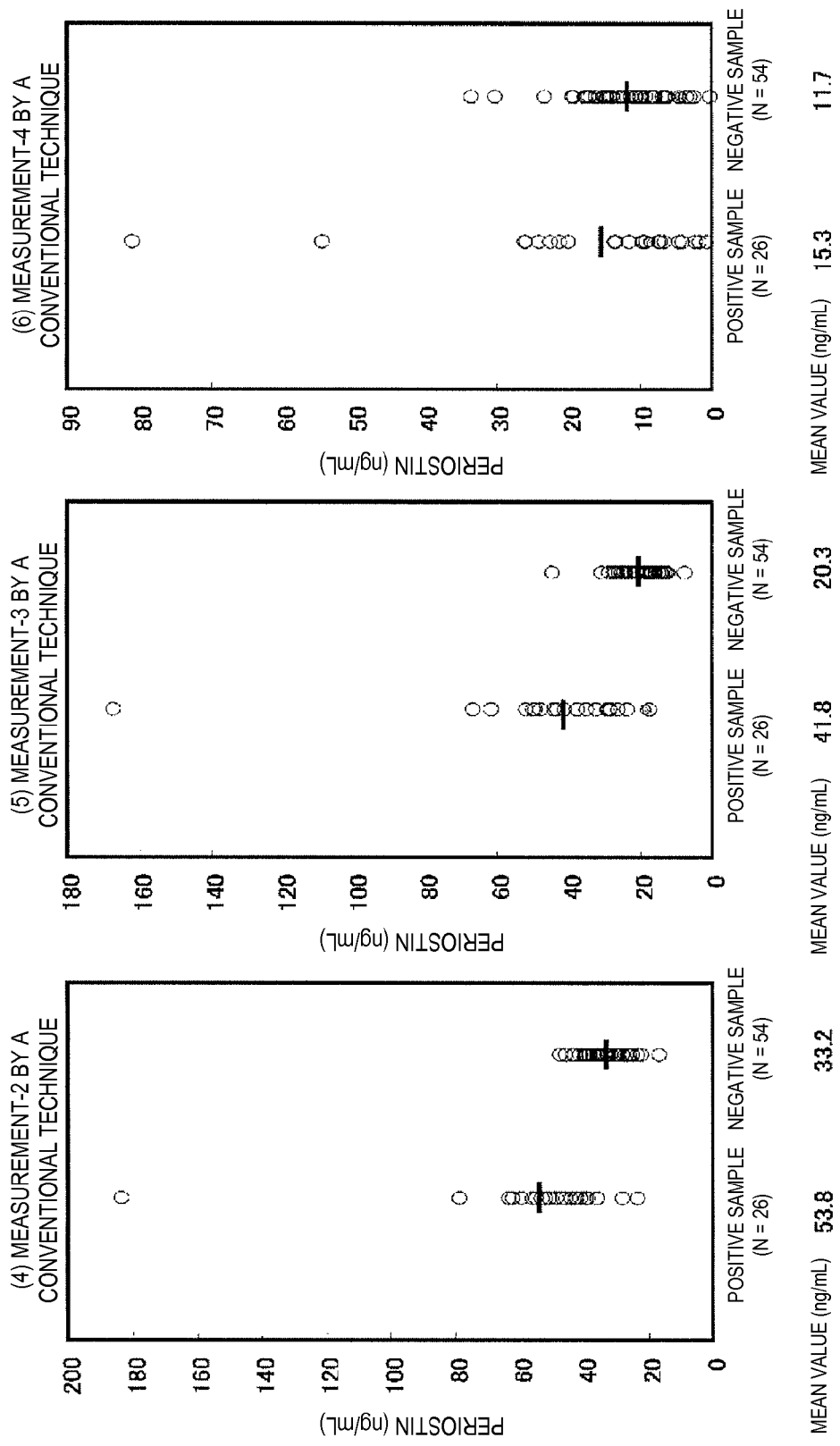
FIG. 14 includes graphs showing the measurement results of periostin in human serum.
Figure 15:
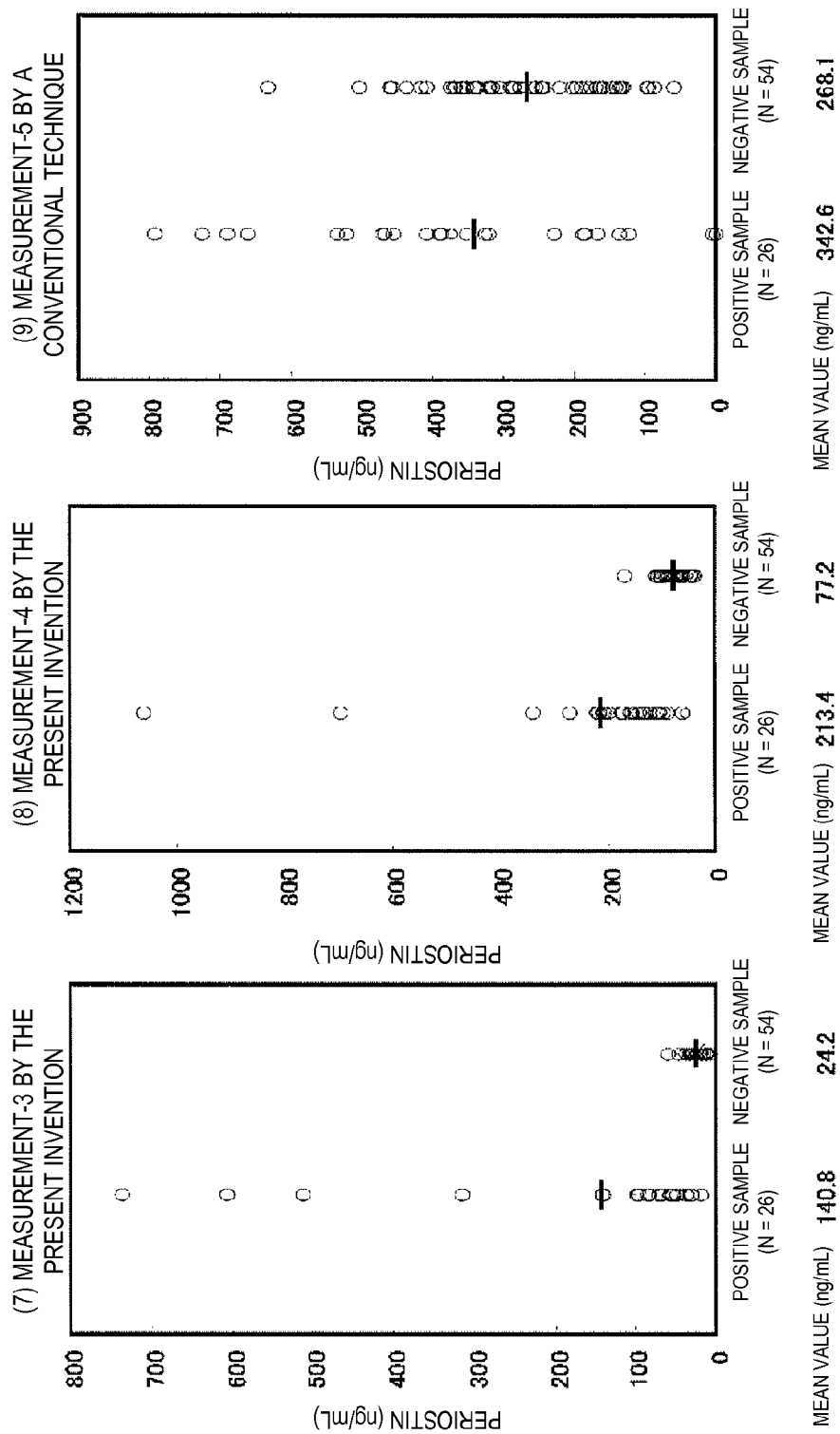
FIG. 15 includes graphs showing the measurement results of periostin in human serum.
Figure 16:
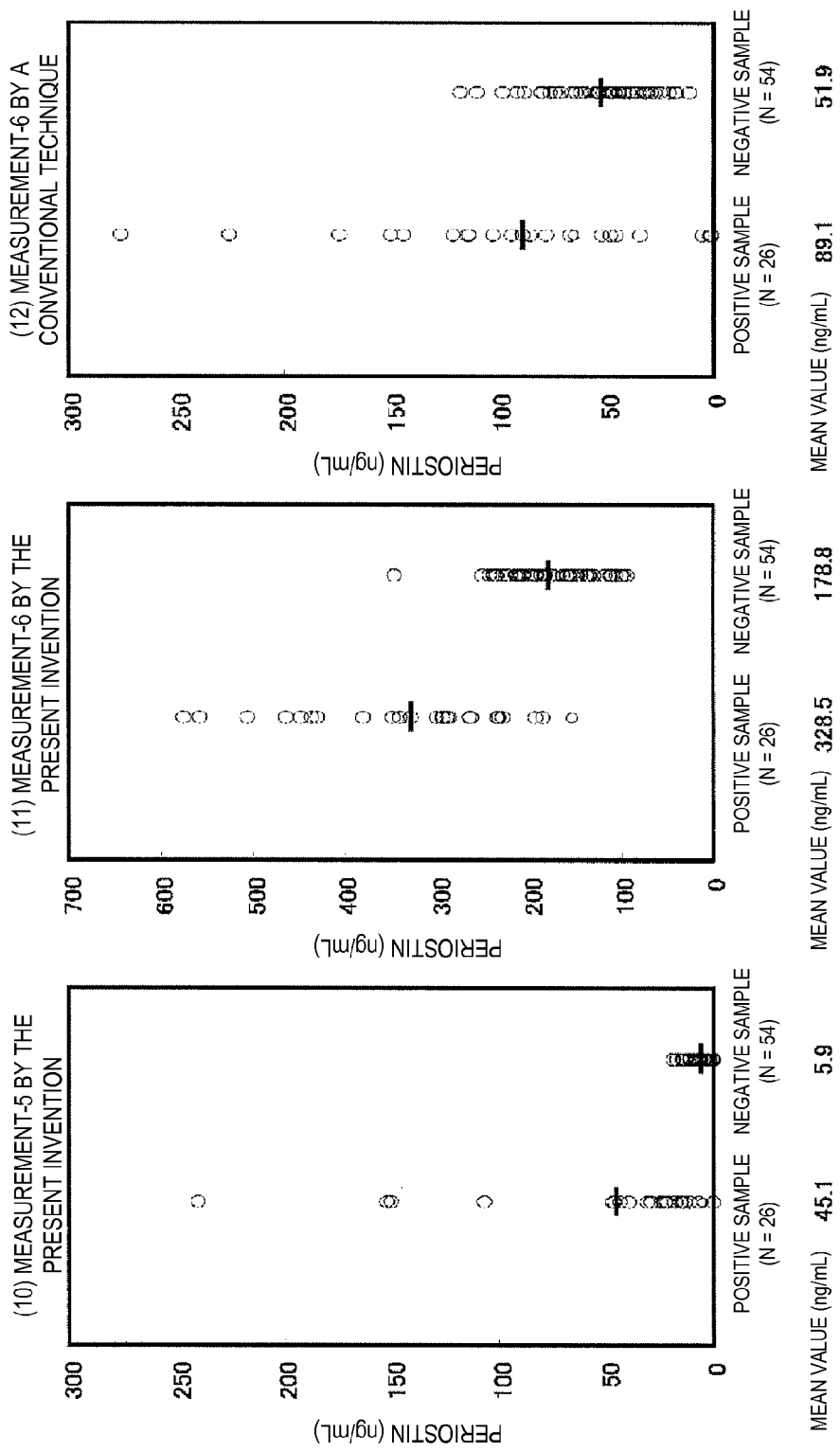
FIG. 16 includes graphs showing the measurement results of periostin in human serum.
Figure 17:
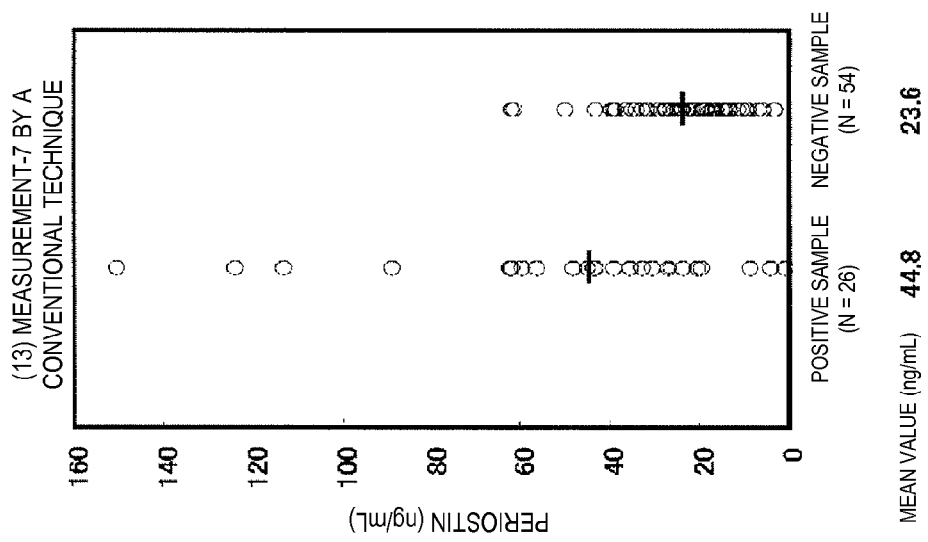
FIG. 17 is a graph showing the measurement results of periostin in human serum.
Figure 19:
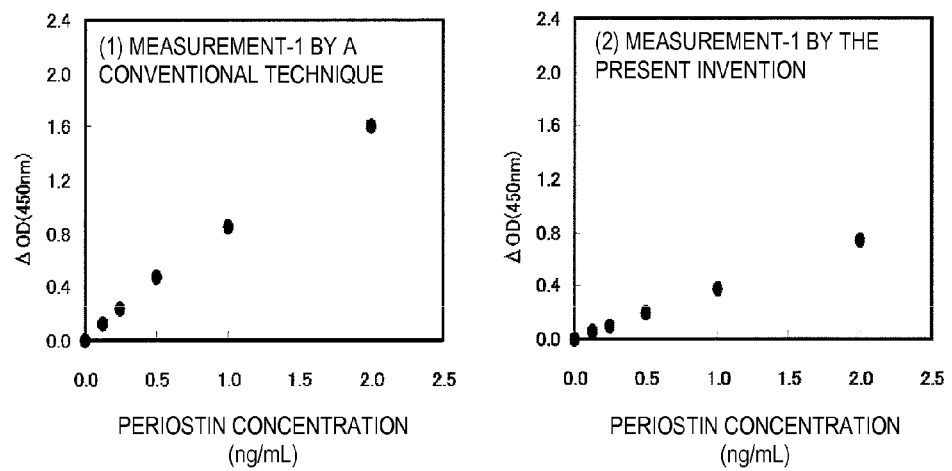
FIG. 19 includes graphs showing calibration curves for measuring periostin in a sample.
Figure 20:
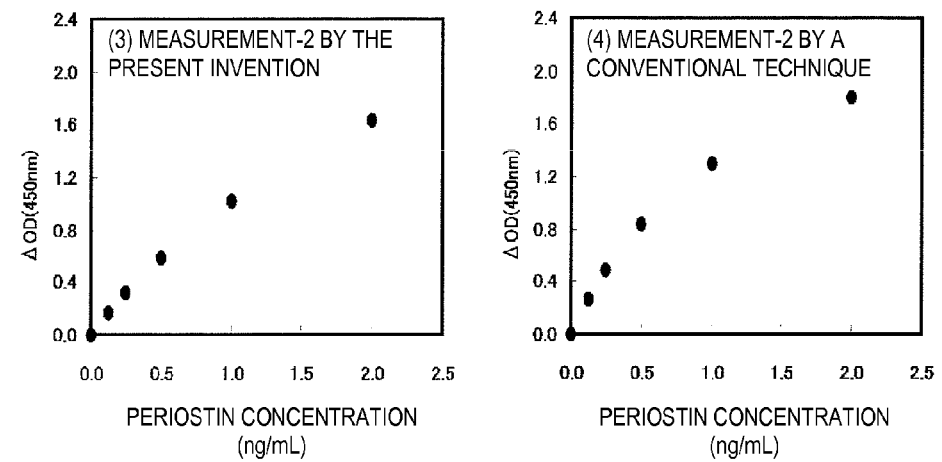
FIG. 20 includes graphs showing calibration curves for measuring periostin in a sample.
Figure 21:
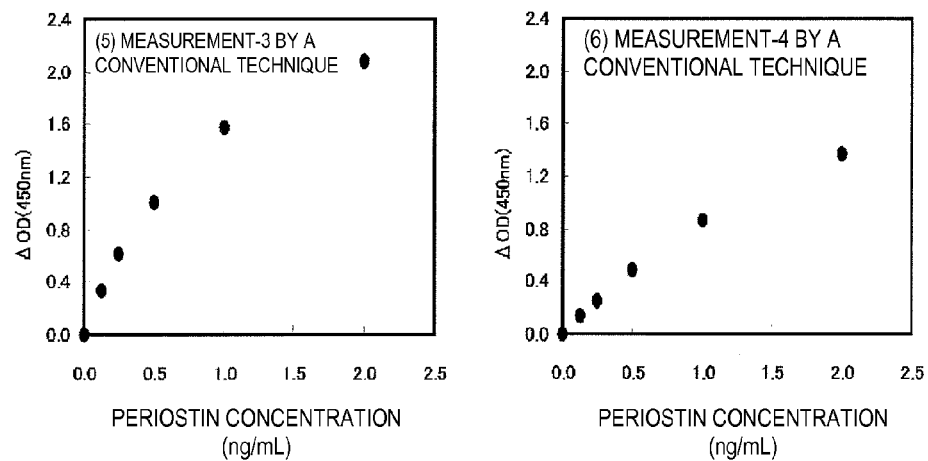
FIG. 21 includes graphs showing calibration curves for measuring periostin in a sample.
Figure 22:
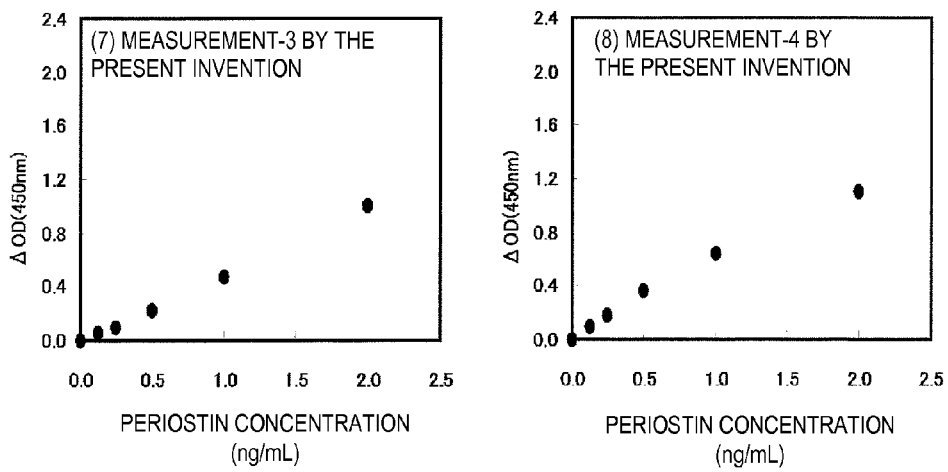
FIG. 22 includes graphs showing calibration curves for measuring periostin in a sample.
Figure 23:
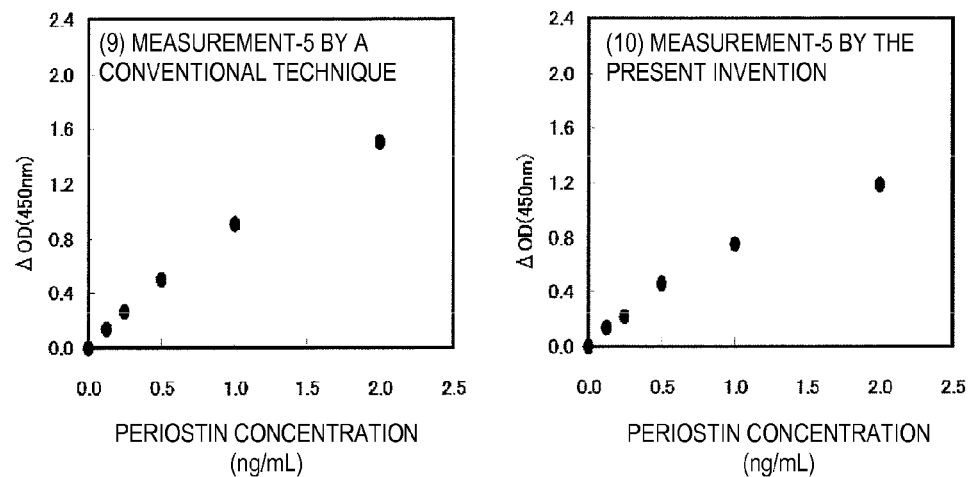
FIG. 23 includes graphs showing calibration curves for measuring periostin in a sample.
Figure 24:
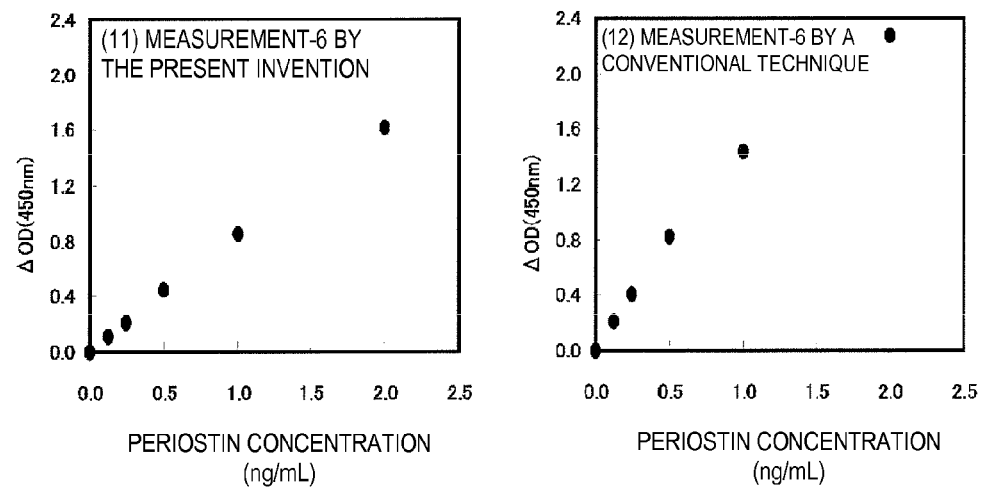
FIG. 24 includes graphs showing calibration curves for measuring periostin in a sample.
Figure 25:
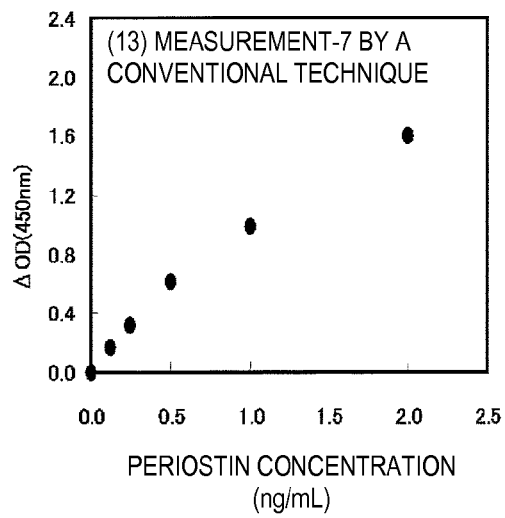
FIG. 25 is a graph showing a calibration curve for measuring periostin in a sample.

3. Results (1) FIG. 13 shows the results of measurements (1) to (3) in 2; FIG. 14 shows the results of measurements (4) to (6) in 2; FIG. 15 shows the results of measurements (7) to (9) in 2; FIG. 16 shows the results of measurements (10) to (12) in 2; and FIG. 17 shows the results of measurement (13) in 2.

In these figures, the horizontal axis indicates the classification of samples subjected to measurement, and the vertical axis indicates the measurements of concentrations (ng/mL) of periostin in the samples.

The symbol "○" plotted in the figures denotes the concentration of periostin contained in each sample.

The mean value (ng/mL) of the measurements of concentrations of periostin contained in the samples is shown at the bottom of each figure.

In calculation of the sensitivity and specificity of each measurement, the cut-off value was set to a concentration that gives a specificity higher than 98% and a highest sensitivity.

In these figures, the lines parallel to the horizontal axes denote the levels of mean values (ng/mL) of the measurements of concentrations of periostin contained in the samples.

(2) FIG. 18 summarizes the measurements (1) to (13) in 2 regarding the immobilized antibody and labeled antibody used in each measurement, the periostin region detected by the immobilized antibody, the periostin region detected by the labeled antibody, the type or types (monomer and/or multimer and/or cleavage product) of periostin measured by the measurement, the sensitivity of the measurement, the specificity of the measurement, the ratio of the mean value of the measured values of positive samples to the mean value of the measured values of negative samples ("the mean value of the measured values of positive samples"/"the mean value of the measured values of negative samples," i.e., the degree of increase in measured values of positive samples relative to those of negative samples), and "the AUC value of the described ROC curve."

(3) FIGS. 13 to 18 demonstrate the followings.

In the cases of not detecting any of the EMI region, the R1 region, the R2 region, and the R3 region of periostin by using an antibody other than "antibodies binding to at least one region selected from the group consisting of the EMI region, the R1 region, the R2 region, and the R3 region of periostin or cleavage products thereof," that is, when periostin cleavage products could not be measured [the cases of measurements (1), (4), (5), (6), (9), (12), and (13) in 2], "the sensitivity of measurement" was 7.7% to 61.5% (mean value: 35.7%); "the specificity of measurement" was 98.1%; "the ratio of the mean value of the measured values of positive samples to the mean value of the measured values of negative samples" ("the mean value of the measured values of positive samples"/"the mean value of the measured values of negative samples," i.e., the degree of increase in measured values of positive samples relative to those of negative samples) was 1.3 to 2.1 times (mean value: 1.7 times); and "the AUC value of the ROC curve" was 0.493 to 0.902 (mean value: 0.738).

In contrast, in the cases of detecting at least one region selected from the group consisting of the EMI region, the R1 region, the R2 region, and the R3 region of periostin by using an "antibody binding to at least one region selected from the group consisting of the EMI region, the R1 region, the R2 region, and the R3 region of periostin or cleavage products thereof," that is, when a periostin cleavage product could be measured [the cases of measurements (2), (3), (7), (8), (10), and (11) in 2], "the sensitivity of measurement" was 73.1% to 96.2% (mean value: 80.8%); "the specificity of measurement" was 98.1%; "the ratio of the mean value of the measured values of positive samples to the mean value of the measured values of negative samples" ("the mean value of the measured values of positive samples"/"the mean value of the measured values of negative samples," i.e., the degree of increase in measured values of positive samples relative to those of negative samples) was 1.8 to 7.7 times (mean value: 4.8 times); and "the AUC value of the ROC curve" was 0.912 to 0.994 (mean value: 0.943).

That is, it is demonstrated that in the case of detecting at least one region selected from the group consisting of the EMI region, the R1 region, the R2 region, and the R3 region of periostin by using an "antibody binding to any of the EMI region, the R1 region, the R2 region, and the R3 region of periostin or cleavage products thereof," "the sensitivity of measurement," "the ratio of the mean value of the measured values of positive samples to the mean value of the measured values of negative samples" ("the mean value of the measured values of positive samples"/"the mean value of the measured values of negative samples," i.e., the degree of increase in measured values of positive samples relative to those of negative samples), and "the AUC value of the ROC curve" are all increased and enhanced to improve the accuracy of the measurement, compared to the case of using an antibody other than "antibodies binding to at least one region selected from the group consisting of the EMI region, the R1 region, the R2 region, and the R3 region of periostin or cleavage products thereof."

Furthermore, in the cases of detecting at least one region selected from the group consisting of the EMI region, the R1 region, the R2 region, and the R3 region of periostin and of capable of measuring a periostin cleavage product but not measuring periostin multimers by using an "antibody binding to at least one region selected from the group consisting of the EMI region, the R1 region, the R2 region, and the R3 region of periostin or cleavage products thereof but not binding to periostin multimers" [the cases of measurements (3), (7), and (10) in 2], "the sensitivity of the measurement" was 73.1% to 96.2% (mean value: 83.4%); "the specificity of the measurement" was 98.1%; "the ratio of the mean value of the measured values of positive samples to the mean value of the measured values of negative samples" ("the mean value of the measured values of positive samples"/"the mean value of the measured values of negative samples," i.e., the degree of increase in measured values of positive samples relative to those of negative samples) was 5.8 to 7.7 times (mean value: 7.1 times), and "the AUC value of the ROC curve" was 0.914 to 0.994 (mean value: 0.950).

That is, it is demonstrated that in the case of detecting at least one region selected from the group consisting of the EMI region, the R1 region, the R2 region, and the R3 region of periostin and of capable of measuring a periostin cleavage product but not measuring periostin multimers by using an "antibody binding to at least one region selected from the group consisting of the EMI region, the R1 region, the R2 region, and the R3 region of periostin or cleavage products thereof but not binding to periostin multimers," "the sensitivity of the measurement," "the ratio of the mean value of the measured values of positive samples to the mean value of the measured values of negative samples" ("the mean value of the measured values of positive samples"/"the mean value of the measured values of negative samples," i.e., the degree of increase in measured values of positive samples relative to those of negative samples), and "the AUC value of the ROC curve" are all further increased and enhanced to further improve the accuracy of the measurement, compared to the case of using an "antibody binding to at least one region selected from the group consisting of the EMI region, the R1 region, the R2 region, and the R3 region of periostin or cleavage products thereof."

It was confirmed from the results that the method of measuring periostin, the reagent for measuring periostin, and the method for improving accuracy in periostin measurement of the present invention can improve, for example, the measurement sensitivity and can improve the measurement accuracy in the measurement of periostin contained in samples.

It was also confirmed from the results that the method of testing for pulmonary fibrosis or interstitial pneumonia of the present invention can improve the measurement sensitivity, specificity, or the like and can improve the measurement accuracy to give an accurate measurement value of periostin and that the method can improve the differentiation of pulmonary fibrosis or interstitial pneumonia patients from healthy subjects and patients affected with other diseases to prevent wrong diagnosis.

Example 13

Measurement of Periostin in Sample

A standard curve (calibration curve) was described by measuring periostin in samples containing known concentrations of periostin.

1. Sample

"Partial-length periostin (Δ17/18/21)" (i.e., "mixture of periostin monomer, multimer, and cleavage product" is known to contain all of periostin monomer, multimer, and cleavage product) in 2 of [1] of II in Reference Example 2 was diluted with a sample diluent [50 mM tris(hydroxymethyl)aminomethane buffer [Tris buffer] (pH 8.0) containing 0.5% casein, 100 mM sodium chloride, and 0.1% sodium azide] to prepare the following reference samples (2) to (6) containing periostin at known concentrations.

A sample diluent [50 mM tris(hydroxymethyl)aminomethane buffer [Tris buffer] (pH 8.0) containing 0.5% casein, 100 mM sodium chloride, and 0.1% sodium azide] not containing periostin was used as a sample (the following reference sample (1)) containing 0 ng/mL of periostin.

(1) Reference sample-1 (periostin concentration: 0 ng/mL)
(2) Reference sample-2 (periostin concentration: 0.125 ng/mL)
(3) Reference sample-3 (periostin concentration: 0.25 ng/mL)
(4) Reference sample-4 (periostin concentration: 0.5 ng/mL)
(5) Reference sample-5 (periostin concentration: 1.0 ng/mL)
(6) Reference sample-6 (periostin concentration: 2.0 ng/mL)

2. Measurement

The periostin concentration in each sample was measured and calculated by enzyme immunosorbentassay (ELISA) using anti-periostin monoclonal antibodies.

The measurement was performed in accordance with the description in (1) to (13) of 2 in Example 12 except for the following matters (a) and (b) to describe each standard curve of "periostin concentration-absorbance," i.e., a calibration curve, for following measurements (1) "Measurement-1 by a conventional technique" to "(13) Measurement-7 by a conventional technique."

(a) Reference samples (1) to (6) in 1 were used as the samples in (d) of (1) of 2 in Example 12, instead of samples (1) and (2) in 1 in Example 12.

(b) The standard curve of "periostin concentration-absorbance" (calibration curve) was described from the absorbance of each reference sample measured in (k) of (1) of 2 in Example 12 instead of the procedure in (l) and (m) of (1) of 2 in Example 12.

(1) Measurement-1 by a conventional technique
(2) Measurement-1 by the present invention (3) Measurement-2 by the present invention
(4) Measurement-2 by a conventional technique
(5) Measurement-3 by a conventional technique
(6) Measurement-4 by a conventional technique
(7) Measurement-3 by the present invention
(8) Measurement-4 by the present invention
(9) Measurement-5 by a conventional technique
(10) Measurement-5 by the present invention
(11) Measurement-6 by the present invention
(12) Measurement-6 by a conventional technique
(13) Measurement-7 by a conventional technique 3. Results (1) The measurement results in 2 are shown in FIGS. 19 to 25.

In these figures, the horizontal axis indicates periostin concentrations (ng/mL) in the samples, and the vertical axis indicates the absorbance ($\Delta$OD) at 450 nm in measurement of each sample.

(2) The standard curves (calibration curves), shown in FIGS. 19 to 25, described in this Example all show an increase in the absorbance obtained with the increase of the periostin concentration in samples to demonstrate the quantitatively of the measurements.

It was confirmed from the results that the method of measuring periostin and the reagent for measuring periostin of the present invention can accurately measure periostin in samples.

Example 14

Preparation of Anti-Periostin Monoclonal Antibody—Seventh Time

An anti-periostin monoclonal antibody was prepared, separately from Examples 1 to 6, in accordance with the description in (1) to (4) in Example 1 (seventh time).

As a result, a clone was established from grown hybridoma cell lines and was named as cell line SS25A.

A rat anti-periostin monoclonal antibody (hereinafter, referred to as "anti-periostin monoclonal antibody (SS25A)") was obtained from a monoclonal antibody-producing cell line SS25A.

Example 15

Preparation of Anti-Periostin Monoclonal Antibody—Eighth Time

An anti-periostin monoclonal antibody was prepared, separately from Examples 1 to 6 and 14, in accordance with the description in (1) to (4) in Example 1 (eighth time).

As a result, a clone was established from grown hybridoma cell lines and was named as cell line SS27A.

A rat anti-periostin monoclonal antibody (hereinafter, referred to as "anti-periostin monoclonal antibody (SS27A)") was obtained from a monoclonal antibody-producing cell line SS27A.

Example 16

Confirmation of Recognition Site of Anti-Periostin Monoclonal Antibody

Each of the anti-periostin monoclonal antibodies obtained in Examples 14 and 15 was investigated for which region of periostin the anti-periostin monoclonal antibody recognizes in accordance with the description in (1) to (8) of 1 in Example 7.

It was confirmed from the measurement results that "anti-periostin monoclonal antibody (SS25A)" obtained in Example 14 bound to only "periostin," "partial-length periostin (R1/R2 regions)," "partial-length periostin (R2 region)," and "partial-length periostin (R1/R2/R3 regions)" among the above-mentioned periostin and partial-length periostins and did not bind to "partial-length periostin (R4 region)," "partial-length periostin (EMI region)" and "partial-length periostin (C-terminal region)."

It was confirmed from the results that "anti-periostin monoclonal antibody (SS25A)" recognized the R2 region of periostin as an epitope.

It was also confirmed from the measurement results that "anti-periostin monoclonal antibody (SS27A)" obtained in Example 15 bound to only "periostin," "partial-length periostin (R1/R2 regions)," and "partial-length periostin (R1/R2/R3 regions)" among the above-mentioned periostin and partial-length periostins and did not bind to "partial-length periostin (R2 region)," "partial-length periostin (R4 region)," "partial-length periostin (EMI region)," and "partial-length periostin (C-terminal region)."

It was confirmed from the results that "anti-periostin monoclonal antibody (SS27A)" recognized the R1 region of periostin as an epitope.

Example 17

Investigation of Reactivity of Anti-Periostin Monoclonal Antibody

The reactivities of the anti-periostin monoclonal antibodies obtained in Examples 14 and 15 to periostin monomer, multimer, and cleavage product were investigated.

1. Measurement (1) "Anti-periostin monoclonal antibody (SS25A)" obtained in Example 14 and "anti-periostin monoclonal antibody (SS27A)" obtained in Example 15 were each subjected to immunoprecipitation treatment, SDS-polyacrylamide gel electrophoresis, and Western blotting in accordance with the description in 1 to 3 of [1] in Example 8.

In addition, "anti-periostin monoclonal antibody (SS18A)" obtained in Example 3, "anti-periostin monoclonal antibody (SS 19A)" obtained in Example 4, and "anti-periostin monoclonal antibody (SS19D)" obtained in Example 4 were also subjected to the above-mentioned procedures as controls.

In the SDS-polyacrylamide gel electrophoresis and the Western blotting, no lanes for negative control were provided.

(2) As a result of the procedures, in the polyvinyl difluoride membrane, the positions corresponding to the molecular weights of the periostin monomer, multimer, and cleavage product recognized and bound by the anti-periostin monoclonal antibodies were colored.

The polyvinyl difluoride membrane subjected to color development was photographed.

The reactivity of each of the anti-periostin monoclonal antibodies to the monomer, multimer, and cleavage product of periostin was investigated by the presence and the position (molecular weight) of coloring on the polyvinyl difluoride membrane.

Figure 26:
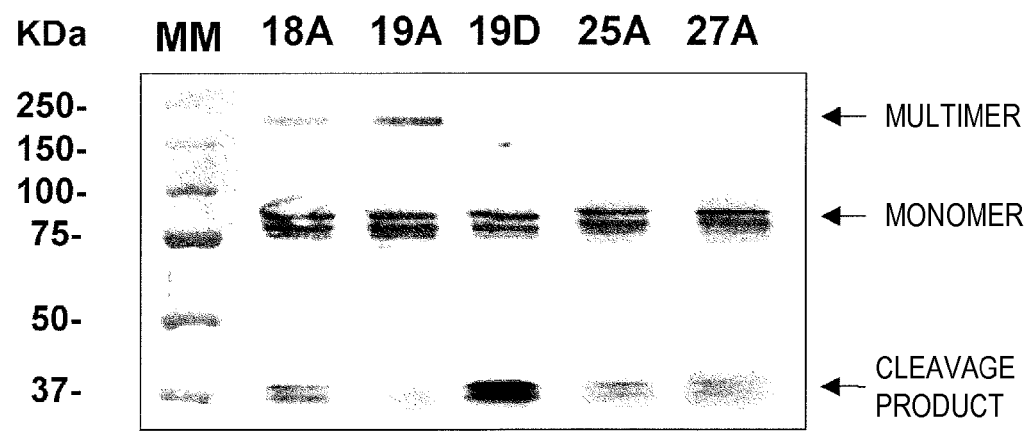
FIG. 26 is a photograph showing the results (polyvinyl difluoride membrane) in investigation of reactivities of the obtained anti-periostin monoclonal antibodies (derived from cell line SS18A, cell line SS19A, cell line SS19D, cell line SS25A, and cell line SS27A) to periostin monomer, multimer, and cleavage product.

2. Results (1) FIG. 26 shows the polyvinyl difluoride membrane photographed in (2) of 1.

In the figure, the lanes show, from the left, the molecular weight markers (lane indicated by "MM"), periostin recognized and bound by "anti-periostin monoclonal antibody (SS18A)" (lane indicated by "18A"), periostin recognized and bound by "anti-periostin monoclonal antibody (SS19A)" (lane indicated by "19A"), periostin recognized and bound by "anti-periostin monoclonal antibody (SS19D)" (lane indicated by "19D"), periostin recognized and bound by "anti-periostin monoclonal antibody (SS25A)" (lane indicated by "25A"), and periostin recognized and bound by "anti-periostin monoclonal antibody (SS27A)" (lane indicated by "27A").

In the figure, the broad band between the molecular weight markers of 150 and 250 KDa represents a periostin multimer (which is presumed as a trimer from the molecular weight) from the molecular weight; the broad band observed from near the molecular weight marker of 75 KDa towards the higher molecular weight side represents a periostin monomer from the molecular weight; and the broad band near the molecular weight marker of 37 KDa represents a periostin cleavage product from the molecular weight.

(2) The figure demonstrates that in the lane of periostin recognized and bound by "anti-periostin monoclonal antibody (SS25A)," coloring was observed at the positions representing the periostin monomer and cleavage product but not observed at the position representing the periostin multimer. It was therefore confirmed that "anti-periostin monoclonal antibody (SS25A)" recognizes and binds to periostin monomer and cleavage product but does not recognize and not bind to periostin multimers.

The figure also demonstrates that in the lane of periostin recognized and bound by "anti-periostin monoclonal antibody (SS27A)," coloring was observed at the positions representing the periostin monomer and cleavage product but not observed at the position representing the periostin multimer. It was therefore confirmed that "anti-periostin monoclonal antibody (SS27A)" recognizes and binds to periostin monomer and cleavage product but does not recognize and not bind to periostin multimers.

That is, the results demonstrate that the following anti-periostin monoclonal antibodies can recognize and bind to periostin cleavage products, but cannot recognize and not bind to periostin multimers.

"Anti-periostin monoclonal antibody (SS25A)"
"Anti-periostin monoclonal antibody (SS27A)"

Cell line SS25A is a monoclonal antibody-producing cell line producing "anti-periostin monoclonal antibody (SS25A)" and has been deposited in the NITE Patent Microorganisms Depositary, National Institute of Technology and Evaluation (2-5-8 Kazusakamatari, Kisarazu-shi, Chiba, Japan) under "Reference No. NITE AP-1285" on Mar. 16, 2012. Cell line SS25A, a monoclonal antibody-producing cell line producing "anti-periostin monoclonal antibody (SS25A)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Jul. 19, 2012 [transfer date: Jul. 19, 2012] (Accession No. NITE BP-1285).

Cell line SS27A is a monoclonal antibody-producing cell line producing "anti-periostin monoclonal antibody (SS27A)" and has been deposited in the NITE Patent Microorganisms Depositary, National Institute of Technology and Evaluation (2-5-8 Kazusakamatari, Kisarazu-shi, Chiba, Japan) under "Reference No. NITE AP-1286" on Mar. 16, 2012. Cell line SS27A, a monoclonal antibody-producing cell line producing "anti-periostin monoclonal antibody (SS27A)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Jul. 19, 2012 [transfer date: Jul. 19, 2012] (Accession No. NITE BP-1286).

(3) The results also demonstrate that in "anti-periostin monoclonal antibody (SS18A)" as a control, coloring was observed at all positions representing the periostin multimer, monomer, and cleavage product. It was therefore confirmed that "anti-periostin monoclonal antibody (SS18A)" recognizes and binds to all of periostin multimer, monomer, and cleavage product.

In "anti-periostin monoclonal antibody (SS19A)," coloring was observed at the positions representing the periostin multimer and monomer but not observed at the position representing the periostin cleavage product. It was therefore confirmed that "anti-periostin monoclonal antibody (SS19A)" recognizes and binds to periostin multimer and monomer but does not recognize and not bind to periostin cleavage products.

In "anti-periostin monoclonal antibody (SS19D)," coloring was observed at the positions representing the periostin monomer and cleavage product but not observed at the position representing the periostin multimer. It was therefore confirmed that "anti-periostin monoclonal antibody (SS19D)" recognizes and binds to periostin monomer and cleavage product but does not recognize and not bind to periostin multimers.

The results of "anti-periostin monoclonal antibody (SS18A)," "anti-periostin monoclonal antibody (SS19A)," and "anti-periostin monoclonal antibody (SS19D)" are the same as the results in Example 8. These results also demonstrated that the procedure and the results in Example 17 are accurate.

Example 18

Measurement of Periostin in Human Serum and ROC Analysis of Measurement Results

The effect of the present invention was confirmed by measuring periostin in human serum, and a Receiver Operating Characteristic (ROC) curve of the measurement results was described for analysis.

[1] ROC Analysis
1. Sample

Samples used were the following human serum (1) and (2).

(1) Positive Sample (39 Samples in Total)

Serum of pulmonary fibrosis patients (20 patients in total) and serum of interstitial pneumonia [associated with collagen vascular disease] patients (19 patients in total) were used as positive samples.

(2) Negative Samples (64 Samples in Total)

Serum of healthy subjects (64 subjects in total) was used as negative samples.

2. Measurement

The periostin concentration in each sample was measured and calculated by enzyme immunosorbentassay (ELISA) using anti-periostin monoclonal antibodies as follows.

<1> Measurement by a Conventional Technique

An ROC curve was described by determining the periostin concentration in each sample through measurement and treatment in accordance with the description in (a) to (n) of (1) of 2 in Example 11.

In the generation of the ROC curve, the assumed distribution was nonparametric, and the confidence level was set to 95%.

This measurement using "anti-periostin monoclonal antibody (SS18A)" as a immobilized antibody and "anti-periostin monoclonal antibody (SS17B)" as a labeled antibody can measure periostin multimer and monomer, as obvious from the investigation results in Example 8 and FIG. 7.

<2> Measurement (i) by the present invention

An ROC curve was described by determining the periostin concentration in each sample through measurement and treatment in accordance with the description in (a) to (n) of (1) of 2 in Example 11 except that "anti-periostin monoclonal antibody (SS20A)" (an antibody recognizing and binding to the EMI region of periostin and recognizing and binding to all of periostin monomer, multimer, and cleavage product) obtained in Example 5 was used instead of "anti-periostin monoclonal antibody (SS18A)" as the anti-periostin monoclonal antibody immobilized to the wells of the microtiter plate in (a) of (1) of 2 in Example 11 and that "anti-periostin monoclonal antibody (SS19D)" (an antibody recognizing and binding to the R3 region of periostin and capable of recognizing and binding to periostin monomer and cleavage product, but not capable of recognizing and binding to periostin multimers) obtained in Example 4 was used instead of "anti-periostin monoclonal antibody (SS17B)" as the anti-periostin monoclonal antibody labeled with biotin in (f) of (1) of 2 in Example 11.

In the generation of the ROC curve, the assumed distribution was nonparametric, and the confidence level was set to 95%.

This measurement using "anti-periostin monoclonal antibody (SS20A)" as a immobilized antibody and "anti-periostin monoclonal antibody (SS19D)" as a labeled antibody can measure periostin monomer and cleavage product, as obvious from the investigation results in Example 8 and FIG. 7.

<3> Measurement (ii) by the present invention

An ROC curve was described by determining the periostin concentration in each sample through measurement and treatment in accordance with the description in (a) to (n) of (1) of 2 in Example 11 except that "anti-periostin monoclonal antibody (SS25A)" (an antibody recognizing and binding to the R2 region of periostin and capable of recognizing and binding to periostin monomer and cleavage product, but not capable of recognizing and binding to periostin multimers) obtained in Example 14 was used instead of "anti-periostin monoclonal antibody (SS18A)" as the anti-periostin monoclonal antibody immobilized to the wells of the microtiter plate in (a) of (1) of 2 in Example 11 and that "anti-periostin monoclonal antibody (SS20A)" (an antibody recognizing and binding to the EMI region of periostin and recognizing and binding to all of periostin monomer, multimer, and cleavage product) obtained in Example 5 was used instead of "anti-periostin monoclonal antibody (SS17B)" as the anti-periostin monoclonal antibody labeled with biotin in (f) of (1) of 2 in Example 11.

In the generation of the ROC curve, the assumed distribution was nonparametric, and the confidence level was set to 95%.

This measurement using "anti-periostin monoclonal antibody (SS25A)" as a immobilized antibody and "anti-periostin monoclonal antibody (SS20A)" as a labeled antibody can measure periostin monomer and cleavage product, as obvious from the investigation results in Examples 8 and 16.

<4> Measurement-(iii) by the Present Invention

An ROC curve was described by determining the periostin concentration in each sample through measurement and treatment in accordance with the description in (a) to (n) of (1) of 2 in Example 11 except that "anti-periostin monoclonal antibody (SS27A)" (an antibody recognizing and binding to the R1 region of periostin and capable of recognizing and binding to periostin monomer and cleavage product, but not capable of recognizing and binding to periostin multimers) obtained in Example 15 was used instead of "anti-periostin monoclonal antibody (SS18A)" as the anti-periostin monoclonal antibody immobilized to the wells of the microtiter plate in (a) of (1) of 2 in Example 11 and that "anti-periostin monoclonal antibody (SS20A)" (an antibody recognizing and binding to the EMI region of periostin and recognizing and binding to all of periostin monomer, multimer, and cleavage product) obtained in Example 5 was used instead of "anti-periostin monoclonal antibody (SS17B)" as the anti-periostin monoclonal antibody labeled with biotin in (f) of (1) of 2 in Example 11.

In the generation of the ROC curve, the assumed distribution was nonparametric, and the confidence level was set to 95%.

This measurement using "anti-periostin monoclonal antibody (SS27A)" as a immobilized antibody and "anti-periostin monoclonal antibody (SS20A)" as a labeled antibody can measure periostin monomer and cleavage product, as obvious from the investigation results in Examples 8 and 16.

Figure 27:
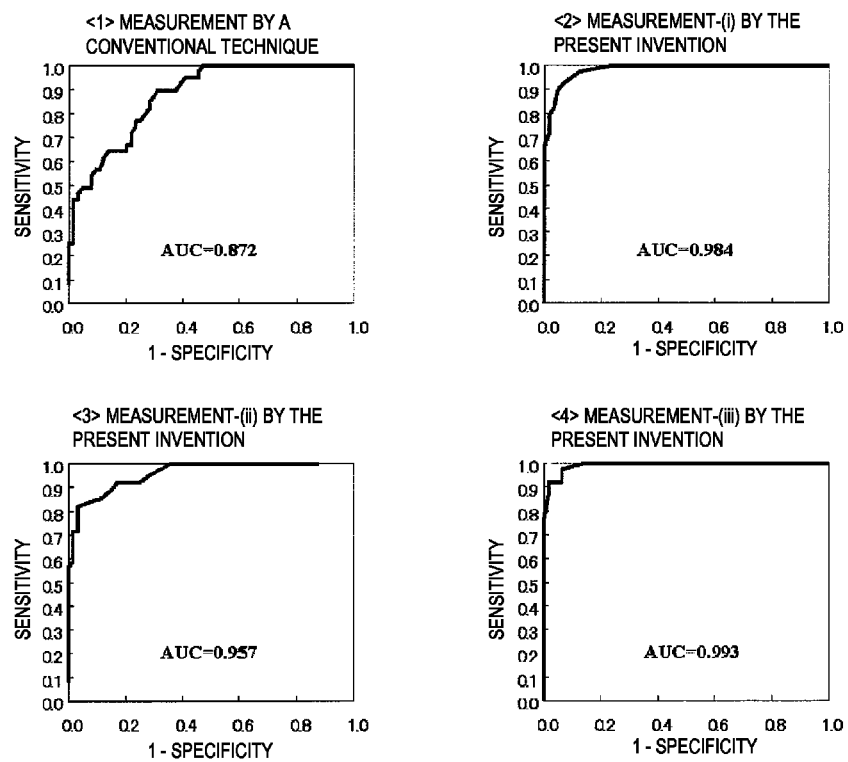
FIG. 27 includes graphs showing the ROC curves of measurement results of periostin in human serum.

3. Results (1) FIG. 27 shows all ROC curves described as described above based on, for example, the measurements results of concentrations of periostin contained in the positive serum samples of pulmonary fibrosis patients and interstitial pneumonia [associated with collagen vascular disease] patients and negative serum samples of healthy subjects.

In the figure, the horizontal axis in each ROC curve indicates the value of "1-specificity" in the measurement, and the vertical axis indicates the "sensitivity" of the measurement.

The "AUC" in each ROC curve in the figure is an abbreviation of Area Under the Curve, and the value thereof denotes the area under the ROC curve. A higher value of the AUC means higher sensitivity and specificity of the measurement, i.e., higher accuracy of the measurement and is therefore preferred in the measurement.

Each ROC curve will now be described.

(2) In "Measurement by a conventional technique" in <1> of 2, i.e., in a measuring system using "anti-periostin monoclonal antibody (SS18A)" recognizing and binding to the R1 region of periostin as a immobilized antibody and "anti-periostin monoclonal antibody (SS17B)" recognizing and binding to the R4 region of periostin as a labeled antibody to detect the R1 region and the R4 region of periostin and capable of measuring periostin multimer and monomer, the AUC value calculated from the ROC curve was 0.872.

(3) In "Measurement-(i) by the present invention" in <2> of 2, i.e., in a measuring system using "anti-periostin monoclonal antibody (SS20A)" recognizing and binding to the EMI region of periostin as a immobilized antibody and "anti-periostin monoclonal antibody (SS19D)" recognizing and binding to the R3 region of periostin as a labeled antibody to detect the EMI region and the R3 region of periostin and capable of measuring periostin monomer and cleavage product, the AUC value calculated from the ROC curve was 0.984.

(4) In "Measurement-(ii) by the present invention" in <3> of 2, i.e., in a measuring system using "anti-periostin monoclonal antibody (SS25A)" recognizing and binding to the R2 region of periostin as a immobilized antibody and "anti-periostin monoclonal antibody (SS20A)" recognizing and binding to the EMI region of periostin as a labeled antibody to detect the R2 region and the EMI region of periostin and capable of measuring periostin monomer and cleavage product, the AUC value calculated from the ROC curve was 0.957.

(5) In "Measurement-(iii) by the present invention" in <4> of 2, i.e., in a measuring system using "anti-periostin monoclonal antibody (SS27A)" recognizing and binding to the R1 region of periostin as a immobilized antibody and "anti-periostin monoclonal antibody (SS20A)" recognizing and binding to the EMI region of periostin as a labeled antibody to detect the R1 region and the EMI region of periostin and capable of measuring periostin monomer and cleavage product, the AUC value calculated from the ROC curve was 0.993.

(6) The results above demonstrate that in the ROC curve (AUC=0.984) of "Measurement-(i) by the present invention" in <2> of 2, the ROC curve (AUC=0.957) of "Measurement-(ii) by the present invention" in <3> of 2, and the ROC curve (AUC=0.993) of "Measurement-(iii) by the present invention" in <4> of 2, detecting at least one region selected from the group consisting of the EMI region, the R1 region, the R2 region, and the R3 region of periostin, i.e., using antibodies binding to periostin cleavage products and not binding to periostin multimers (i.e., capable of measuring periostin cleavage products but not capable of measuring periostin multimers), the AUC values were, in all measurements, significantly higher than those of the ROC curve (AUC=0.872) of "Measurement by a conventional technique" in <1> of 2 detecting a region other than "the EMI region, the R1 region, the R2 region, and the R3 region of periostin," i.e., detecting the R4 region and/or the C-terminal region of periostin and not capable of measuring periostin cleavage products. The results therefore demonstrate significant improvements in the sensitivity and specificity, i.e., the accuracy, of each measurement.

That is, it was confirmed from the results that the method of measuring periostin, the reagent for measuring periostin, and the method for improving accuracy in periostin measurement of the present invention can improve the measurement sensitivity, specificity, or the like and can improve the measurement accuracy.

It was also confirmed from the results that the method of testing for pulmonary fibrosis or interstitial pneumonia of the present invention can improve the measurement sensitivity, specificity, or the like and can improve the measurement accuracy to give an accurate measurement value of periostin and that the method can improve the differentiation of pulmonary fibrosis or interstitial pneumonia patients from healthy subjects and patients affected with other diseases to prevent wrong diagnosis.

[2] Investigation of Effect (e.g., the Sensitivity of the Measurement) of the Present Invention 1. Sample Samples used were the following human serum (1) and (2).

(1) Positive Sample (39 Samples in Total)

The serum of the pulmonary fibrosis patients (20 patients in total) and interstitial pneumonia [associated with collagen vascular disease] patients (19 patients in total) in (1) of 1 in [1] were used as positive samples.

(2) Negative Sample (64 Samples in Total)

The serum of healthy subject (64 subjects in total) in (2) of 1 in [1] was used as negative samples.

2. Measurement

<1> Measurement by a Conventional Technique

The periostin concentration in each sample was determined through measurement and treatment in accordance with the description in <1> of 2 in [1].

<2> Measurement-(i) by the Present Invention

The periostin concentration in each sample was determined through measurement and treatment in accordance with the description in <2> of 2 in [1].

<3> Measurement-(ii) by the Present Invention

The periostin concentration in each sample was determined through measurement and treatment in accordance with the description in <3> of 2 in [1].

<4> Measurement-(iii) by the Present Invention

The periostin concentration in each sample was determined through measurement and treatment in accordance with the description in <4> of 2 in [1].

3. Results (1) FIG. 28 summarizes the measurements <1> to <4> in 2 regarding the immobilized antibody and labeled antibody used in each measurement, the periostin region detected by the immobilized antibody, the periostin region detected by the labeled antibody, the type or types (monomer and/or multimer and/or cleavage product) of periostin measured by the measurement, the sensitivity of the measurement, the specificity of the measurement, the ratio of the mean value of the measured values of positive samples to the mean value of the measured values of negative samples ("the mean value of the measured values of positive samples"/"the mean value of the measured values of negative samples," i.e., the degree of increase in measured values of positive samples relative to those of negative samples), and "the AUC value of the described ROC curve."

(2) FIG. 28 demonstrates the followings.

In the case of not detecting any of the EMI region, the R1 region, the R2 region, and the R3 region of periostin by using an antibody other than "antibodies binding to at least one region selected from the group consisting of the EMI region, the R1 region, the R2 region, and the R3 region of periostin or cleavage products thereof," that is, when periostin cleavage products could not be measured [the case of measurement <1> in 2], "the sensitivity of measurement" was 43.6%; "the specificity of measurement" was 98.4%; "the ratio of the mean value of the measured values of positive samples to the mean value of the measured values of negative samples" ("the mean value of the measured values of positive samples"/"the mean value of the measured values of negative samples," i.e., the degree of increase in measured values of positive samples relative to those of negative samples) was 2.8 times; and "the AUC value of the ROC curve" was 0.872.

In contrast, in the case of detecting at least one region selected from the group consisting of the EMI region, the R1 region, the R2 region, and the R3 region of periostin and of capable of measuring a periostin cleavage product but not measuring periostin multimers by using an "antibody binding to at least one region selected from the group consisting of the EMI region, the R1 region, the R2 region, and the R3 region of periostin or cleavage products thereof and not binding to periostin multimers" [the cases of measurements <2>, <3>, and <4> in 2], "the sensitivity of measurement" was 71.8% to 92.3% (mean value: 81.2%); "the specificity of measurement" was 98.4%; "the ratio of the mean value of the measured values of positive samples to the mean value of the measured values of negative samples" ("the mean value of the measured values of positive samples"/"the mean value of the measured values of negative samples," i.e., the degree of increase in measured values of positive samples relative to those of negative samples) was 3.6 to 16.1 times (mean value: 8.6 times); and "the AUC value of the ROC curve" was 0.957 to 0.993 (mean value: 0.978).

That is, it is demonstrated that in the case of detecting at least one region selected from the group consisting of the EMI region, the R1 region, the R2 region, and the R3 region of periostin and of capable of measuring a periostin cleavage product but not measuring periostin multimers by using an "antibody binding to at least one region selected from the group consisting of the EMI region, the R1 region, the R2 region, and the R3 region of periostin or cleavage products thereof but not binding to periostin multimers," "the sensitivity of the measurement," "the ratio of the mean value of the measured values of positive samples to the mean value of the measured values of negative samples" ("the mean value of the measured values of positive samples"/"the mean value of the measured values of negative samples," i.e., the degree of increase in measured values of positive samples relative to those of negative samples), and "the AUC value of the ROC curve" are all significantly increased and enhanced to improve the accuracy of the measurement, compared to the case of using an antibody other than "antibodies binding to at least one region selected from the group consisting of the EMI region, the R1 region, the R2 region, and the R3 region of periostin or cleavage products thereof."

The results above also revealed that the method of measuring periostin, the reagent for measuring periostin, and the method for improving accuracy in periostin measurement of the present invention can improve, for example, the measurement sensitivity and can improve the measurement accuracy.

It was also confirmed from the results that the method of testing for pulmonary fibrosis or interstitial pneumonia of the present invention can improve the measurement sensitivity, specificity, or the like and can improve the measurement accuracy to give an accurate measurement value of periostin and that the method can improve the differentiation of pulmonary fibrosis or interstitial pneumonia patients from healthy subjects and patients affected with other diseases to prevent wrong diagnosis.

Accession Numbers

Cell line SS19D is a monoclonal antibody-producing cell line producing "anti-periostin monoclonal antibody (SS19D)" and has been deposited in the NITE Patent Microorganisms Depositary, National Institute of Technology and Evaluation (2-5-8 Kazusakamatari, Kisarazu-shi, Chiba, Japan) under "Accession No. NITE P-1068" on Feb. 22, 2011. Cell line SS19D, a monoclonal antibody-producing cell line producing "anti-periostin monoclonal antibody (SS19D)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Feb. 7, 2012 [transfer date: Feb. 9, 2012] (Accession No. NITE BP-1068).

Cell line SS16A is a monoclonal antibody-producing cell line producing "anti-periostin monoclonal antibody (SS16A)" and has been deposited in the NITE Patent Microorganisms Depositary, National Institute of Technology and Evaluation (2-5-8 Kazusakamatari, Kisarazu-shi, Chiba, Japan) under "Reference No. NITE AP-1281" on Mar. 16, 2012. Cell line SS16A, a monoclonal antibody-producing cell line producing "anti-periostin monoclonal antibody (SS16A)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Jul. 19, 2012 [transfer date: Jul. 19, 2012] (Accession No. NITE BP-1281).

Cell line SS18A is a monoclonal antibody-producing cell line producing "anti-periostin monoclonal antibody (SS18A)" and has been deposited in the NITE Patent Microorganisms Depositary, National Institute of Technology and Evaluation (2-5-8 Kazusakamatari, Kisarazu-shi, Chiba, Japan) under "Reference No. NITE AP-1282" on Mar. 16, 2012. Cell line SS18A, a monoclonal antibody-producing cell line producing "anti-periostin monoclonal antibody (SS18A)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Jul. 19, 2012 [transfer date: Jul. 19, 2012] (Accession No. NITE BP-1282).

Cell line SS19C is a monoclonal antibody-producing cell line producing "anti-periostin monoclonal antibody (SS19C)" and has been deposited in the NITE Patent Microorganisms Depositary, National Institute of Technology and Evaluation (2-5-8 Kazusakamatari, Kisarazu-shi, Chiba, Japan) under "Reference No. NITE AP-1283" on Mar. 16, 2012. Cell line SS19C, a monoclonal antibody-producing cell line producing "anti-periostin monoclonal antibody (SS19C)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Jul. 19, 2012 [transfer date: Jul. 19, 2012] (Accession No. NITE BP-1283).

Cell line SS20A is a monoclonal antibody-producing cell line producing "anti-periostin monoclonal antibody (SS20A)" and has been deposited in the NITE Patent Microorganisms Depositary, National Institute of Technology and Evaluation (2-5-8 Kazusakamatari, Kisarazu-shi, Chiba, Japan) under "Reference No. NITE AP-1284" on Mar. 16, 2012. Cell line SS20A, a monoclonal antibody-producing cell line producing "anti-periostin monoclonal antibody (SS20A)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Jul. 19, 2012 [transfer date: Jul. 19, 2012] (Accession No. NITE BP-1284).

Cell line SS25A is a monoclonal antibody-producing cell line producing "anti-periostin monoclonal antibody (SS25A)" and has been deposited in the NITE Patent Microorganisms Depositary, National Institute of Technology and Evaluation (2-5-8 Kazusakamatari, Kisarazu-shi, Chiba, Japan) under "Reference No. NITE AP-1285" on Mar. 16, 2012. Cell line SS25A, a monoclonal antibody-producing cell line producing "anti-periostin monoclonal antibody (SS25A)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Jul. 19, 2012 [transfer date: Jul. 19, 2012] (Accession No. NITE BP-1285).

Cell line SS27A is a monoclonal antibody-producing cell line producing "anti-periostin monoclonal antibody (SS27A)" and has been deposited in the NITE Patent Microorganisms Depositary, National Institute of Technology and Evaluation (2-5-8 Kazusakamatari, Kisarazu-shi, Chiba, Japan) under "Reference No. NITE AP-1286" on Mar. 16, 2012. Cell line SS27A, a monoclonal antibody-producing cell line producing "anti-periostin monoclonal antibody (SS27A)," has been transferred to international deposition by an application for transferring the domestic deposition to the international deposition submitted to the NITE Patent Microorganisms Depositary, National Institute of Technology and Evaluation (2-5-8 Kazusakamatari, Kisarazu-shi, Chiba, Japan) on Jul. 19, 2012 [transfer date: Jul. 19, 2012] (Accession No. NITE BP-1286).

The invention claimed is:

1. An isolated antibody produced by a hybridoma cell line selected from the group consisting of SS19D having an accession number NITE BP-1068, SS25A having an accession number NITE BP-1285, and SS27A having an accession number NITE BP-1286, wherein the antibody specifically binds to at least one region of periostin or a cleavage product thereof wherein the at least one region is selected from the group consisting of an R1 region having an amino acid sequence consisting of SEQ ID NO:6, an R2 region having an amino acid sequence consisting of SEQ ID NO:8, and an R3 region having an amino acid sequence consisting of SEQ ID NO:10; and wherein the antibody does not bind to periostin multimers.

2. A reagent for measuring periostin or a cleavage product thereof contained in a sample, the reagent comprising an antibody produced by a hybridoma cell line selected from the group consisting of SS19D having an accession number NITE BP-1068, SS25A having an accession number NITE BP-1285, and SS27A having an accession number NITE BP-1286, wherein the antibody specifically binds to at least one region of periostin or a cleavage product thereof wherein the region is selected from the group consisting of an R1 region having an amino acid sequence consisting of SEQ ID NO:6, an R2 region having an amino acid sequence consisting of SEQ ID NO:8 and an R3 having an amino acid sequence consisting of SEQ ID NO:10 and wherein the antibody does not bind to periostin multimers.

* * * * *